US009180252B2

(12) United States Patent
Gelblum et al.

(10) Patent No.: US 9,180,252 B2
(45) Date of Patent: Nov. 10, 2015

(54) BELLOWS SYRINGE FLUID DELIVERY SYSTEM

(71) Applicant: MEDRAD, INC., Indianola, PA (US)

(72) Inventors: Eugene A Gelblum, Mt. Lebanon, PA (US); Jill Denesvich, Pittsburgh, PA (US); Edward J Rhinehart, Monroeville, PA (US); Barry L Tucker, Verona, PA (US); Mark Trocki, Cheswick, PA (US); John Puskar-Pascewicz, Pittsburgh, PA (US); Matthew Beale, Pittsburgh, PA (US); Matthew Sass, Pittsburgh, PA (US)

(73) Assignee: Bayer Medical Care Inc., Indianola, PA (US)

( * ) Notice: Subject to any disclaimer, the term of this patent is extended or adjusted under 35 U.S.C. 154(b) by 117 days.

(21) Appl. No.: 13/834,624

(22) Filed: Mar. 15, 2013

(65) Prior Publication Data

US 2013/0281940 A1  Oct. 24, 2013

Related U.S. Application Data

(60) Provisional application No. 61/636,049, filed on Apr. 20, 2012.

(51) Int. Cl.
| | |
|---|---|
| *A61M 5/178* | (2006.01) |
| *A61M 37/00* | (2006.01) |
| *A61M 5/24* | (2006.01) |
| *A61M 5/145* | (2006.01) |
| *A61M 5/148* | (2006.01) |

(52) U.S. Cl.
CPC ............ *A61M 5/2425* (2013.01); *A61M 5/148* (2013.01); *A61M 5/1452* (2013.01); *A61M 5/14546* (2013.01)

(58) Field of Classification Search
CPC ............ A61M 5/2425; A61M 5/1452; A61M 5/14546; A61M 5/148; A61M 5/1456
USPC ............... 604/212–214, 216, 132, 133, 95.03
See application file for complete search history.

(56) References Cited

U.S. PATENT DOCUMENTS

| | | | |
|---|---|---|---|
| 798,093 | A | 8/1905 | Dean |
| 937,029 | A | 10/1909 | Strong et al. |

(Continued)

FOREIGN PATENT DOCUMENTS

| | | |
|---|---|---|
| DE | 29818399 | 2/2000 |
| EP | 1086661 A2 | 3/2001 |

(Continued)

OTHER PUBLICATIONS

International Search Report and Written Opinion of the International Searching Authority in counterpart PCT Application No. PCT/US/2013/035884 filing date Apr. 10, 2013.

(Continued)

*Primary Examiner* — Rebecca E Eisenberg
(74) *Attorney, Agent, or Firm* — Joseph L. Kent; David Schramm; James R. Stevenson

(57) ABSTRACT

A bellows assembly for a fluid delivery system is a multi-component device that includes a cylindrical pressure jacket and a bellows syringe that is received within the pressure jacket. The bellows syringe includes a cap member and a bellows member. The bellows syringe in one embodiment is adapted to be secured to the pressure jacket by the cap member. The cap member is formed with a discharge port, which may be formed as conventional luer fitting. The discharge port is disposed coaxially within an annular wall on the outward facing side of the cap member and may be recessed within the annular wall. The bellows member is a hollow body that includes a series of bellows sections or rings. A distal end of the bellow member is formed with a discharge neck terminating in a discharge port, and the proximal end is formed with a closed end wall.

23 Claims, 81 Drawing Sheets

(56) References Cited

U.S. PATENT DOCUMENTS

| | | |
|---|---|---|
| 2,514,575 A | 7/1950 | Hein et al. |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,673,561 A | 3/1954 | Peterson, Jr. |
| 2,688,963 A | 9/1954 | Smith |
| 2,688,964 A | 9/1954 | Smith |
| 2,717,598 A | 9/1955 | Kranso |
| 2,911,972 A | 11/1959 | Scholcoff |
| 2,935,067 A | 5/1960 | Bernanrd |
| 2,950,717 A | 8/1960 | Edouard |
| 3,155,281 A | 11/1964 | Stracey |
| 3,161,194 A | 12/1964 | Chapman |
| 3,161,195 A | 12/1964 | Sinclair et al. |
| 3,172,577 A | 3/1965 | Hartung |
| 3,190,619 A | 6/1965 | Penney et al. |
| 3,231,139 A | 1/1966 | Bernard |
| 3,301,293 A | 1/1967 | Santelli |
| 3,340,869 A | 9/1967 | Arthur |
| 3,390,821 A | 7/1968 | Joseph |
| 3,411,503 A | 11/1968 | Santomieri |
| 3,442,424 A | 5/1969 | Prussin et al. |
| 3,471,058 A | 10/1969 | Latham et al. |
| 3,473,524 A | 10/1969 | Drewe |
| 3,474,844 A | 10/1969 | Lindstrom et al. |
| 3,506,163 A | 4/1970 | Rauth et al. |
| 3,527,215 A | 9/1970 | Witt |
| 3,557,788 A | 1/1971 | Swartz |
| 3,613,963 A | 10/1971 | Berkmuller |
| 3,618,846 A | 11/1971 | Poli |
| 3,826,409 A | 7/1974 | Chilcoate |
| 3,873,003 A | 3/1975 | Seiferth et al. |
| 3,938,514 A | 2/1976 | Boucher |
| 4,006,736 A | 2/1977 | Kranys et al. |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,349,129 A | 9/1982 | Amneus |
| 4,411,656 A | 10/1983 | Cornett, III |
| 4,526,296 A | 7/1985 | Berger et al. |
| 4,677,980 A | 7/1987 | Reilly et al. |
| 4,743,243 A | 5/1988 | Vaillencourt |
| 4,753,638 A | 6/1988 | Peters |
| 4,758,226 A | 7/1988 | Carre |
| 4,773,458 A | 9/1988 | Touzani |
| 4,850,807 A | 7/1989 | Frantz |
| 5,000,739 A | 3/1991 | Kulisz et al. |
| 5,147,311 A | 9/1992 | Pickhard |
| 5,201,438 A | 4/1993 | Norwood |
| 5,209,372 A | 5/1993 | Norwood |
| 5,236,204 A | 8/1993 | Hempel |
| 5,238,150 A | 8/1993 | Williams |
| 5,240,130 A | 8/1993 | Osbakk |
| 5,242,422 A | 9/1993 | Schneberger et al. |
| 5,269,428 A | 12/1993 | Gilbert |
| 5,300,031 A * | 4/1994 | Neer et al. ............ 604/154 |
| 5,333,761 A | 8/1994 | Davis et al. |
| 5,353,961 A | 10/1994 | Debush |
| 5,370,250 A | 12/1994 | Gilbert |
| 5,378,233 A | 1/1995 | Haber et al. |
| 5,383,858 A | 1/1995 | Reilly et al. |
| 5,397,157 A | 3/1995 | Hempel et al. |
| 5,520,653 A | 5/1996 | Reilly et al. |
| 5,573,129 A | 11/1996 | Nagata et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,683,369 A | 11/1997 | Tsukada |
| 5,731,053 A | 3/1998 | Kuhn et al. |
| D394,212 S | 5/1998 | Mazda |
| 5,758,789 A | 6/1998 | Shin et al. |
| 5,779,675 A | 7/1998 | Reilly et al. |
| 5,785,691 A | 7/1998 | Vetter et al. |
| 5,794,107 A | 8/1998 | Russell |
| D397,930 S | 9/1998 | Mazda |
| D397,931 S | 9/1998 | Mazda |
| D397,932 S | 9/1998 | Mazda |
| D397,933 S | 9/1998 | Mazda |
| 5,836,922 A | 11/1998 | Hansen et al. |
| 5,873,861 A | 2/1999 | Hitchins et al. |
| 5,899,889 A | 5/1999 | Futagawa et al. |
| 5,913,844 A | 6/1999 | Ziemba et al. |
| RE36,377 E | 11/1999 | Gilbert |
| 5,979,326 A | 11/1999 | Ohinata |
| 6,062,437 A | 5/2000 | Mascitelli |
| 6,077,252 A | 6/2000 | Siegel |
| 6,083,204 A | 7/2000 | Malerba et al. |
| 6,105,815 A | 8/2000 | Mazda |
| 6,142,976 A | 11/2000 | Kubo |
| 6,216,915 B1 | 4/2001 | Harman et al. |
| 6,250,505 B1 | 6/2001 | Petit |
| 6,273,152 B1 | 8/2001 | Buehler et al. |
| 6,315,761 B1 | 11/2001 | Shcherbina et al. |
| 6,319,235 B1 | 11/2001 | Yoshino |
| 6,332,876 B1 | 12/2001 | Poynter et al. |
| 6,485,471 B1 | 11/2002 | Zivitz et al. |
| 6,544,246 B1 | 4/2003 | Niedospial, Jr. |
| 6,558,358 B2 | 5/2003 | Rosoff et al. |
| 6,620,134 B1 | 9/2003 | Trombley, III et al. |
| 6,634,524 B1 | 10/2003 | Helmenstein |
| 6,652,489 B2 | 11/2003 | Trocki et al. |
| 6,702,143 B2 | 3/2004 | Wang |
| 6,726,657 B1 | 4/2004 | Dedig et al. |
| 6,773,417 B2 | 8/2004 | Fitzgibbons et al. |
| 6,840,164 B2 | 1/2005 | Eastman |
| 6,866,039 B1 | 3/2005 | Wright et al. |
| 6,869,419 B2 | 3/2005 | Dragan et al. |
| RE38,770 E | 8/2005 | Gilbert |
| 7,004,213 B2 | 2/2006 | Hansen |
| 7,011,650 B2 | 3/2006 | Rosoff et al. |
| 7,192,549 B2 | 3/2007 | Hansen |
| 7,250,039 B2 | 7/2007 | Fitzgerald |
| 7,309,463 B2 | 12/2007 | Hansen |
| 7,419,478 B1 | 9/2008 | Reilly et al. |
| 7,497,843 B1 | 3/2009 | Castillo et al. |
| 7,513,378 B2 | 4/2009 | Mori et al. |
| 7,740,792 B2 | 6/2010 | Haury et al. |
| 7,802,691 B2 | 9/2010 | Musalek |
| 8,133,203 B2 | 3/2012 | Hack |
| 2002/0091361 A1 | 7/2002 | Rosoff et al. |
| 2003/0210985 A1 | 11/2003 | Feygin et al. |
| 2007/0167910 A1 | 7/2007 | Tennican et al. |
| 2011/0218499 A1 | 9/2011 | Cahen |
| 2013/0163364 A1 | 6/2013 | Park |

FOREIGN PATENT DOCUMENTS

| | | |
|---|---|---|
| FR | 1288915 A | 3/1962 |
| GB | 2214819 A | 9/1989 |
| WO | 9820920 | 5/1998 |
| WO | 9924098 | 5/1999 |
| WO | 2008002483 | 1/2008 |
| WO | 2013163364 | 10/2013 |

OTHER PUBLICATIONS

International Preliminary Report on Patentability from corresponding PCT Application No. PCT/US2013/037763, Jul. 2013.
International Preliminary Report on Patentability from corresponding PCT Application No. PCT/US2013/035884, Jun. 2013.
International Search Report for Counterpart PCT Application No. PCT/US1999/027574, Jun. 2000.

\* cited by examiner

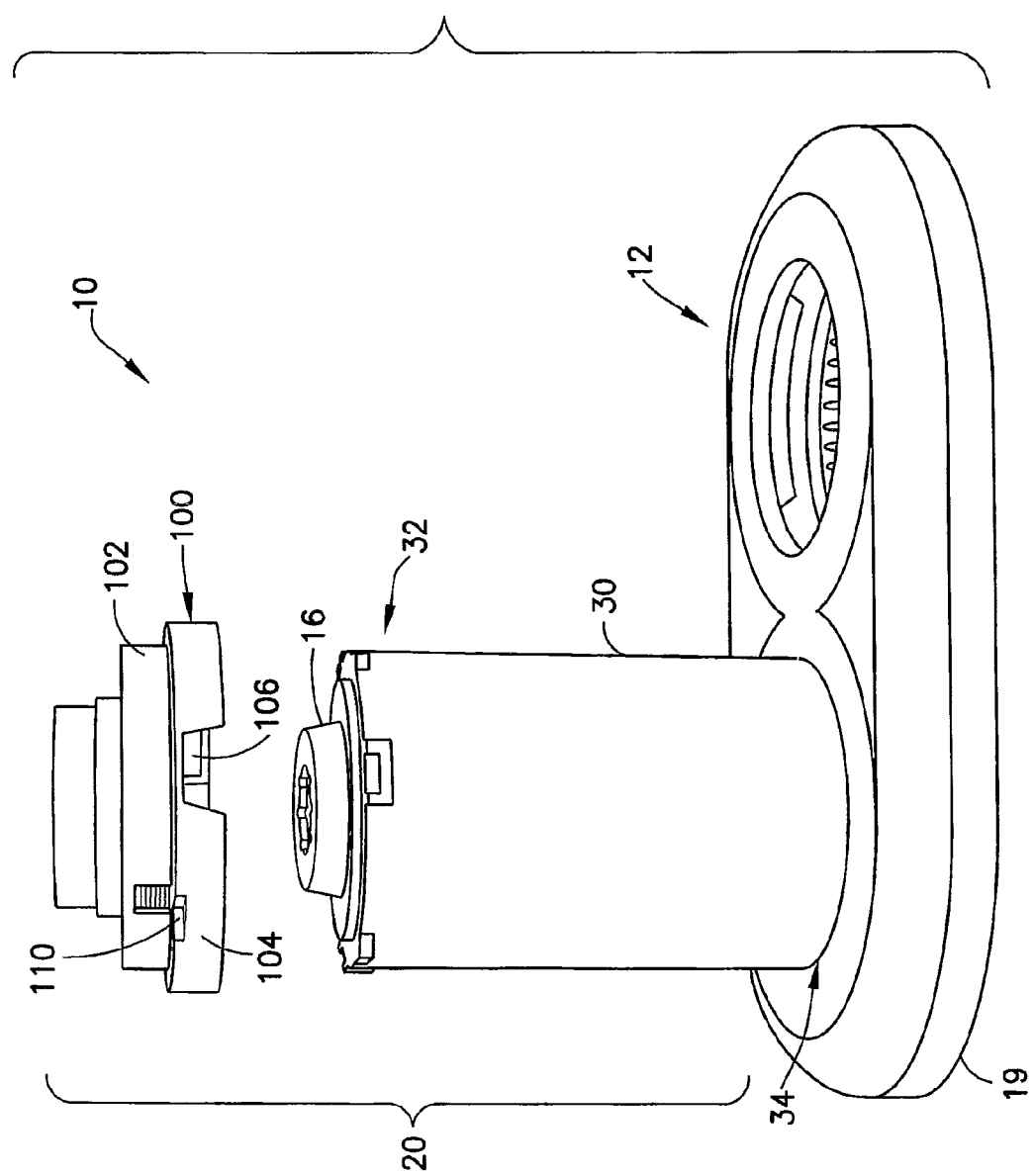

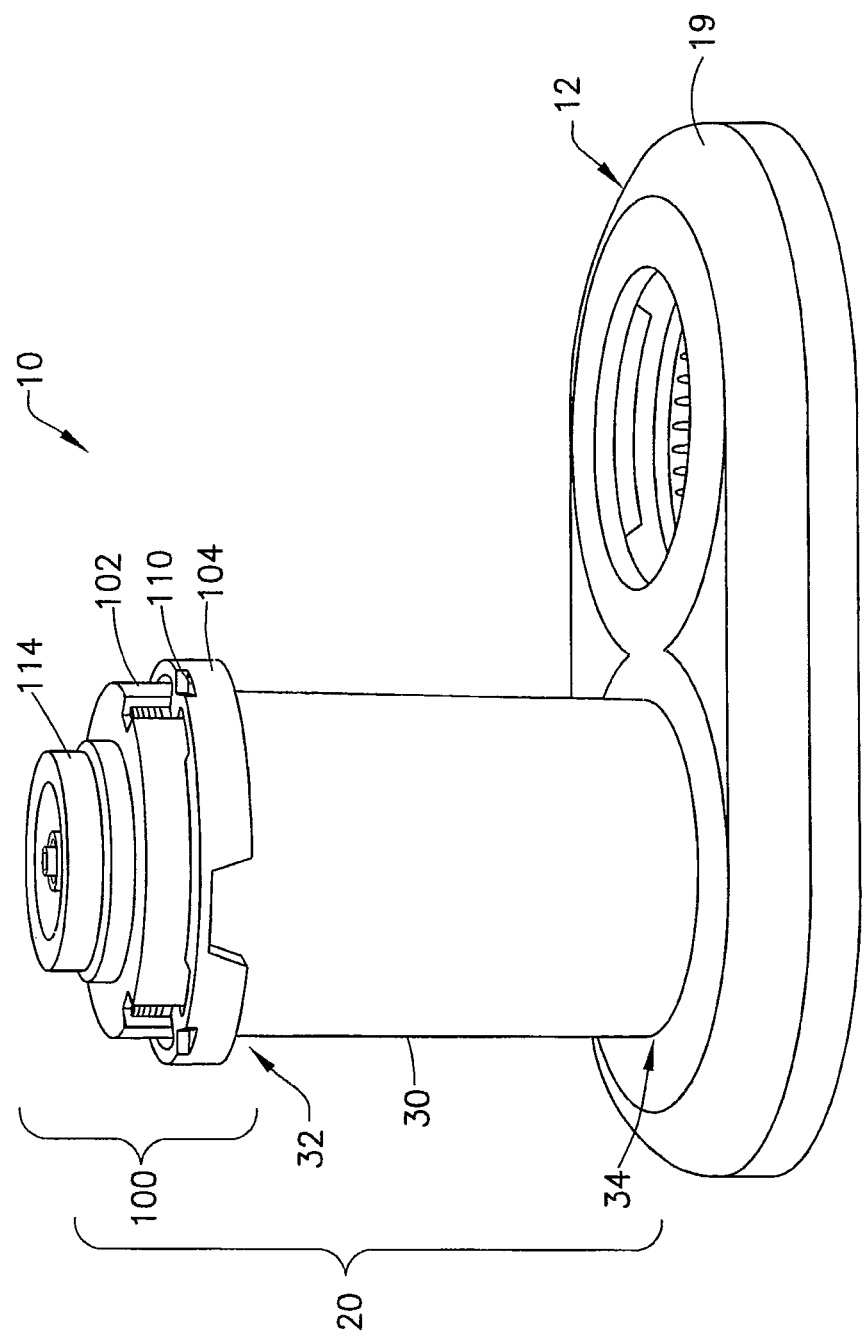

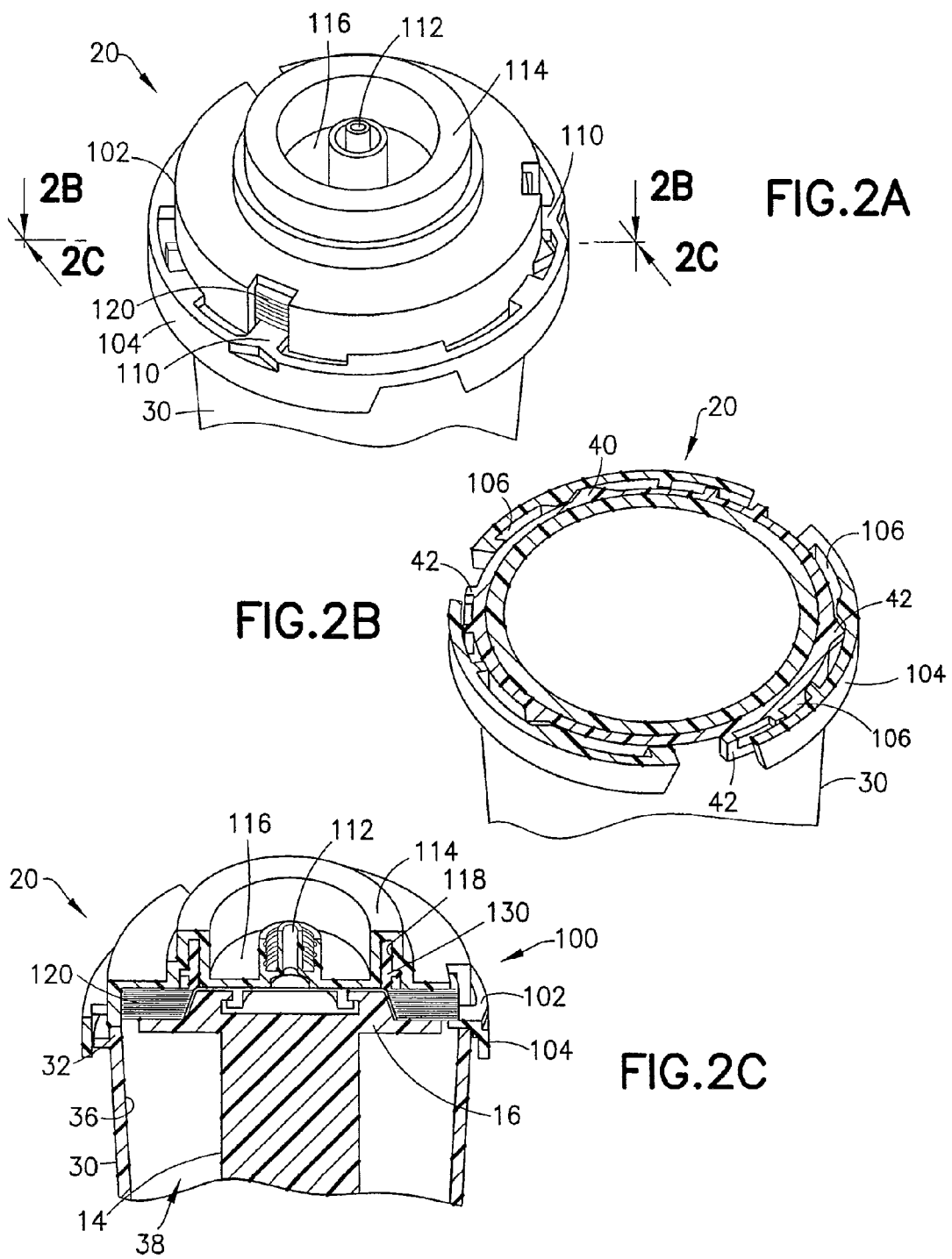

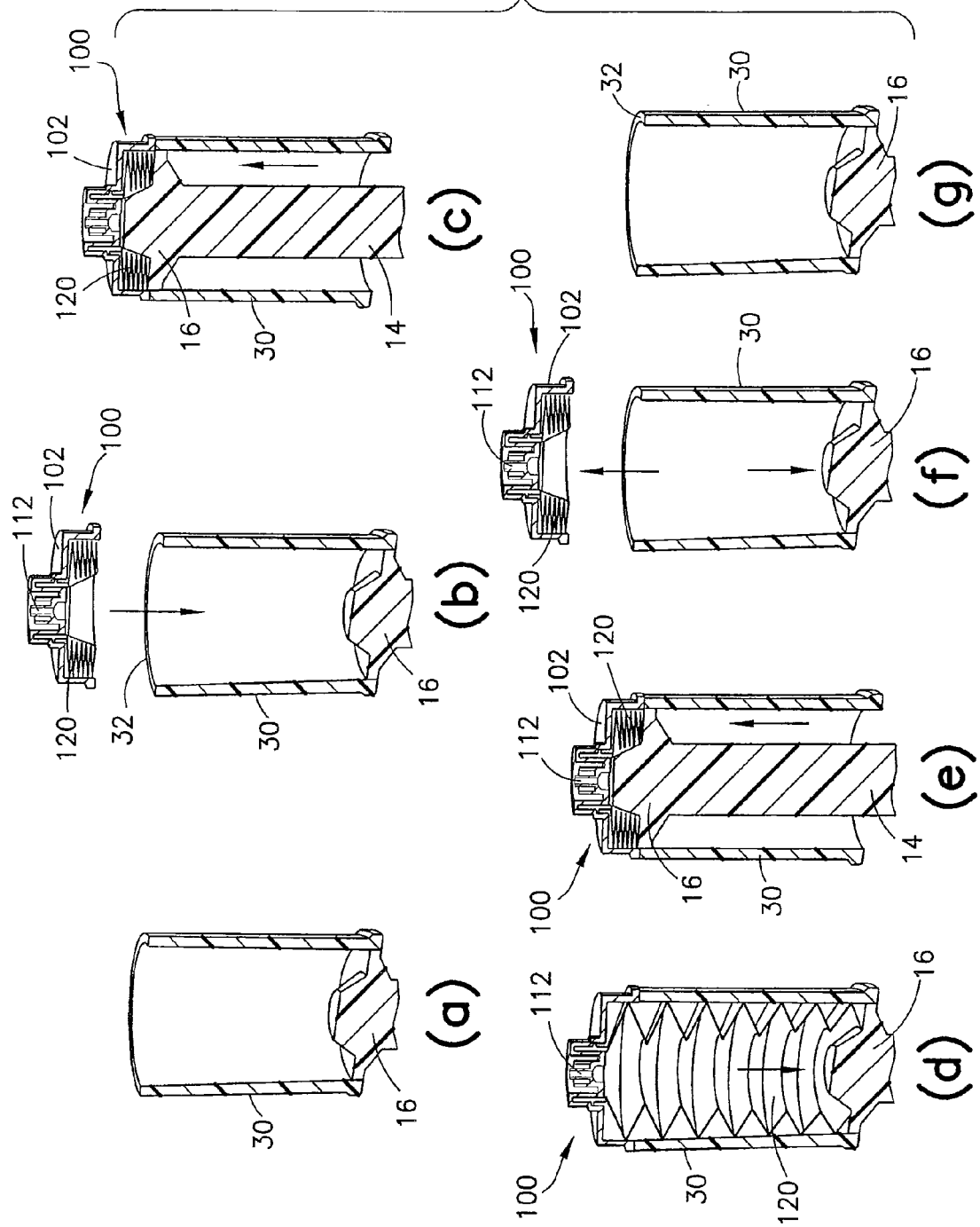

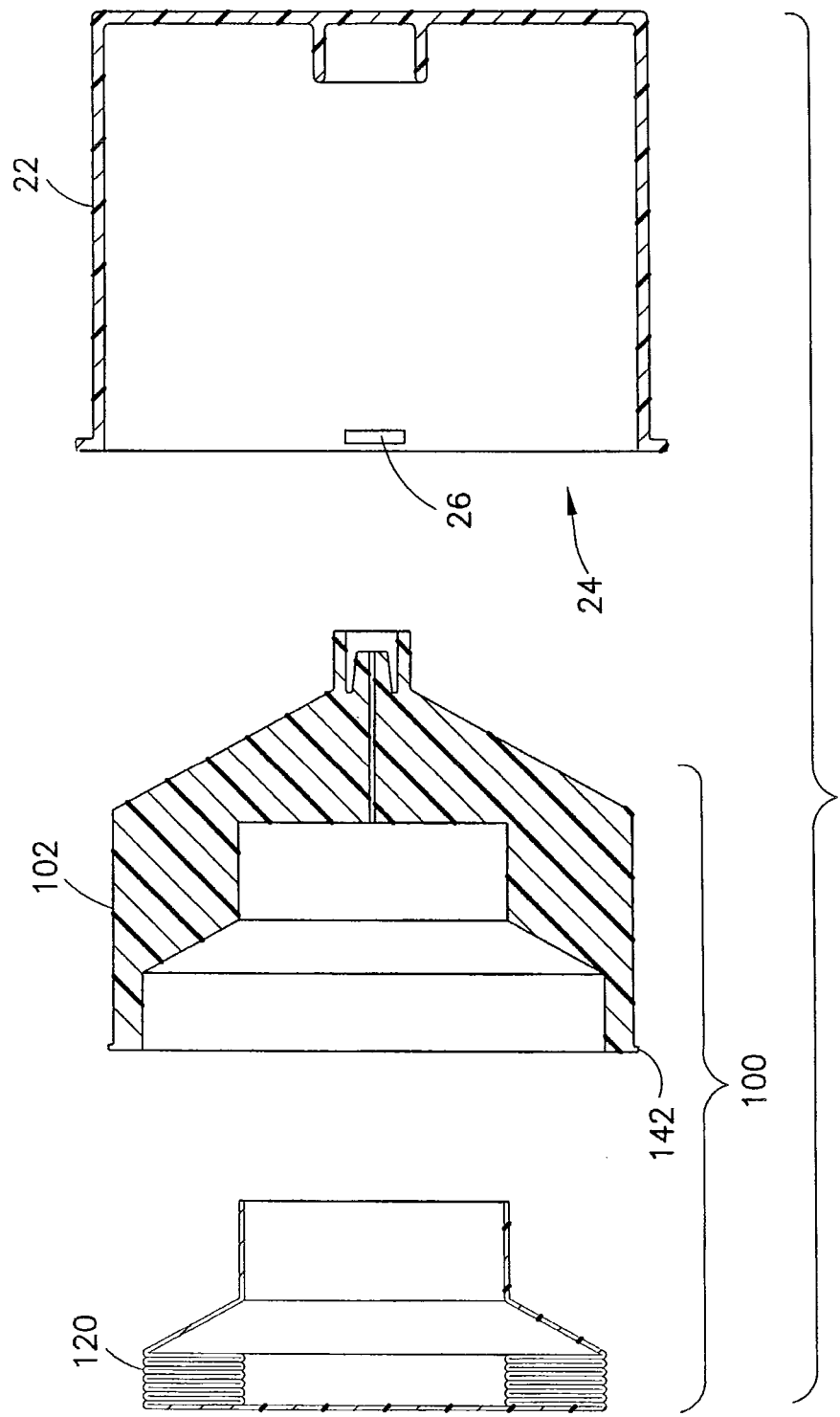

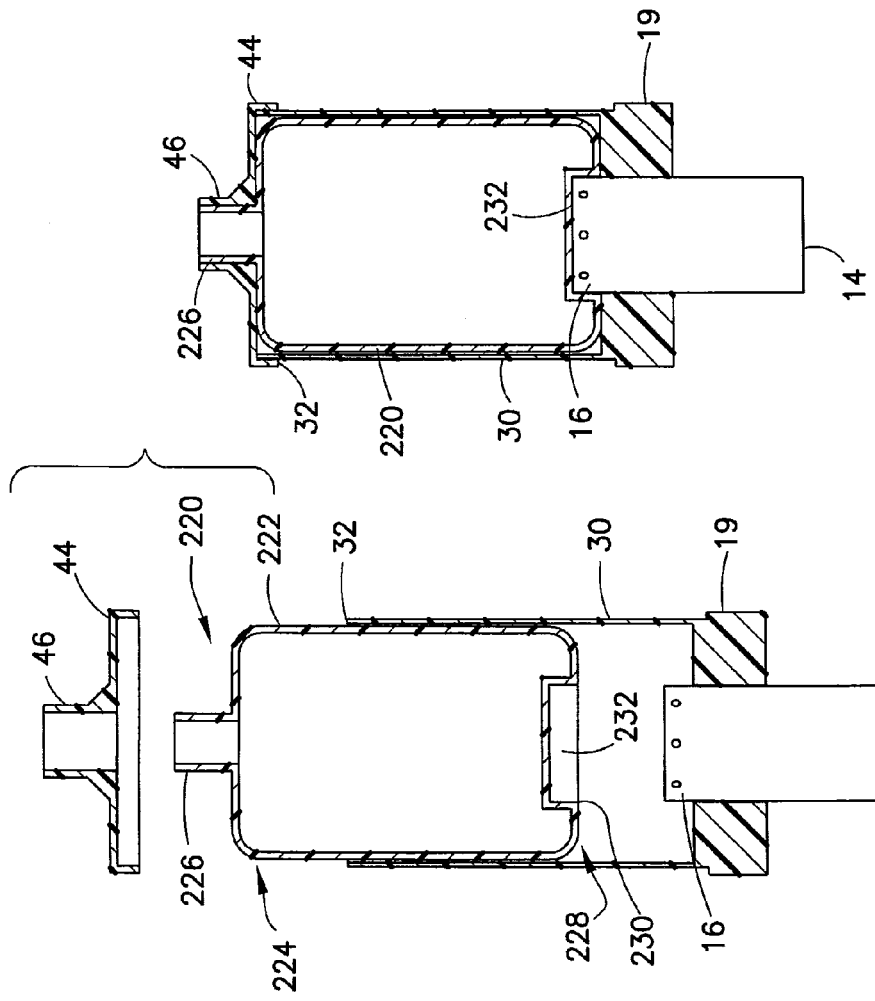
FIG.6C
FIG.6B
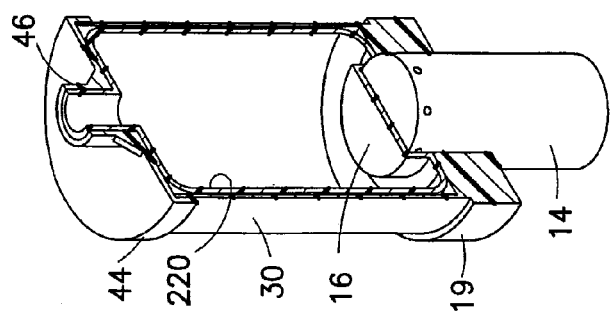
FIG.6A

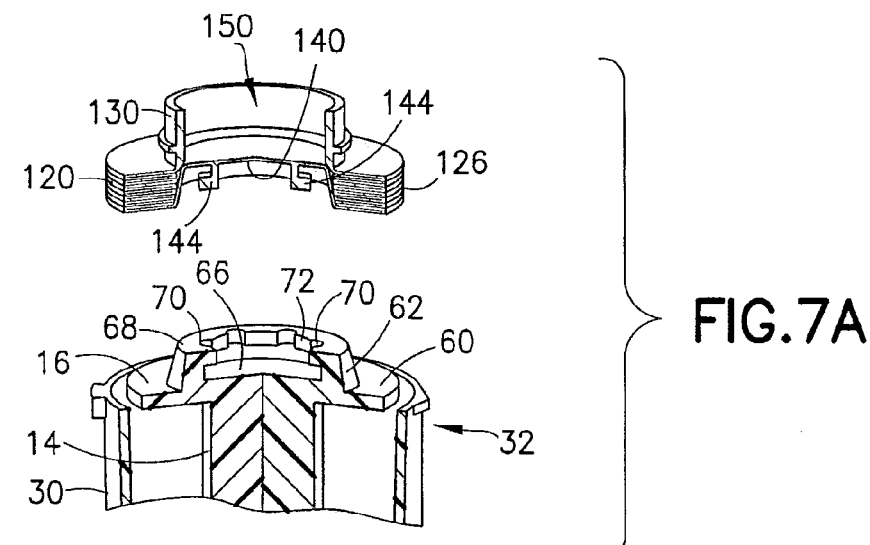
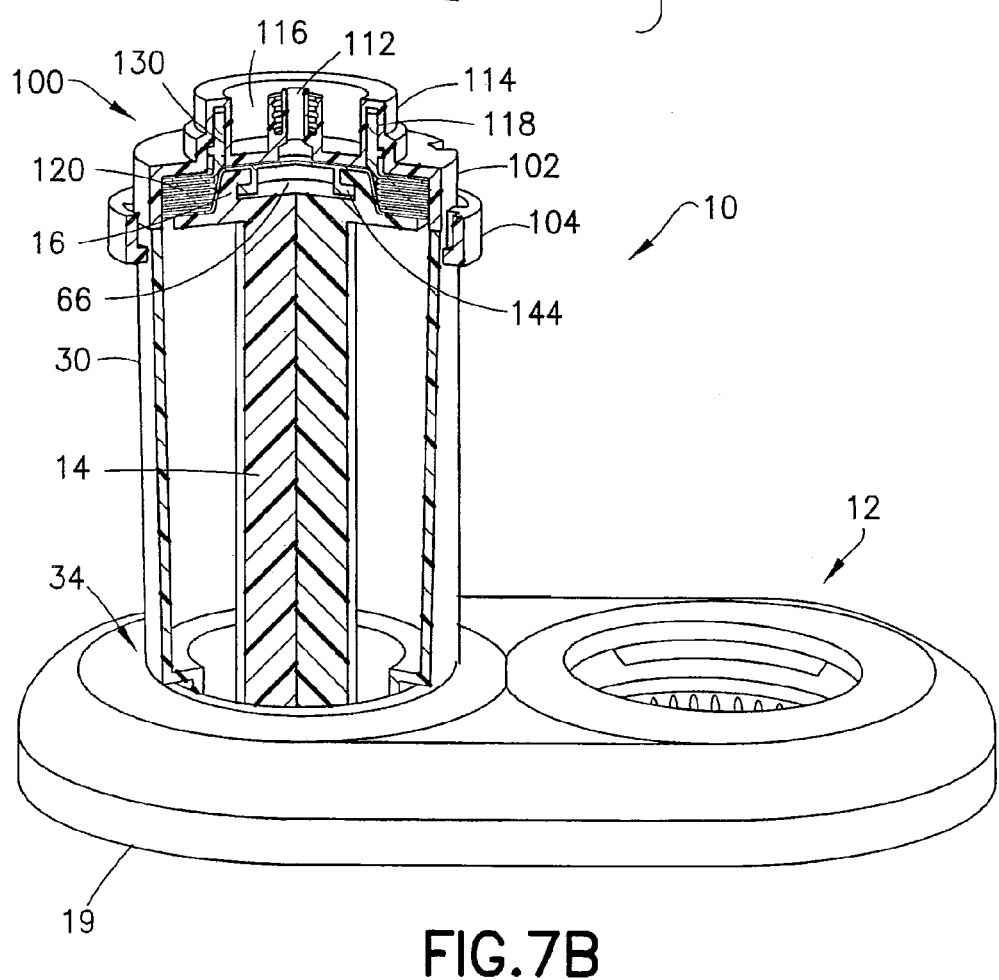

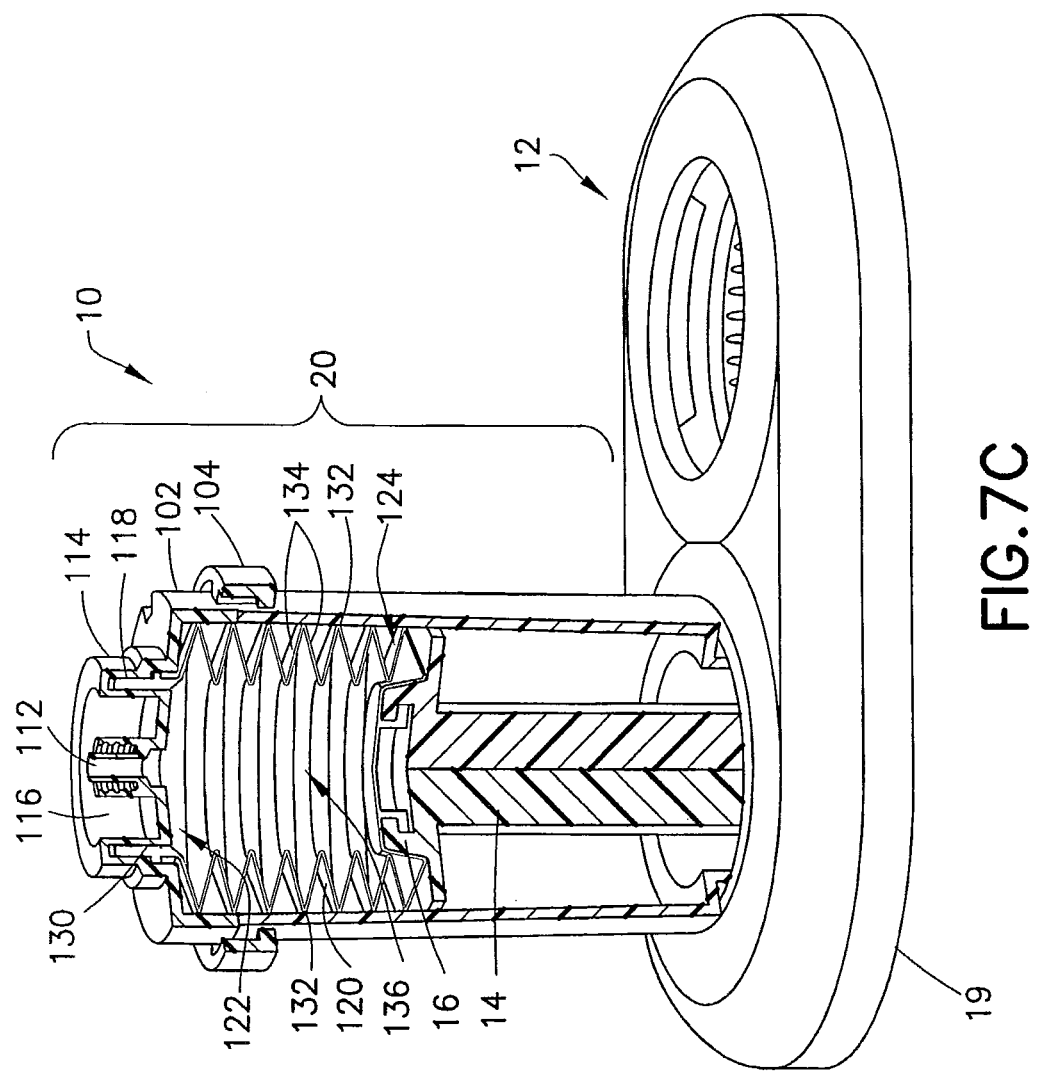

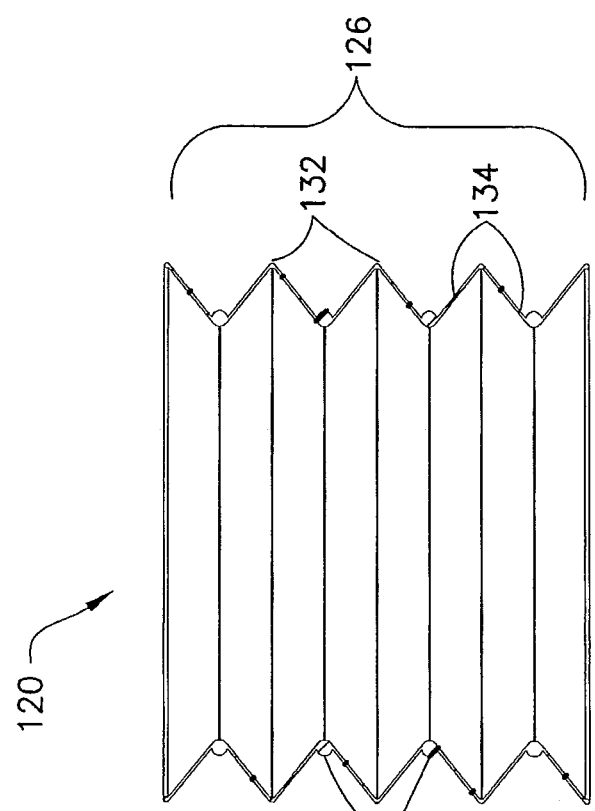
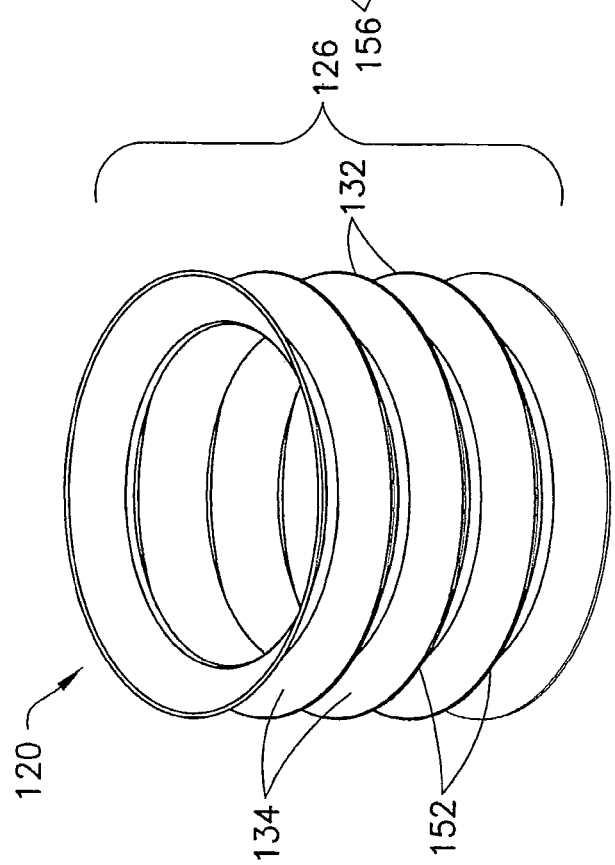
FIG.22D
FIG.22C

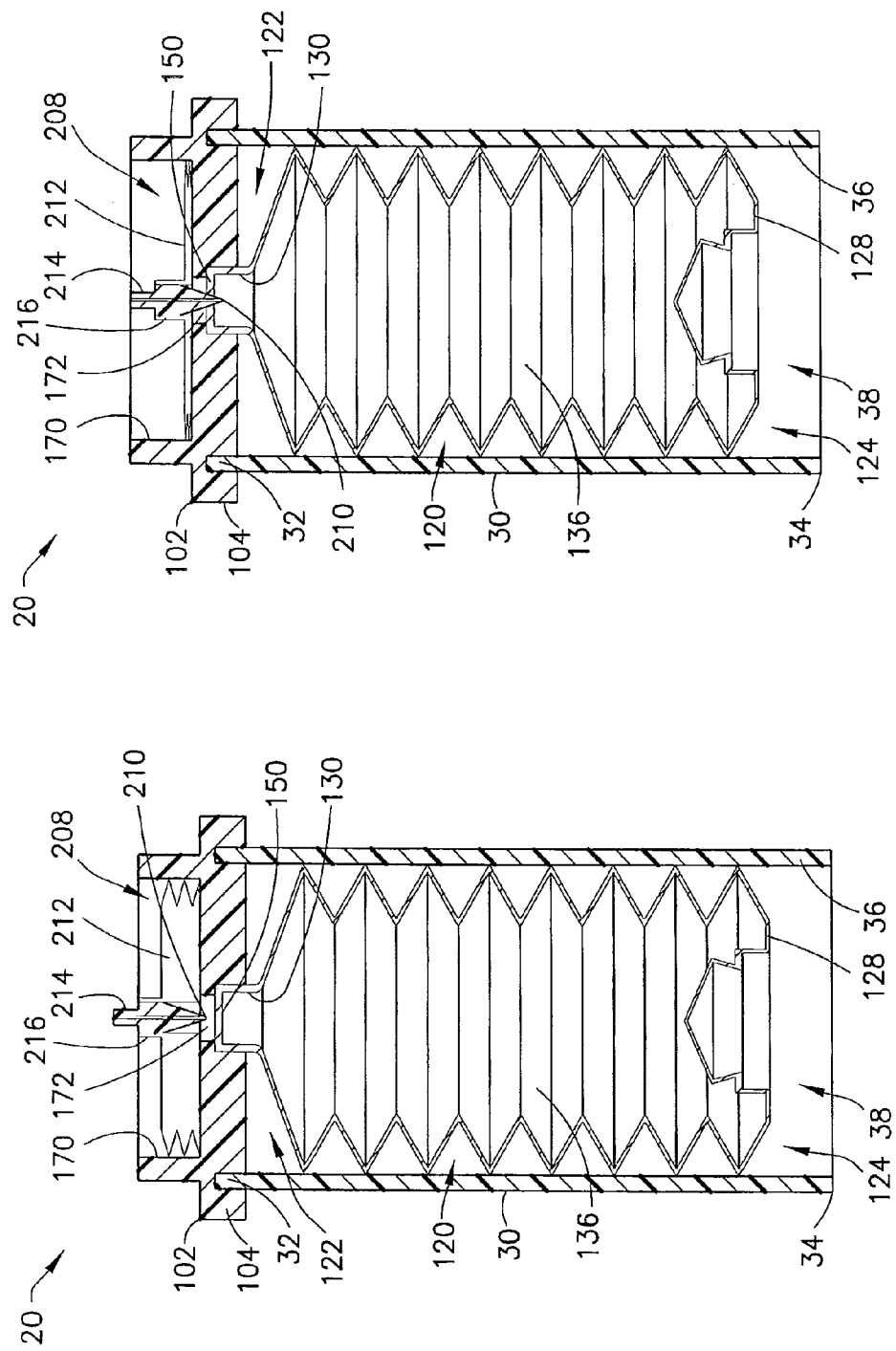

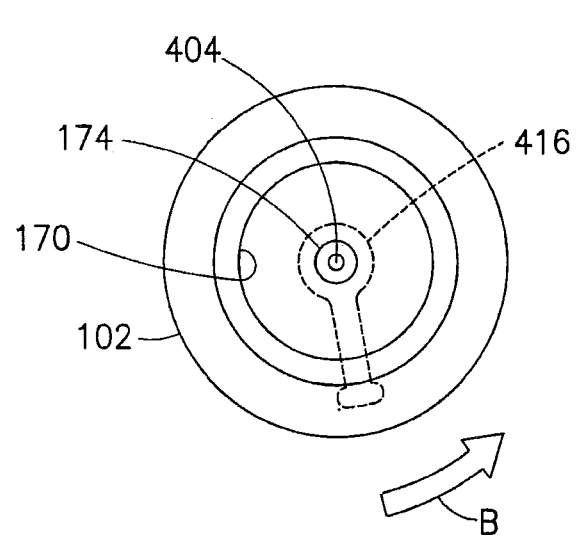
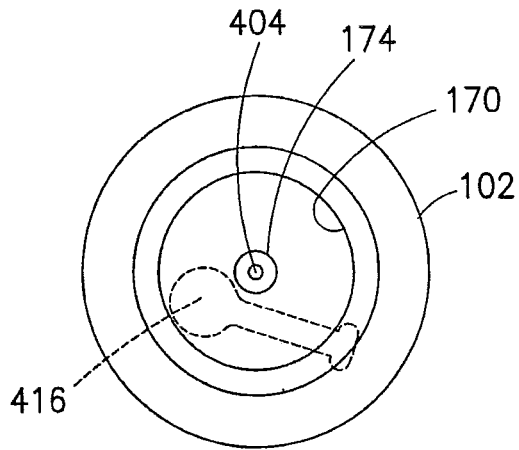
FIG.31B   FIG.31C
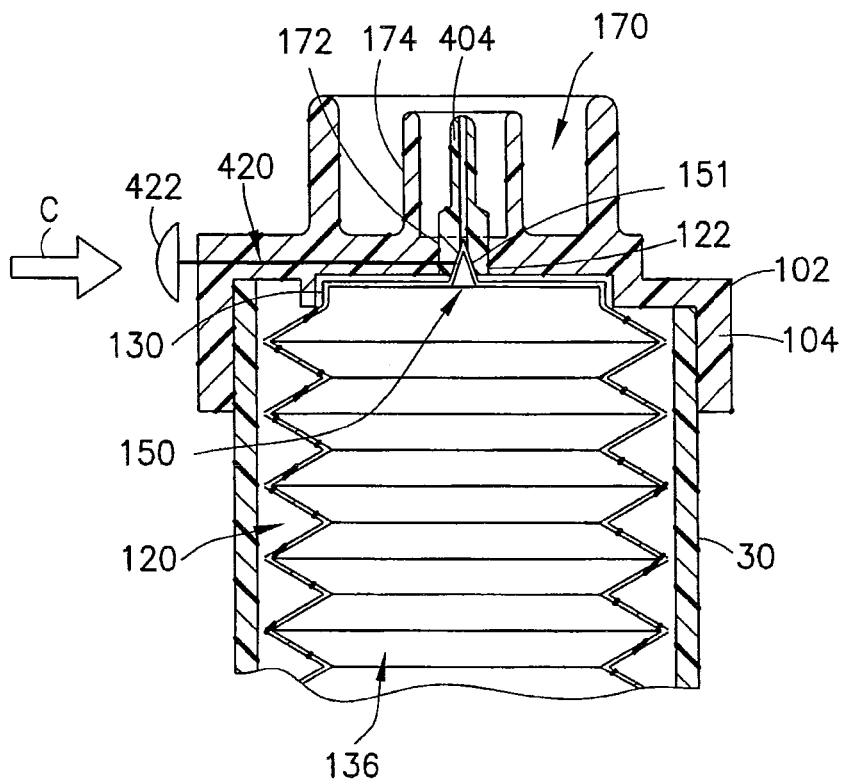
FIG.32

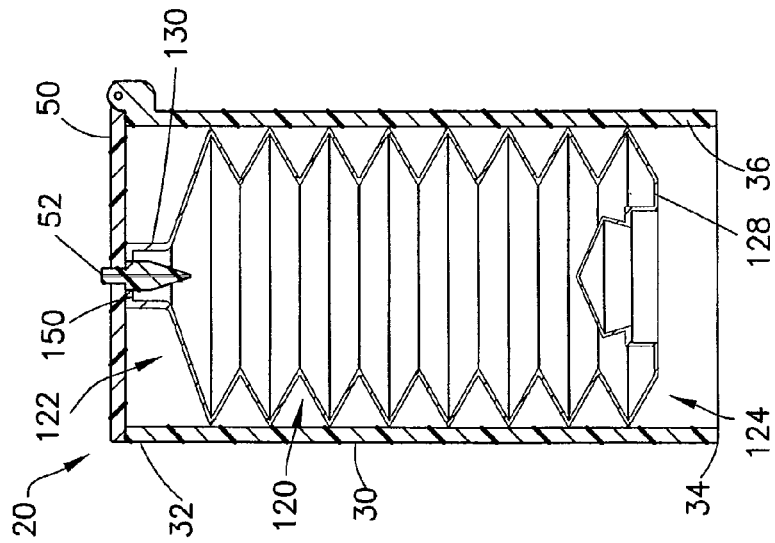
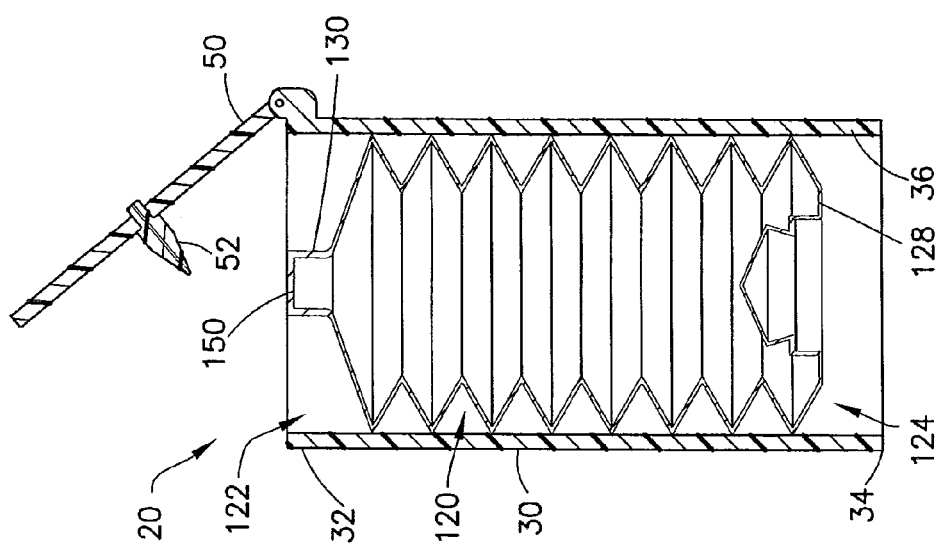
FIG.33B
FIG.33A

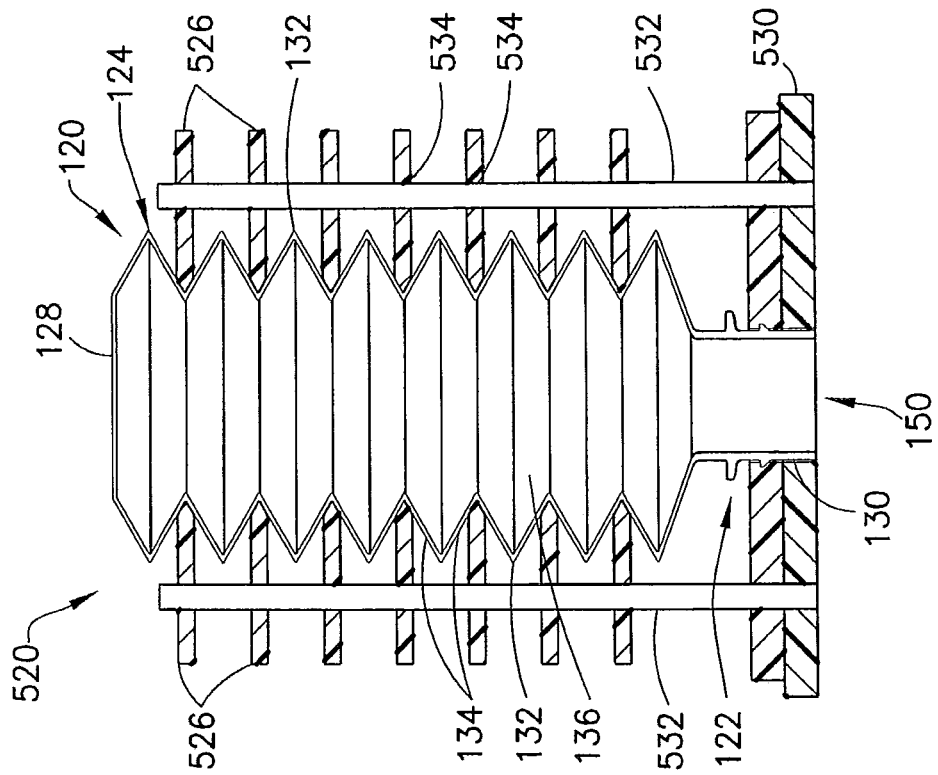
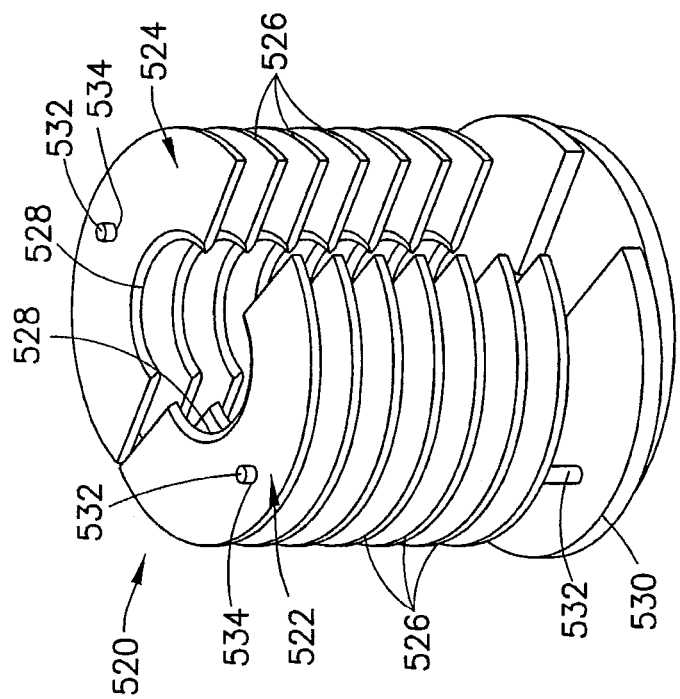
FIG.35B
FIG.35A

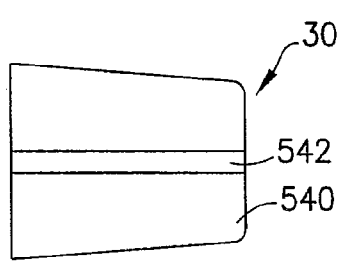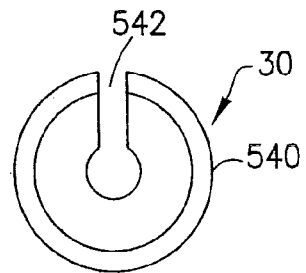
FIG.36A          FIG.36B
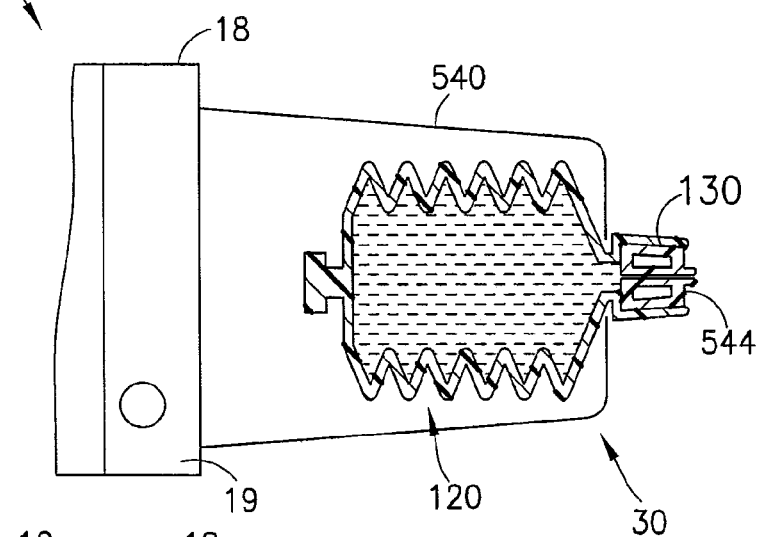
FIG.36C
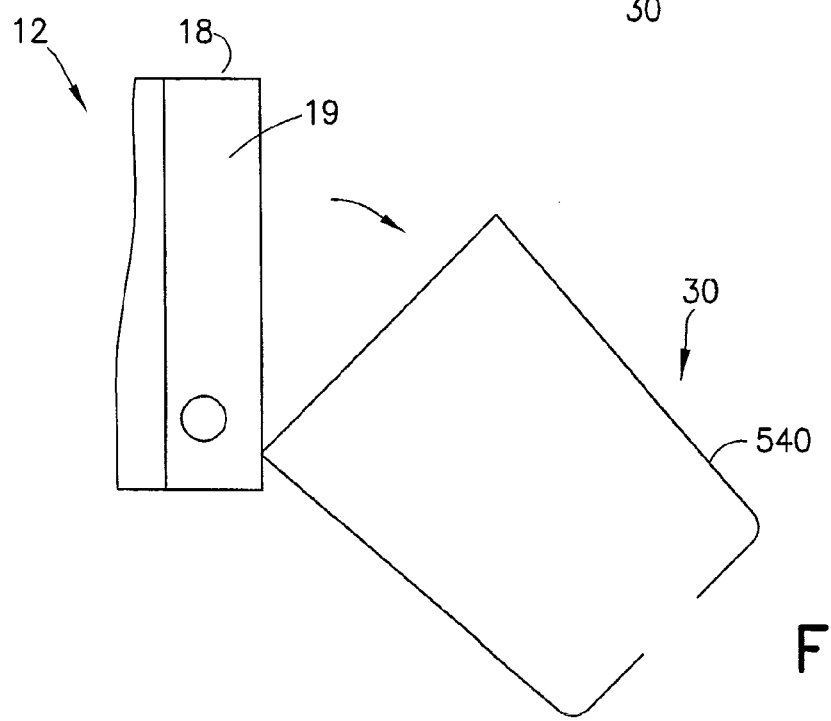
FIG.36D

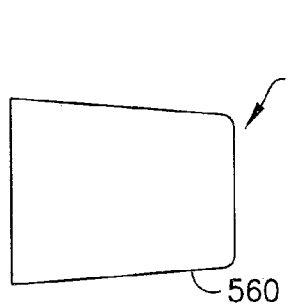
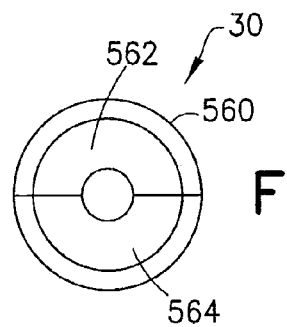
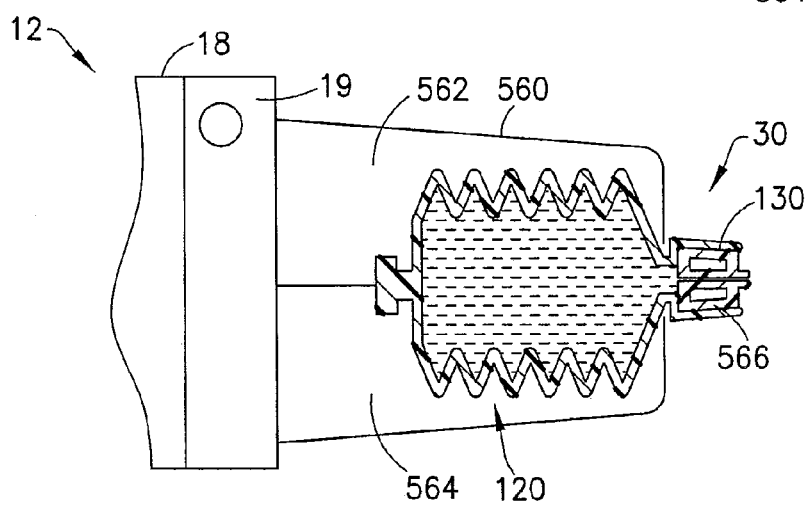
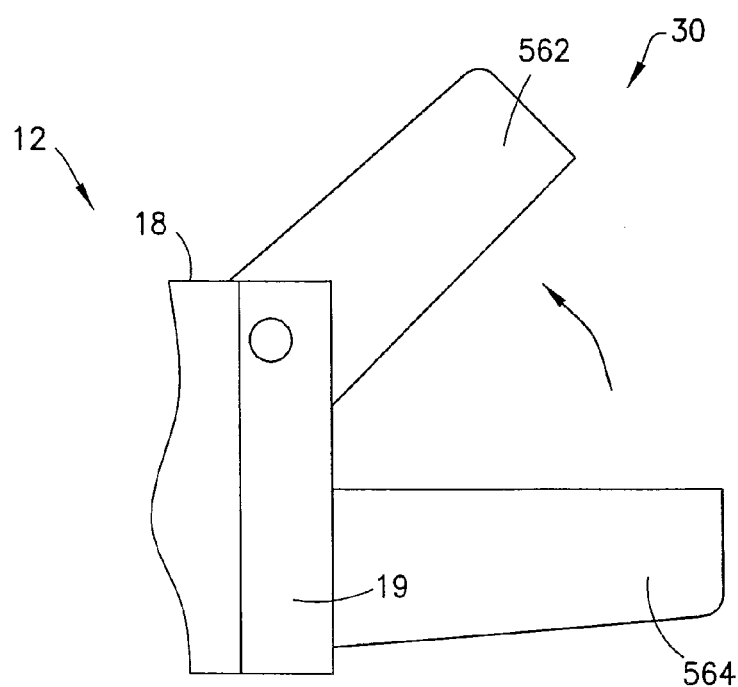

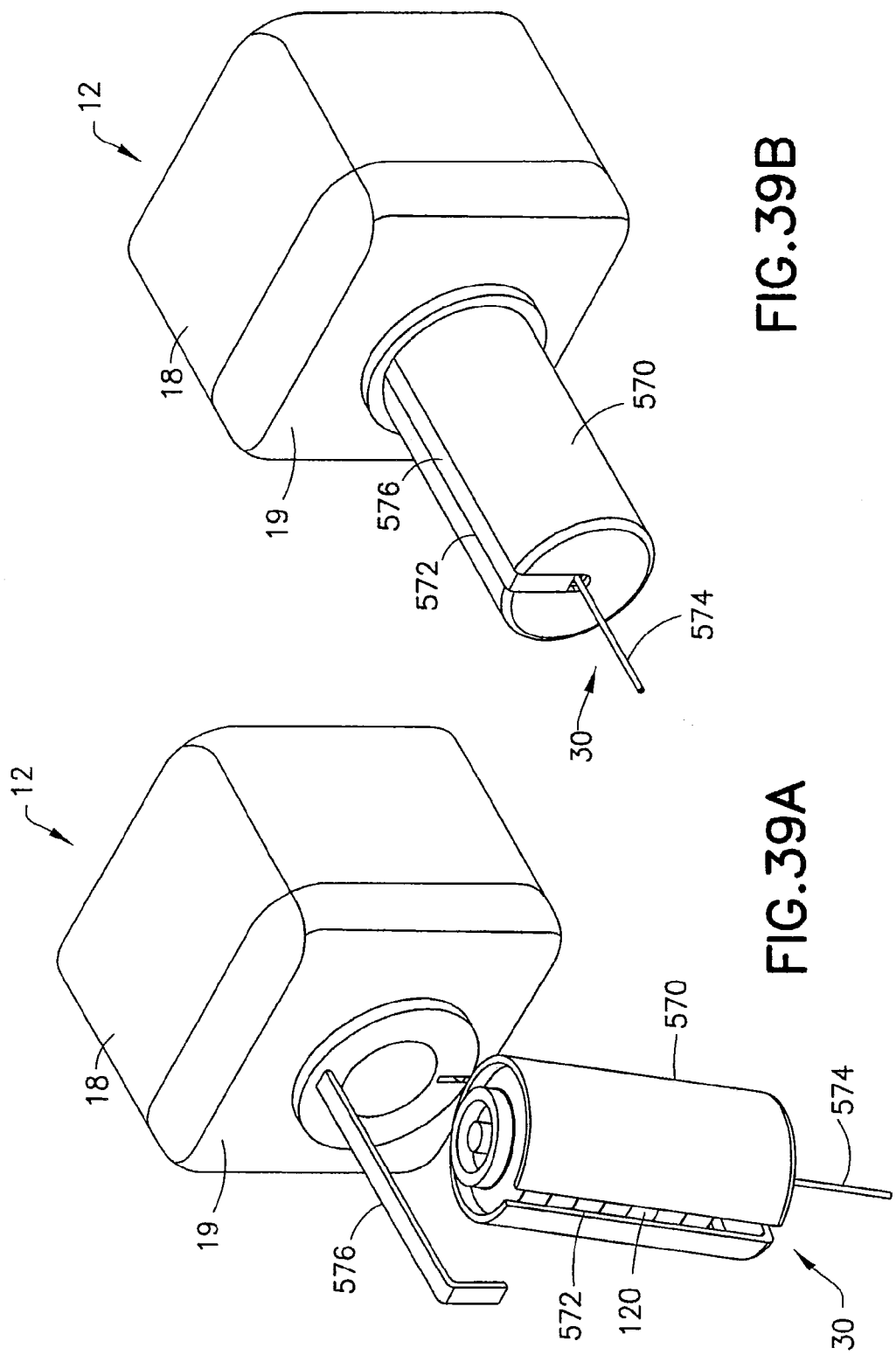

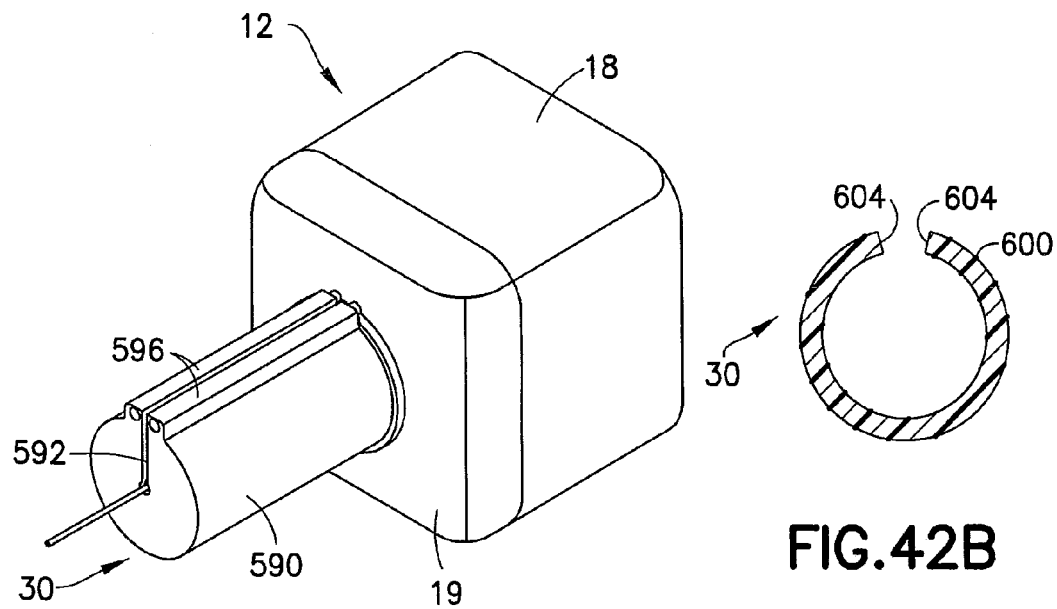
FIG.41C
FIG.42B
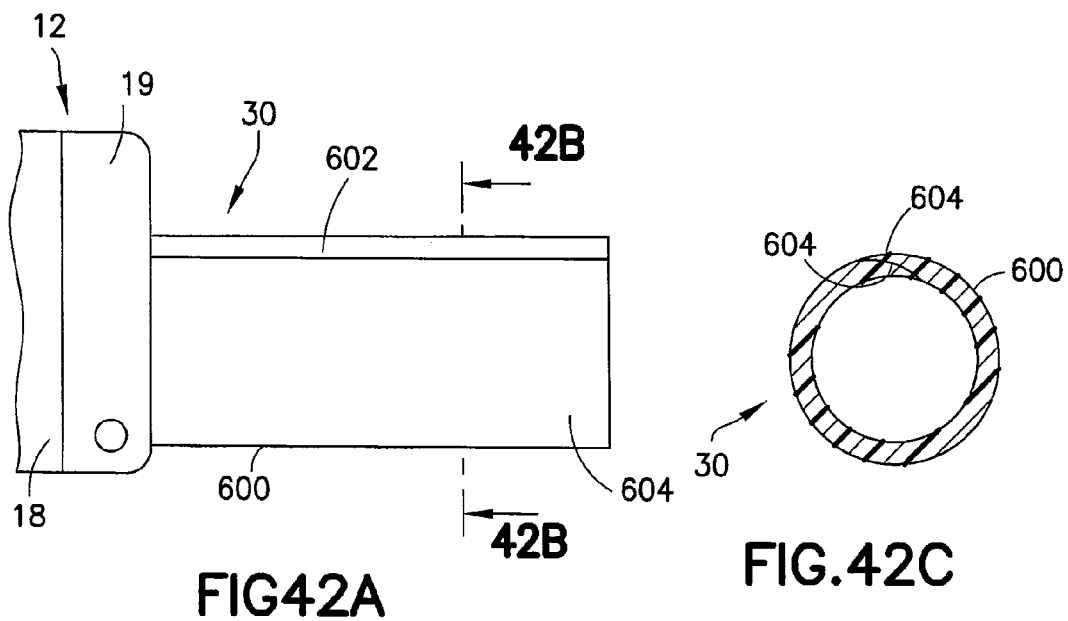
FIG42A
FIG.42C

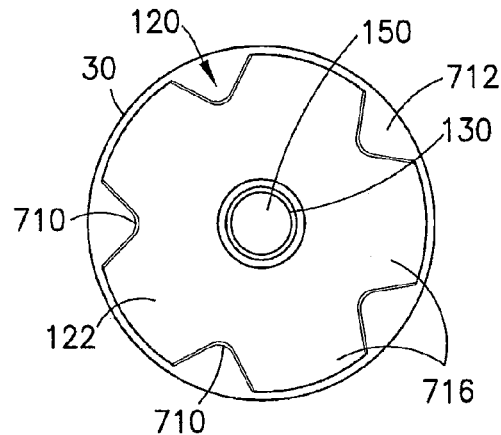
FIG.49B
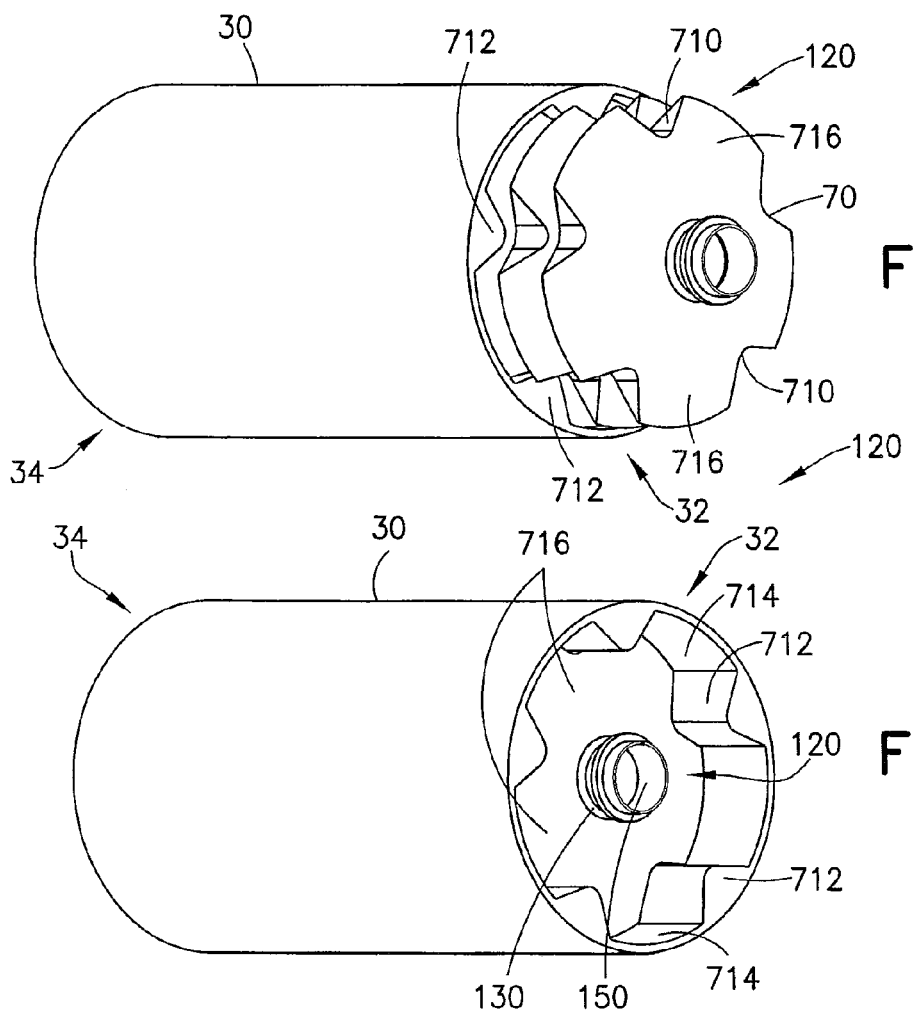
FIG.49C
FIG.49D

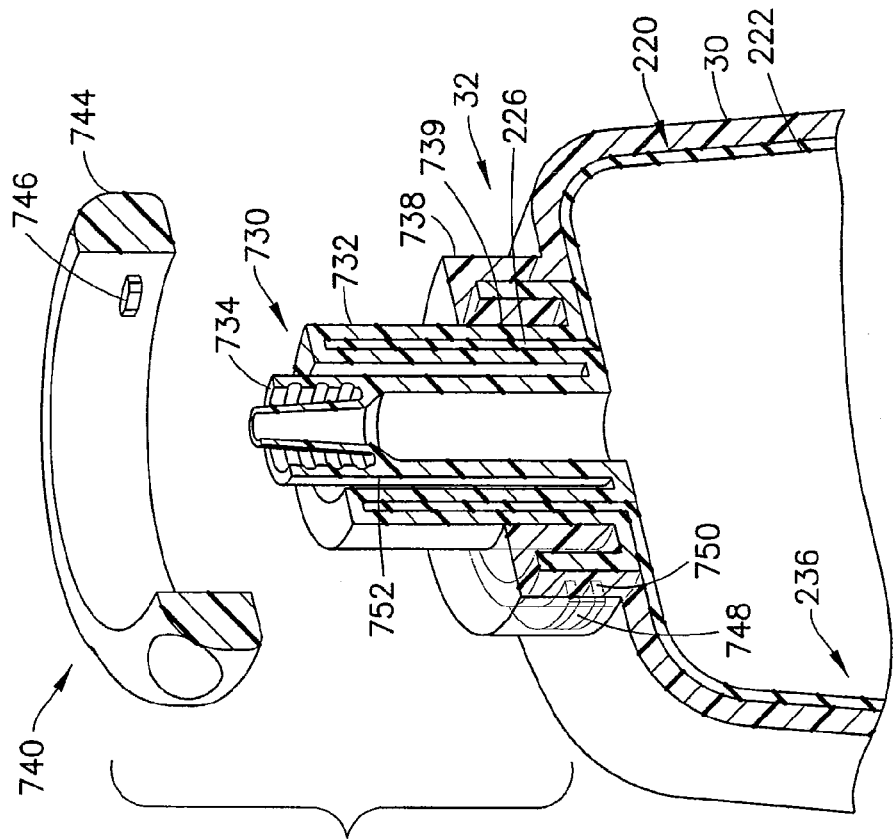
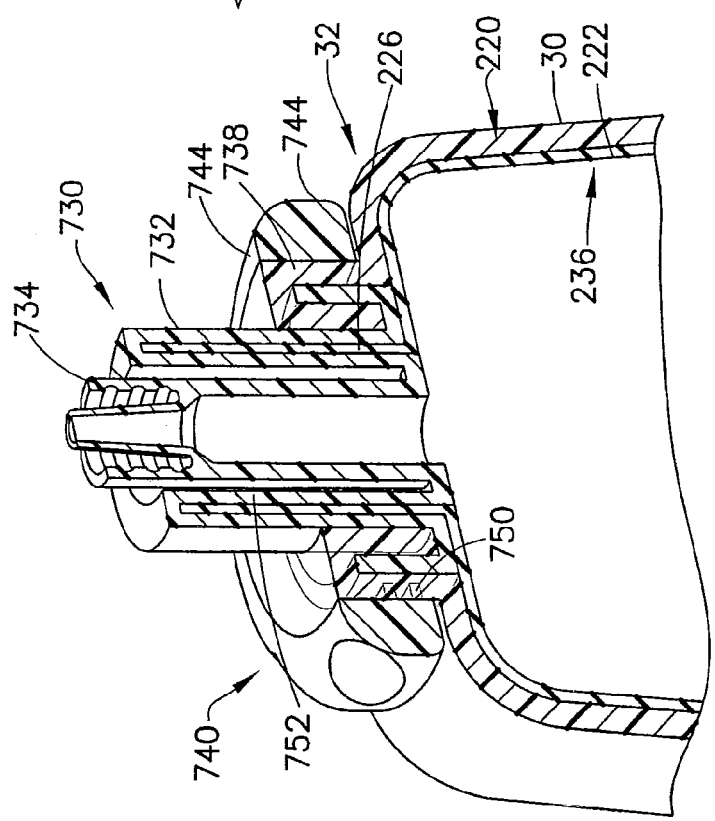
FIG. 51C
FIG. 51B

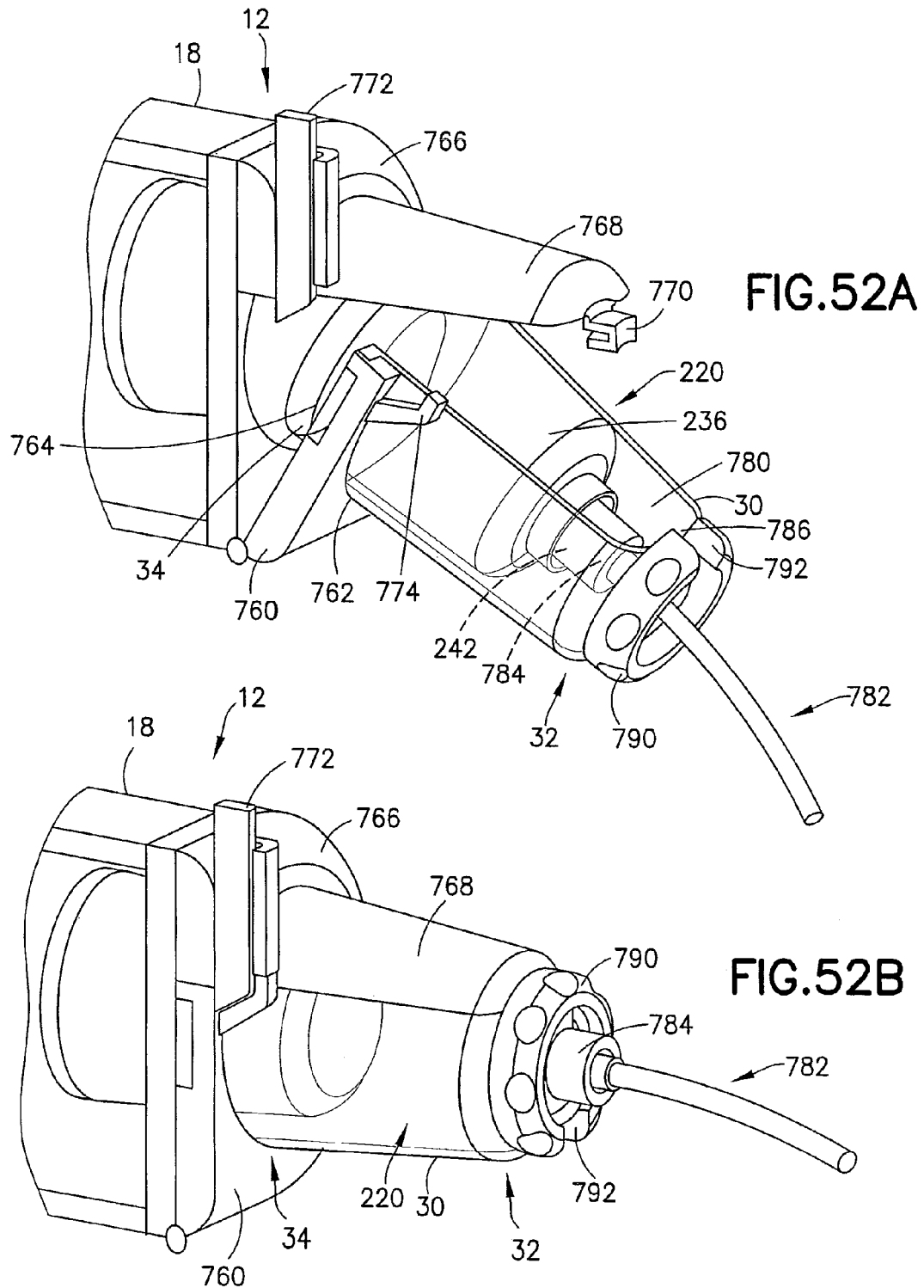

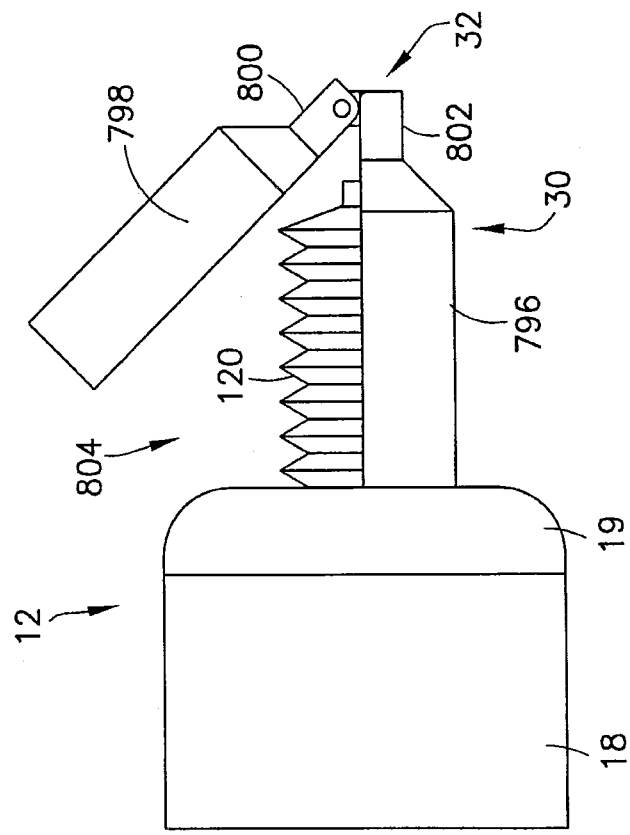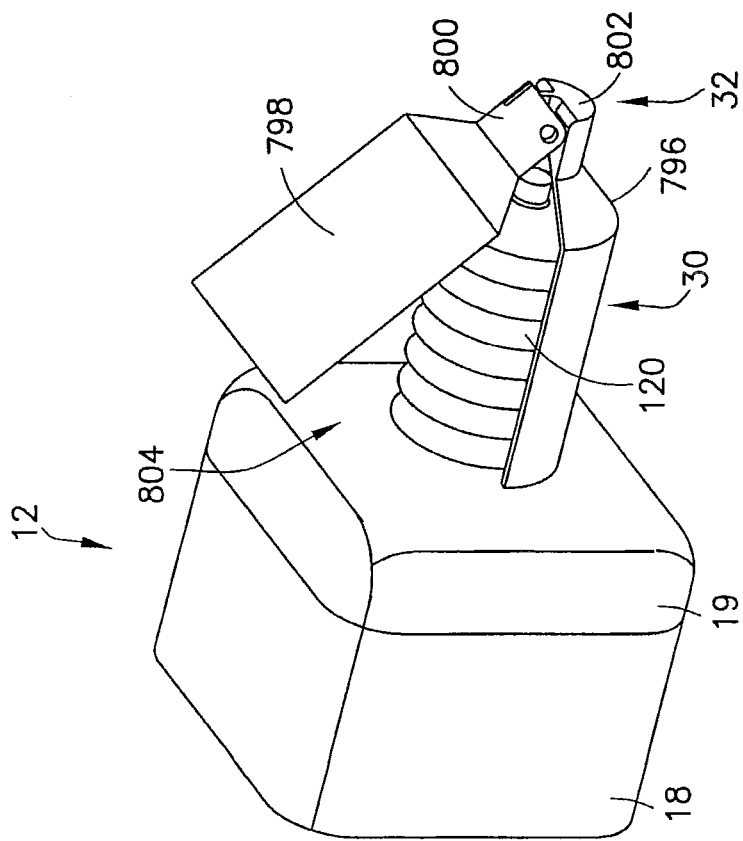

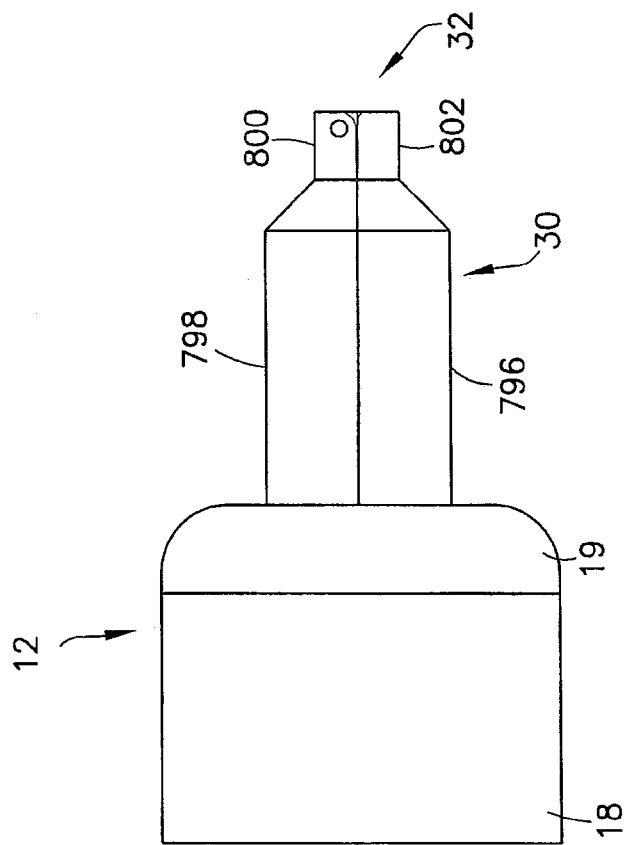
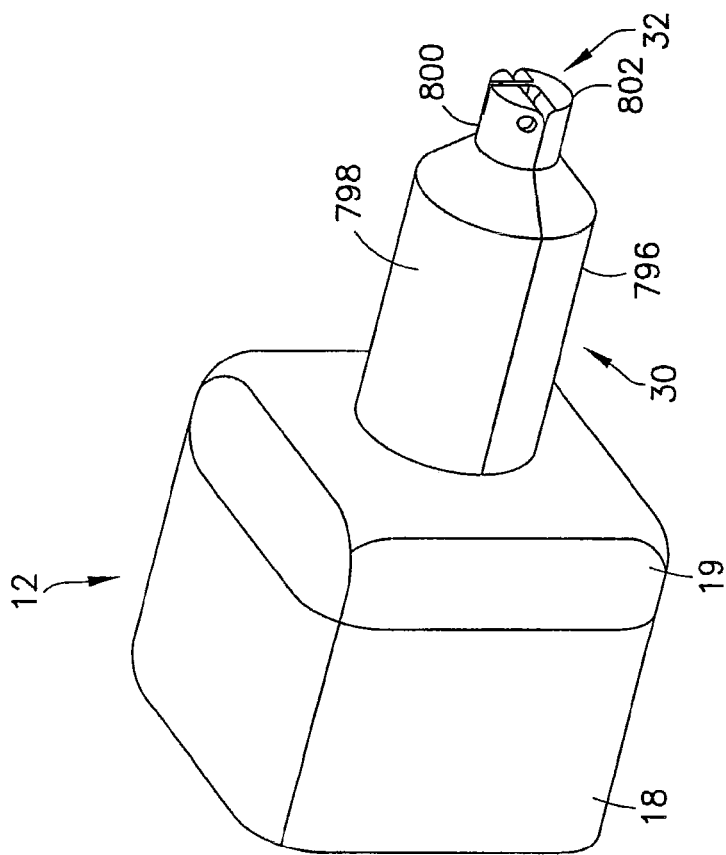
FIG.54D
FIG.54C

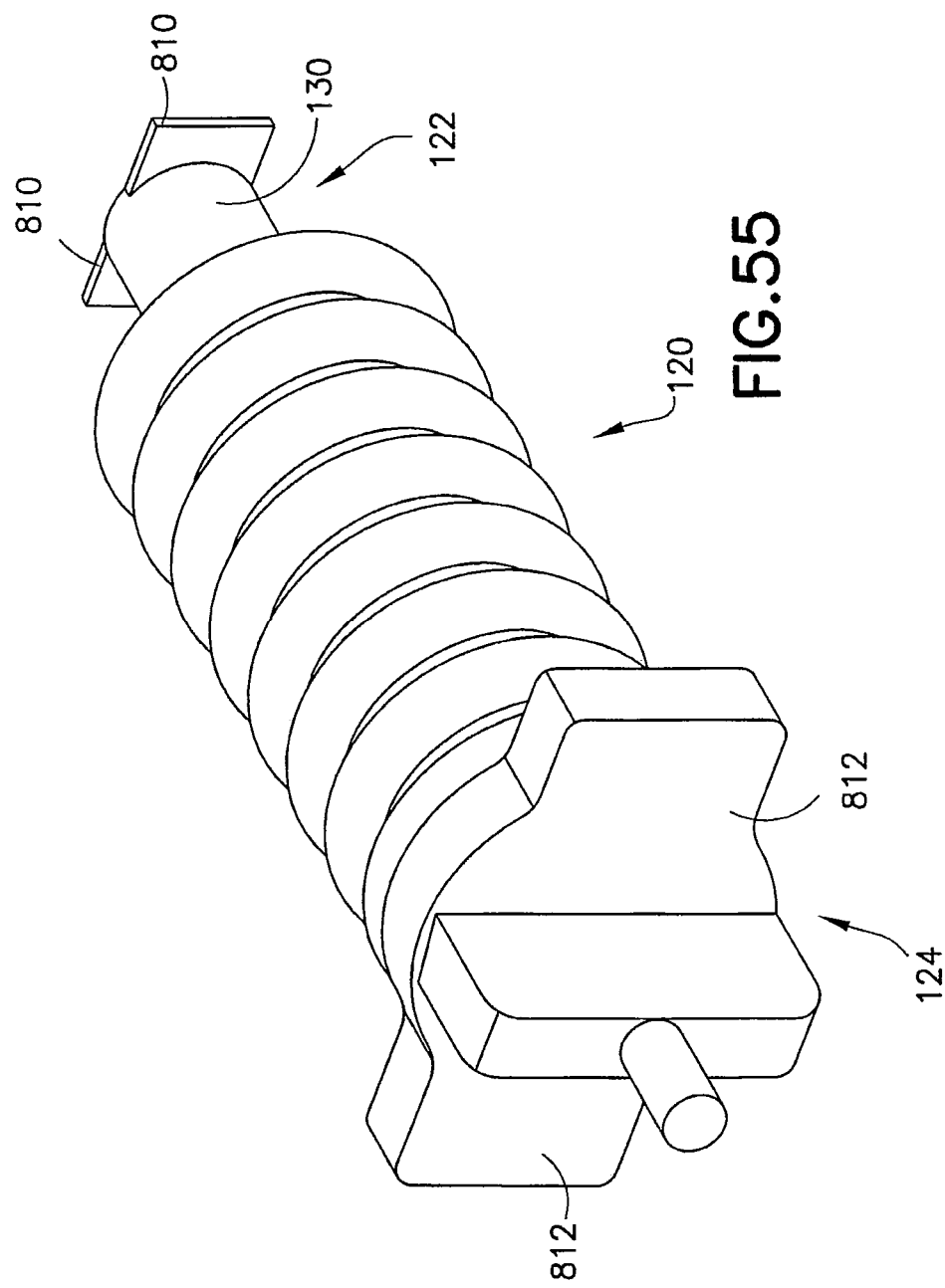

BELLOWS SYRINGE FLUID DELIVERY SYSTEM

CROSS REFERENCE TO RELATED APPLICATION

This application claims the benefit of U.S. Provisional Application No. 61/636,049 filed Apr. 20, 2012 and entitled "Bellows Syringe Fluid Delivery System", the disclosure of which is incorporated herein by reference.

BACKGROUND OF THE INVENTION

1. Field of the Invention

The present disclosure is related to the medical field and, more particularly, disposable syringes used in the medical field in which all or part of the syringe may be disposed of after a single use. The present disclosure is further related to the use of disposable syringe, ampoules, and fluid containers adapted for association with controlled, programmable fluid injection apparatuses.

2. Description of Related Art

Disposable ampoules containing liquid medicaments are known in the medical field for use with a reusable type holder, such as hypodermic injectors. For example, U.S. Pat. No. 2,950,717 to Bouet discloses such an ampoule for use used with a syringe-type holder having at one end a hypodermic needle and, at a second end, a piston adapted to engage the disposable ampoule loaded into the syringe holder. The ampoule is in the form of bellows-like tubular element having a disk-shaped end wall adapted to engage the piston disposed in the syringe holder.

U.S. Pat. No. 2,514,575 to Hein discloses a syringe that encloses a hollow flexible container used to hold medicament, which may be in the form of a liquid, emulsion, paste, and the like. The container may be connected at a proximal end thereof directly to a plunger disposed in the syringe barrel. The container is introvertable into itself so that action of the plunger toward a closed end of the syringe barrel causes the container to introvert and expel liquid or another material from the container.

U.S. Pat. No. 5,147,311 to Pickhard discloses a syringe-type injection device that has a housing in which is arranged a holder for a deformable, medicament-containing ampoule having a bellows-type shape. An injection needle is provided at one end of the syringe injection device which communicates with the interior of the ampoule. A driving device is linked to the other end region of the ampoule, and which is used to dispense a medicament material held in the ampoule via the injection needle.

U.S. Pat. No. 5,899,889 to Futagawa et al. discloses a prefilled syringe having a barrel with a distal end forming a needle-connecting portion and an open proximal end. A plastic tubular container is disposed in the barrel and has a flexible hollow cylindrical body used to contain a liquid medicament previously charged therein. A plunger is inserted into the barrel through the open proximal end and is slidably held therein. The tubular container is held in the barrel so that an end or tip thereof may be placed in a lumen of the needle-connecting portion of the barrel. In use, as the hollow cylindrical body is emptied of fluid, the wall of the hollow cylindrical body is squeezed into a space between the barrel and the plunger as the plunger is pushed into the barrel.

U.S. Patent Application No. 2002/0091361 to Rosoff et al. discloses a multiple-dose syringe including a barrel with a closed end and an open end. The closed end has an injection port adapted to receive a needle. A plunger is slidably disposed through the open end of the barrel. A container is connected to an end of the plunger to move with the plunger. The container has a deformable shell with an opening at a forward end thereof A predetermined quantity of fluid is sealed in the deformable shell by a closure member disposed over the opening. The container is slidably disposed in the barrel and includes a seal proximal to the forward end to form a first cavity in the barrel with a volume that is adjustable by moving the container in the barrel with the plunger so that fluid can be selectively drawn into and expelled from the first cavity. After at least a substantial portion of the fluid is expelled from the first cavity, the shell is configured to collapse by further pressure applied by the plunger to expel the predetermined quantity of fluid contained therein.

U.S. Pat. No. 6,332,876 to Poynter et al. discloses a compressible syringe including a bellows. The disclosed syringe bellow has rearward frusto-conical bellows walls that are thicker than its forward frusto-conical bellows walls. The bellow walls converge in an apex, with the rearward frusto-conical wall at a first angle with respect to a plane perpendicular to the longitudinal axis of the syringe and intersecting the apex, and with the forward frusto-conical wall being at a second angle with respect to the plane and with the first angle being greater than the second angle. The bellows rings increase in diameter successively from the rearward to the forward portion of the syringe U.S. Pat. No. 6,620,134 to Trombley, III et al. discloses a syringe system that includes a barrel, a plunger slidably disposed within the barrel, and a collapsible cartridge in the barrel. The collapsible cartridge is inserted within the barrel and collapses as the plunger is advanced within the barrel to pressurize fluid within the collapsible cartridge. The collapsible cartridge includes a passage through which fluid passes when pressurized by the plunger.

U.S. Pat. No. 6,869,419 to Dragan et al. discloses an ampoule having a body portion, a sealed end portion, and a sealed delivery portion. The ampoule is adapted for use in a delivery syringe system for controllably dispensing a low viscosity material, such as a liquid, gel, or paste. The ampoule has sealed rear portions adapted to mate with a plunger of a syringe so as to facilitate controlled dispensing of the low viscosity material. The syringe has a plunger adapted to grasp the collapsed ampoule, facilitating removal, as well as breach openings positioned to provide controlled initial flow of the dispensed low viscosity material.

It is also known in the medical field to use bellows-type ampoules and containers in association with controlled, programmable fluid injection apparatuses. One such example may be found in U.S. Pat. No. 5,000,739 to Kulisz et al. The Kulisz patent discloses a programmable pump with three separate components, namely, a driver, a reservoir, and a fluid tubing set connector. The driver provides an electromechanical assembly adapted to cause fluid to flow from the reservoir. The driver can be programmed for varying flow rates and alternating on/off delivery cycles through the control of switches externalized on the driver face. The top of the bellows reservoir includes a port, and the bottom includes a septum for filling by a needle. The tubing set connector subsequently connects to a port connector of the bellows reservoir. The tubing set connector provides an interface to any standard luer-type tubing set which then connects to a needle for infusion.

U.S. Pat. No. 6,485,471 to Zivitz et al. discloses a fluid-delivery apparatus for delivering a medicament to a patient. The apparatus includes a housing defining a passageway, a bellowed ampoule positioned to lie in the passageway of the housing, and a piston. The bellowed ampoule includes a body with first and second ends and is formed to define a cavity configured to contain the medicament. The piston presses the second end of the ampoule toward the first end to dispense the medicament from the cavity. The fluid-delivery apparatus includes a piston-drive system that is configured to apply a force to the piston to dispense medicament from the ampoule. The piston-drive mechanism includes a torque-production system and an actuator system. The torque-production system includes a gear train operated by an electric motor and is adapted to apply a torque to a lead screw to move a drive nut and into engagement with the piston. The drive motor is actuated by a motor driver and engages with the gear train via a motor shaft.

Further, U.S. Patent Application Publication No. 2011/0218499 to Cahen discloses a device for injecting a fluid for medical use. The device includes a cylindrical component wherein a container for receiving the injection fluid is provided. The container has a bellows-shaped body made of deformable material and includes a tip through which fluid passes. The cylindrical component or base has a bottom wall through which an axially translatable piston rod is guided, and a top wall. The container has circular bellows-type rings. The distal end of the piston has a shape complementing the shape of a corresponding cavity in the bottom wall of the container. An activating mechanism may be connected to the piston to impart force to the piston and eject the injection fluid from the container.

SUMMARY OF THE INVENTION

In one embodiment, a bellows syringe for a fluid delivery system is disclosed, comprising a cap member and a bellows member. The cap member defines an internal cavity and a discharge port, and further comprising a depending skirt portion. The skirt portion may comprise a plurality of radially-inward extending tab members. The bellows member is disposed in the internal cavity and held in a compressed state in the internal cavity by engagement between the cap member and a proximal end of the bellows member, such as engagement between the tab members and the proximal end of the bellows member.

The proximal end of the bellows member is closed and a distal end of the bellows member defines a discharge port in fluid communication with the discharge port on the cap member. The closed proximal end of the bellows member may comprise depending attachment members for attaching the bellows member to a piston head of a piston element. The attachment members may be disposed in an end pocket defined in the closed proximal end of the bellows member.

The discharge port on the cap member may be recessed within an annular wall on a distal end of the cap member. The bellows member may comprise a distal end defining a discharge neck that forms a discharge port in fluid communication with the discharge port on the cap member, and the discharge neck is seated within an interior annular groove in the cap member for securing the discharge neck to the cap member. The bellows syringe may be packaged in a protector cap having an open end sealed by a removable seal.

In another embodiment, the bellows syringe for a fluid delivery system comprises a cap member, a bellows member, and a base member. The cap member defines an internal cavity and a discharge port, and further comprises a depending skirt portion comprising a plurality of radially-inward extending tab members. The bellows member is disposed in the internal cavity and held in a compressed state in the internal cavity. The base member comprises a plate portion and a central portion of optional annular shape. The plate portion comprises a plurality of upward-extending retaining tabs engaged with the catch members to maintain the bellows member in the compressed state in the internal cavity. The locations for the retaining tabs and catch members may be reversed. The proximal end of the bellows member may be closed and the central portion of the base member may be seated within an end pocket defined in the closed proximal end of the bellows member. The central portion may define a circumferential groove and the bellows member may comprise a cooperating rib engaging the circumferential groove for securing the plate portion to the proximal end of the bellows member. The central portion defines an end pocket for receiving a piston head of a piston element, and wherein the end pocket comprises internal elements to engage the piston head.

Another embodiment described herein is directed to a bellows assembly for association with a fluid delivery system. The bellows assembly comprises a pressure jacket and a bellows syringe, which comprises a cap member and a bellows member. The pressure jacket has a distal end and a proximal end and defines a throughbore therebetween. The bellows syringe is adapted for connection to the distal end of the pressure jacket. The cap member defines an internal cavity and a discharge port, and further comprises a depending skirt portion. The skirt portion may comprise a plurality of radially-inward extending tab members. The bellows member is disposed in the internal cavity and held in a compressed state in the internal cavity by engagement between the cap member and a proximal end of the bellows member, such as between the tab members and the proximal end of the bellows member.

The proximal end of the bellows member may be closed and a distal end of the bellows member may define a discharge port in fluid communication with the discharge port on the cap member. The closed proximal end of the bellows member may comprise depending attachment members for attaching the bellows member to a piston head of a piston element operable in the throughbore of the pressure jacket. The attachment members may be disposed in an end pocket defined in the closed proximal end of the bellows member.

A plurality of circumferentially-spaced mounting flanges may be provided on the distal end of the pressure jacket. A plurality of tabs members may further be provided on the distal end of the pressure jacket and located between each the mounting flanges, respectively. Mating or receiving slots may be defined in the skirt portion of the cap member to receive the mounting flanges for securing the bellows syringe to the distal end of the pressure jacket. The cap member may be rotated relative to the distal end of the pressure jacket to seat the mounting flanges in the mating slots in the cap member. This rotational motion may be used to cause the tab members on the distal end of the pressure jacket to engage the tab members on the skirt portion of the cap member and release the tab members on the skirt portion of the cap member from engagement with the proximal end of the bellows member.

In another embodiment, the tab members on the skirt portion of the cap member are formed as a plurality of catch members, and the bellows syringe further comprises a base member. The base member comprises a plate portion and a central portion. The plate portion comprises a plurality of upward-extending retaining tabs engaged with the catch members to maintain the bellows member in the compressed state in the internal cavity. The locations for the retaining tabs and catch members may be reversed. The central portion may be seated within an end pocket defined in a closed proximal end of the bellows member. The central portion may define a circumferential groove and the bellows member may comprise a cooperating rib engaging the circumferential groove for securing the plate portion to the proximal end of the bellows member. The distal end of the pressure jacket may comprise a plurality of tab members each defining a transverse slot, and the plate portion may engage the transverse slots to secure the bellows syringe to the pressure jacket.

In another embodiment, a fluid delivery system is provided, comprising a power fluid injector, a pressure jacket, and a bellows syringe. The fluid injector comprises a reciprocally operable piston element. The pressure jacket has a distal end and a proximal end and defines a throughbore therebetween. The pressure jacket proximal end is engaged with the fluid injector such that the piston element is operable in the throughbore. The bellows syringe is adapted for connection to the distal end of the pressure jacket. The bellows syringe comprises a cap member and a bellows member. The cap member defines an internal cavity and a discharge port, and further comprises a depending skirt portion. The skirt portion may comprise a plurality of radially-inward extending tab members. The bellows member is disposed in the internal cavity and held in a compressed state in the internal cavity by engagement between the cap member and a proximal end of the bellows member, such as between the tab members and the proximal end of the bellows member. The proximal end of the bellows member may be closed and a distal end of the bellows member may define a discharge port in fluid communication with the discharge port on the cap member. The closed proximal end of the bellows member may comprise depending attachment members for attaching the bellows member to a piston head of the piston element operable in the throughbore of the pressure jacket. The attachment members may be disposed in an end pocket defined in the closed proximal end of the bellows member.

In another embodiment of the fluid delivery system, the tab members on the skirt portion of the cap member may be formed as a plurality of catch members, and the bellows syringe may further comprise a base member comprising a plate portion and a central portion, typically an annular shaped portion. The plate portion comprises a plurality of upward-extending retaining tabs engaged with the catch members to maintain the bellows member in the compressed state in the internal cavity. The locations for the retaining tabs and catch members may be reversed. The central portion may define an end pocket formed with internal elements adapted to receive radially-extendable retaining pins on a piston head of the piston element to secure the base member to the piston head.

In another embodiment of the fluid delivery system, the proximal end of the bellows member may be closed and define an end pocket formed with internal elements adapted to receive radially-extendable retaining pins on a piston head of the piston element to secure the closed proximal end of the bellows member to the piston head.

Additionally, the proximal end of the pressure jacket may be pivotally connected to the power fluid injector. Further, the pressure jacket may define a split-top opening for passage therethrough of a fluid tubing set connected to a discharge port on the bellows member.

In another embodiment, a bellows syringe for a fluid delivery system generally comprises a cap member defining an internal cavity and a discharge port, the cap member further comprising a depending skirt portion, and a bellows member disposed in the internal cavity and held in a compressed state in the internal cavity by engagement between the cap member and a proximal end of the bellows member. The skirt portion may comprise a plurality of radially-inward extending tab members engaged with the proximal end of the bellows member to hold the bellows member in the compressed state in the internal cavity. The proximal end of the bellows member may be closed and a distal end of the bellows member may define a discharge port in fluid communication with the cap member discharge port. The closed proximal end of the bellows member may comprise at least one attachment member for attaching the bellows member to a piston head of a piston element. The least one attachment member may be disposed in an end pocket defined in the closed proximal end of the bellows member. The at least one attachment member may comprise a button element adapted to be engaged by a piston element comprising a plurality of jaw members. The bellows member may comprise a distal end defining a discharge neck that defines a discharge port in fluid communication with the cap member discharge port, and the discharge neck may be seated within an interior annular groove in the cap member for securing the discharge neck to the cap member.

A base member may be provided as part of the bellows syringe and comprise a plate portion and a central portion, typically an annular shaped portion. One of the skirt portion and the plate portion may comprise a plurality of retaining tabs engaged with catch members provided on the other of the skirt portion and the plate portion to hold the bellows member in the compressed state in the internal cavity.

The proximal end of the bellows member may be closed and the distal end of the bellows member may define a discharge port in fluid communication with the cap member discharge port. The bellows member may comprise a distal end defining a discharge neck that defines a discharge port in fluid communication with the cap member discharge port, and the discharge neck may be seated within an interior annular groove in the cap member for securing the discharge neck to the cap member. The central portion may define a circumferential groove and the bellows member may comprise a cooperating rib engaging the circumferential groove for securing the plate portion to the proximal end of the bellows member. The central portion may define an end pocket for receiving a piston head of a piston element, and the end pocket may comprise at least one internal element to engage the piston head.

A further embodiment is directed to a bellows assembly for association with a fluid delivery system. The bellows assembly may comprise a pressure jacket having a distal end and a proximal end and defining a throughbore therebetween, and a bellows syringe adapted for connection to the distal end of the pressure jacket. The bellow syringe may comprise a cap member defining an internal cavity and a discharge port, the cap member further comprising a depending skirt portion, and a bellows member disposed in the internal cavity and held in a compressed state in the internal cavity by engagement between the cap member and a proximal end of the bellows member. A base member may be provided as part of the bellows syringe and comprise a plate portion and a central portion, typically an annular shaped portion. One of the skirt portion and the plate portion may comprise a plurality of retaining tabs engaged with catch members provided on the other of the skirt portion and the plate portion to hold the bellows member in the compressed state in the internal cavity. The distal end of the pressure may comprise a plurality of tab members each defining a slot, and the plate portion may be adapted to engage the slots to secure the bellows syringe to the pressure jacket. Additionally, a plurality of circumferentially-spaced mounting flanges may be provided on the distal end of the pressure jacket, and a plurality of tab members may be provided on the distal end of the pressure jacket and provided between the mounting flanges, respectively. Mating slots may be defined in the skirt portion of the cap member to receive the mounting flanges for securing the bellows syringe to the distal end of the pressure jacket, such that when the cap member is rotated to seat the mounting flanges in the mating slots in the cap member, and this rotational motion causes the tab members on the distal end of the pressure jacket to engage the tab members on the skirt portion of the cap member and release the tab members on the skirt portion of the cap member from engagement with the proximal end of the bellows member.

Yet a further embodiment is a fluid delivery system comprising a fluid injector comprising a reciprocally operable piston element having a piston head, a pressure jacket having a distal end and a proximal end and defining a throughbore therebetween, the pressure jacket proximal end engaged with the fluid injector such that the piston element is operable in the throughbore, and a bellows syringe adapted for connection to the distal end of the pressure jacket. The bellows syringe generally comprises a cap member defining an internal cavity and a discharge port, the cap member further comprising a depending skirt portion, and a bellows member disposed in the internal cavity and held in a compressed state in the internal cavity by engagement between the cap member and a proximal end of the bellows member.

A particular embodiment is directed to a bellows syringe for a fluid delivery system comprising a cap member defining an internal cavity and a discharge port, the cap member further comprising a depending skirt portion, and a bellows member disposed in the internal cavity and held in a compressed state in the internal cavity by engagement between the cap member and a proximal end of the bellows member.

The skirt portion may comprise a plurality of radially-inward extending tab members engaged with the proximal end of the bellows member to hold the bellows member in the compressed state in the internal cavity.

The proximal end of the bellows member may be closed and a distal end of the bellows member may define a discharge port in fluid communication with the cap member discharge port, and the closed proximal end of the bellows member may comprise at least one attachment member for attaching the bellows member to a piston head of a piston element. The at least one attachment member may be disposed in an end pocket defined in the closed proximal end of the bellows member. The at least one attachment member may comprise a button element adapted to be engaged by a piston element comprising a plurality of jaw members.

The bellows syringe may further comprise a base member comprising a plate portion and a central portion, and one of the skirt portion and the plate portion may comprise a plurality of retaining tabs engaged with catch members provided on the other of the skirt portion and the plate portion to hold the bellows member in the compressed state in the internal cavity. The central portion may define a circumferential groove and the bellows member may comprise a cooperating rib engaging the circumferential groove for securing the plate portion to the proximal end of the bellows member. The central portion may define an end pocket for receiving a piston head of a piston element, and the end pocket may comprise at least one internal element to engage the piston head.

A further embodiment is a bellows assembly for association with a fluid delivery system comprising a pressure jacket having a distal end and a proximal end and defining a throughbore therebetween and a bellows syringe adapted for connection to the distal end of the pressure jacket. The bellows syringe may comprise a cap member defining an internal cavity and a discharge port, the cap member further comprising a depending skirt portion, and a bellows member may be disposed in the internal cavity and held in a compressed state in the internal cavity by engagement between the cap member and a proximal end of the bellows member.

The skirt portion may comprise a plurality of radially-inward extending tab members engaged with the proximal end of the bellows member to hold the bellows member in the compressed state in the internal cavity.

The proximal end of the bellows member may be closed and a distal end of the bellows member may define a discharge port in fluid communication with the cap member discharge port, and the closed proximal end of the bellows member may comprise at least one attachment member for attaching the bellows member to a piston head of a piston element. The at least one attachment member may be disposed in an end pocket defined in the closed proximal end of the bellows member. The at least one attachment member may comprise a button element adapted to be engaged by a piston element comprising a plurality of jaw members.

The bellows syringe may further comprise a base member comprising a plate portion and a central portion, and one of the skirt portion and the plate portion may comprise a plurality of retaining tabs engaged with catch members provided on the other of the skirt portion and the plate portion to hold the bellows member in the compressed state in the internal cavity. The central portion may define a circumferential groove and the bellows member may comprise a cooperating rib engaging the circumferential groove for securing the plate portion to the proximal end of the bellows member. The central portion may define an end pocket for receiving a piston head of a piston element, and the end pocket may comprise at least one internal element to engage the piston head.

The distal end of the pressure jacket may comprise a plurality of tab members each defining a slot, and the plate portion may be adapted to engage the slots to secure the bellows syringe to the pressure jacket.

The bellows assembly may further comprise a plurality of circumferentially-spaced mounting flanges on the distal end of the pressure jacket, and a plurality of tab members on the distal end of the pressure jacket and provided between the mounting flanges, respectively. Mating slots may be defined in the skirt portion of the cap member to receive the mounting flanges for securing the bellows syringe to the distal end of the pressure jacket. The cap member may be rotated to seat the mounting flanges in the mating slots in the cap member, and the rotational motion may cause the tab members on the distal end of the pressure jacket to engage the tab members on the skirt portion of the cap member and release the tab members on the skirt portion of the cap member from engagement with the proximal end of the bellows member.

Another embodiment is directed to a fluid delivery system, comprising a fluid injector comprising a reciprocally operable piston element having a piston head, a pressure jacket having a distal end and a proximal end and defining a throughbore therebetween, the pressure jacket proximal end engaged with the fluid injector such that the piston element is operable in the throughbore, and a bellows syringe adapted for connection to the distal end of the pressure jacket. The bellows syringe generally comprises a cap member defining an internal cavity and a discharge port, the cap member further comprising a depending skirt portion, and a bellows member disposed in the internal cavity and held in a compressed state in the internal cavity by engagement between the cap member and a proximal end of the bellows member.

The skirt portion may comprise a plurality of radially-inward extending tab members engaged with the proximal end of the bellows member to hold the bellows member in the compressed state in the internal cavity.

The proximal end of the bellows member may be closed and a distal end of the bellows member may define a discharge port in fluid communication with the cap member discharge port, and the closed proximal end of the bellows member may comprise at least one attachment member for attaching the bellows member to a piston head of a piston element. The at least one attachment member may be disposed in an end pocket defined in the closed proximal end of the bellows member. The at least one attachment member may comprise a button element adapted to be engaged by a piston element comprising a plurality of jaw members.

The bellows syringe may further comprise a base member comprising a plate portion and a central portion, and one of the skirt portion and the plate portion may comprise a plurality of retaining tabs engaged with catch members provided on the other of the skirt portion and the plate portion to hold the bellows member in the compressed state in the internal cavity. The central portion may define a circumferential groove and the bellows member may comprise a cooperating rib engaging the circumferential groove for securing the plate portion to the proximal end of the bellows member. The central portion may define an end pocket for receiving a piston head of a piston element, and the end pocket may comprise at least one internal element to engage the piston head.

The distal end of the pressure jacket may comprise a plurality of tab members each defining a slot, and the plate portion may be adapted to engage the slots to secure the bellows syringe to the pressure jacket.

The bellows assembly may further comprise a plurality of circumferentially-spaced mounting flanges on the distal end of the pressure jacket, and a plurality of tab members on the distal end of the pressure jacket and provided between the mounting flanges, respectively. Mating slots may be defined in the skirt portion of the cap member to receive the mounting flanges for securing the bellows syringe to the distal end of the pressure jacket. The cap member may be rotated to seat the mounting flanges in the mating slots in the cap member, and the rotational motion may cause the tab members on the distal end of the pressure jacket to engage the tab members on the skirt portion of the cap member and release the tab members on the skirt portion of the cap member from engagement with the proximal end of the bellows member.

Further details and advantages of the various embodiments described in detail herein will become clear upon reviewing the following detailed description of the various embodiments in conjunction with the accompanying drawing figures.

BRIEF DESCRIPTION OF THE DRAWINGS

FIGS. 1B-1D are perspective views showing a bellows assembly according to one embodiment and operational steps of attaching the bellows syringe to a cylindrical pressure jacket associated with a powered fluid injector.

FIG. 2A is a top perspective view of the bellows assembly.

FIG. 2B is a cross-sectional view taken along lines 2B-2B in FIG. 2A.

FIG. 2C is a cross-sectional view taken along lines 2C-2C in FIG. 2A.

FIG. 3 is a sequence of cross-sectional, partial perspective, and partially cut-away views showing attachment of the bellows syringe to the pressure jacket of the bellows assembly, and operation of a plunger element in the pressure jacket.

FIG. 4C is an exploded view of the bellows syringe and the protector cap or retainer shown in FIG. 4A.

FIGS. 6A-6F schematically in cross-section and in partial perspective and cut-away view illustrate another embodiment wherein a fluid container is inserted into the pressure jacket, and illustrate operational steps for interfacing a piston element to a proximal end of the fluid container.

FIG. 7A is a perspective, exploded, and partial cross-sectional view showing the bellows syringe and a portion of the pressure jacket of the bellows assembly.

FIG. 7B is a perspective and partial cross-sectional view showing the bellows syringe of FIG. 7A, and showing a piston element engaged with the proximal end of a bellows member of the bellows syringe.

FIG. 7C is a perspective and partial cross-sectional view showing the bellows syringe of FIG. 7A, and showing a piston element engaged with the proximal end of a bellows member and withdrawing the bellows member into the pressure jacket.

FIGS. 22C-22D are respectively a perspective view and a side view of the bellows portion of the bellows member shown in FIGS. 22A-22B after molding to form the stiffening ribs as part of the bellows portion of the bellows member.

FIGS. 27A-27B are schematic cross-sectional views of the bellows syringe associated with a pressure jacket, and showing a collapsible piercing connector cap used to access the bellows member of the bellows syringe.

FIG. 31B is a schematic top plan view of the bellows syringe of FIG. 31A and showing the rotational plate in a position to block a fluid path with the bellows member.

FIG. 31C is a schematic top plan view of the bellows syringe of FIG. 31B and showing the rotational plate in a position establishing the fluid path with the bellows member.

FIG. 32 is a partial cross-sectional view of the bellows syringe associated with a pressure jacket, and showing a cap member with a cutting blade operable via an external button and used to access the bellows member of the bellows syringe.

FIG. 33A is a schematic cross-sectional view showing a pressure jacket with a pivotal door having a piercing fluid connector element used to access the bellows member of the bellows syringe when loaded in the pressure jacket, and showing the pivotal door in an open position.

FIG. 33B is a schematic cross-sectional view showing a pressure jacket with a pivotal door as shown in FIG. 33A, and showing the pivotal door in a closed position.

FIG. 35A is a perspective view of a clam shell support scaffold used support the bellows member of the bellows syringe either alone or in combination with the embodiment shown in FIG. 34.

FIG. 35B is a schematic cross-sectional view showing the clam shell support scaffold of FIG. 35A supporting the bellows member of the bellows syringe.

FIG. 36A is a top view of a pressure jacket for supporting the bellows member according to one embodiment.

FIG. 36B is an end view of a pressure jacket for supporting the bellows member according to one embodiment.

FIGS. 36C-36D are schematic views of a fluid injector with a pivotally mounted split-top pressure jacket, as shown in FIGS. 36A-36B, for supporting the bellows member.

FIG. 38A is a top view of a pressure jacket for supporting the bellows member according to one embodiment.

FIG. 38B is an end view of a pressure jacket for supporting the bellows member according to one embodiment.

FIGS. 38C-38D are schematic cross-sectional views of a fluid injector with a split-front pressure jacket, as shown in FIGS. 38A-38B, for supporting the bellows member.

FIGS. 39A-39B are schematic perspective views of a fluid injector with a pivotally mounted split-top pressure jacket body for supporting the bellows member, and the housing of the fluid injector further having an appendage for closing the split-top.

FIGS. 41A-41C are schematic perspective views of a fluid injector in which an split-top pressure jacket body for supporting the bellows member is telescopically and pivotally connected to the fluid injector housing by a slide plate.

FIG. 42A is a schematic cross-sectional view a fluid injector with a split-top pressure jacket body for supporting the bellows member, with the pressure jacket body being resiliently flexible to permit opening and closing of the split-top to allow passage of a fluid tubing set through the split-top opening.

FIG. 42B is a transverse cross-sectional view of the pressure jacket shown in FIG. 42A taken along lines 42B-42B.

FIG. 42C is a transverse cross-sectional view of the pressure jacket shown in FIG. 42A according to another embodiment.

FIG. 49B is an end view of the bellows member and pressure jacket of FIG. 49A.

FIG. 49C is a perspective view of the bellows member partially loaded into the pressure jacket of FIG. 49A.

FIG. 49D is a perspective view showing the bellows member fully loaded into the pressure jacket of FIG. 49A.

FIG. 51B is a perspective and partial cross-sectional view of the fluid container of FIG. 51A with locking finger elements of the chuck mechanism removed for clarity.

FIG. 51C is a perspective and partial cross-sectional view of the fluid container of FIG. 51A with a locking collar of the chuck mechanism exploded from the fluid connector fitting.

FIG. 52A is perspective view of a fluid injector in which an open top pressure jacket is hinged to the fluid injector housing and a locking ring is used to secure the pressure jacket to the fluid injector housing in the closed position, and showing the pressure jacket in an open position.

FIG. 52B is perspective view of a fluid injector in which an open top pressure jacket is hinged to the fluid injector housing and a locking ring is used to secure the pressure jacket to the fluid injector housing in the closed position, and showing the pressure jacket in the closed position.

FIG. 54A is a perspective view of the fluid injector with a split or clam shell pressure jacket that pivots open at a distal end to form a mouth opening facing the fluid injector body, with the pressure jacket shown in an opened position.

FIG. 54B is a side view of the fluid injector shown in FIG. 54A.

FIG. 54C is a perspective view of the fluid injector of FIG. 54A with the pressure jacket shown in a closed position.

FIG. 54D is side view of the fluid injector as shown in FIG. 54C.

FIG. 55 is a perspective view of another embodiment of the bellows member of the bellows syringe having outward-extending radial tabs at the distal end and at the proximal end for engaging corresponding receiving slots in a pressure jacket.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, features, and operational sequences illustrated in the accompanying drawing figures and described herein are simply exemplary and should not be considered as limiting.

Figure 1A:
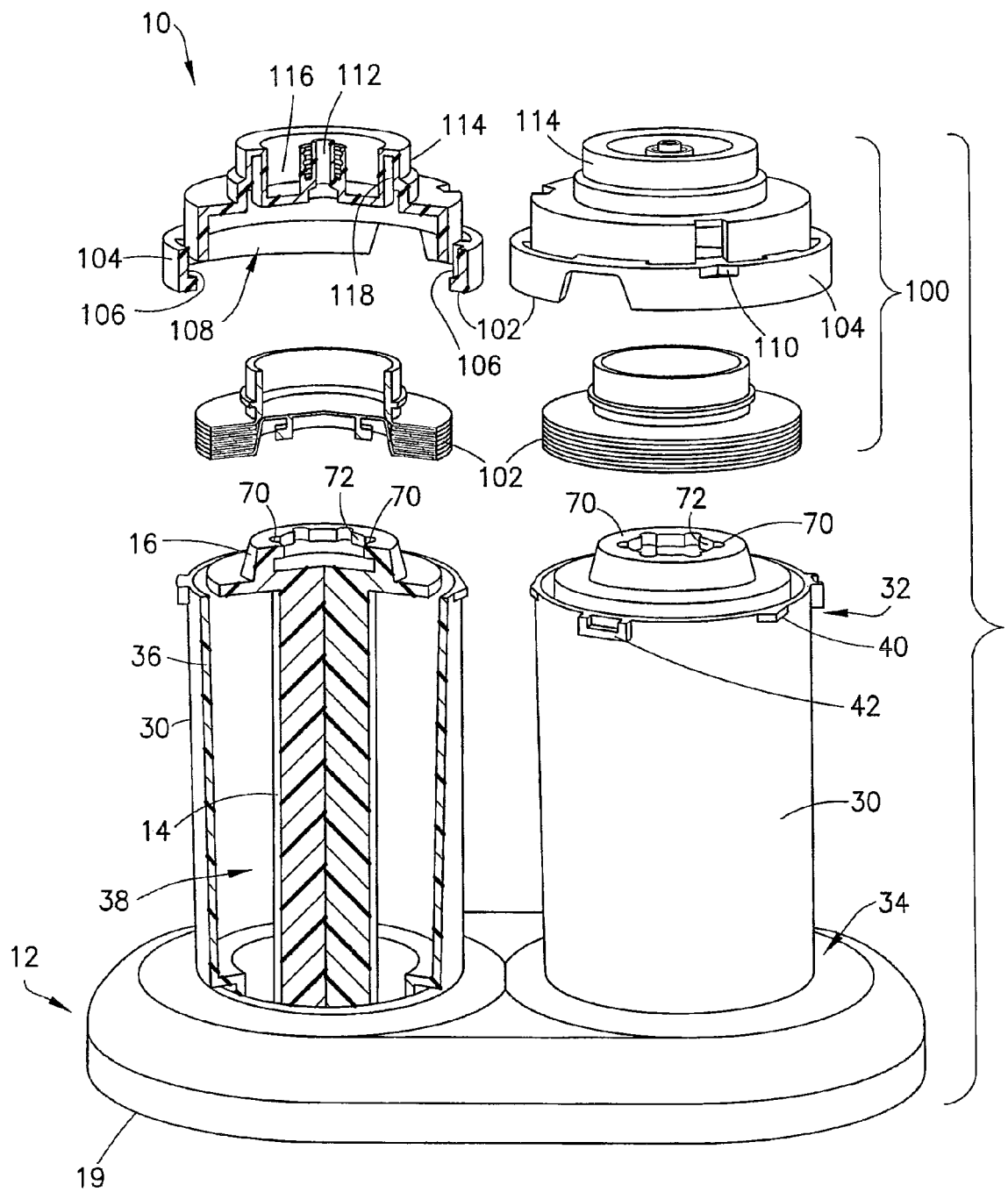
FIG. 1A is a perspective, exploded, and partially cut-away view of adjacent bellows assemblies each incorporating a bellows syringe according to one embodiment.
Figure 1C:
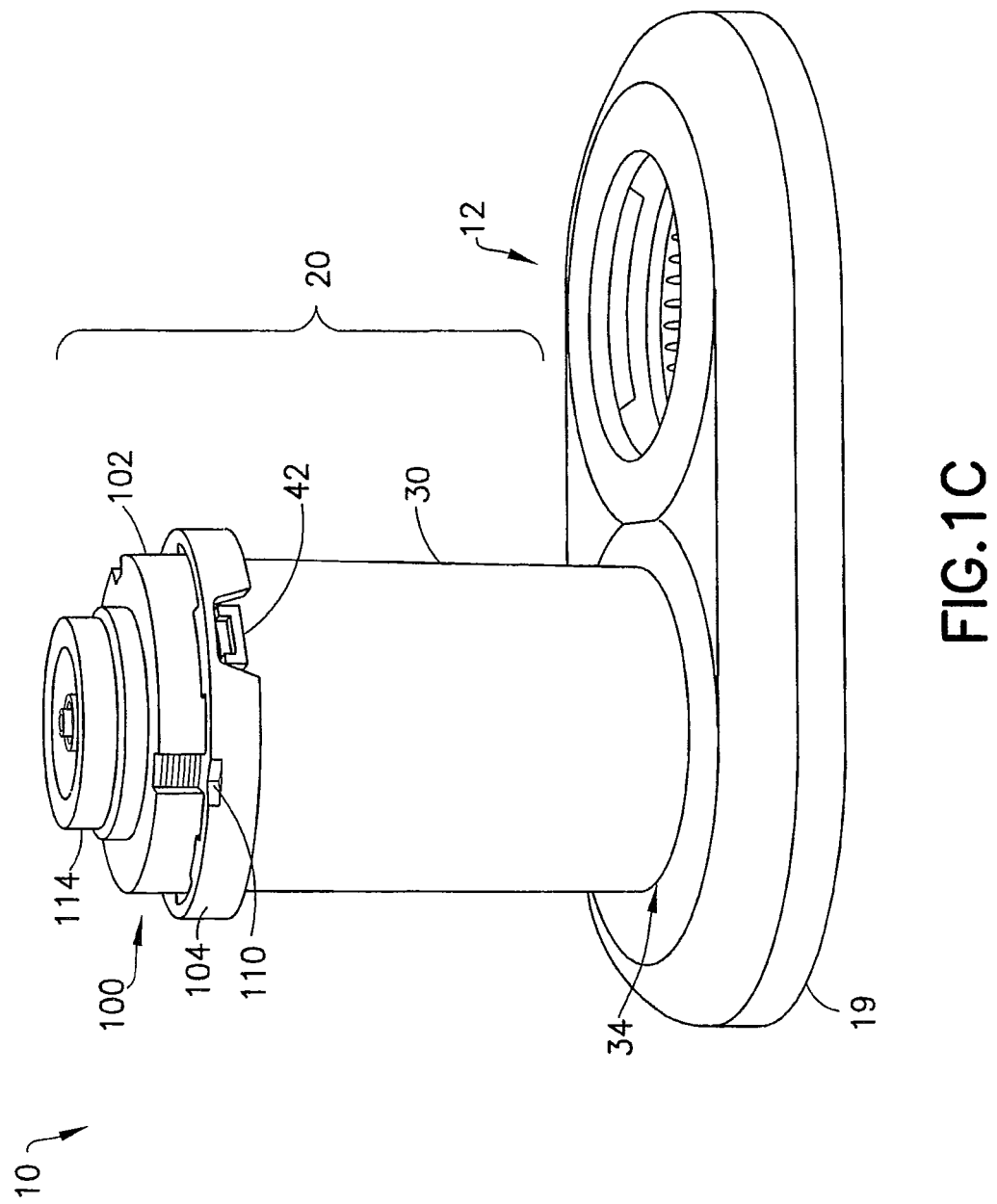

Referring initially to FIGS. 1-2 and 7, a fluid delivery system 10 generally comprises a powered fluid injector head 12, such as a Stellant® powered injector platform manufactured by Medrad, Inc. Only a face portion 19 of the powered fluid injector head is shown in FIGS. 1A-1D and 7A-7C but other figures, such as FIG. 10C discussed herein, illustrate a suitable fluid injector head 12 for use in the various embodiments described herein. A bellows assembly 20 comprising a cylindrical body or pressure jacket 30 and a bellows syringe 100, may be associated with the fluid injector head 12 (hereinafter "fluid injector 12") as described in detail herein with respect to several embodiments. As is known in the medical field, injecting contrast media into the bloodstream of patients enables visualization of various pathologies through X-Ray, Computed Tomography (CT), Magnetic Resonance (MR), or other medical imaging modalities. Contrast delivery is most effective and efficient using a powered fluid injector, such as the Stellant® powered fluid injector, that can be programmed to deliver specific amounts of contrast agent and/or saline at specific flow rates. A powered fluid injector may be used in diagnosing stroke, heart disease, cancer, vascular disease, physical injury, digestive disorder, etc. The fluid injector 12 comprises one or more linearly reciprocal piston elements 14 which each have a distal piston interface or piston head 16 adapted to engage a bellows syringe 100 of the bellows assembly 20. The piston element or elements 14 are enclosed within a housing 18 as shown, for example, in FIG. 10C discussed herein, and specific details of a powered injector platform and syringe elements used therewith may be found in U.S. Pat. No. 5,383,858 to Reilly et al.; U.S. Pat. No. 5,873,861 to Hitchins et al.; and U.S. Pat. No. 6,652,489 to Trocki et al., all assigned to Medrad, Inc. and each incorporated herein by reference for disclosure related to the foregoing elements. This disclosure is explicitly not limited to utilizing the bellows syringe 100 with contrast media but may be used for any medicinal fluid to be delivered to a patient. The face plate portion 19 of the fluid injector 12 is specifically shown in FIGS. 1A-1D.

The bellows assembly 20 is a multi-component device and generally comprises a cylindrical body or pressure jacket 30 and a bellows syringe 100 that interfaces with the pressure jacket 30. The bellows syringe 100 comprises a cap member or element 102 and a bellows member or element 120. The bellows syringe 100 is adapted for use in CT, MR, and like procedures and operable at typical operating pressures of about 200-400 psi, as examples, and the bellows member 120 may be expanded to hold fluid volumes on the order of 200 ml. The bellows syringe 100 is adapted to be secured to the pressure jacket 30 by the cap member 102. Each of the foregoing components is discussed hereinafter in detail.

The cylindrical body or pressure jacket 30 is a unitary, typically cylindrical body having a distal end 32 and a proximal end 34 and is typically a reusable component, while the bellows syringe 100 is typically a single-use component. The pressure jacket 30 has a sidewall 36 that defines a throughbore 38 between the distal and proximal ends 32, 34. The proximal end 34 is adapted to interface with the fluid injector 12 and includes mounting structure (not shown) positioned to engage the front end or face plate 19 of the housing 18 of the fluid injector 12 to properly seat the pressure jacket 30 relative to the fluid injector 12. As an example, two opposed bayonet attachment flanges (not shown) may be provided on the proximal end 34 for interfacing with the fluid injector face plate 19 to secure the pressure jacket 30 to the fluid injector 12. The distal end 32 of the pressure jacket 30 is formed with exterior circumferentially-spaced exterior tabs 40 and exterior circumferentially-spaced mounting flanges 42. The mounting flanges 42 are spaced circumferentially around the distal end 32 of the pressure jacket 30, with the tabs 40 located between the mounting flanges 42. The pressure jacket 30 may be made of any suitable plastic material, desirably a clear plastic material, such as, but not limited to, polycarbonate, acrylic, or polyester.

Further details relating to desirable mounting structures used to properly interface the pressure jacket 30 with the fluid injector 12 may be found in the foregoing Medrad, Inc. patents which discuss similar interfacing features for securing a Stellant® CT syringe to a Stellant® fluid injector. In accordance with this disclosure, the pressure jacket 30 may have interfacing structure for attaching the pressure jacket 30 to a Stellant® fluid injector. However, this description is provided for exemplary purposes and the proximal end 34 of the pressure jacket 30 may have any suitable configuration for interfacing with any suitable powered fluid injector known in the medical field for powered fluid delivery applications. The Stellant® fluid injector and the proximal end features of a Stellant® syringe, as described in the foregoing Medrad, Inc. patents, are provided for exemplary purposes only and should not be considered limiting. For example, the interface between the proximal end 34 of the pressure jacket 30 and fluid injector 12 may take other front-loading arrangements as disclosed in the foregoing Trocki et al. patent, or in U.S. Pat. No. 7,419,478 to Reilly et al. and assigned to Medrad, Inc. (additionally incorporated herein by reference). An adapter may also be used to connect the pressure jacket 30 to the fluid injector 12 as disclosed in U.S. Pat. No. 5,520,653 to Reilly et al., or in U.S. Pat. No. 7,497,843 to Castillo et al. and U.S. Pat. No. 6,726,657 to Dedig et al., all assigned to Medrad, Inc. and incorporated herein by reference for these teachings. All of the foregoing Medrad, Inc. patents disclose various apparatus and methods for mounting a syringe body or pressure jacket to a fluid injector, whether a single-syringe fluid injector or multi-syringe fluid injector and, further, disclose various apparatus and methods for interfacing a syringe plunger with a piston element of the fluid injector. Thus, these patents are incorporated by reference into this disclosure at least for teaching apparatuses and methods for interfacing the pressure jacket 30 to the fluid injector 12 and, further, for interfacing the piston element or elements 14 of the fluid injector 12 with the bellows member 120, or additional components or elements provided on the bellows member 120 when disposed within the pressure jacket 30, as described herein. Further, the housing 18 of the fluid injector 12 may comprise a light ring (not shown) that can encompass all or part of the axial length of the pressure jacket 30 and all or part of the bellows syringe 100 to sterilize the pressure jacket 30 and all or part of the bellows syringe 100 with ultraviolet light (UV). Additionally, the pressure jacket 30 may comprise a barrier or membrane (not shown) within the bore 38 near the proximal end 34 of the pressure jacket 30 that acts as a barrier to keep fluid from entering the fluid injector housing 18 in the event of failure of the bellows member 120. The barrier forms a reservoir chamber that catches spilled fluid.

In one embodiment, the cap member 102 is used to secure the bellows syringe 100 to the pressure jacket 30. The cap member 102, in the embodiment illustrated, comprises a depending ring or skirt portion 104 that is approximately equal to or slightly larger than the outer diameter of the pressure jacket 30. The skirt portion 104 is formed with receiving slots 106, such as bayonet slots, for engagement with the mounting flanges 42 provided on the distal end 32 of the pressure jacket 30. Accordingly, when the bellows syringe 100 is mounted on the distal end 32 of the pressure jacket 30 and rotated in a clockwise or, conversely, a counterclockwise direction depending on the opening orientation of the bayonet slots 106, the bellows syringe 100 is secured onto the pressure jacket 30. The cap member 102 further defines an internal cavity 108 wherein the bellows member 120 is disposed and held in a compressed, transport, or pre-use state. The bellows member 120 is typically held in a compressed and locked state or pre-use state in the bellows syringe 100 by retaining tabs 110 formed as part of the skirt portion 104 of the cap member 102 and which extend radially-inward to engage the bottom of the bellows member 120 to maintain the bellows member 120 in the compressed or pre-use state. The exterior tabs 40 are located on the distal end 32 of the pressure jacket 30 so that when the cap member 102 is placed on the distal end 32 and rotated so that the receiving slots 106 receive the mounting flanges 42, the exterior tabs 40 engage or interact with the retaining tabs 110 and cause the retaining tabs 110 to disengage from the bellows member 120. Thus, the retaining tabs 110 are automatically "unlocked" from the bellows member 120 as the cap member 102 is placed onto the distal end 32 of the pressure jacket 30 and the cap member 102 is rotated to secure the cap member 102 to the pressure jacket 30. Once placed in association with the pressure jacket 30 and "unlocked", the bellows syringe 100 is then ready for use in a medical procedure. The retaining tabs 110 are formed to extend radially inward from the skirt portion 104 of the cap member 102, and the skirt portion 104 may be formed to be resiliently flexible in the vicinity of the tabs 110 to permit the retaining tabs 110 to flex and disengage from the bellows member 120 as the cap member 102 is rotated on the distal end 32 of the pressure jacket 30 to secure the assembly of the bellows syringe 100 to the pressure jacket 30. Alternatively, the retaining tabs 110 may be formed to be resiliently flexible on the skirt portion 104 of the cap member 102 to flex and disengage from the bellows member 120 as the cap member 102 is rotated on the distal end 32 of the pressure jacket 30 to secure the assembly of the bellows syringe 100 to the pressure jacket 30.

The cap member 102 may be further formed with a discharge port 112, which may be formed as conventional luer fitting. The discharge port 112 is disposed coaxially within an annular wall 114 on the outward facing side of the cap member 102 and may be recessed within the annular wall 114, such as within an annular cavity 116 defined by the annular wall 114, to promote sterility of the discharge port 112. The recessing of the discharge port 112 in the annular cavity 116 aids in avoiding finger-contact with the discharge port 112 as a user loads the bellows syringe 100 onto pressure jacket 30. Further, the cap member 102 may be formed with an interior annular recess or groove 118 for receiving and securing the discharge portion of the bellows member 120 as described further herein.

The bellows member 120, when extended, generally comprises a hollow body that includes a forward or distal end 122, a rearward or proximal end 124, and an intermediate bellows portion as generally indicated by reference numeral 126. The rearward or proximal end or portion 124 defines a closed end wall 128. The rearward portion of the bellows portion 126 connects to the closed end wall 128, and a forward portion of the bellows portion 126 defines a discharge neck 130 opposite the closed end wall 128. The discharge neck 130 is adapted to be received in the interior annular recess or groove 118 in the cap member 102 and may be secured permanently therein, adhesively secured therein, or be removably secured therein such as by a friction fit connection or other suitable mechanical connection. The discharge neck 130 terminates in a discharge port 150 (see, for example, FIGS. 7D-7F discussed herein) that may have, according to one non-limiting embodiment, a fracturable closure seal (discussed herein) for sterility purposes, such as pierceable foil or elastomeric seal. The bellows portion 126 is formed with a plurality of bellows sections or bellows rings 132 between the neck 120 and the closed end wall 128, which form the bellows portion 126. The bellows sections or rings 132 are defined by frusto-conical wall sections 134 providing the bellows member 120 with a hollow interior 136. The discharge neck 130 defines passageway 138 leading to the hollow interior 136 generally defined by the bellows portion 126 of the bellows member 120. The closed end wall 128 may be shaped to interface directly with the piston head 16 on the piston element 14 of a fluid injector 12. For example, the closed end wall 128 may define a receiving end pocket 140 for interfacing directly with a similarly-shaped piston head 16. In particular, the depicted embodiment of the piston head 16 comprises a radial end flange 60 and a distal end abutment 62 shaped to match the interior shape of the receiving end pocket 140. The closed end wall 128 may alternatively include an attached rigid base element or part that defines the receiving end pocket 140 for engaging with the piston head 16 in a like manner.

The bellows member 120 of the bellows syringe 100 essentially forms a collapsible fluid container that may be axially expanded by action of the piston element 14 once the piston head 16 is mechanically engaged in the receiving end pocket 140. This expansion occurs as the piston element 14 withdraws axially in the pressure jacket 30, and this axially withdrawing movement fills the hollow interior 136 of the bellows member 120 with a desired medical fluid. This axially withdrawing movement of the piston element 14 axially expands the bellows member 120 along the compressed bellows portion 126. Once filled with the desired medical fluid, an opposite movement of the piston element 14 axially collapses the bellows member 120 along bellows portion 126 to eject the medical fluid via the discharge neck 130 and discharge port 150; further specific details of the operation of the bellows member 120 in conjunction with the piston element 14 are presented herein.

FIG. 3 illustrates a sequence for attaching the bellows syringe 100 to the pressure jacket 30 to form the bellows assembly 20. In FIG. 3, the pressure jacket 30 has already been connected or otherwise associated with a fluid injector (not shown in FIG. 3) at step a. The bellows syringe 100 in step b is secured onto the distal and 32 of the cylinder body 30 as described previously. Next, at step c, the piston element 14 of the fluid injector 12 is extended to engage the bellows member 120. In this step, the piston head 16 is seated in engagement with the end pocket 140 in the closed end wall 128 of the bellows member 120 and is secured in the end pocket 140 with any suitable mechanical connection to permit the plunger element 14 to operate the bellows member 120 in the proximal and distal directions. In step d, the piston element 14 retracts and elongates the bellows member 120 and, in particular, elongates the bellows portion 126 by separating the bellows sections or rings 132. In this step, the hollow interior 136 of the bellows member 120 may filled with fluid from an external sourced connected to the discharge port 112 on the cap member 102. Once the bellows member 120 is filled with a desired amount of fluid, the piston element 14 can be controlled to the reverse direction, as shown at step e, to expel fluid from the hollow interior 136 of the bellows member 120. The fluid passes through the passageway 138 defined by the discharge neck 130 and discharges from the bellows syringe 100 via the discharge port 112 on the cap member 102. Once the fluid is dispensed from the bellows syringe 100, the bellows syringe 100 may be removed at step f from the pressure jacket 30 by reversing the loading process described previously. The used bellows syringe 100 may then be discarded as medical waste. The piston element 14 is withdrawn axially in the pressure jacket 30 and, at step g, the pressure jacket 30 is ready for attachment of a new, sterile bellows syringe 100.

Figure 4A:
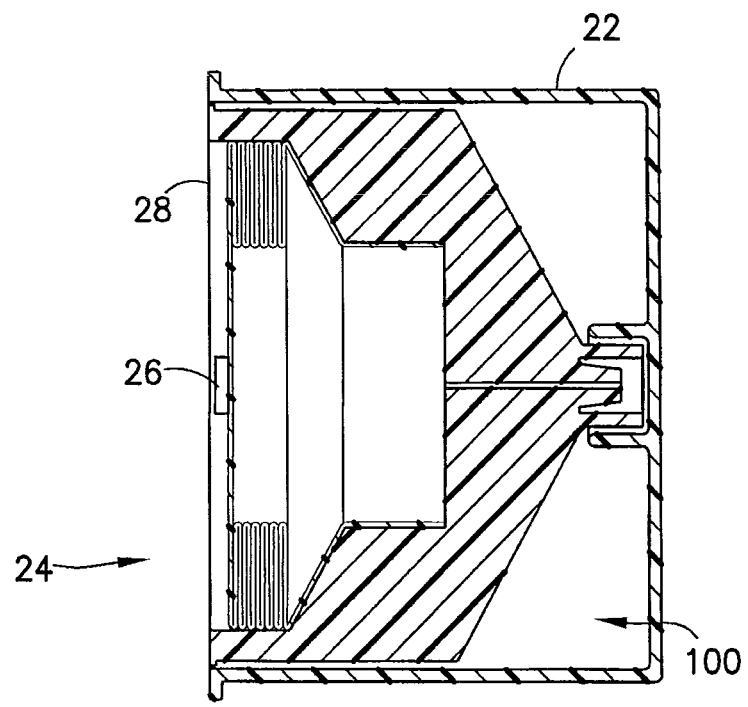
FIG. 4A is a schematic cross-sectional view of the bellows syringe enclosed by a protector cap or retainer.
Figure 4B:
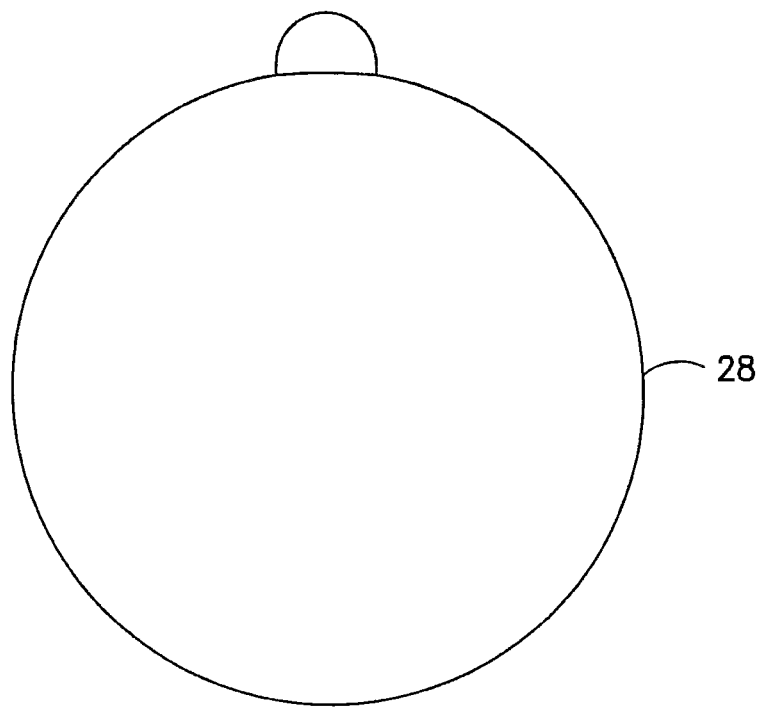
FIG. 4B is a plan view of a peel open seal for the protector cap or retainer shown in FIG. 4A.

As the bellows syringe 100 is suited for single-patient use, features may be provided to maintain the sterility of the bellows syringe 100 prior to use. Referring to FIGS. 4A-4C, the bellows syringe 100 may be packaged within a protector cap or retainer 22. The protector cap or retainer 22 is generally in the form or a disposable dust cap having an open end 24. Internal retaining tabs 26 are provided in the protector cap 22. The retaining tabs 26 are adapted to engage mating or corresponding exterior retaining tabs 142 on the cap member 102. The exterior retaining tabs 142 are provided on the skirt portion 104 of the cap 102. A peel-open rear seal 28 encloses the open end 24 of the protector cap 22 and maintains the sterility of the interior space within the protector cap 22 wherein the bellows syringe 100 is disposed. The bellows syringe 100, as enclosed by the protector cap 22 and peel-open rear seal 28, may be packaged in a blister package for shipment to a medical facility.

Figures 5A, 5B:
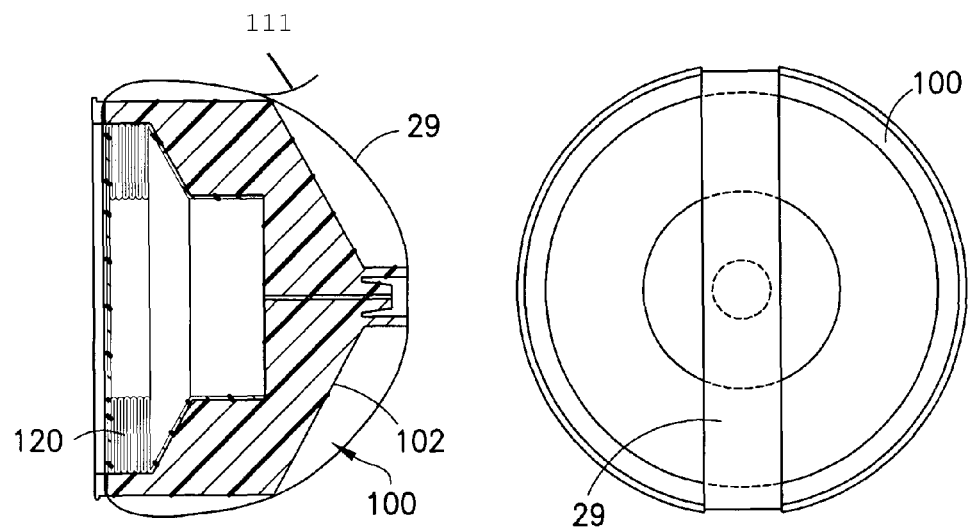
FIG. 5A is a schematic cross-sectional view of the bellows syringe enclosed by a tamper-evident seal strip.
FIG. 5B is a top view of the bellows syringe sealed by the tamper-evident seal strip shown in FIG. 5A.
Figure 5C:
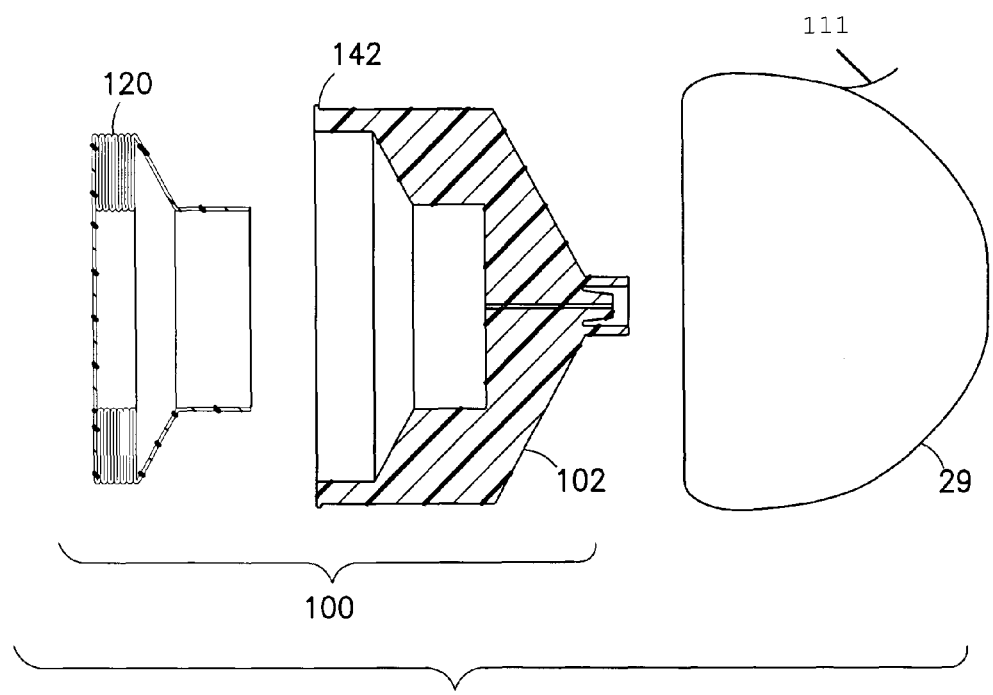
FIG. 5C is an exploded side view of the bellows syringe and the tamper-evident seal strip shown in FIG. 5A.
Figure 6F:
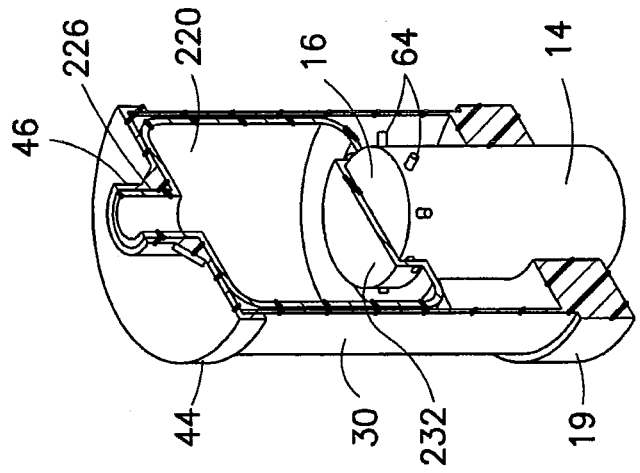
Figure 6E:
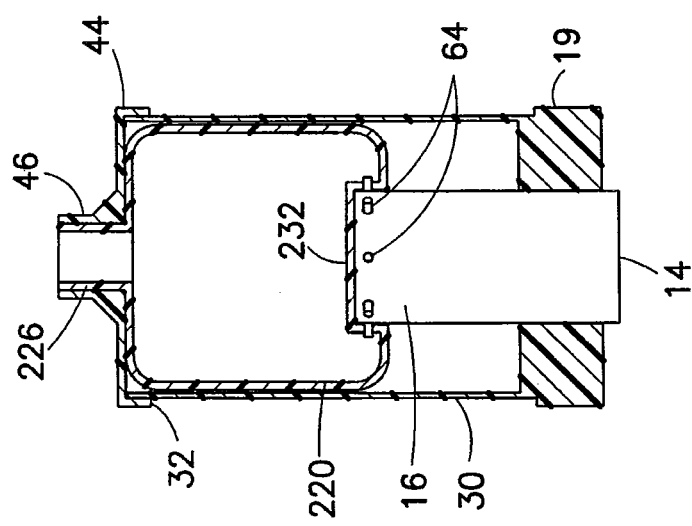
Figure 6D:
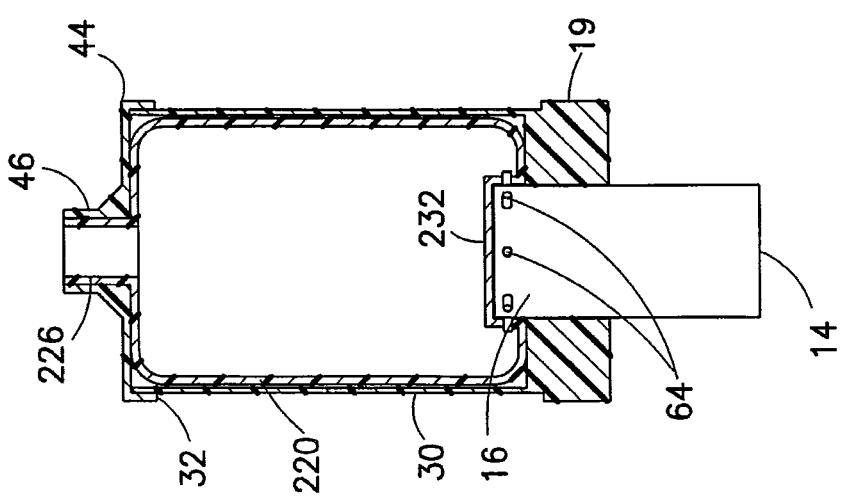

A modification or enhancement of the foregoing packaging method for maintaining sterility of the bellows syringe 100 is shown in FIGS. 5A-5C. In this modification or enhancement, the bellows syringe 100 is enclosed by a tamper-evident seal strip 29. The tamper-evident strip 29 extends around the bellows syringe 100 such that the tamper-evident strip 29 covers the discharge port 112 on the cap member 102. In the embodiments of the bellows syringe 100 shown in FIGS. 4-5, the cap member 102 is shown formed without the annular wall 114 surrounding the discharge port 112. Hence, there is a need in this embodiment to protect the discharge port 112 from contamination, such as by inadvertent finger-contact with a user who is handling the bellows syringe 100. A pull tab 111 may be provided as part of the tamper-evident strip 29 to facilitate removal of the strip 29 from the bellows syringe 100. The bellows syringe 100 having the tamper-evident strip 29 affixed thereto may be sealed in the protector cap 22 described above in connection with FIGS. 4A-4C.

Figure 8:
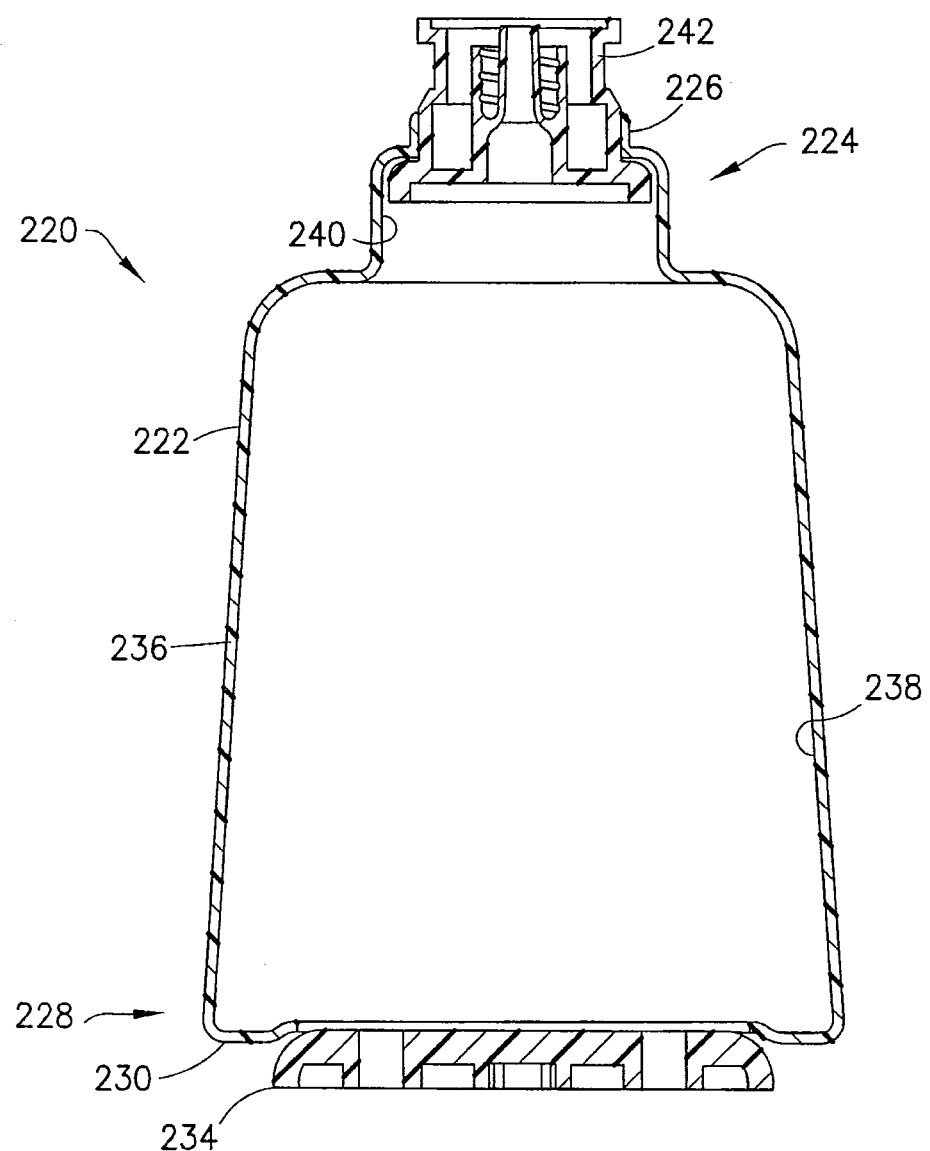
FIG. 8 is a schematic cross-sectional view of a tapered wall fluid container having rigid end part or base according to another embodiment.

Referring to FIGS. 6A-6F and FIG. 8 another embodiment is schematically illustrated wherein a fluid container 220 is inserted into the cylindrical pressure jacket 30 associated with a fluid injector 12. The pressure jacket 30 in this embodiment has the same general form as described hereinabove, and the bellows syringe 100 may likewise be used with the pressure jacket 30 and related components discussed herein with appropriate modifications to the cap member 102, the bellows member 120, and the pressure jacket 30. The fluid container 220 may have a soft, pliable body 222 having a distal end 224 with a discharge port 226, for example similar to the discharge port 112 described previously, and a proximal end 228 with a closed end wall 230. The closed end wall 230 defines a receiving end pocket 232 therein to receive the piston head 16 of the piston element 14, and this structure may be applied to the bellows member 120 as well, such as configuring the end pocket 140 in a similar manner to end pocket 232. The closed end wall 230 may alternatively include a rigid base element or part that defines the receiving end pocket 232 for the piston head 16, as shown in FIG. 8. Even though fluid container 220 is illustrated for use in the pressure jacket/pressure jacket 30 shown FIGS. 6A-6F, as noted, the bellows syringe 100 may also be used in the embodiment depicted in FIGS. 6A-6F. A retaining cap 44 may be associated with the pressure jacket 30 to enclose the open distal end 32 of the pressure jacket 30 and retain the fluid container 220 or the bellows syringe 100 therein. The retaining cap 44 may be formed to mechanically connect to the distal end 32 of the pressure jacket 30, and may comprise a discharge port 46 that is axially aligned with the discharge port 226 on the fluid container 30. As a further alternative, a similar discharge port to the discharge port 226 may be provided on the bellows member 120 at the distal end 122 thereof so that the bellows member 120 is made suitable for use in the embodiment depicted in FIGS. 6A-6F without need of the cap member 102, and use of this modified embodiment is further discussed immediately hereinafter.

In use, the fluid container 220 or bellows member 120 is loaded into the pressure jacket 30 through the open distal end 32 of the pressure jacket 30 and the retaining cap 44 is placed on the distal end 32 of the pressure jacket 30. As an example, a threaded connection or like mechanical connection may be provided between the retaining cap 44 and the distal end 32 of the pressure jacket 30. In the present embodiment, the piston head 16 of the piston element 14 is provided with radially-extendable retaining pins 64 which are initially recessed into the piston head 16 as shown in FIGS. 6A-6F. Thus, when the fluid container 220 or bellows member 120 is initially placed into the pressure jacket 30, the retaining pins 64 are in their recessed configuration and do not interfere with the placement of piston head 16 into the respective end pockets 232, 140 in the fluid container 220 or the bellows member 120. Next, when the retaining cap 44 is rotated to secure the threaded or like mechanical connection between the retaining cap 44 and the pressure jacket 30, this rotational motion may also be used to impart rotation to the fluid container 220 or the bellows member 120, such as by a suitable inter-engagement between the discharge port 46 and the discharge port 226 on the fluid container 30 (or between a like discharge port 226 provided on the bellows member 120 and the discharge port 226) and this rotational motion also causes the fluid container 220 or bellows member 120 to rotate on the piston head 16. As this rotational motion occurs, the respective end pockets 232, 140 in the fluid container 220 or bellows member 120 rotationally act upon the piston head 16 and cause the retaining pins 64 to extend radially outward from the piston head 16 to grip the body of the respective fluid container 220 or bellows member 120 in the respective end pockets 232, 140. The gripping connection in the respective end pockets 232, 140 may take the form of internal structures or elements to provide fixed engagement in the respective end pockets 232, 140 to permit an interlocked connection to be established between the end pockets 232, 140 and the piston head 16, (see as examples the internal structures or elements 72 in FIGS. 7A and internal structures or elements 1020 in FIGS. 57-58 discussed herein). Once the piston element 14 and the affixed disposable component, either the fluid container 220 or bellows member 120, are connected, movement of the piston element 14 in a forward/distal direction causes the fluid container 220 or the bellows member 120 to dispense fluid received into the fluid container 220 or bellows member 120 via the discharge port 226, or a like discharge port on the bellows member 120. Counter-rotation of the retaining cap 44 and pressure jacket 30 in the opposite direction from that described in the foregoing, cause the retaining pins 64 to retract radially into the piston head 16, thereby disengaging the interlocked connection between the piston head 16 and the fluid container 220 or bellows member 120. Typically, the fluid container 220 or bellows member 120 is prefilled with fluid. The pliable, yet self-supporting, nature of the fluid container body 222 permits the end wall 230 to introvert into the fluid container body 222, and a sidewall 236 of the fluid container body 222 may fold inward against itself in a manner similar to that shown in the Hein patent (U.S. Pat. No. 2,514, 575) described previously and incorporated herein by reference. However, it will be understood that the body 222 of the fluid container 220 is sufficiently rigid to be self-supporting when placed on end, yet pliable enough to permit the end wall 230 to introvert into the interior of the fluid container body 222 so that the sidewall 236 may fold inward against itself radially between the sidewall 236 and the interior wall of the pressure jacket 30.

Referring specifically to FIGS. 7A-7G, the bellows assembly 20, described previously in connection with FIGS. 1-3, is further shown interfacing with a fluid injector 12 and, in particular, a face plate 19 of the fluid injector 12. In this embodiment, the pressure jacket 30 of the bellows assembly 20 may interface with the face plate 19 in the manner described previously. The bellows member 120 of the bellows syringe 100 is formed such that the rotational motion used to connect the bellows syringe 100 to the cylindrical portion 30, as described previously, also connects the bellows member 120 to the piston element 14 of the fluid injector 12. In this embodiment, the closed end wall 128 of the bellows member 120 is formed with an opposing pair of attachment members or catches 144 that extend proximally from the closed end wall 128. The distal end abutment 62 on the piston head 16 of the piston elements 14 is formed with a distal end opening or cavity 66 defined by an annular end wall 68. The annular end wall 68 defines a pair of opposing slots 70 and internal structures or elements 72 for receiving and engaging the retaining pins 64. The pair of opposing slots 70 is situated so that as the bellows syringe 100 is seated onto the distal end 32 of the pressure jacket 30, the attachment members 144 on the bellows member 120 pass through the opposing slots 70. Accordingly, as the bellows syringe 100 is seated onto the distal end 32 of the pressure jacket 30 the attachment members 144 on the bellows member 120 pass through the opposing slots 70, and the rotational movement of the cap member 102 used to secure the bellows syringe 100 onto the pressure jacket 30 simultaneously causes the attachment members 144 to seat into engagement with the annular end wall 68 and secure the bellows member 120 in engagement with the piston element 14. In particular, in this embodiment, the attachment members 144 are adapted to seat into engagement with the internal structures or elements 72 internally of the annular end wall 68 and secure the bellows member 120 in engagement with the piston element 14.

Figures 7D, 7E:
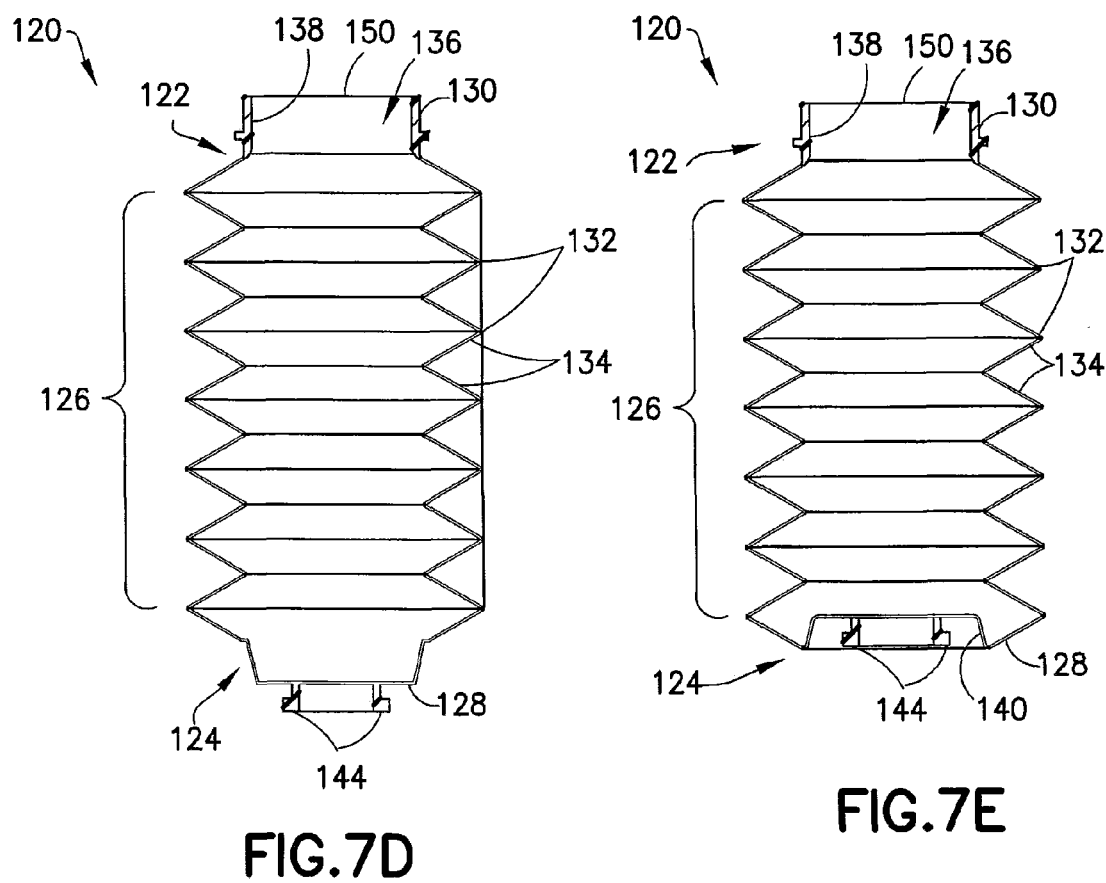
FIGS. 7D and 7E are respective perspective and partial cross-sectional views of the bellows member of the bellows syringe in isolation, and further illustrating a push-in end wall of the bellows member.
Figure 7F:
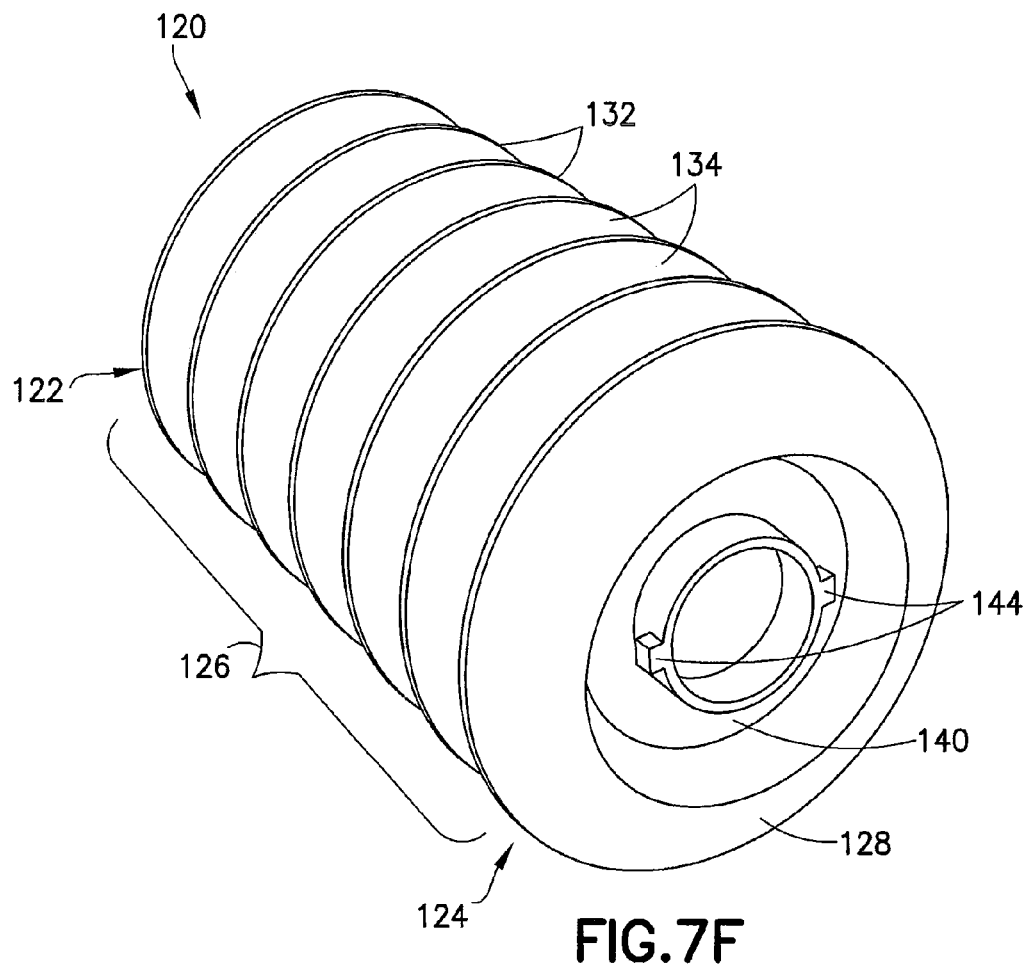
FIG. 7F is a perspective view of the bellows member viewed on end.
Figure 7G:
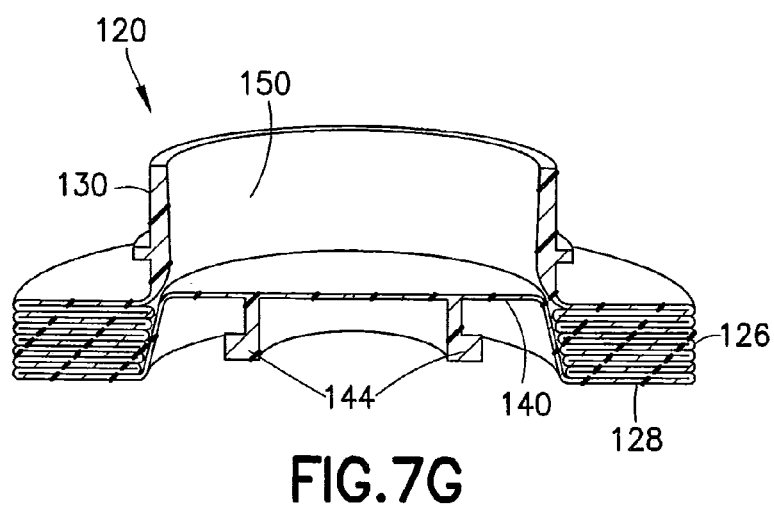
FIG. 7G is a perspective cross-sectional view of the bellows member shown in a compressed state.

FIG. 7D shows the bellows member 120 in a state after manufacturing, typically a blow molding formation operation, and prior to associating the bellows member 120 with the cap member 102. As illustrated, the closed end wall 128 of the bellows member 120 is formed so that the closed end wall 128 extends or projects proximally from the bellows member 120 or is "extroverted". The bellows member 120 may be provided in this configuration for attachment to the piston head 16 of the piston element 14, as described in the foregoing. Once the connection between the attachment members or catches 144 and the annular end wall 68 of the piston head 16 is made by the methodology described above, distal movement of the piston element 14 causes the closed end wall 128 to fold inward or "introvert" into the nearest bellows section or ring 132 and into the configuration shown in FIG. 7E. The open discharge neck 130 may terminate in a sealed or open discharge port 150 for the bellows member 120.

Figure 7H:
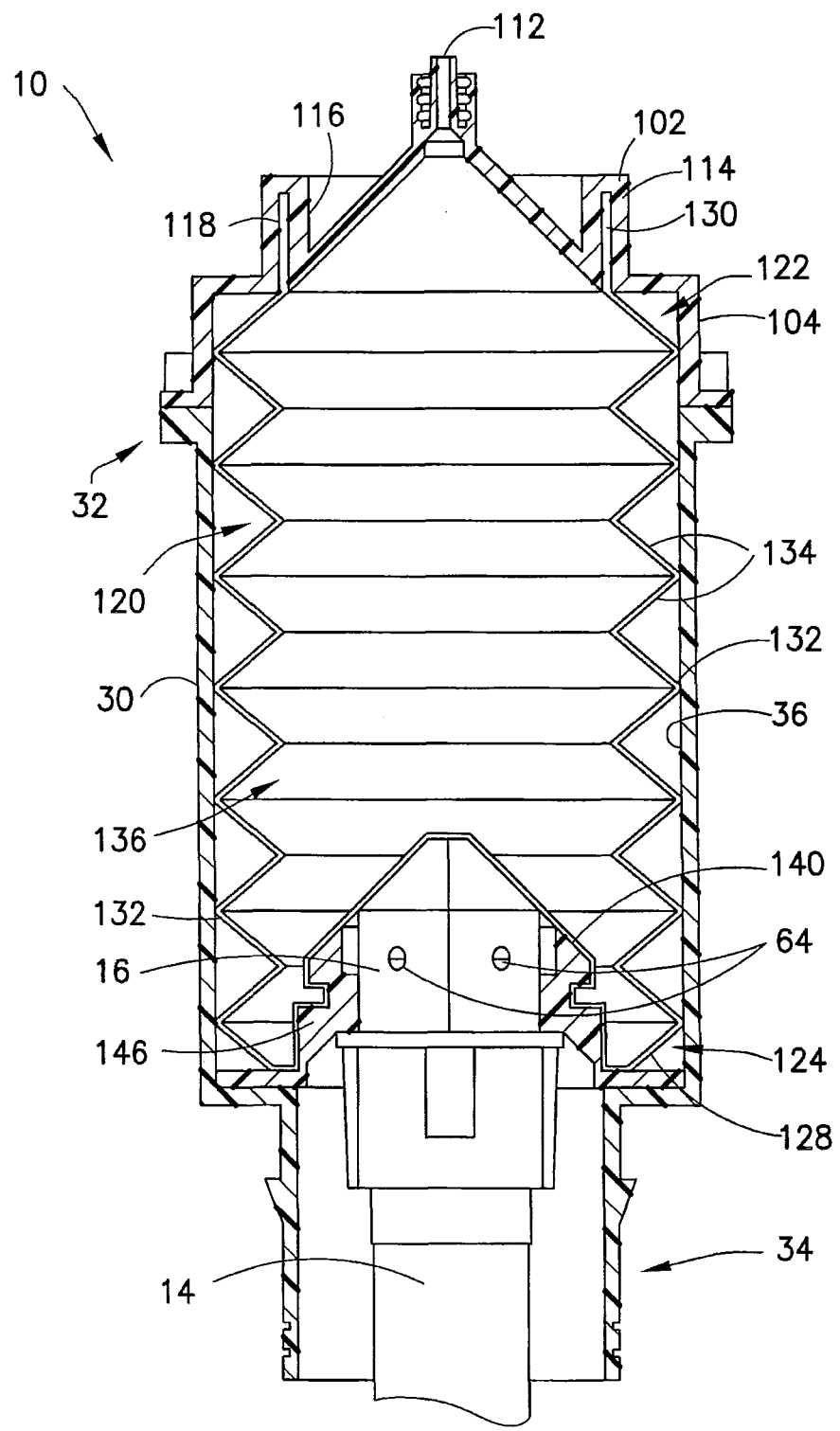
FIG. 7H is a cross-sectional view showing the bellows member with a rigid end part or base provided on a closed end wall of the bellows member and engagement of the piston element therewith.

Referring to FIG. 7H, in a further variation of the embodiment shown in FIGS. 7A-7G, a rigid base element or end part 146 may be molded or otherwise affixed, such as by adhesive, to the closed end wall 128 of the bellows member 120. The end part 146 provides a means for engagement of the piston head 16 to the bellows member 120. For example, the end part 146 may define an end pocket similar to the end pocket 140 described previously, or may take a conventional interface form such as a suitable configuration to mate with piston heads or tips of a Stellant® powered fluid injector platform, which has a push-pin piston head arrangement comprised by the retaining pins 64 discussed previously. An advantage of the rigid end part 146 is improved predictability in the deformation of the bellows sections or rings 132 during expansion and contraction of the bellows member 120 because the piston elements 14 of the fluid injector 12 push and pull against a rigid base part or plate rather than on the body of the bellows member 120, which is typically made of a less rigid plastic material that is capable of deformation.

In FIG. 8, the fluid container 220 according to a modified embodiment is provided with a rigid end part or base 234 that may be molded or otherwise affixed, such as by adhesive, to the closed end wall 230 of the fluid container body 222. In FIG. 8, the fluid container 220 is further shown with a container body 222 having a sidewall 236 having an optional tapered shape. The tapered sidewall 236 tapers at an angle of approximately 18°, or between 15-25°, and the rigid end part 234 and pliable, yet self-supporting, nature of the fluid container body 222 permits the end wall 230 to introvert into the fluid container body 222, and the tapering of the sidewall 236 provides additional radial clearance around the circumference of the rigid end part 234 so that the material forming the sidewall 236 may gather or overlap radially outward of the circumferential edge of the rigid end part 234 as the piston element 14 moves distally or forward into the fluid container body 222. The fluid container 220 may be formed without a tapered sidewall 236. As illustrated in FIG. 8, the fluid container body 222 defines an interior space or volume 238. Further, the discharge port 226 of the fluid container 220 is formed with an open passageway or opening 240 that is sealed by a fluid connector fitting or element 242 such as a conventional luer fitting or element. The tapered sidewall 236 may be tapered in either direction (e.g., as illustrated tapering from wide at the proximal end 228 to narrow at the distal end 224 or vice versa). The rigid end part 234 may be applied to any of the fluid container 220, fluid container 320 (discussed herein in connection with FIGS. 10A-10C), or bellows member 120 in this disclosure. As noted previously, it will be understood that the body 222 of the fluid container 220 is sufficiently rigid to be self-supporting when placed on end, yet pliable enough to permit the end wall 230 to introvert into the interior of the fluid container body 222 so that the sidewall 236 may fold inward against itself radially between the sidewall 236 and the interior wall of the pressure jacket 30. Thus, the fluid container 220 is an axially collapsible fluid container in a manner similar to the bellows member 120, but in a different manner wherein the sidewall 236 introverts into the interior of the fluid container body 222 and folds inward against itself; and the foregoing introverting, axially collapsing feature of the fluid container 220 is equally applicable to all of the straight-sided and tapered-sided fluid containers described in this disclosure, such as fluid container 320 described herein. FIG. 10B, discussed herein illustrates the introverting feature of the fluid container 320. The use of the rigid end part 234 does not materially change the foregoing introverting, axially collapsing operation of the fluid container 220 and like fluid containers described in this disclosure.

Figure 9A:
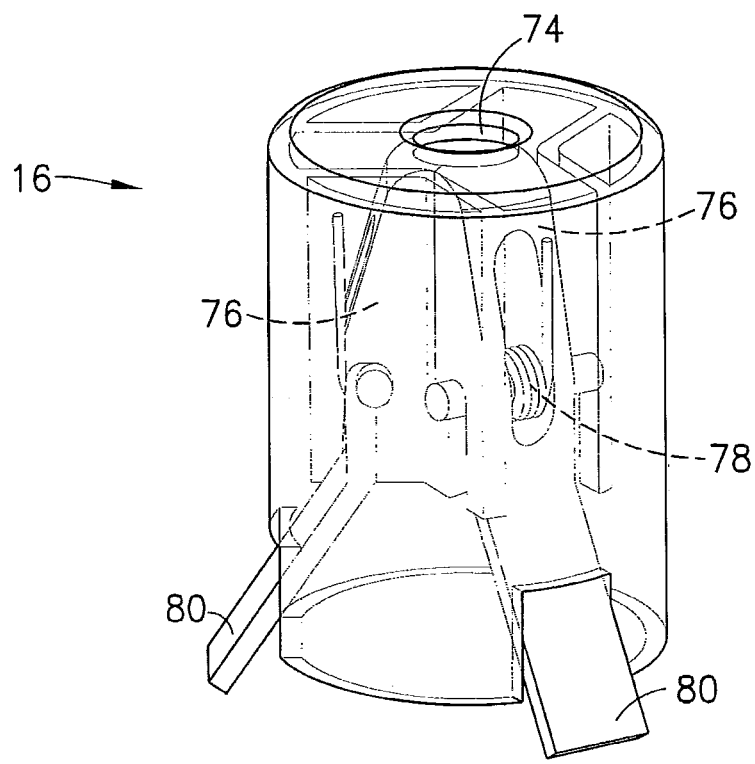
FIG. 9A is a perspective view partially in phantom of a piston element adapted to interface with a structure on the proximal end of the bellows member or a fluid container.
Figure 9B:
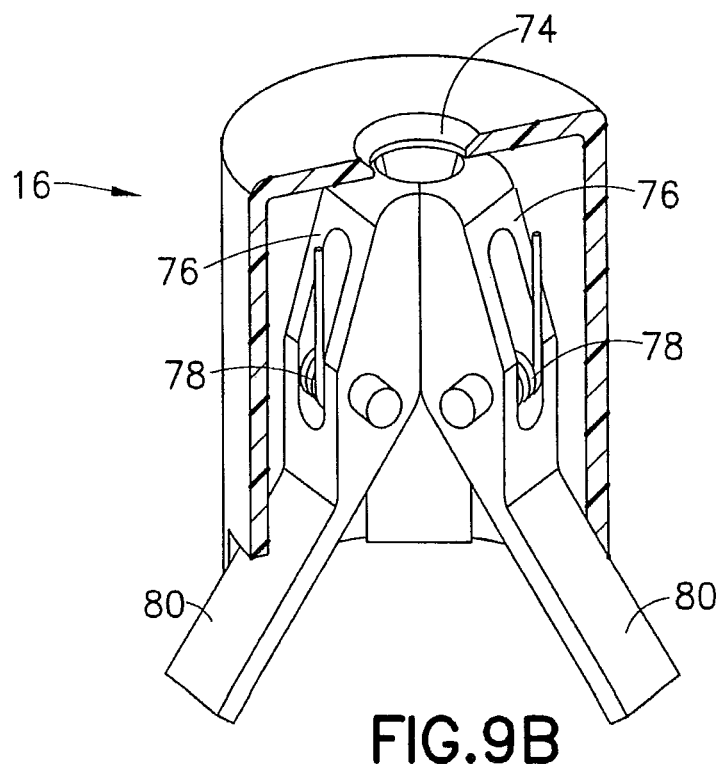
FIG. 9B is a perspective and partial cross-sectional view of the piston element shown in FIG. 9A.
Figure 9C:
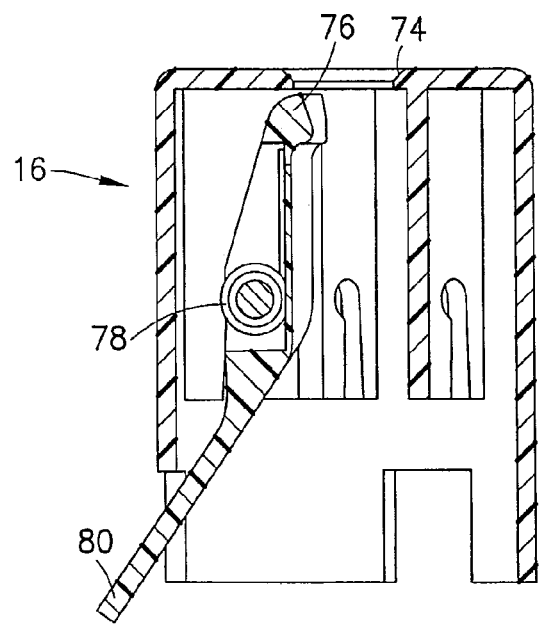
FIG. 9C is a cross-sectional view of the piston element shown in FIG. 9A.

Referring next to FIGS. 9A-9C, another embodiment of the piston head 16 for the piston element(s) 14 of the fluid injector 12 is shown. The piston head 16 shown in FIGS. 9A-9C may be used in any of the various embodiments of the fluid injector 12 discussed in this disclosure. In this embodiment, the bellows member 120 or fluid container 220 comprises a button or like structure (shown in FIGS. 24-26) on the proximal closed end wall 128, 230 that is fits within a hole or opening 74 in the piston head 16. In particular, as the button or like structure is received into the hole or opening 74, the button engages a plurality of pivotal jaws 76, which are held closed by respective torsion springs 78, and urges the respective jaws 76 apart. Once the jaws 76 pass over the button, the torsion springs 78 cause the jaws 76 to snap onto a stem or like structure connecting the button to the closed end wall 128, 230 of the bellows member 120 or fluid container 220, respectively. In this embodiment, the bellows member 120 or fluid container 220 may be loaded into the pressure jacket 30 in the manner described previously to position the button or like element in axial alignment with the hole 74 in the piston head 16. Then, the piston element 14 may be driven forward until the button or like structure is received into the hole 74 in the piston head 16. To disconnect the bellows member 120 or fluid container 220 from the piston head 16, at a prescribed point during a retracting movement of the piston element 14, respective lever tabs 80 on the pivotal jaws 76 contact a surface or abutment that forces the pivot jaws 76 open, thereby permitting removal of the bellows member 120 or fluid container 220 from the pressure jacket 30.

Figure 10A:
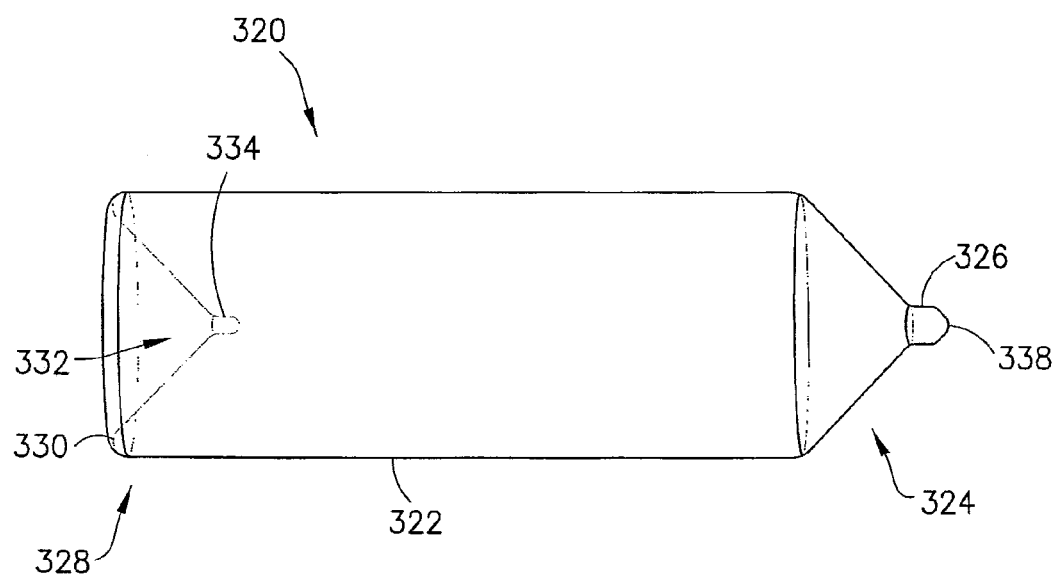
FIG. 10A is a perspective view of a prefilled fluid container according to another embodiment and comprising a rupture-ready tip.
Figure 10B:
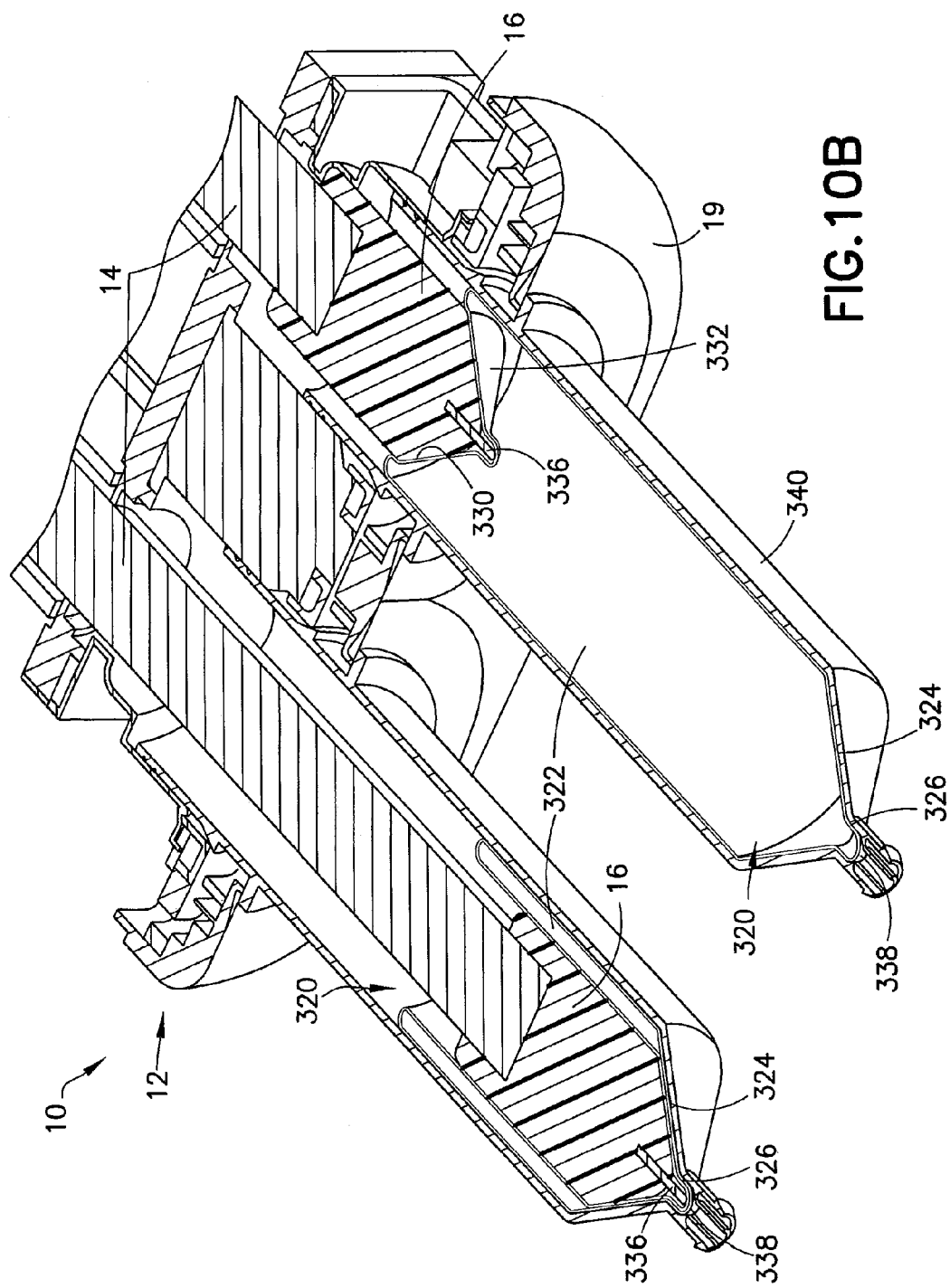
FIG. 10B is a perspective and cross-sectional view showing the fluid container shown in FIG. 10A loaded in a syringe connected to a dual-syringe powered fluid injector.
Figure 10C:
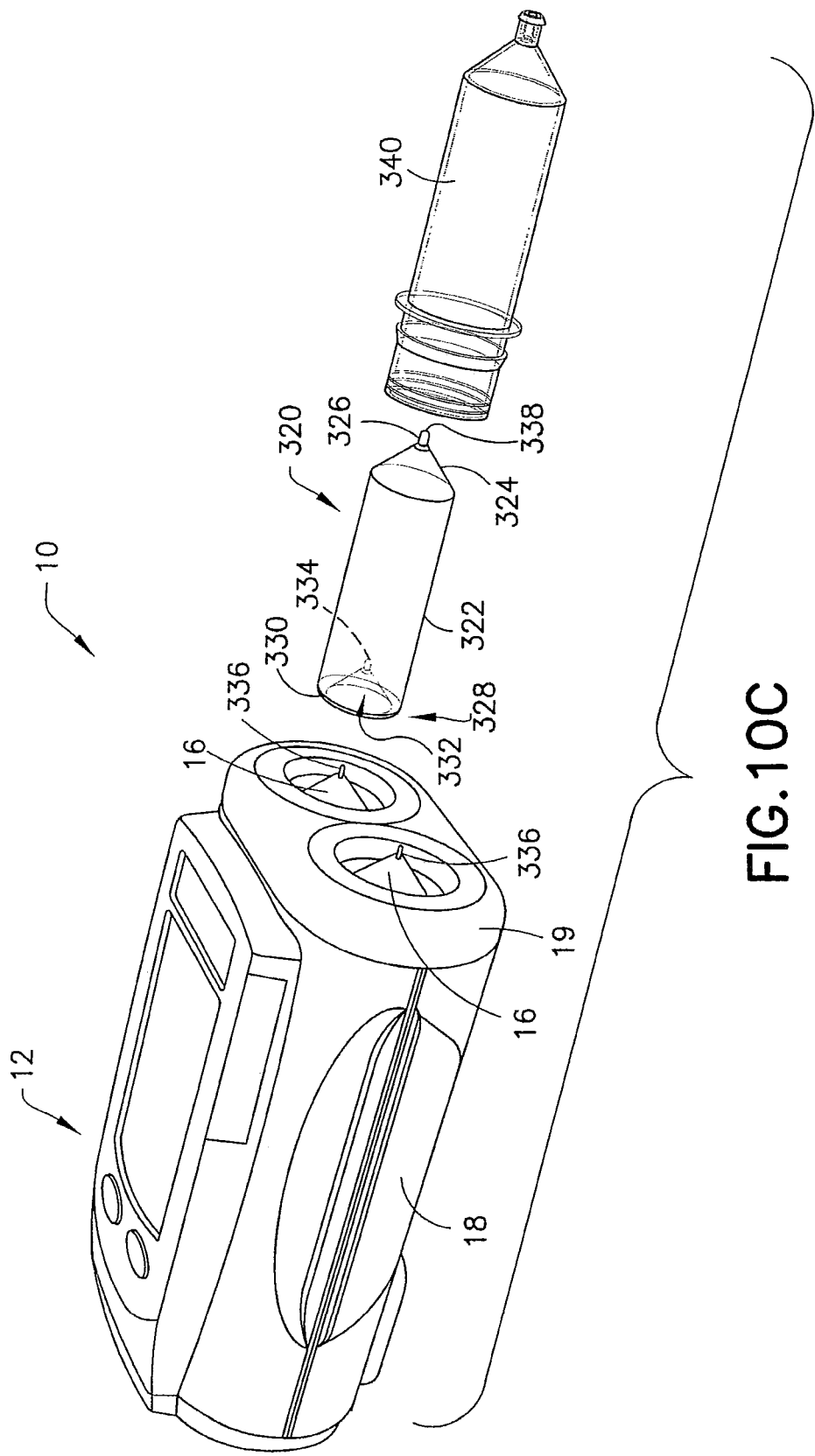
FIG. 10C is an exploded perspective view of the fluid container, syringe, and dual-syringe powered fluid injector shown in FIG. 10A.

Referring further to FIGS. 10A-10C, a multi-syringe type fluid injector 12 is illustrated. In this embodiment, the fluid injector 12 is adapted to accept a disposable fluid container 320 according to another embodiment as illustrated in FIG. 10A. The fluid container 320 in this embodiment has a soft, pliable, yet self-supporting body 322 having a conical distal end 324 terminating in a discharge port 326, and a proximal end 328 with a closed end wall 330. The closed end wall 330 defines a receiving end pocket 332 therein to receive the piston head 16 of the piston element 14 of the fluid injector 12. The closed end wall 330 may alternatively include a rigid end part or base or plate (not shown) that defines the receiving end pocket 332 for the piston head 16, in a similar manner to other embodiments discussed previously. Even though a two (2) syringe fluid injector 12 is illustrated, the present fluid container 320 may be used in a single syringe-type fluid injector 12. The end pocket 332 further defines a tip receptor 334 for a corresponding tip element 336 on the piston head 16 of the piston element 14. Further, the discharge port 326 is fully sealed by a rupture ready tip 338.

The present fluid container 320 is adapted for use as a disposable liner or prefilled container in a reusable or disposable syringe 340, which is adapted to directly engage the fluid injector 12 and, in particular, the face plate 19 of the fluid injector housing 18. The syringe 340 is generally operable as a pressure jacket in this embodiment, and a suitable construction for the syringe 340 and the fluid injector 12 in this embodiment may be found in U.S. Pat. No. 7,419,478 to Reilly, et al. assigned to Medrad, Inc. and incorporated herein by reference. The Reilly, et al. patent includes syringe details for the syringe 340, and details for interfacing the syringe 340 to the fluid injector 12. The fluid container 320 may be made by a blowing-filling-capping (BFC) technique, also referred to in the relevant field of endeavor as blow-mold-seal (BFS), wherein the fluid container body 322 is blow-molded, filled with the desired medical fluid such as contrast media, and aseptically sealed by sealing the discharge port 326 with an integrally formed/molded rupture-ready tip 338. The BFC technique permits the fluid container 320 to be formed, filled, and sealed typically in one machine or apparatus and these steps may be accomplished under sterility maintained conditions, limiting the possibility of introducing contaminates in the formed, filled, and sealed fluid container 320. The rupture-ready tip 338 is formed as part of the molding process at the conclusion of filling of the fluid container body 322. A sterility-enhanced preformed and prefilled fluid container 320 results from the BFC process. The rupture-ready tip 338 may be designed for external puncture by a fluid conducting tubing set attached to the tip 338 by a user, or may be designed to reliably burst when a preset internal pressure is reached in the fluid container 320 as the piston element 14 moves distally or forward in the fluid container body 322.

Several embodiments herein describe a process using a pre-form, which is then molded to final shape. While BFS/BFC techniques do not use pre-forms, injection-blowmolding (IBM) and injection stretch-blow-molding (ISBM) do use pre-forms, and such techniques may be used with the pre-forms set forth in this disclosure.

Figure 11A:
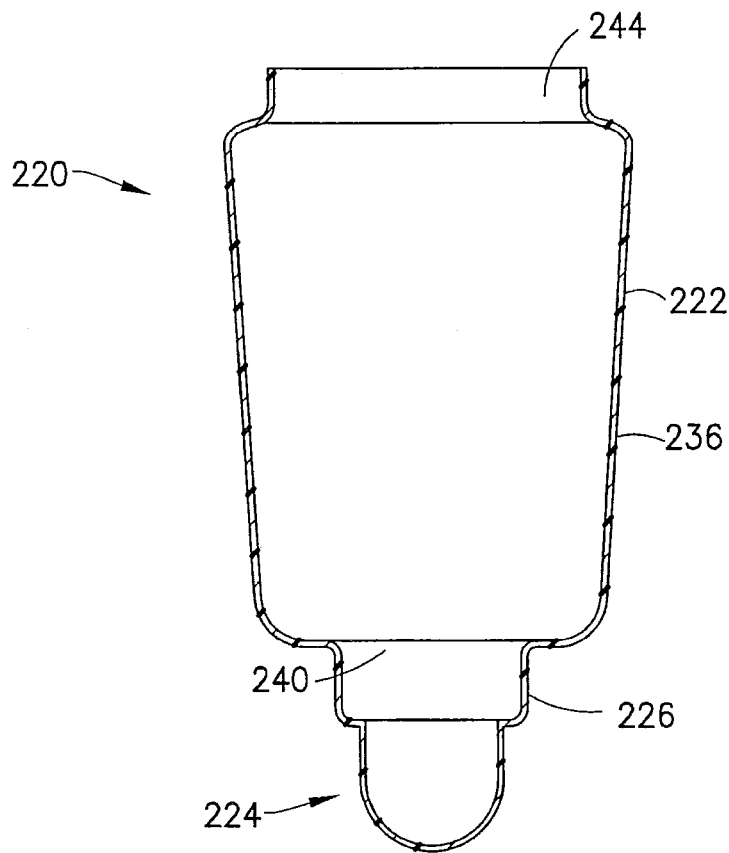
FIG. 11A is a cross-sectional view of a fluid container according to another embodiment formed and filled by a blow-fill-cap (BFC) process.
Figure 11B:
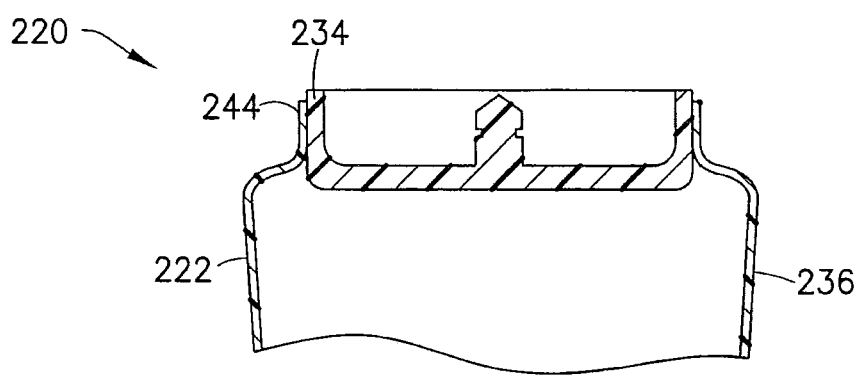
FIG. 11B is a partial cross-sectional view of the fluid container of FIG. 11A, wherein a rigid end part or base is used to seal a wide proximal end of the fluid container.
Figure 11C:
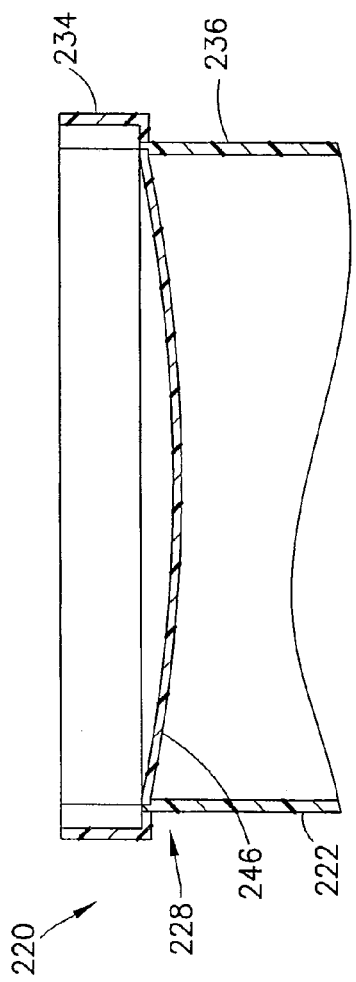
FIG. 11C is a partial cross-sectional view of a modification of the fluid container of FIG. 11A, wherein a flexible membrane is used to seal the wide proximal end of the fluid container and further comprises an optional rigid end part or base.

Referring to FIGS. 11A-11C, a BFC process may be used to form any of the fluid containers described in this disclosure, including fluid containers 220, 320 and, further, bellows member 120. In FIGS. 11A-11C, an exemplary BFC process may be used to form the fluid container 220 shown in FIG. 8, discussed previously, and this fluid container 220 is referenced hereinafter only for exemplary purposes for discussing the features and processes exemplified by FIGS. 11A-11C. The illustration of fluid container 220 as specifically depicted in FIGS. 11A-11C should not be considered limiting. In the BFC process, the fluid container body 222 is blow-molded via an open proximal end 244, which is the wider end of the fluid container body 222. The fluid exit end or distal end 224 is formed as the closed end of the fluid container body 222 and is the narrow end of the fluid container body 222. The discharge port 226 in this embodiment is formed as the sealed end of the fluid container body 222. After the fluid container body 222 is formed, the formed fluid container body 222 is filled with the desired medical fluid. Once the fluid container body 222 is filled with fluid, the rigid end part 234 is used to seal the open proximal end 244, and the end part 234 may be molded to or otherwise secured to the fluid container body 222, for example, by adhesive. Once the end part 234 is installed, the fluid container 220 is ready for use as a prefilled container. In FIG. 11C, as an alternative, the formed fluid container body 222 may be sealed with a flexible membrane 246. As illustrated, in this variation of the fluid container 220, the sidewall 236 need not be tapered, as discussed previously, and the lack of tapering does not retard the ability of the fluid container body 222 to flex or roll and introvert into itself from the proximal end 228 toward the distal end 224. Further, the end part 234 may optionally be molded to or otherwise secured to the fluid container body 222 as in previous embodiments.

Figure 12:
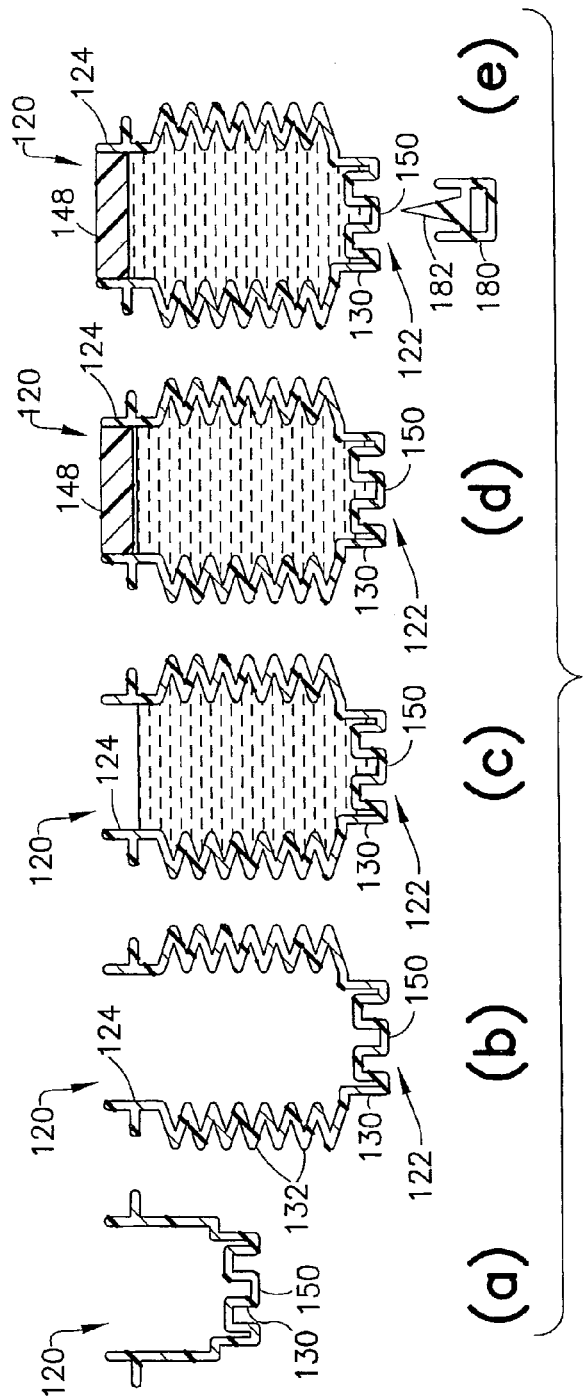
FIG. 12 is a sequence of schematic cross-sectional views showing manufacturing, filling, and sealing of the bellows member of the bellows syringe in which the proximal end of the bellows is sealed with a sealing element or plug.

Referring to FIG. 12, the bellows member 120 may also be formed using a BFC process. In FIG. 12, a sequence of molding, filling, and sealing the bellows member 120 according to an exemplary BFC process is schematically illustrated. The sequence starts at step a where the body of the bellows member 120 is provided as a molded pre-form, and followed at step b where the bellows portion 126 comprising bellows sections or rings 132 is formed, such as by blow-molding. At step c, the formed bellows member 120 is filled with fluid from an open proximal end 124 in this embodiment. At step d, the open proximal end 124 is sealed with a sealing element or plug 148, to complete the prefilled bellows member 120. In this embodiment, the discharge neck 130 is sealed closed to form a closed or sealed discharge port 150 during the blow-molding process, as filling is accomplished via the open proximal end 124. A connector element 180 having a piercing feature or element 182 may be used to access the sealed discharge port 150 at step e.

Figure 13:
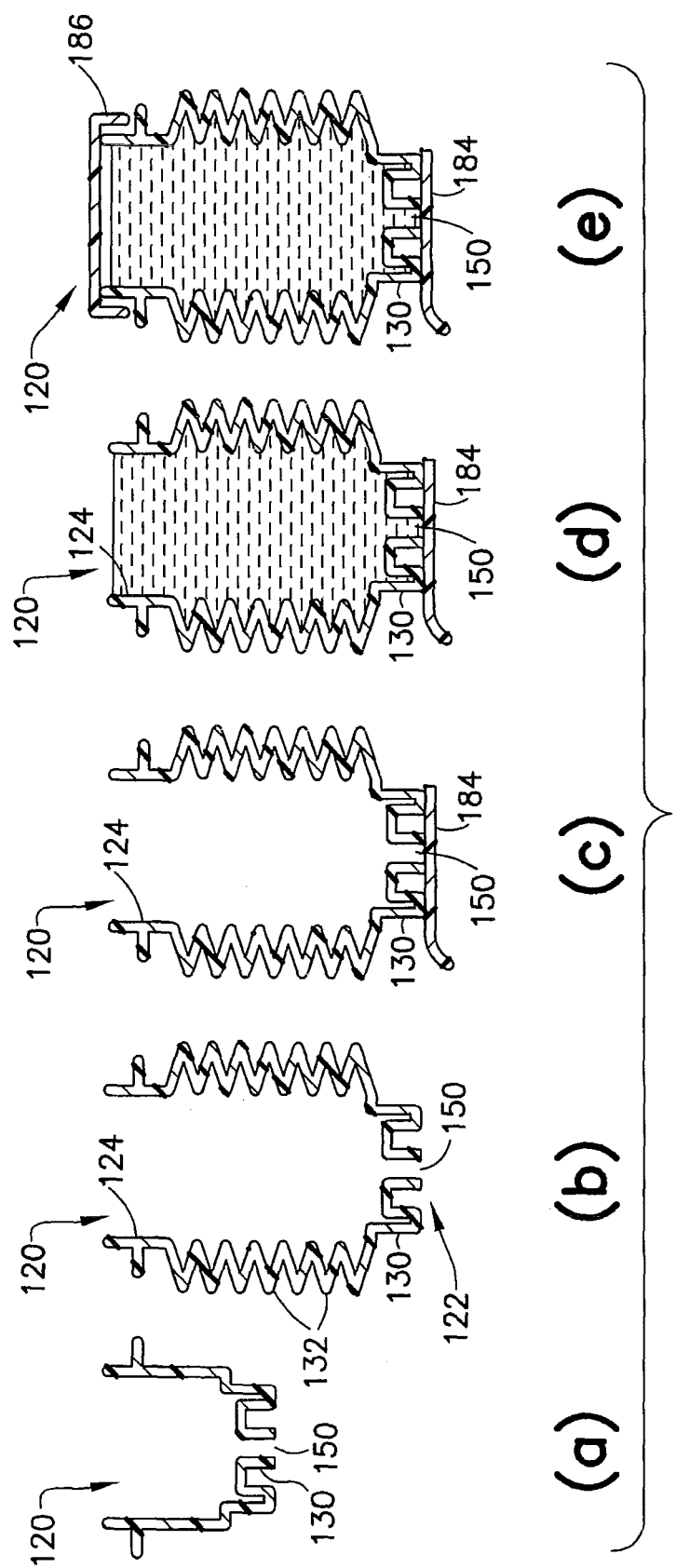
FIG. 13 is a sequence of schematic cross-sectional views showing manufacturing, filling, and sealing of the bellows member of the bellows syringe and sealing of opposing open ends of the bellows member with aseptic seals.

Referring to FIG. 13, an alternative sequence of molding, filling, and sealing the bellows member 120 according to an exemplary BFC process is schematically illustrated. The sequence starts at step a where the body of the bellows member 120 is provided as a molded pre-form, but now with an open discharge port 150 at the distal end 122, and followed at step b where the bellows portion 126 comprising bellows sections or rings 132 is formed, such as by blow-molding. At step c, an aseptic seal 184, such as a foil membrane, is applied to the discharge port 150 which is formed as part of the discharge neck 130 of the bellows member 120. At step d, the formed bellows member 120 is filled with fluid from the open proximal end 124. At step e, a second aseptic seal 186 is applied to the open proximal end 124 to seal the open proximal end 124 and complete the prefilled bellows member 120.

Figure 14:
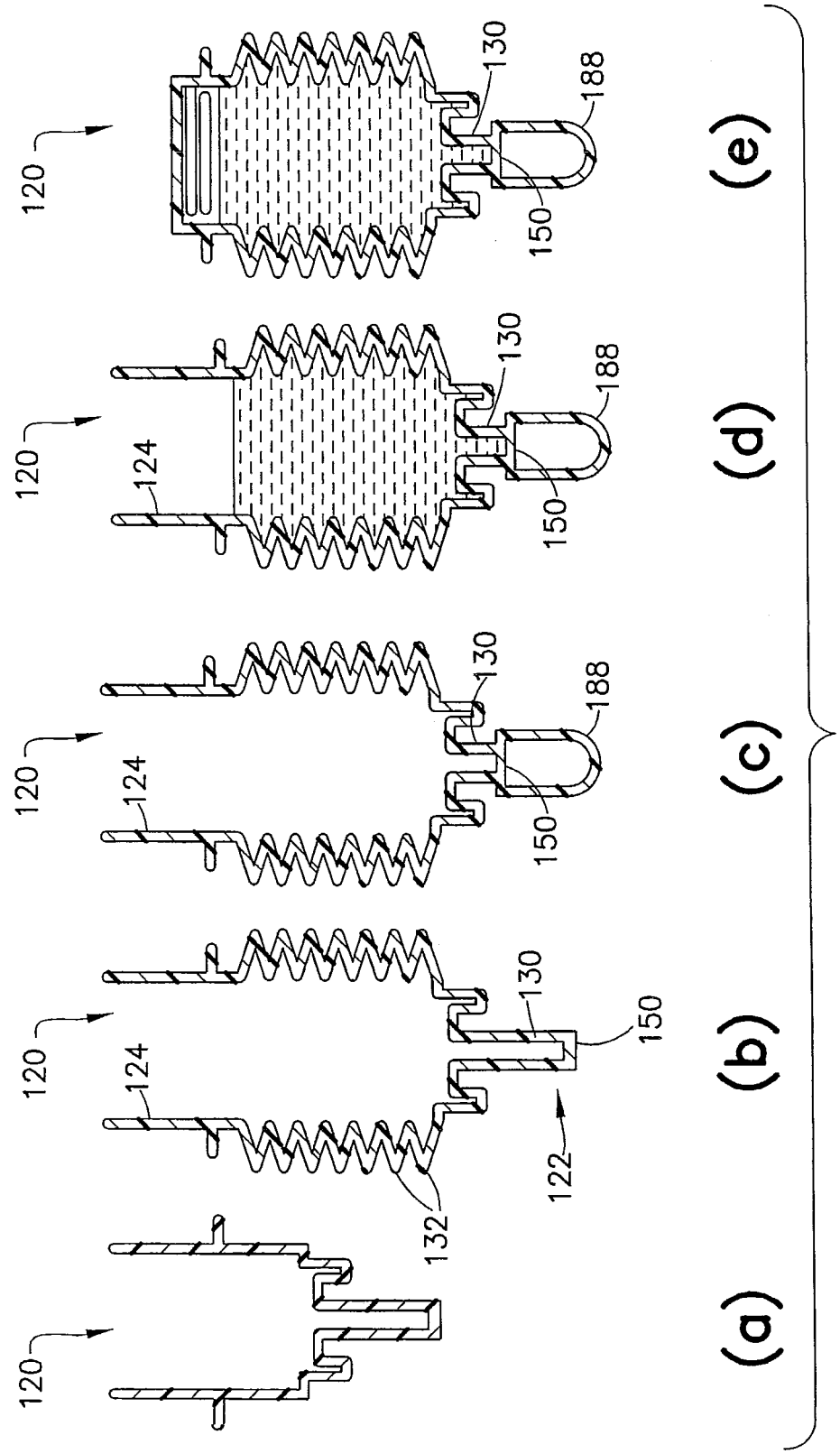
FIG. 14 is a sequence of schematic cross-sectional views showing manufacturing, filling, and sealing of the bellows member of the bellows syringe, and mechanical sealing of opposing open ends of the bellows member.

Referring to FIG. 14, another sequence of molding, filling, and sealing the bellows member 120 according to an exemplary BFC process is schematically illustrated. The sequence starts at step a where the body of the bellows member 120 is provided as a molded pre-form, again with a closed discharge port 150 at the distal end 122, but now the discharge port 150 is provided at the end of a discharge neck 130 having an elongated form. At step b, the bellows portion 126 comprising bellows sections or rings 132 is formed, such as by blow-molding. At step c, a break-away tab 188 is crimped or otherwise mechanically formed into the elongated discharge neck 130. At step d, the formed bellows member 120 is filled with fluid from the open proximal end 124. At step e, the open proximal end 124 is sealed closed, for example by a crimping or like mechanical closure process, to complete the prefilled bellows member 120.

Figure 15:
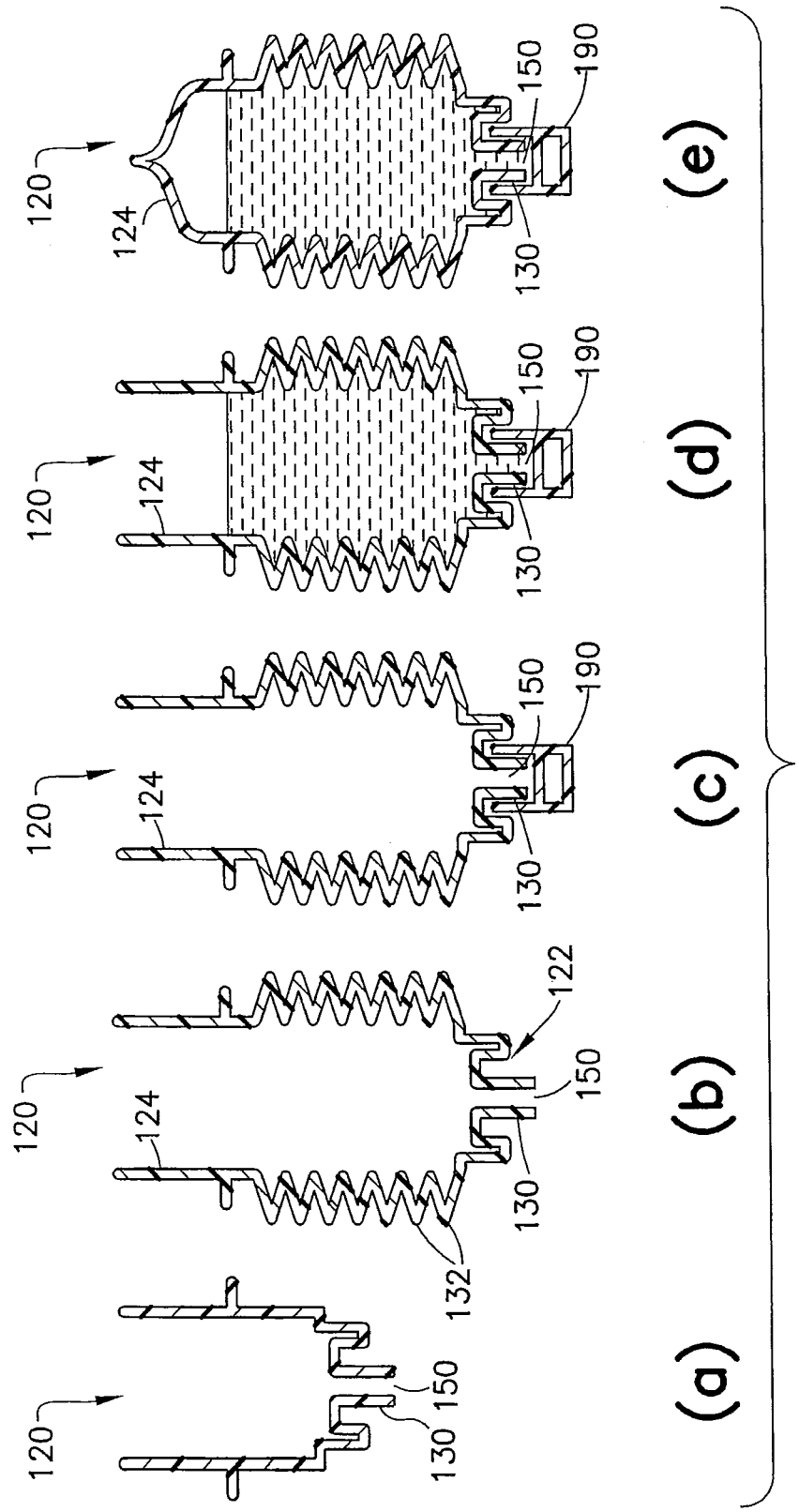
FIG. 15 is a sequence of schematic cross-sectional views showing manufacturing, filling, and sealing of the bellows member of the bellows syringe, and mechanical sealing of one open end of the bellows member while a second open end is sealed with a closure or cap.

Referring to FIG. 15, another sequence of molding, filling, and sealing the bellows member 120 according to an exemplary BFC process is schematically illustrated. The sequence starts at step a where the body of the bellows member 120 is provided as a molded pre-form, but now with an open discharge port 150 at the distal end 122, and followed at step b where the bellows portion 126 comprising bellows sections or rings 132 is formed, such as by blow-molding. At step c, a mechanical closure or cap 190 is applied to the discharge neck 130 to seal the discharge port 150. At step d, the formed bellows member 120 is filled with fluid from the open proximal end 124. At step e, the open proximal end 124 is sealed, for example by a crimping process or like mechanical closure process, to complete the prefilled bellows member 120.

Figure 16:
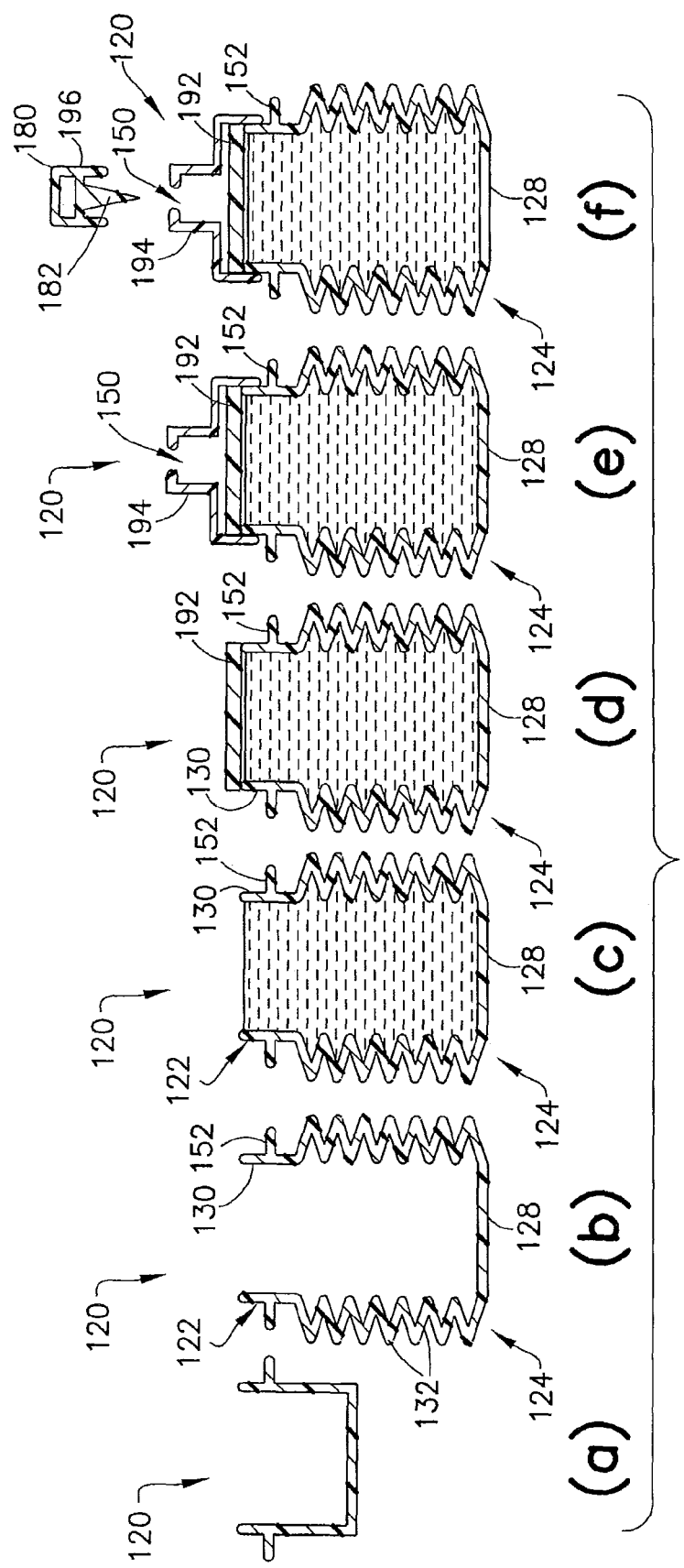
FIG. 16 is a sequence of schematic cross-sectional views showing manufacturing, filling, and sealing of the bellows member of the bellows syringe, and sealing of an open end by an aseptic seal and a mechanically applied interface closure or cap.

Referring to FIG. 16, another sequence of molding, filling, and sealing the bellows member 120 according to an exemplary BFC process is schematically illustrated. The sequence starts at step a where the body of the bellows member 120 is provided as a molded pre-form, but with an open distal end 122, and followed at step b where the bellows portion 126 comprising bellows sections or rings 132 is formed, such as by blow-molding. The molded pre-form or formed bellows member 120 may be provided with an exterior circumferential flange 152. At step c, the formed bellows member 120 is filled with fluid from the open distal end 122 in this embodiment, and the discharge neck 130 is sealed at step d with an aseptic membrane 192, such as a foil membrane, or molded membrane or crimped shaped membrane. At step e, a mechanical interface closure or cap 194 is applied to the sealed discharge neck 130 to abut the exterior circumferential flange 152 to complete the prefilled bellows member 120. At step f, the connector element 180 having a piercing feature 182, discussed previously, may be used to access the sealed discharge neck 130 by attachment to the interface cap or closure 194 and puncturing the aseptic membrane 192. The piercing feature 182 of the connector element 180 may be disposed within a shielded housing 196.

Figure 17:
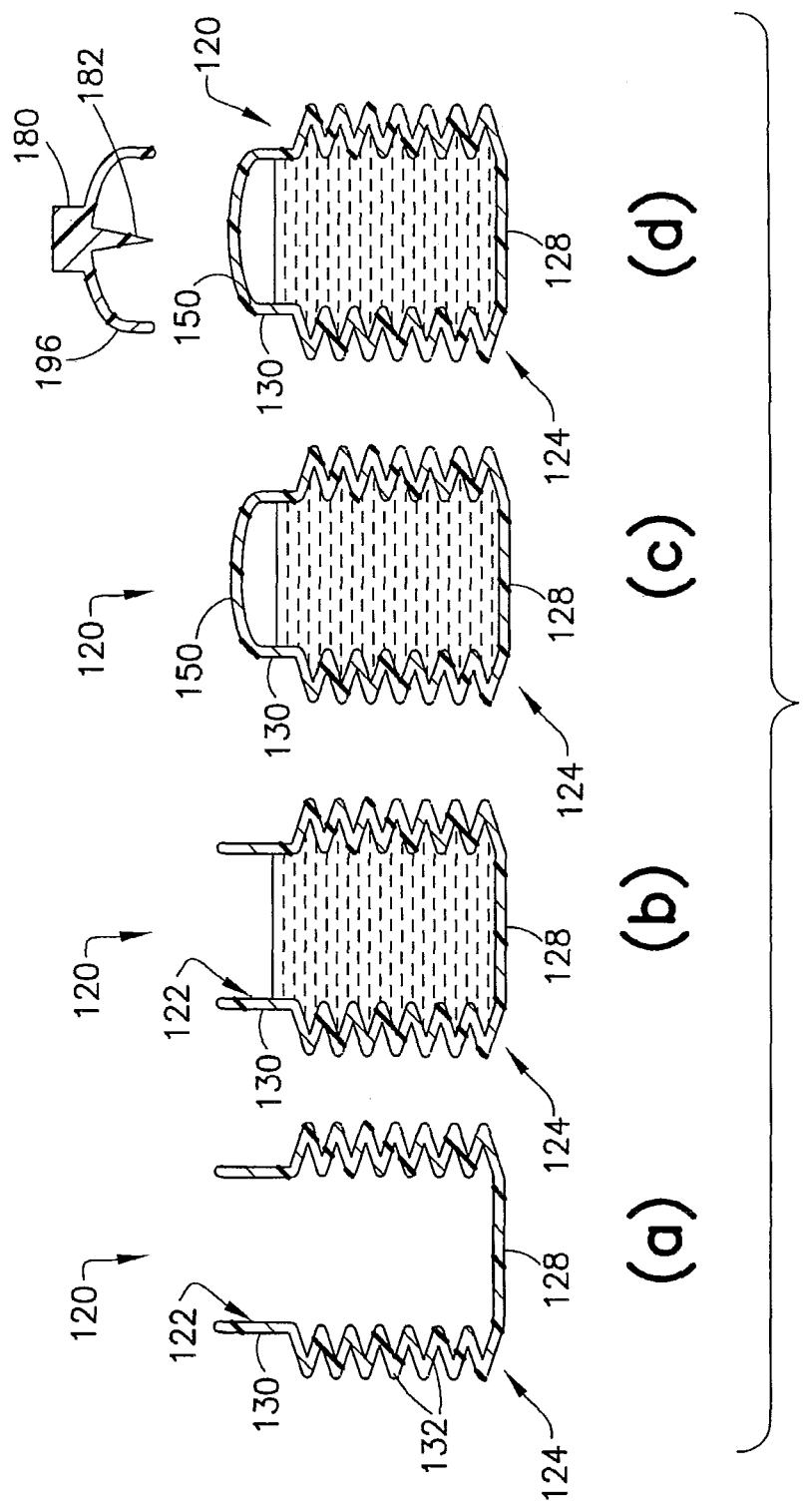
FIG. 17 is a sequence of schematic cross-sectional views showing manufacturing, filling, and sealing of the bellows member of the bellows syringe, and mechanical sealing of an open end of the bellows member.

Referring to FIG. 17, another sequence of molding, filling, and sealing the bellows member 120 according to an exemplary BFC process is schematically illustrated. The sequence starts at step a where the body of the bellows member 120 is extrusion blow-molded while retaining an open distal end 122, followed at step b where the formed bellows member 120 is filled with fluid from the open distal end 122 in this embodiment. At step c, the discharge neck 130 is sealed using a crimping process or like mechanical process to form a closed discharge port 150 that may be punctured. For example, the connector element 180 having a piercing feature 182, discussed previously, may be used to access the sealed discharge port 150, such as at step d. The connector element 180 may be part of a press-on fluid tubing set and can be used to manually pierce the sealed discharge port 150, or the connector element 180 may be held as part of or connected to the pressure jacket 30 and the piercing of the discharge port 150 may be accomplished during the action of loading the bellows member 120 into the pressure jacket pressure jacket 30.

Figure 18:
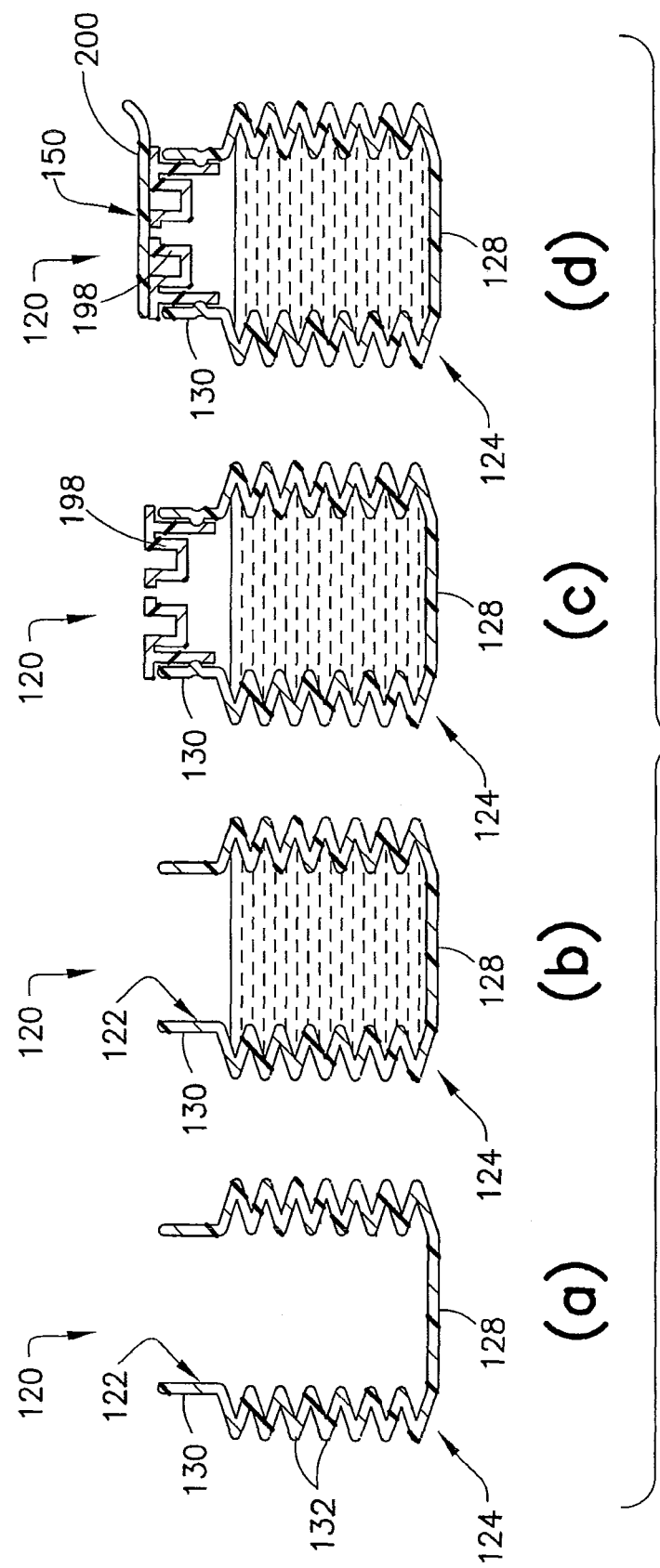
FIG. 18 is a sequence of schematic cross-sectional views showing manufacturing, filling, and sealing of the bellows member of the bellows syringe, and sealing of an open end of the bellows member by a fluid connector fitting and an aseptic seal.

Referring to FIG. 18, another alternative sequence of molding, filling, and sealing the bellows member 120 according to an exemplary BFC process is schematically illustrated. The sequence starts at step a where the body of the bellows member 120 is extrusion blow-molded while retaining an open distal end 122, followed at step b where the formed bellows member 120 is filled with fluid from the open distal end 122 in this embodiment, and the discharge neck 130 is sealed at step c by a separately-molded, drop-in fluid connector fitting 198 that is placed in the discharge neck 130. The fluid connector fitting 198 is sealed with an aseptic seal 200 such as a foil membrane, such as at step d. The connector element 180, discussed previously, having a piercing feature 182 may be used to access the sealed discharge port 150 in this embodiment. As an example, the connector element 180 may be part of a press-on fluid tubing set and can be used to manually pierce the sealed discharge port 150, or the connector element 180 may be held as of part or connected to the pressure jacket 30 and the piercing of the discharge port 150 may be accomplished during the action of loading the bellows member 120 into the pressure jacket 30.

Figure 19:
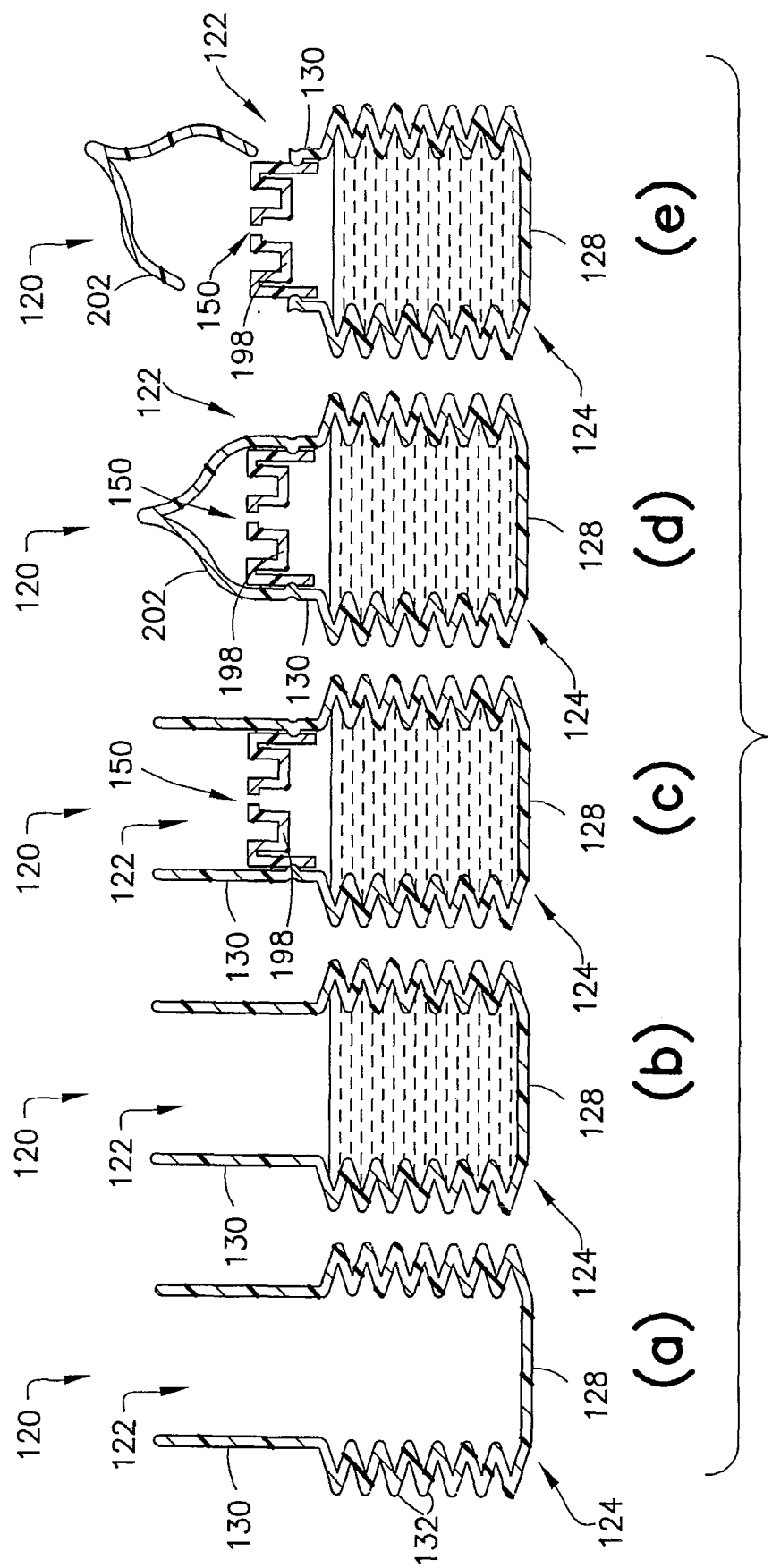
FIG. 19 is a sequence of schematic cross-sectional views showing manufacturing, filling, and sealing of the bellows member of the bellows syringe, and sealing of an open end of the bellows member by a fluid connector fitting and followed by additional mechanical sealing of the open end.

Referring to FIG. 19, another sequence of molding, filling, and sealing the bellows member 120 according to an exemplary BFC process is schematically illustrated. The sequence starts at step a where the body of the bellows member 120 is extrusion blow-molded while retaining an open distal end 122 and an elongated discharge neck 130 in this embodiment. At step b, the formed bellows member 120 is filled with fluid from the open distal end 122. At step c, the discharge neck 130 is closed by a separately-molded, drop-in fluid connector fitting 198 that is placed in the discharge neck 130. The fluid connector fitting 198 is sealed by a mechanical crimping process or otherwise sealed in the discharge neck 130 at step d to form a break-away cover 202 at the distal end 122. The portion of the discharge neck 130 that is used to form the break-away cover 202 may be made frangible by use, for example, of a score line, and the break-away cover 202 may be removed at step e to permit access to the fluid connector fitting 198.

Figure 20:
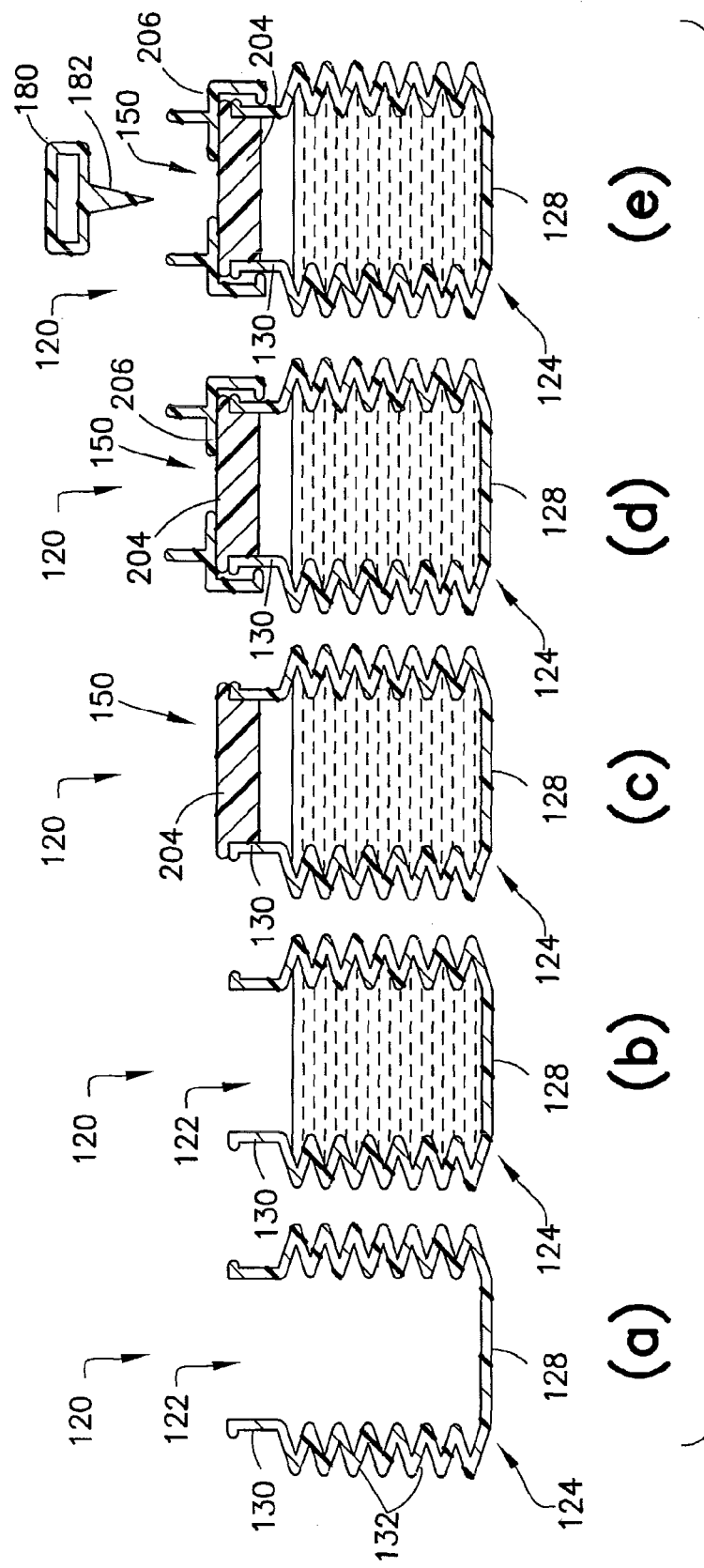
FIG. 20 is a sequence of schematic cross-sectional views showing manufacturing, filling, and sealing of the bellows member of the bellows syringe, and sealing of an open end of the bellows member by a pierceable septum.

Referring to FIG. 20, another sequence of molding, filling, and sealing the bellows member 120 according to an exemplary BFC process is schematically illustrated. The sequence starts at step a where the body of the bellows member 120 is extrusion blow-molded while retaining an open distal end 122. At step b, the formed bellows member 120 is filled with fluid from the open distal end 122. At step c, the discharge neck 130 is sealed by a pierceable septum 204 that is placed in the discharge neck 130. At step d, a cap 206 may be applied to the distal end 122 to enclose the discharge neck 130 and partially enclose the top of the septum 204. The connector element 180, discussed previously, having a piercing feature 182 may be used to access the septum 204 as shown at step e.

Figure 21B:
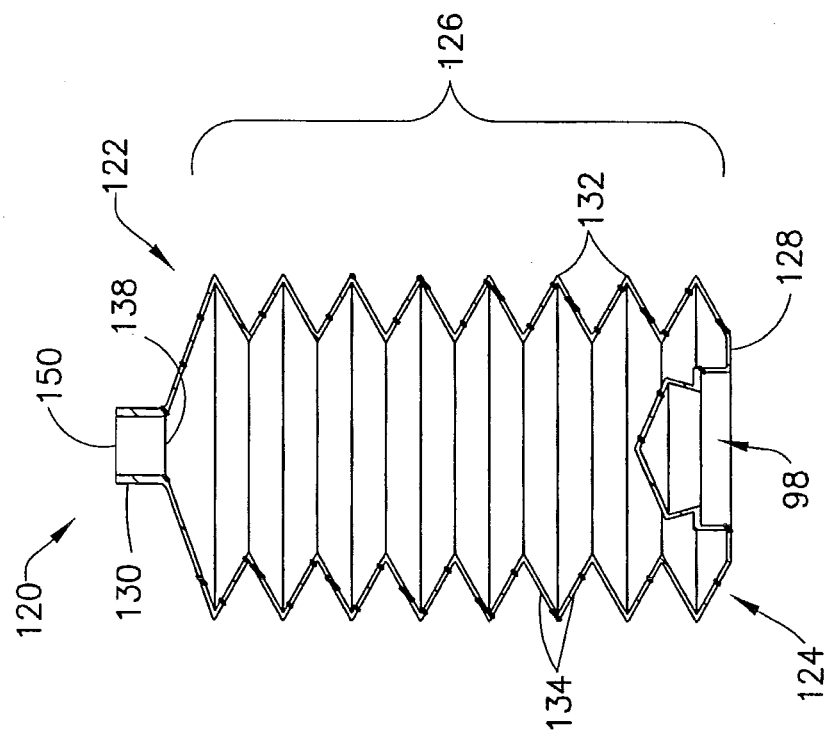
FIGS. 21A-21B are respective schematic cross-sectional views of a fluid container and a bellows member wherein integral piston engagement features are formed as part of the closed end of the fluid container or bellows member as part of a molding process.
Figure 21A:
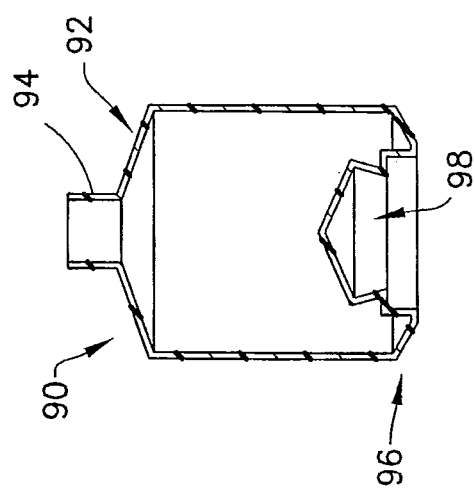

Referring to FIGS. 21A-21B, the bellows member 120 and fluid containers 220, 320 of this disclosure may be made by a combination of injection molding and, further, blow-molding. In FIG. 21A, a schematic fluid container pre-form 90 is shown formed by an injection molding process. This process results in a fluid container pre-form having a distal end 92 with an open discharge port 94 and a proximal end 96 formed with integral piston engagement features 98 that are formed as part the closed proximal end 96. In FIG. 21B, the pre-form 90 is blow-molded to form the bellows member 120 having the features described previously, but the bellows member 120 retains the integral piston engagement features 98 as part of the closed end wall 128 thereof.

Figure 22B:
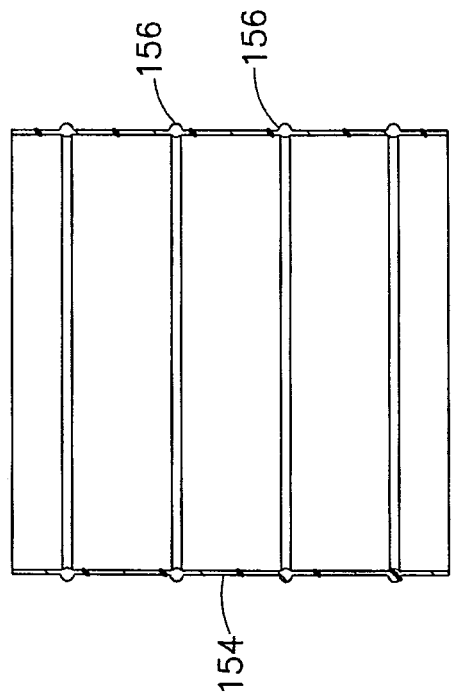
FIGS. 22A-22B are respectively a perspective view and a side view of a bellows portion of the bellows member wherein strengthening stiffening ribs are provided on the bellows portion prior to further molding.
Figure 22A:
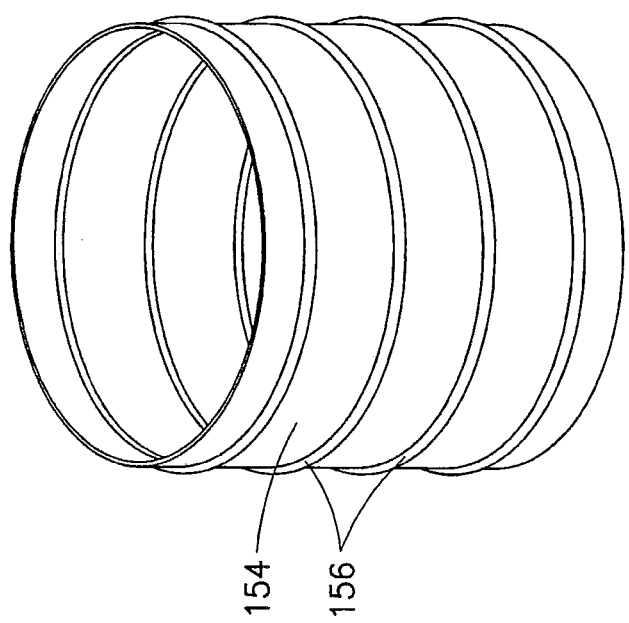

Referring to FIGS. 22A-22B and FIGS. 22C-22D, the bellows member 120 may be formed initially as a pre-form that may be subsequently blow-molded. In the present figures, the bellows portion 126 only is shown as a tube-shaped pre-form 154 and stiffening ribs 156 may be added. The stiffening ribs 156 may be made of the same material as the pre-form or a different material, but is typically non-elastomeric material. The pre-form 154 may then be blow-molded to form the bellows portion 126 of the bellows member 120, as shown in FIGS. 22C-22D, with the bellows sections or rings 132 being formed between the respective stiffening ribs 156. These figures illustrate another method for forming the bellows portion 126 of the bellows member 120.

Figure 23A:
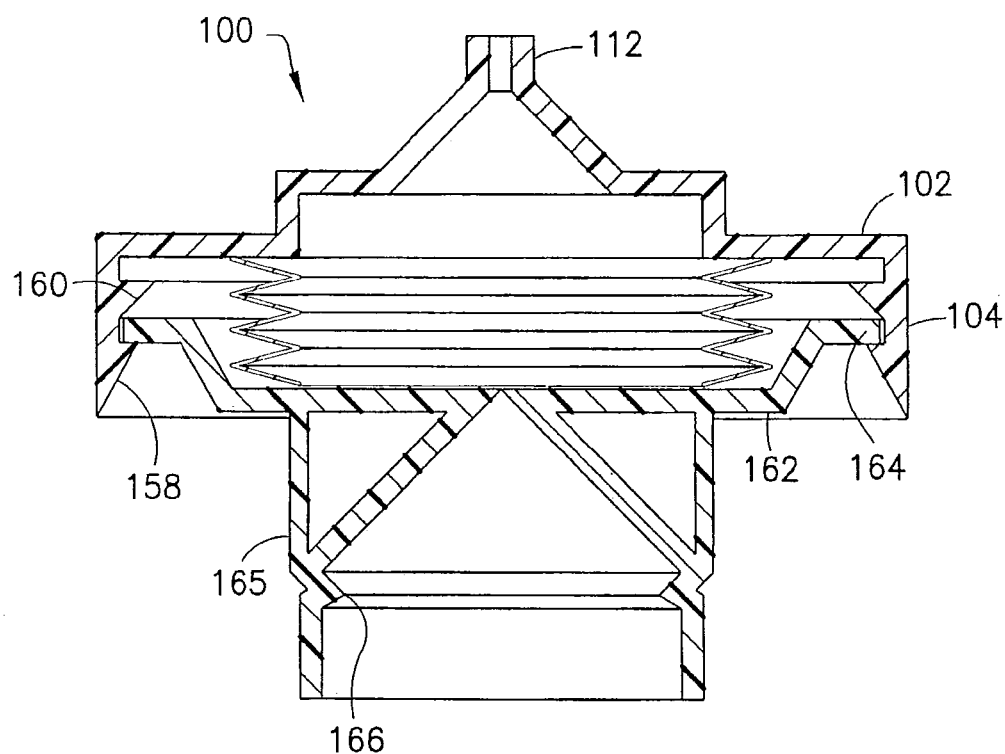
FIGS. 23A-23B are respectively a schematic cross-sectional view and a schematic cross-sectional and perspective view showing the bellows syringe in a compressed state prior to use according to another embodiment.
Figure 23B:
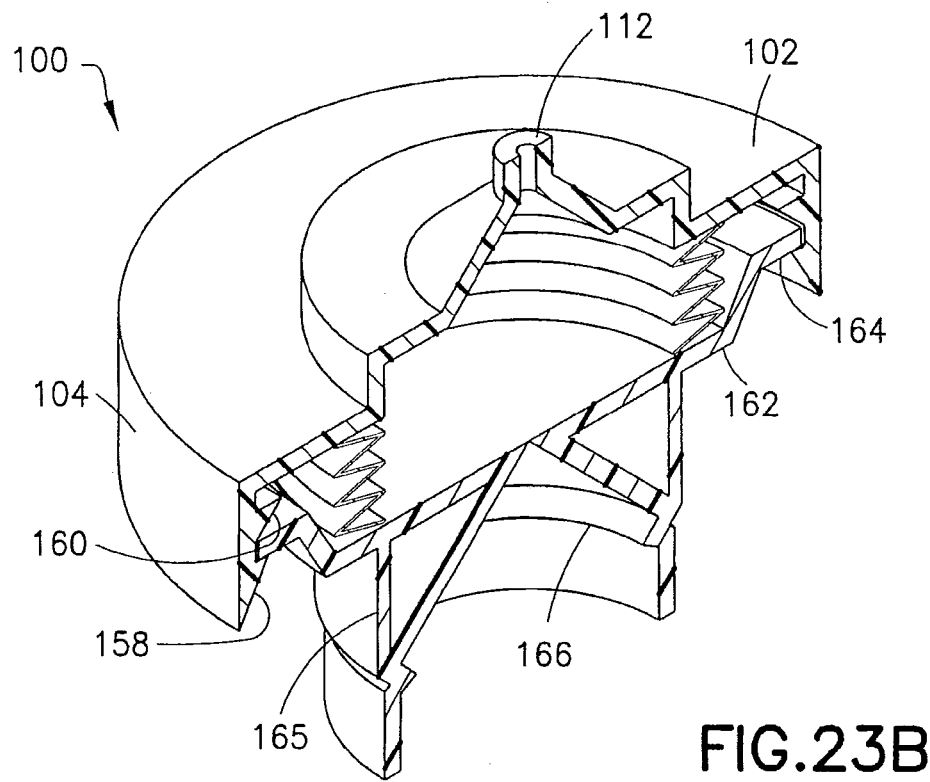
Figure 23C:
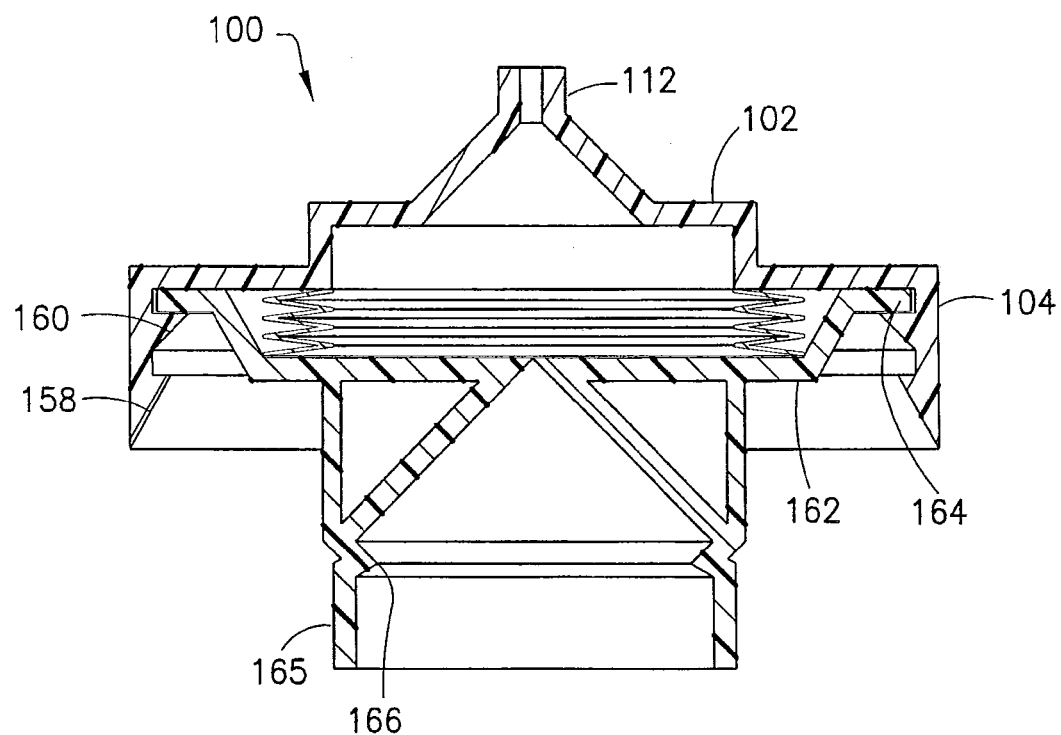
FIGS. 23C-23D are respectively a schematic cross-sectional view and a schematic cross-sectional and perspective view showing the bellows syringe in a compressed state after use according to the embodiment shown in FIGS. 23A-23B.
Figure 23D:
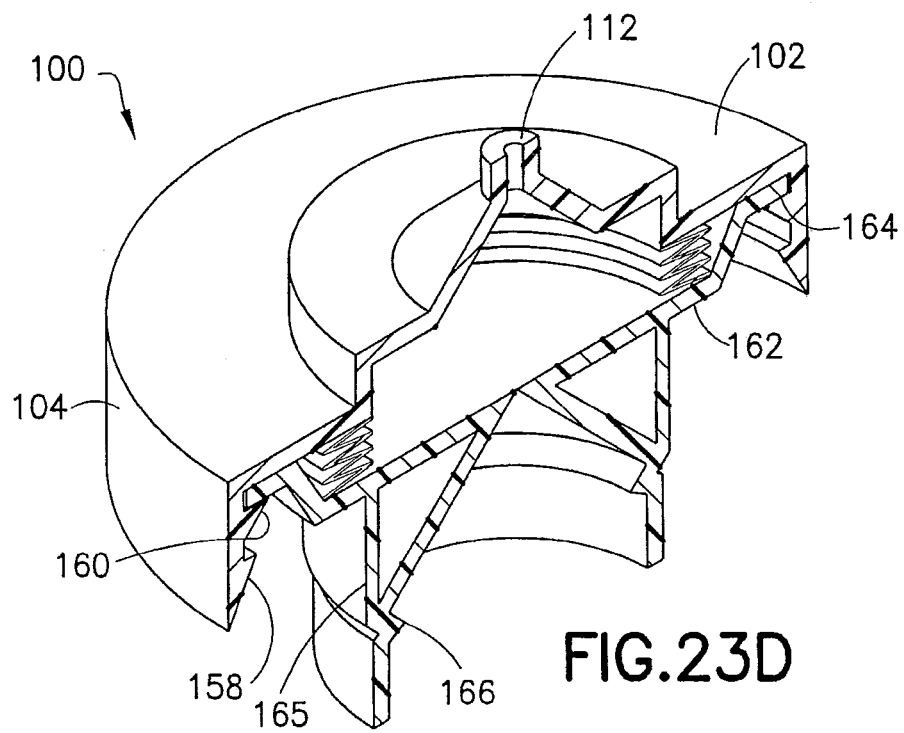

Referring to FIGS. 23A-23D, the bellows syringe 100 may be shipped in a compressed configuration, as noted previously. In the illustrated embodiment, the bellows syringe 100 is shipped in a first locked state which may be unlocked for use. Once used, the bellows syringe 100 may be placed in a second, permanently locked state to prevent undesirable reuse of the used bellows syringe 100. For example, the cap member 102 may comprise a first set of locking tabs 158 and a second, interior set of locking tabs 160 disposed axially along the skirt portion 104 of the cap member 102. A base member 162 may be provided on the end wall 128 at the proximal end 124 of the bellows member 120. The base member 162 comprises a circumferential lip or rim 164 adapted to interface with the two (2) sets of locking tabs 158, 160. The base member 162 may further comprise a depending cylindrical portion 165 adapted to interface with the piston head 16 of the piston element 14 of the fluid injector 12. The bellows syringe 100 may be initially provided in a sealed blister package and the like, with the circumferential lip or rim 164 on the base member 162 engaged with the first set of locking tabs 158 as shown in FIGS. 23A-23B. This engagement may be unlocked, for example, by action of the piston head 16 of the piston element 14 of the fluid injector 12, such as when the piston head 16 initially engages piston engagement structure 166 provided in the depending cylindrical portion 165 of the base member 162. Once the engagement between the circumferential lip or rim 164 on the base member 162 and the first set of locking tabs 158 is released, the bellows syringe 100 is operable as described previously. Once the useful life of the bellows syringe 100 has been exhausted, the piston element 14 of the fluid injector 12 may be operated to push the base member 162 into the cap member 102 so that the circumferential lip or rim 164 on the base member 162 engages with the second, interior set of locking tabs 160, as shown in FIGS. 23C-23D. This second engagement may be a permanent connection so that the bellows syringe 100 cannot be reused without significant impairment of or damage to the physical components of the bellows syringe 100. The concepts described in connection with FIGS. 23A-23D may be applied to any of the embodiments of the bellows syringe 100 in this disclosure.

Figure 24:
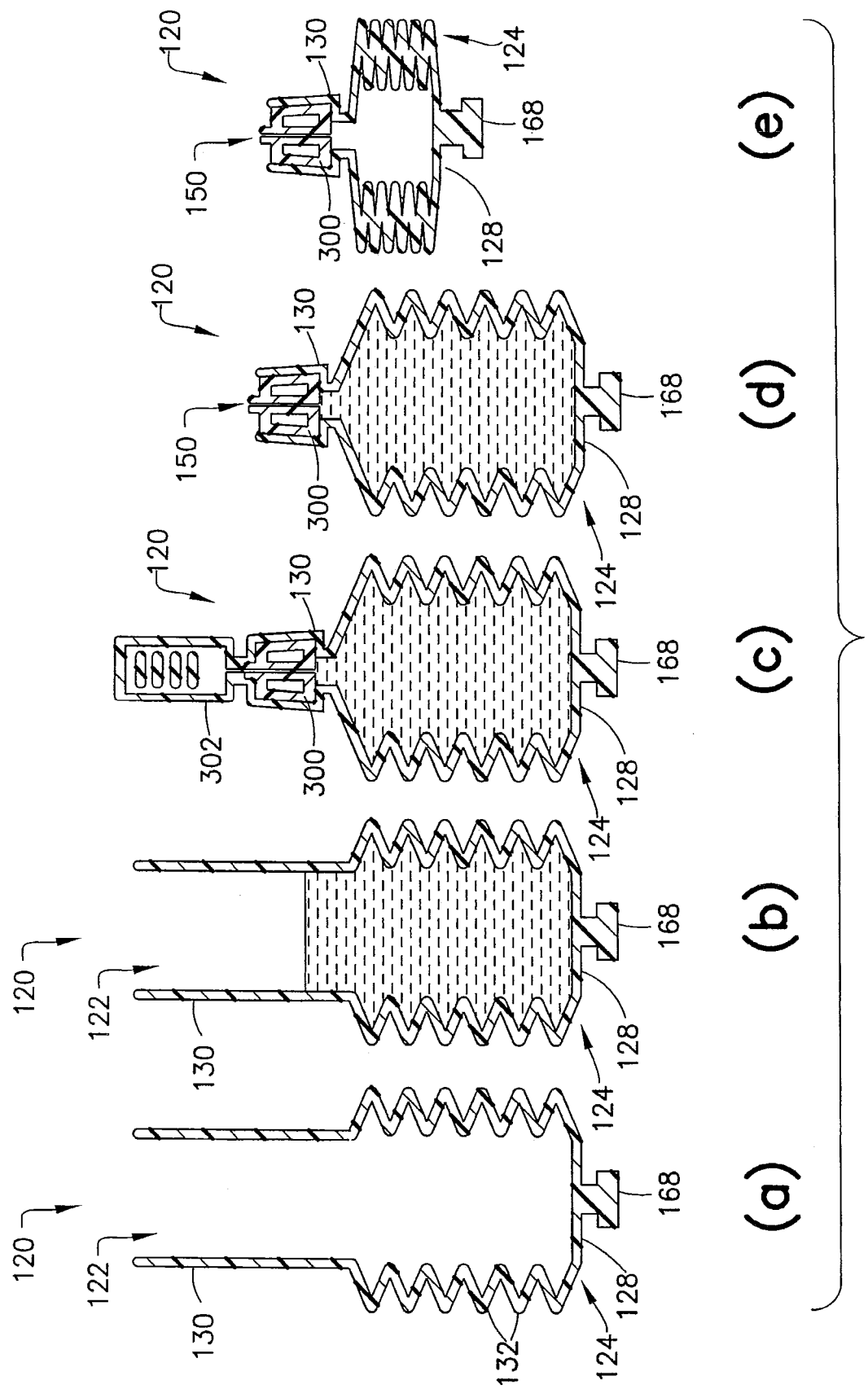
FIG. 24 is a sequence of schematic cross-sectional views showing filling of the bellows member of the bellows syringe, and sealing of an open end of the bellows member by a fluid connector fitting followed by mechanical sealing to form a break-away tab.
Figure 25:
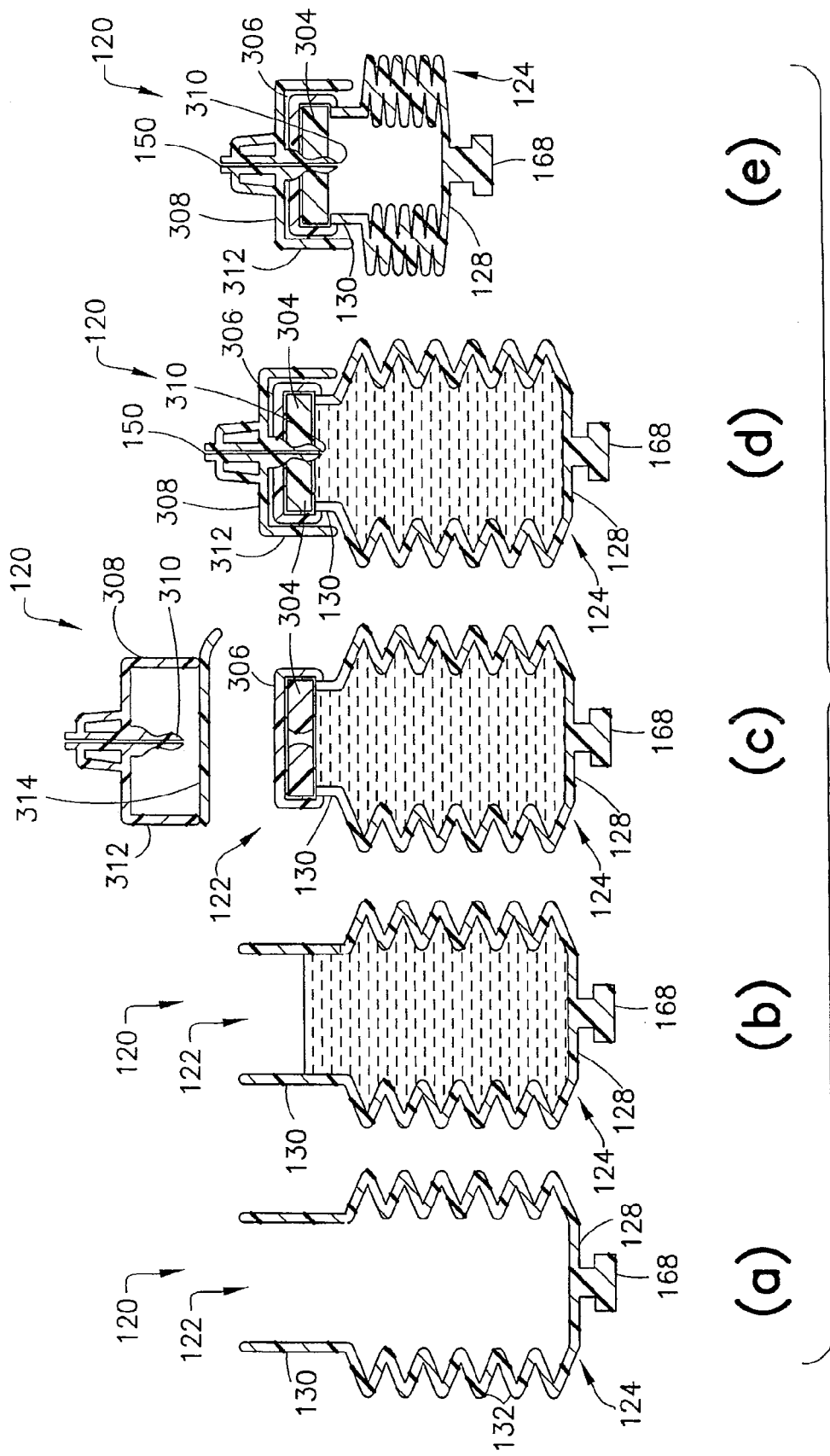
FIG. 25 is a sequence of schematic cross-sectional views showing filling of the bellows member of the bellows syringe, and sealing of an open end of the bellows member by a pierceable septum followed by mechanical sealing to enclose the pierceable septum.
Figure 26:
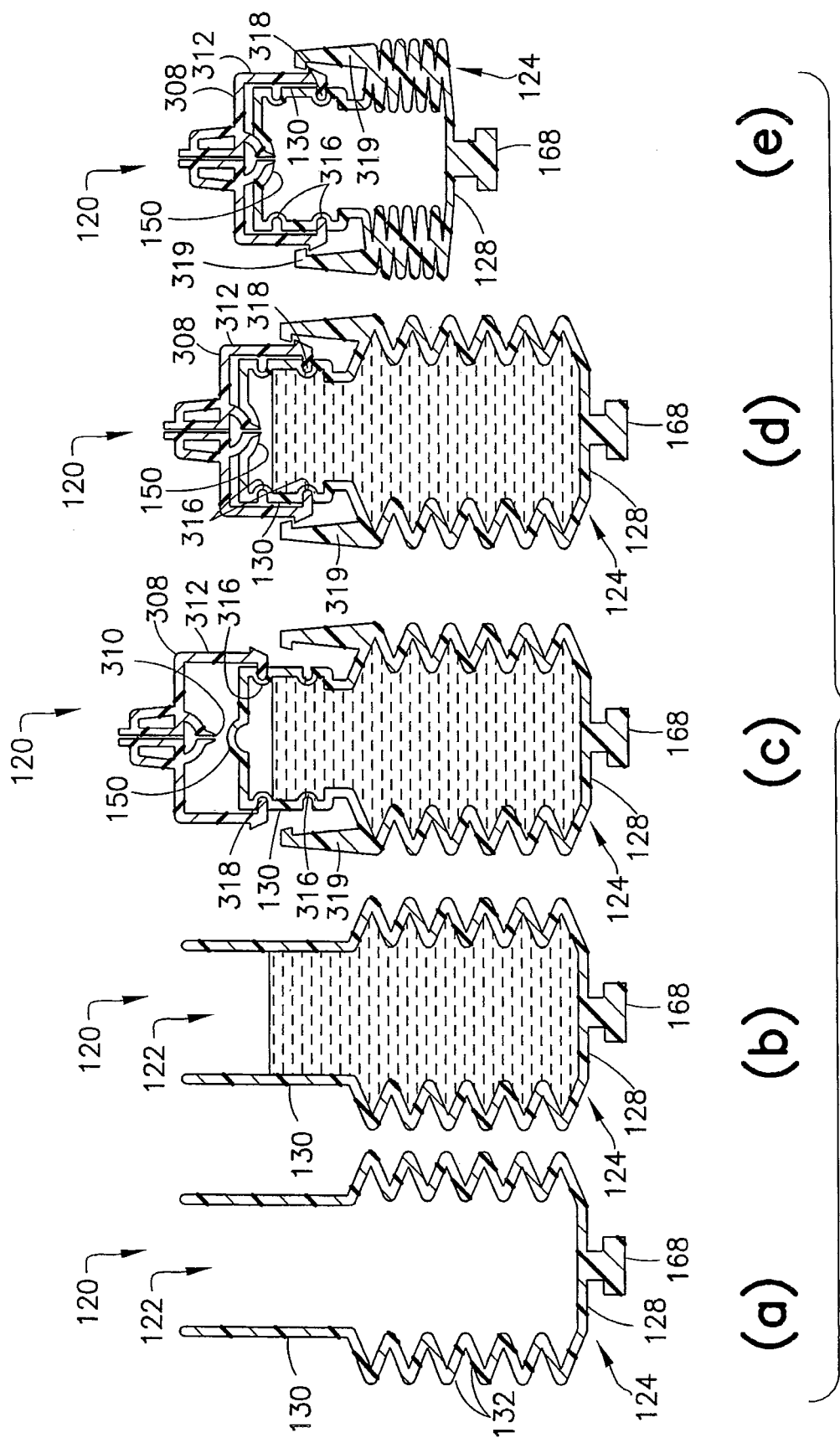
FIG. 26 is a sequence of schematic cross-sectional views showing filling of the bellows member of the bellows syringe, and sealing of an open end of the bellows member by mechanical sealing to form a sealed elongated discharge neck.

Referring to FIGS. 24-26, various tubing connection elements may be associated with the bellows member 120 of the bellows syringe 100. FIGS. 24-26 show the bellows member 120 with a button element or like structure 168 on the proximal closed end wall 128 that is used to interface with the piston head 16 shown in FIGS. 9A-9C. Fluid containers 220, 320 may also have the button element 168, as mentioned previously in connection with fluid container 220.

In FIG. 24, a sequence for molding, filling, and sealing the bellows member 120 is schematically illustrated. The sequence starts at step a where the body of the bellows member 120 is extrusion blow-molded, provided as an injection-molded component, etc., while retaining an open distal end 122 and an elongated discharge neck 130 in this embodiment. At step b, the formed bellows member 120 is filled with fluid through the open distal end 122. At step c, the discharge neck 130 is closed by a separately-molded, drop-in fluid connector fitting 300 that is placed in the discharge neck 130. At step c, the fluid connector fitting 300 is sealed by mechanical crimping or otherwise sealed to seal the discharge neck 130 and to form a break-away tab 302 at the distal end 122. The break-away tab 302 is frangible and may be removed at step d to permit access to the fluid connector fitting 300. Fluid may be dispensed from the bellows member 120 until empty as shown at step e.

In FIG. 25, another sequence for molding, filling, and sealing the bellows member 120 is schematically illustrated. The sequence starts at step a where the body of the bellows member 120 is extrusion blow-molded, provided as an injection-molded component, etc., while again retaining an open distal end 122 and an elongated discharge neck 130 in this embodiment. At step b, the formed bellows member 120 is filled with fluid through the open distal end 122. At step c, the discharge neck 130 is closed and sealed by a separately-molded, drop-in septum 304 and an enclosing mechanical cap fitting 306 that is engaged with the discharge neck 130. A fluid connector element 308 having a piercing feature or element 310 may be used to access the septum 304. The piercing element 310 may be enclosed in a shield or housing portion 312 of the fluid connector element 308, and a peel-away membrane or seal 314 may enclose the shield or housing portion 312 to shield the piercing element 310. Fluid may be dispensed from the bellows member 120 until empty as shown at step e. The piercing element 310 is operable as the discharge port 150 in this embodiment.

In FIG. 26, another sequence for molding, filling, and sealing the bellows member 120 is schematically illustrated. The sequence starts at step a where the body of the bellows member 120 is extrusion blow-molded, provided as an injection-molded component, etc., while again retaining an open distal end 122 and an elongated discharge neck 130 in this embodiment. At step b, the formed bellows member 120 is filled with fluid through the open distal end 122. At step c, the discharge neck 130 is closed and seal by a mechanical crimping process or like processes, and one or more circumferential grooves or recesses 316 are defined in the discharge neck 130. Also at step c, the fluid connector element 308 according to the previous embodiment is attached to the discharge neck 130. The fluid connector element 308 again has a piercing feature or element 310 enclosed within a the shield or housing portion 312, and a peel-away membrane or seal 314 (shown in FIG. 25) may also be used to enclose the shield or housing portion 312 to shield the piercing element 310. The shield or housing portion 312 comprises one or more distal tabs 318 adapted to engage the circumferential grooves or recesses 316 defined in the discharge neck 130 of the bellows member 120. The distal tab or tabs 318 may alternatively be a continuous rib. The circumferential groove or recess 316 in the discharge neck 130 closest to the sealed discharge port 150 provides a mounting location for the fluid connector element 308 so that the bellows member 120 may be transported. When it is desired to access the interior 136 of the bellows member 120, the user may press down on the fluid connector element 308 so that the distal tabs 318 on the shield or housing portion 312 are displaced from engagement with the upper circumferential groove or recess 316 and engage the next circumferential groove or recess 316 located axially downward on the discharge neck 130 and the piercing element 310 simultaneously pierces the sealed discharge port 150 at the end of the discharge neck 130 of the bellows member 120. Fluid may be dispensed from the bellows member 120 until empty as shown at step e. Upward-directed locking arms 319 may be provided on the bellows member 120 to engage the distal tabs 318 on the shield or housing portion 312 to secure the shield or housing portion 312 in the pierced state shown in steps d and e.

Referring to FIGS. 27A-27B, the bellows assembly 20 is shown with the bellows syringe 100 loaded in the cylindrical body or pressure jacket 30. In this embodiment, a piercing connector cap 208 is provided to access the discharge port 150 at the end of the discharge neck 130 of the bellows member 120. The cap member 102 defines a distal cavity 170 to house the piercing connector cap 208. The piercing connector cap 208 comprises a piercing element 210 supported and activated by a collapsible body 212. The piercing element 210 defines a central passageway 214 therethrough to permit fluid to pass through the piercing element 210. The piercing element 210 is disposed over an opening 172 in the cap member 102. Additionally, the collapsible body 212 comprises a connector tip 216 that coincides with the opening 172 in the cap member 102 to permit fluid to pass through the cap member 102. In use, the piercing connector cap 208 is pressed downward by a user of the bellows assembly 20 so that the collapsible body 212 collapses into the compressed state shown in FIG. 27B. As the collapsible body 212 compresses downward, the piercing element 210 is pushed into the opening 172 in the cap member 102 to puncture the discharge port 150 at the end of the discharge neck 130 of the bellows member 120 and establish fluid communication with the interior 136 of the bellows member 120 via the passageway 214. An external fluid tubing set (not shown) may be connected to the connector tip 216 to permit the contents of the bellows member 120 to be conducted to a patient. While the piercing connector cap 208 may be operated manually, a mechanical component or structure on the external fluid tubing set may also be used to automatically activate the piercing connector cap 208, for example, as part of the connecting process for interfacing the fluid tubing set to the connector tip 216 and, thus, establish a fluid connection with the discharge port 150 on the bellows member 120. The piercing connector cap 208 is desirably sealed in the distal cavity 170 in the cap member 102 in a substantially fluid-tight manner.

Figure 28A:
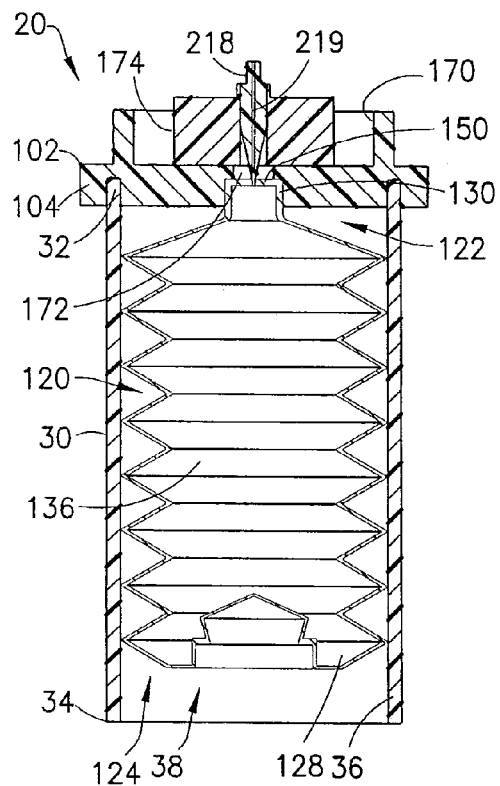
FIGS. 28A-28B are schematic cross-sectional views of the bellows syringe associated with a pressure jacket, and showing a rotational piercing element used to access the bellows member of the bellows syringe.
Figure 28B:
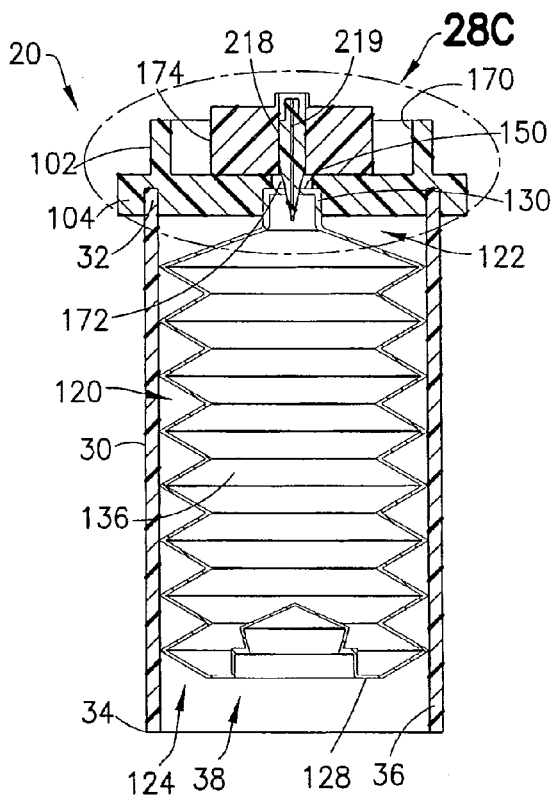
Figure 28C:
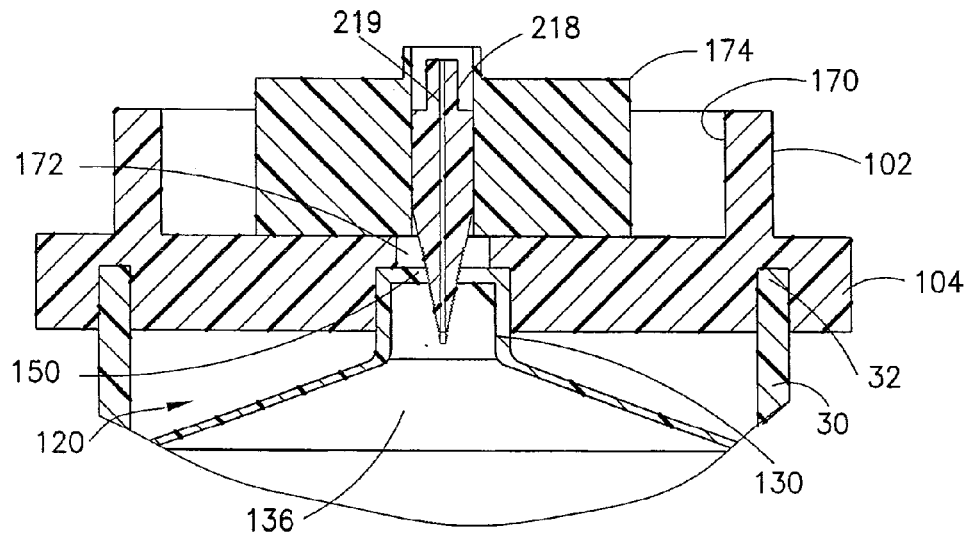
FIG. 28C is a detail view of Detail 28C in FIG. 28B.

In FIGS. 28A-28C, the bellows assembly 20 in another embodiment is shown with the bellows syringe 100 loaded in the cylindrical body or pressure jacket 30. In this embodiment, the cap member 102 again defines a distal cavity 170, and now comprises an integral or attached fluid connector tip 174 connected to the cap member 102 to permit fluid to pass through the opening 172 in the cap member 102. A rotational piercing element 218 defining a central passageway 219 is disposed in the fluid connector tip 174. The piercing element 218 may be in threaded engagement in the opening 172 in the cap member 102, and an external fluid tubing set (not shown) is used to rotate the piercing element 218 in the opening 172 to a position where the piercing element 218 punctures the discharge port 150 at the end of the discharge neck 130 of the bellows member 120 and establish fluid communication with the interior 136 of the bellows member 120 via the passageway 219. For example, the fluid tubing set may be adapted for a threaded engagement with the fluid connector tip 174 and may comprise a mechanical component or structure to engage and rotate the piercing element 218 in the opening 172. The piercing element 218 need not be in threaded engagement in the opening 172 to effect puncturing of the discharge port 150 on the bellows member 120 as the piercing element 218 may simply be pushed into the discharge port 150 by the action of connecting the fluid tubing set to the fluid connector tip 174. However, the threading on the piercing element 218 is desirable for use in piercing or accessing the discharge port 150, enlarging the engagement between these two components, and securing the engagement therebetween in a similar manner to the operation of a wood screw or drywall screw.

Figure 29:
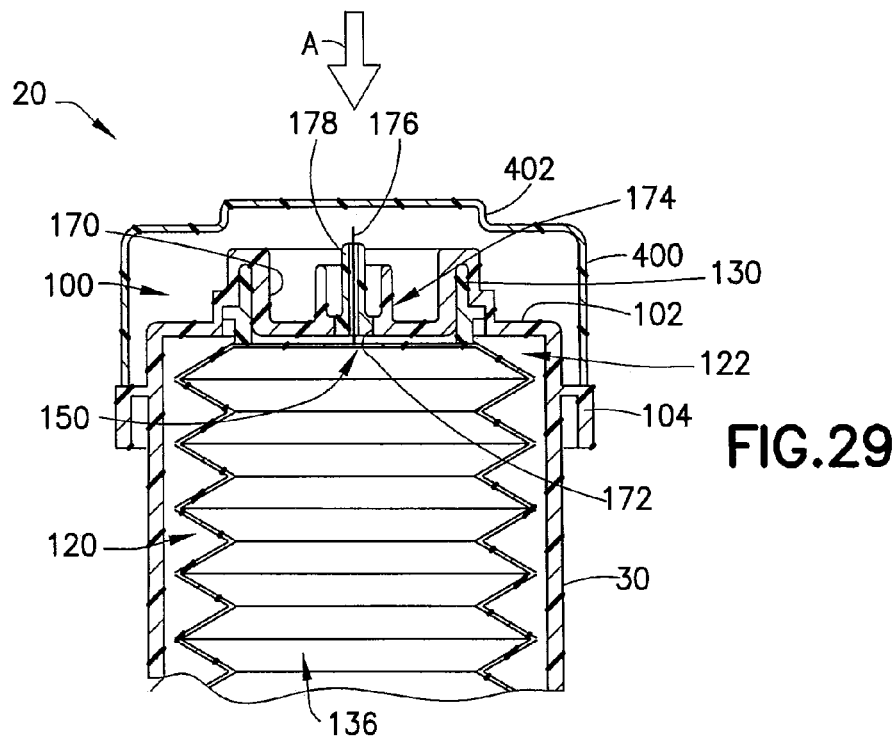
FIG. 29 is a partial cross-sectional view showing the bellows syringe connected to a pressure jacket, and further showing a removable cap having a central button and a piercing pin or needle cannula used to access the bellows member of the bellows syringe.

Referring to FIG. 29, the bellows assembly 20 in another embodiment is shown with the bellows syringe 100 loaded in the pressure jacket 30. In this embodiment, the cap member 102 again defines a distal cavity 170 and has a fluid connector tip 174 connected to the opening 172 in the cap member 102 to permit fluid to pass through the cap member 102. A piercing pin or needle cannula 176 is disposed and axially movable in a central post portion 178 within the fluid connector tip 174. A removable cap 400 is disposed over the cap member 102 and engaged with the cap member 102 by any suitably removable manner, such as being snap-fit onto the cap member 102. The removable cap 400 comprises a central button 402 disposed over the piercing pin or needle cannula 176 that a user may depress in the direction of arrow A to cause the piercing pin or needle cannula 176 to move axially downward and pierce the discharge port 150 at the end of the discharge neck 130 of the bellows member 120 to establish fluid communication with the interior 136 of the bellows member 120. If desired, the piercing pin or needle cannula 176 may be connected to the central button 402 so that, after piercing the discharge port 150, the piercing needle 176 may be removed along with the removable cap 400. Alternatively, the piercing needle cannula 176 when pushed into the central post 178 in the fluid connector tip 174 may form part of the fluid conducing pathway through the fluid connector tip 174 to a fluid tubing set (not shown) connected to the fluid connector tip 174. In either configuration, the pressing of the central button 402 establishes fluid communication with the interior 136 of the bellows member 120 in this embodiment.

Figure 30A:
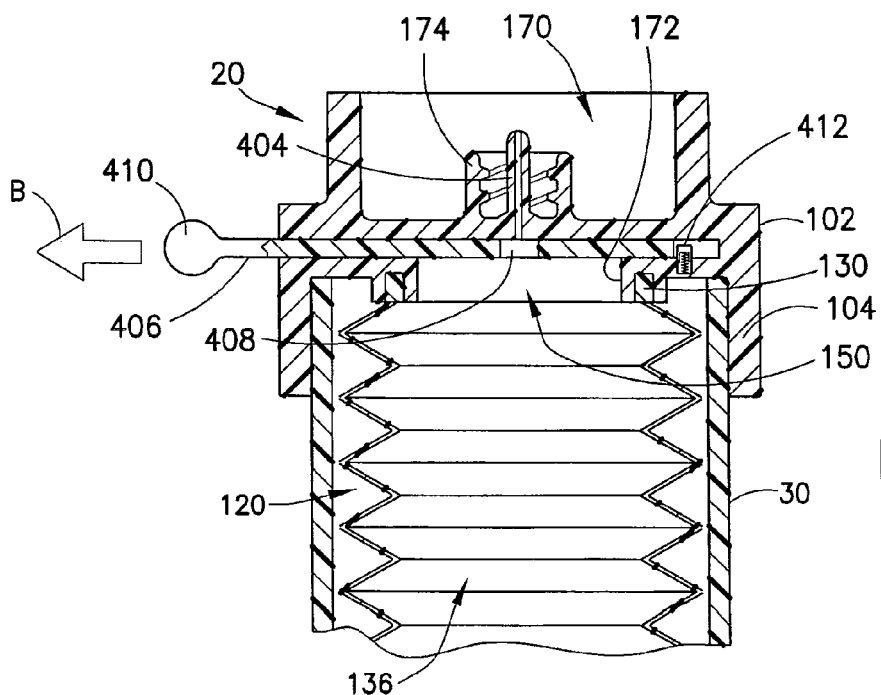
FIG. 30A is a schematic cross-sectional view of the bellows syringe having a cap member with a slide plate used to establish fluid communication with the bellows member, and showing the slide plate in an aligned position to establish a fluid path with the bellows member.
Figure 30B:
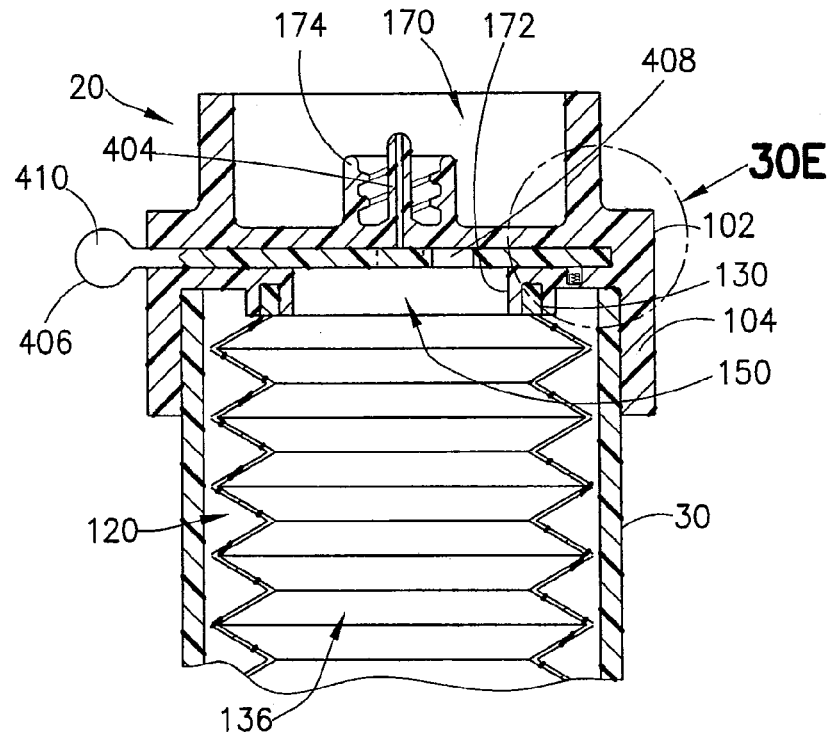
FIG. 30B is a schematic cross-sectional view of the bellows syringe of FIG. 30A showing the slide plate in an unaligned position to block the fluid path with the bellows member.
Figure 30E:
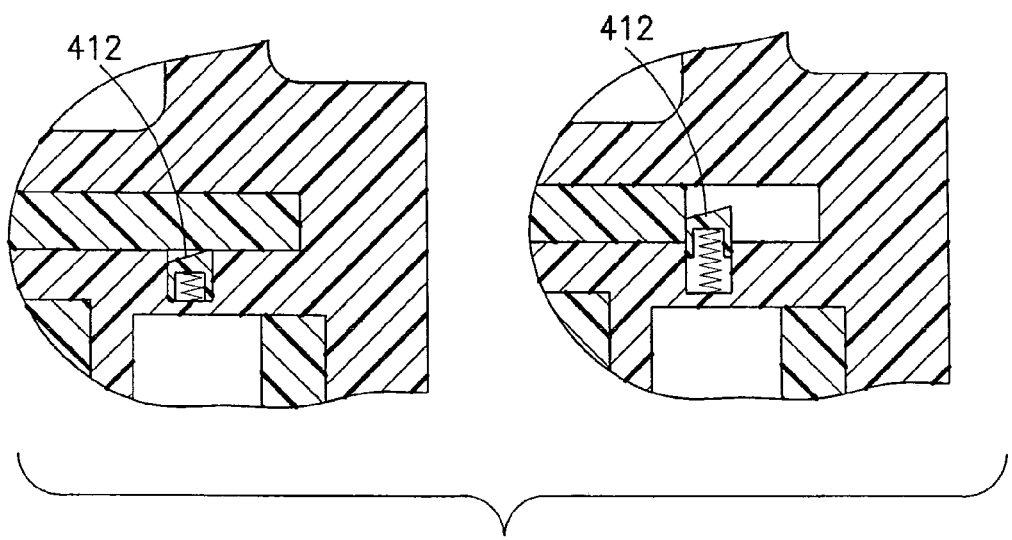
FIG. 30E is a detail view of Detail 30E in FIG. 30B.
Figures 30C, 30D:
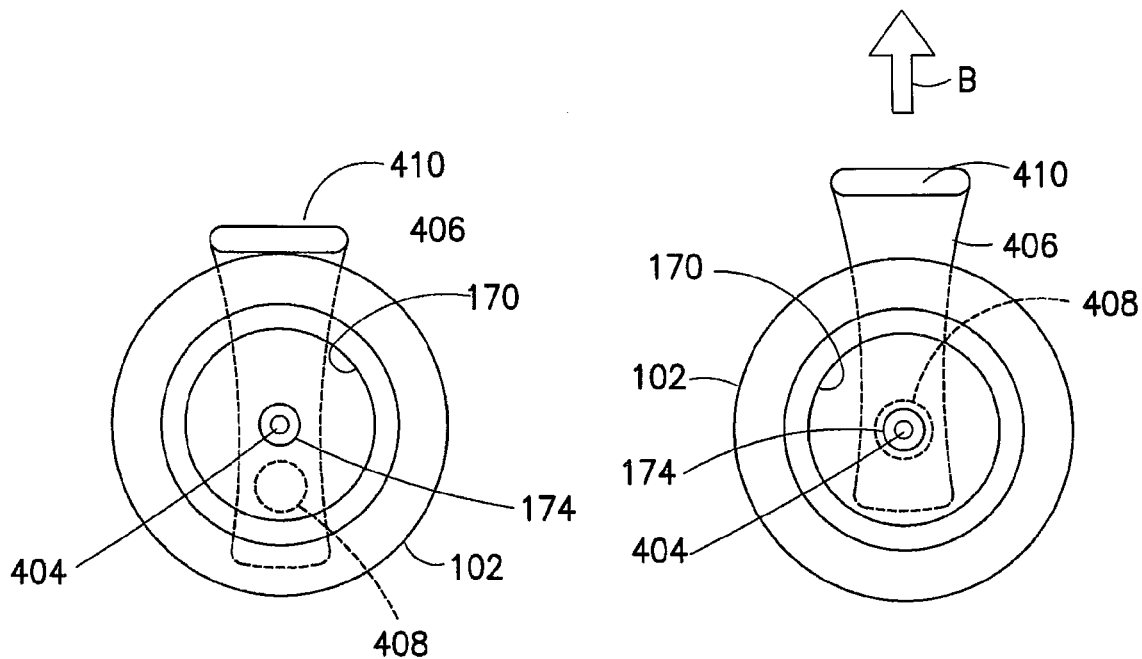
FIG. 30C is a schematic top plan view of the bellows syringe of FIG. 30A and showing the slide plate in the aligned position to establish the fluid path with the bellows member.
FIG. 30D is a schematic top plan view of the bellows syringe of FIG. 30B and showing the slide plate in the unaligned position to block the fluid path with the bellows member.

Referring to FIGS. 30A-30E, the bellows assembly 20 in another embodiment is shown with the bellows syringe 100 loaded in the pressure jacket 30. In this embodiment, the cap member 102 again defines a distal cavity 170 and a fluid connector tip 174 is connected to the opening 172 in the cap member 102 to permit fluid to pass through the cap member 102. A luer-type fluid connector element 404 may be disposed in the fluid connector tip 174 in this embodiment and be in fluid communication with the opening 172. A slide plate 406 is movable associated with the cap member 102 and, in particular, is movable transversely relative to the cap member 102 in the direction of arrow B to create and close a fluid path to the discharge port 150 of the bellows member 120. For example, in one embodiment, the slide plate 406 defines an opening 408 which permits a fluid connection to be established between the fluid connector element 404 and the discharge port 150 on the bellows member 120 when the slide plate 406 is positioned to generally align the opening 408 with the fluid connector element 404 and the discharge port 150 as shown in FIG. 30A. When the slide plate 406 is pushed or pulled relative to the cap member 102 using a push or pull tab 410 on the slide plate 406, the opening 408 is displaced from the connecting fluid path alignment as shown in FIG. 30B, which closes the fluid path. FIGS. 30C-30D show top views of the cap member 102 with the slide plate 406 in the unaligned and aligned positions, respectively. FIG. 30C shows the slide plate 406 in the unaligned position where the opening 408 is unaligned with the fluid connector element 404 and the open discharge port 150 in this embodiment to close a flow path and permit fluid flow. FIG. 30D shows the slide plate 406 in the aligned position where the opening 408 is aligned with the fluid connector fitting 404 and the discharge port 150 to open the flow path and prevent fluid flow. A spring-biased stopper 412 may be disposed adjacent an end of the slide plate 406 to secure the slide plate 406 in the aligned position. The spring-biased stopper 412 may be depressed by action of the slide plate 406 to permit the slide plate 406 to be placed into the blocking or unaligned position.

Figure 31A:
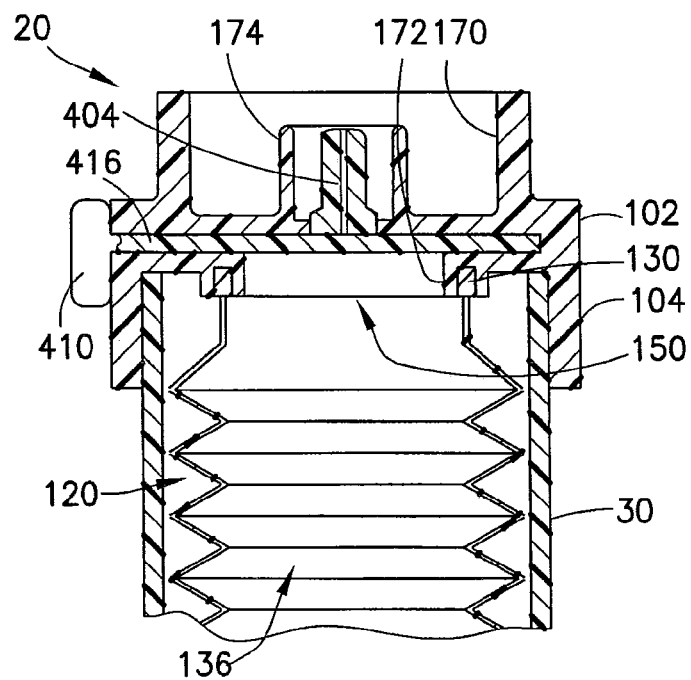
FIG. 31A is a schematic cross-sectional view of the bellows syringe with a cap member with a rotational plate having an off-set feature used to establish fluid communication with the bellows member.

Referring to FIGS. 31A-31C, in a variation of the bellows assembly 20 described in connection with. FIGS. 30A-30E, the slide plate 406 is replaced by a rotational plate 416 that is off-center or off-axis relative to the opening 172 in the cap member 102 and alternately covers and uncovers the fluid path between the fluid connector element 404 and the discharge port 150 on the bellows member 120 depending on the rotational position of the rotational plate 416. As shown in FIGS. 31B-31C, as the rotational plate 416 is rotated relative to the cap member 102 in the direction of arrow B, the rotational plate 416 moves from a first position covering the fluid path between the connector element 404 and the discharge port 150 on the bellows member 120, as shown in FIG. 31B, to a second position wherein the fluid path between the connector element 404 and the discharge port 150 on the bellows member 120 is open or uncovered, as shown in FIG. 31C.

Referring to FIG. 32, the bellows assembly 20 in another embodiment is shown with the bellows member 120 loaded in the cylindrical body or pressure jacket 30. In this embodiment, the cap member 102 again defines a distal cavity 170 and a fluid connector tip 174 fluidly connected to the opening 172 in the cap member 102 to permit fluid to pass through the cap member 102. In this embodiment, a cutting blade 420 is provided as part of the cap member 102 and is operable via an external button 422 which is used to move the cutting blade 420 transversely in the cap member 102. As an example, the discharge port 150 at the end of the discharge neck 130 of the bellows member 120 may define a pointed tip 151 extending into the opening 172 in the cap member 102 and the cutting blade 420 may be disposed to cut the protruding or pointed tip 151 when the external button 422 is pressed, which causes lateral or transverse movement of the cutting blade 420 in the direction of arrow C. The central post 178 (see FIG. 29) in the fluid connector tip 174 may form part of the fluid conducing pathway through the fluid connector tip 174 which connects to a fluid tubing set (not shown).

Referring to FIGS. 33A-33B, the bellows assembly 20 in another embodiment is shown with the bellows syringe 100 loaded in the pressure jacket 30. In this embodiment, a pivotal door 50 is hinged to the pressure jacket 30 to close the open distal end 32 of the pressure jacket 30. The pivotal door 50 comprises a fluid connector element 52 that is integral or removably associated with the pivotal door 50. The fluid connector element 52 comprises a piercing tip or element 54 adapted to pierce the discharge port 150 at the end of the discharge neck 130 of the bellows member 120 to establish fluid communication with the interior 136 of the bellows member 120. A catch or lock may be provided to secure the pivotal door 50 in the closed position with the fluid connector element 52 interfaced with the discharge port 150 on the bellows member 120. The connector element 52 may be adapted to be connected to a fluid tubing set (not shown), which may be a conventional medical fluid tubing set.

Figure 34:
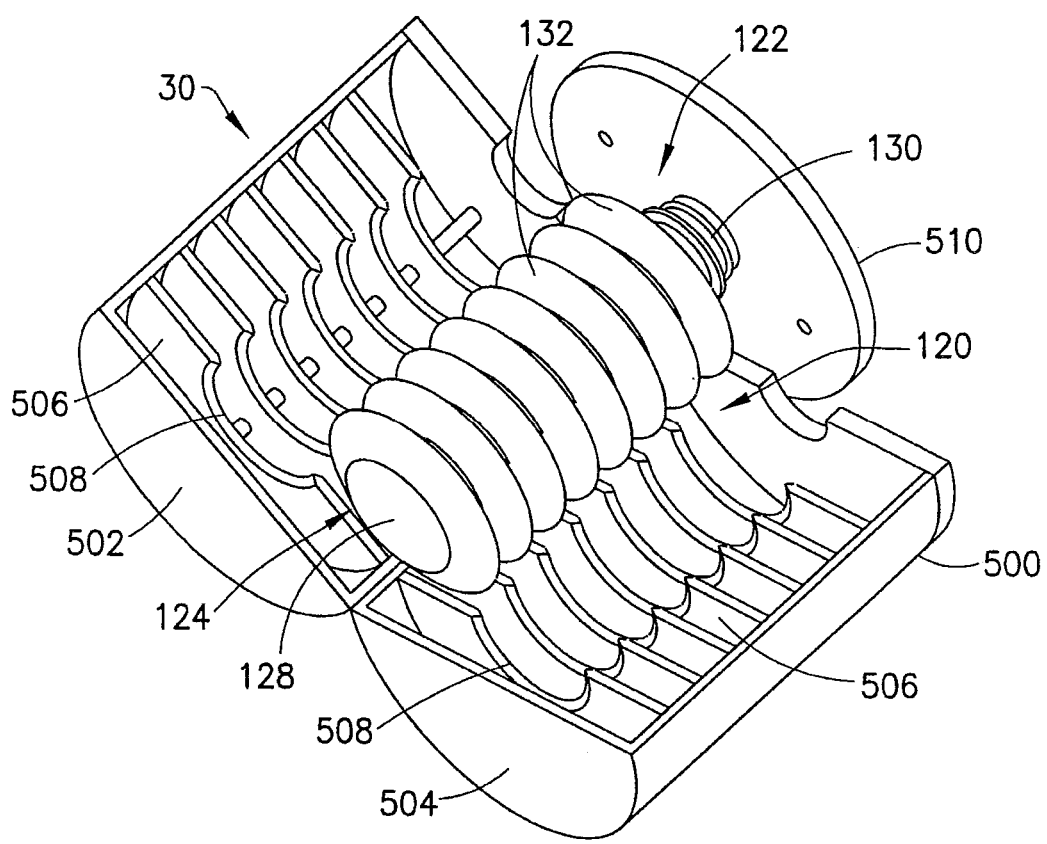
FIG. 34 is a perspective view of a clam shell pressure jacket body used to support the bellows member of the bellows syringe according to one embodiment.

FIG. 34 shows an embodiment of the pressure jacket 30 having a pressure jacket body 500 that is formed by two (2) clam shell portions 502, 504 that are hinged together to close around a bellows member 120 of the bellows syringe 100. The interiors of each of the clam shell portions 502, 504 support rib support member 506 which define cut-out areas or portions 508 that are adapted to support the bellows sections or rings 132 of the bellows member 120 between the individual bellows sections or rings 132. The rib support members 506 support the individual bellows sections or rings 132 when the bellows member 120 is under pressure and help prevent the individual bellows sections or rings 132 from bulging radially outward. An end cap 510 may be provided to support the discharge neck 130 of the bellows member 120 in the pressure jacket body 500. The rib support members 506 are axially compressible according to the concepts described below in connection with FIGS. 35A-35B.

Referring to FIGS. 35A-35B, as an application to or augmentation of the foregoing pressure jacket 30 with a clam shell pressure jacket body 500, a ring support scaffold 520 comprising two ring clam shell portions 522, 524 are hinged together to close around the bellows member 120 of the bellows syringe 100. In this embodiment, the support scaffold 520 may be an external skeleton attached to the bellows member 120 to support the individual bellows sections or rings 132 for the same reasons discussed above in connection with the clam shell pressure jacket body 500 of FIG. 34. The clam shell portions 522, 524 comprise individual rib support members 526 which define cut-out areas or portions 528 that are adapted to support the individual bellows sections or rings 132 of the bellows member 120 between the individual bellows sections or rings 132 on the bellows member 120. The ring support scaffold 520 may be attached to the bellows member 120 and loaded along with the bellows member 120 into the pressure jacket 30 if desired. A support base 530 may be provided to support the support scaffold 520. The support base 530 comprises two (2) support arms 532 that extend upward from the base 520. The support arms 532 are received in respective sets of registered openings 534 in the individual rib support members 526 to control the axial compression characteristics of the bellows member 120. Accordingly, if desired, the base 530 may be loaded along with the bellows member 120 and attached ring support scaffold 520 when loaded into the pressure jacket 30 as shown, for example, in FIG. 34. Thus, the ring support scaffold 520 may be part of the pressure jacket 30 shown in FIG. 34 or a separate structure loaded into the pressure jacket 30 shown in FIG. 34.

In the embodiments shown in FIGS. 34 and 35A-35B, supporting the minor diameters of the bellows portion 126 helps to prevent swell to help control retained fluid capacitance in the bellows member 120 and minimize/eliminate chaotic movement of the bellows member 120 as it collapses during operation. Furthermore, the structural support supplied by the embodiments shown in FIGS. 34 and 35A-35B apply tension between the minor and major diameters of the bellow portion 126, which allows for more controlled collapse. For additional control of retained fluid capacitance, the major diameter and even the sides of the bellows portion 126 could be fully supported and minimize or even eliminate the retained fluid capacitance in the bellows syringe 100. These embodiments contemplate a flexible and movable pressure jacket. To allow for the flexibility, the materials for the pressure jacket 500 could be a high tensile strength fabric such as those constructed of Nylon® or Spectra® ballistic materials. The fabric could also be segmented like ribbons to allow for visibility of the fluid contents. The movable segments described above slide along the support arms 532 as the bellows member 120 is compressed, minimizing the chaotic collapse of the each bellows ring or segment 132. Alternatively, the segments or individual rib support members 526 could be driven by a programmable servo-motor to provide a controlled fluid injection. This method can replace a typical motor/ball-screw arrangement in the fluid injector 12 which drives the plunger element 14.

Referring to FIGS. 36A-36B, a fluid injector 12 is shown with a pressure jacket 30 with a split-top pressure jacket body 540 that is pivotally connected to the fluid injector housing 18, such as to the face plate 19. The split-top pressure jacket body 540 is used to support the bellows member 120 of the bellows syringe 100, and the split-top pressure jacket body 540 defines a split-top opening 542 to allow insertion and removal of bellows member 120 while a fluid tubing set (not shown) is connected to a fluid connector 544 disposed in the discharge neck 130 of the bellows member 120. The split-top pressure jacket body 540 may be pivotally connected to the face plate 19 of the fluid injector 12. In this embodiment, the bellows member 120 is breach-loaded into the split-top pressure jacket body 540.

Figures 37A, 37B:
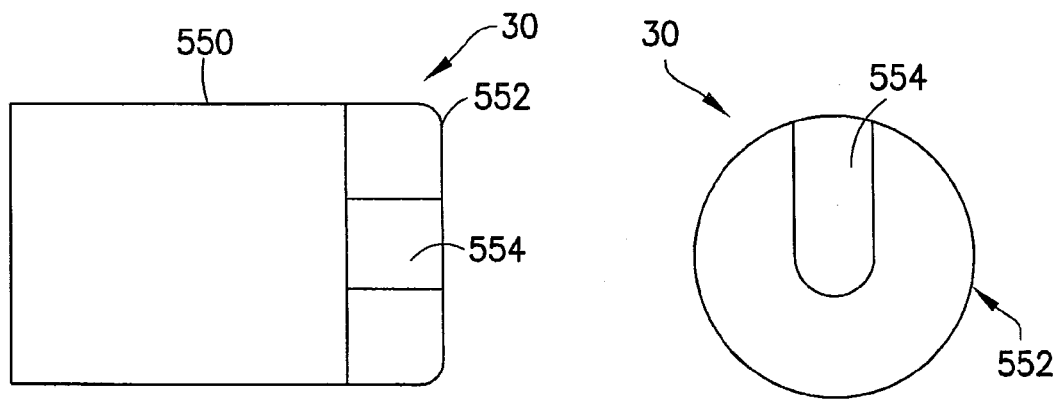
FIG. 37A is a top view of a pressure jacket for supporting the bellows member according to one embodiment.
FIG. 37B is an end view of a pressure jacket for supporting the bellows member according to one embodiment.
Figure 37C:
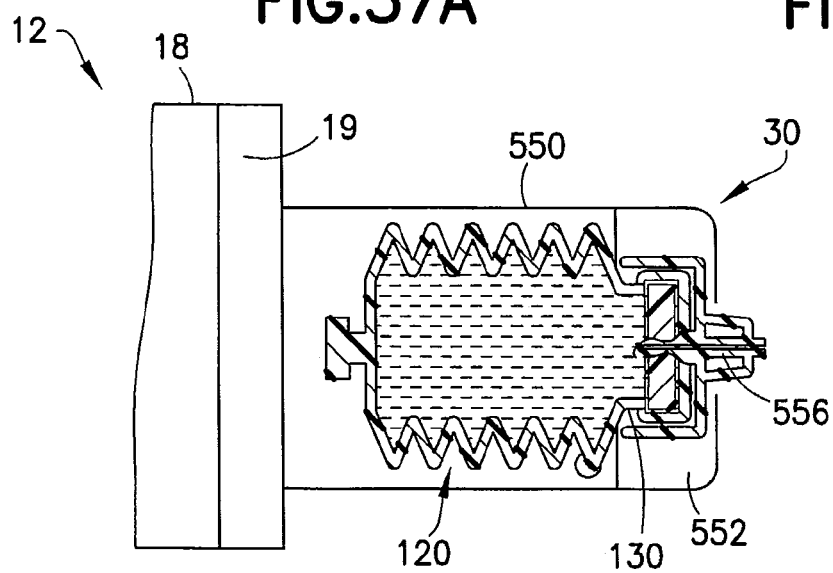
FIGS. 37C-37D are schematic views of a fluid injector with a pressure jacket, as shown in FIGS. 37A-37B, for supporting the bellows member and having a pivotal front end plate with a split-top opening.
Figure 37D:
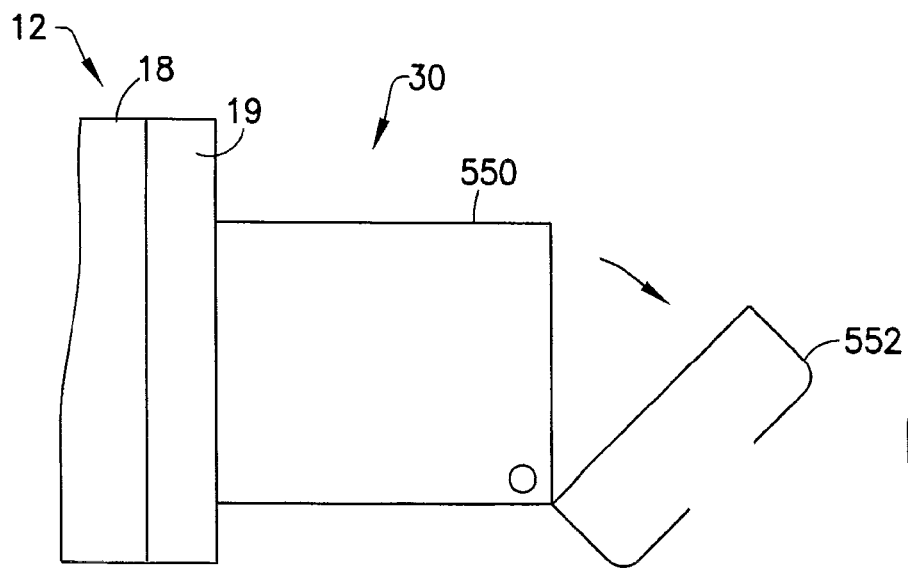

Referring to FIGS. 37A-37B, a fluid injector 12 is shown with a pressure jacket 30 with a cylindrical pressure jacket body 550 that has a pivotally connected front end plate 552. The front end plate 552 defines split-top opening 554. In this embodiment, the bellows member 120 is front-loaded into the pressure jacket body 550 by pivoting the front end plate 552 downward. The split-top opening 554 allows insertion and removal of bellows member 120 while a fluid tubing set is connected to a fluid connector 556 disposed in the discharge neck 130 of the bellows member 12.

Referring to FIGS. 38A-38B, a fluid injector 12 is shown with a pressure jacket 30 having split-front or front-loading clam shell pressure jacket body 560 connected to the fluid injector 12. The split-front pressure jacket body 560 comprises two (2) opposed shell portions 562, 564, with one of the shell portions 562 pivotally connected to the face plate 19 of the housing 18 of the fluid injector 12 and the other of the shell portions 564 fixedly secured to the face plate 19 of the housing 18 of the fluid injector 12. The front-opening nature of the pressure jacket 560 permits the bellows member 120 to be loaded therein from the front, and the pivoting shell portion 562 permits the insertion and removal of bellows member 120 while a fluid tubing set is connected to a fluid connector 566 disposed in the discharge neck 130 of the bellows member 12.

Referring to FIGS. 39A-39B, a fluid injector 12 is shown with a pressure jacket 30 with another embodiment of a split-top pressure jacket body 570. The split-top pressure jacket body 570 is used to support the bellows member 120 of the bellows syringe 100, and the split-top pressure jacket body 570 defines a split-top opening 572 to allow insertion and removal of bellows member 120 while a fluid connector tubing set 574 is connected to the discharge neck 130 of the bellows member 120. The split-top pressure jacket body 570 may be pivotally connected to the face plate 19 of the housing of the fluid injector 12 and, in this embodiment, the bellows member 120 is breach-loaded into the split-top pressure jacket body 570. The fluid injector housing 18 further comprises a filling appendage 576 that extends outward to fill the split-top opening 572 when the split-top pressure jacket 570 is pivoted to the closed position.

Figure 40A:
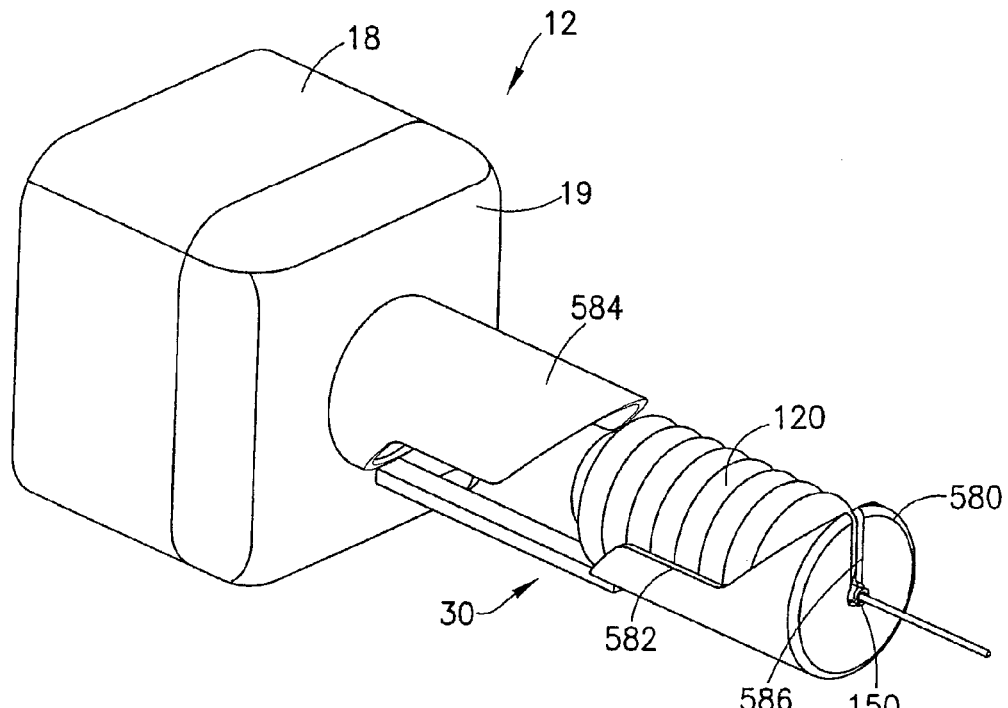
FIGS. 40A-40B are schematic perspective views of a fluid injector in which a split-front pressure jacket body for supporting the bellows member is telescopically connected to the housing of the fluid injector and a split-top or slot is enclosable by a roof portion of the fluid injector housing.
Figure 40B:
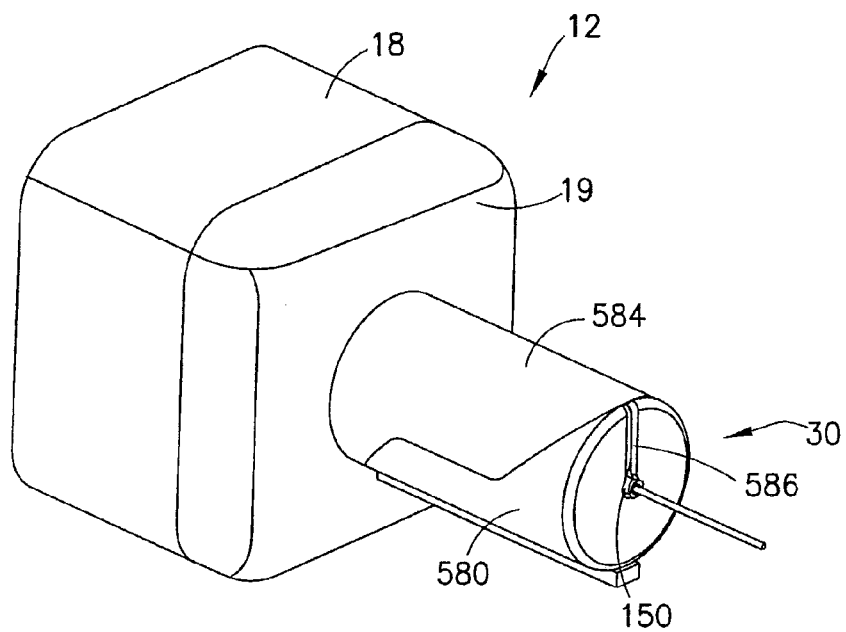

Referring to FIG. 40A-40B, a fluid injector 12 is shown with a pressure jacket 30 having an open-top pressure jacket body 580 that is telescopically connected to the face plate 19 of the housing 18 of the fluid injector 12. The open-top pressure jacket body 580 is used to support the bellows member 120 of the bellows syringe 100. The open-top pressure jacket body 580 defines an open-top 582 to allow insertion and removal of bellows member 120 while a fluid tubing set (not shown) is connected to the discharge port 150 of the bellows member 120. The open-top pressure jacket body 580 may be telescopically connected to the fluid injector housing 18 to extend outward therefrom to reach a loading position for the bellows member 120, and then be retracted to a closed position relative to the fluid injector housing 18 which encloses the open-top 582. In this embodiment, the bellows member 120 is top-loaded into the open-top pressure jacket body 580 via the open-top 582. The fluid injector housing 18 comprises a projecting roof portion 584 which encloses the open-top 582 of the pressure jacket body 580 when the open-top pressure jacket body 580 is in the closed position engaged with the fluid injector housing 18. A slot opening 586 is provided in the distal end of the pressure jacket body 580 to accommodate fluid tubing.

Figure 41A:
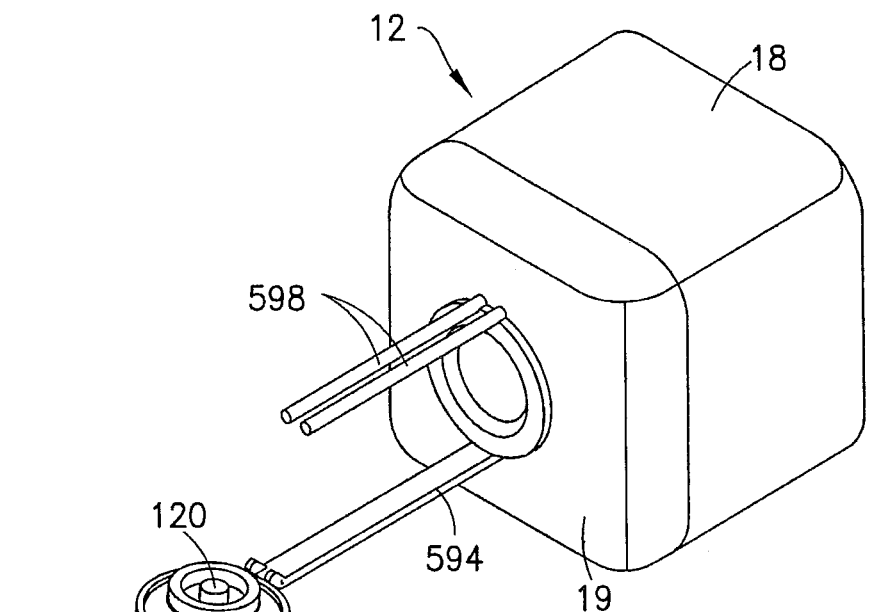
Figure 41B:
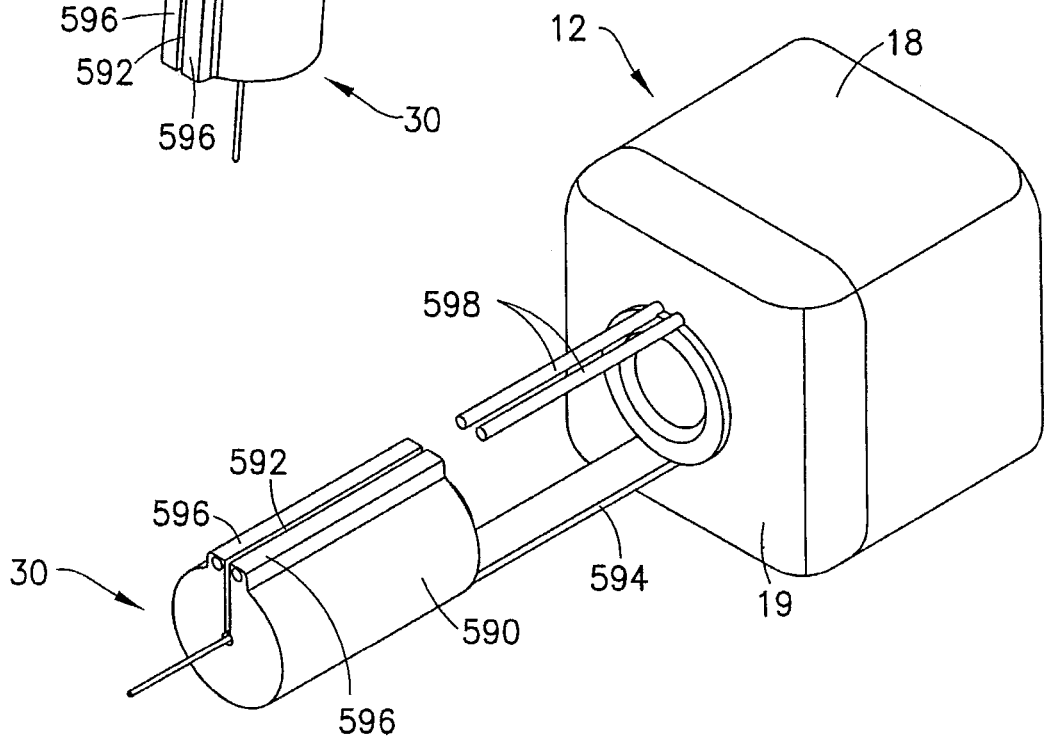

Referring to FIGS. 41A-41C, a fluid injector 12 is shown with a pressure jacket 30 having split-top pressure jacket body 590 that is telescopically and pivotally connected to the face plate 19 of the housing 18 of the fluid injector 12. The split-top pressure jacket body 590 is used to support the bellows member 120 of the bellows syringe 100, and defines a split-top opening 592 to allow insertion and removal of bellows member 120 while a fluid tubing set (not shown) is connected to the discharge port 150 of the bellows member 120. The split-top pressure jacket body 590 is pivotally connected to a slide plate 594 that is telescopically connected to the fluid injector housing 18. The slide plate 594 is extendable outward from fluid injector housing 18 to reach an extended position where the split-top pressure jacket body 590 may be pivoted downward to allow breach-loading of the bellows member 120 into the pressure jacket body 590. The split-top opening 592 in the pressure jacket body 590 may be flanked by two (2) tubular members 596. The tubular members 596 are adapted to receive two (2) tubular support members 598 that extend outward from the face plate 19 of the fluid injector housing 18. In use, once the bellows member 120 is loaded into the pressure jacket body 590, the pressure jacket body 590 may be pivoted upward on the slide plate 594 until the support members 598 are aligned with the tubular members 596 provided on opposing sides of the split-top opening 592. The pressure jacket body 590 may then be telescopically moved toward fluid injector housing 18 by the slide plate 594 and the support members 598 slide into the tubular member 596 to secure the circumferential support around the bellows member 120 and aid in supporting the pressure jacket body 590 to the fluid injector housing of the fluid injector 12.

Referring to FIGS. 42A-42C, a fluid injector 12 is shown with a pressure jacket 30 comprising a split or peel-open pressure jacket body 600 that is telescopically and/or pivotally connected to the face plate 19 and the housing 18 of the fluid injector 12. As in previous embodiments, the pressure jacket 30 is used to support the bellows member 120 of the bellows syringe 100, and is adapted to define a split-top opening 602 to allow insertion and removal of the bellows member 120 while a fluid tubing set (not shown) is connected to the discharge port 150 of the bellows member 120. For example, the pressure jacket body 600 may then be telescopically and pivotally associated with to the fluid injector housing 18, for example, on the slide plate 594 discussed in the previous embodiment, so that the pressure jacket body 600 may be extended outward from the fluid injector housing 18 and pivoted downward to permit breach-loading of the bellows member 120 therein. In this embodiment, the pressure jacket body 600 is resiliently deformable so that when the pressure jacket body 600 is in an extended telescoped position and pivoted downward, the bellows member 120 may be breach-loaded into the into the pressure jacket body 600. The pressure jacket body 600 may be peeled or deflected open along the split-top opening 602 to allow passage of fluid tubing (not shown) through the formed split-top opening 602. The split-top opening 602 may be formed when the two (2) side or edges 604 of the pressure jacket body 600 are pulled apart. Thus, to load the bellows member 120 into the pressure jacket body 600, the pressure jacket body 600 is telescoped outward from the fluid injector housing 18 and pivoted downward and the bellows member 120 is breach-loaded therein. The two (2) sides or edges 604 of the body of the pressure jacket body 600 may then be pulled apart to form the split-top opening 602 to allow passage of a fluid tubing set (not shown) through the formed split-top opening 602. The resilient sides 604 may then be released. As an alternative, as shown in FIG. 42C, the two (2) sides or edges 604 of the body of the pressure jacket body 600 may be provided in an overlapping configuration and are pulled apart to form the split-top opening 602 to allow passage of a fluid tubing set (not shown) through the formed split-top opening 602. The sides or edges 604 may then be released so the resilient pressure jacket body 600 returns to its original state wherein the sides or edges 604 return to their original overlapping configuration; this configuration helps retain the shape of the pressure jacket body 600 when under pressure.

Figure 43A:
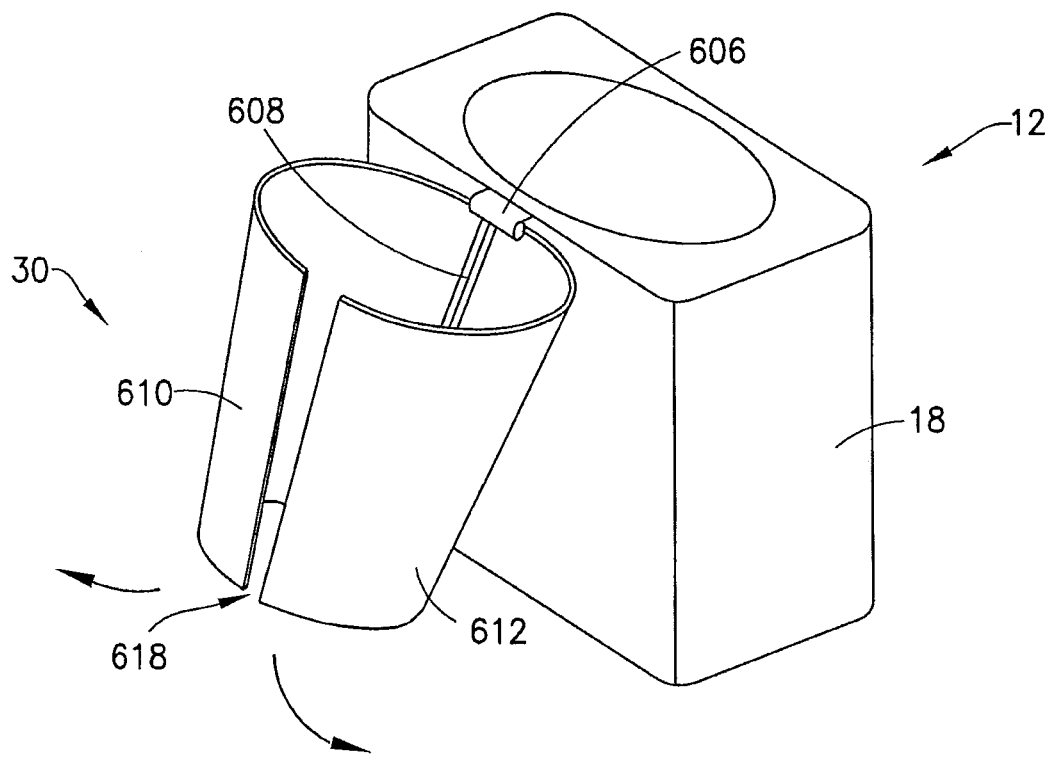
FIGS. 43A-43B are schematic perspective views of a fluid injector with a pivotally connected clam shell pressure jacket hinged to the body of the fluid injector.
Figure 43B:
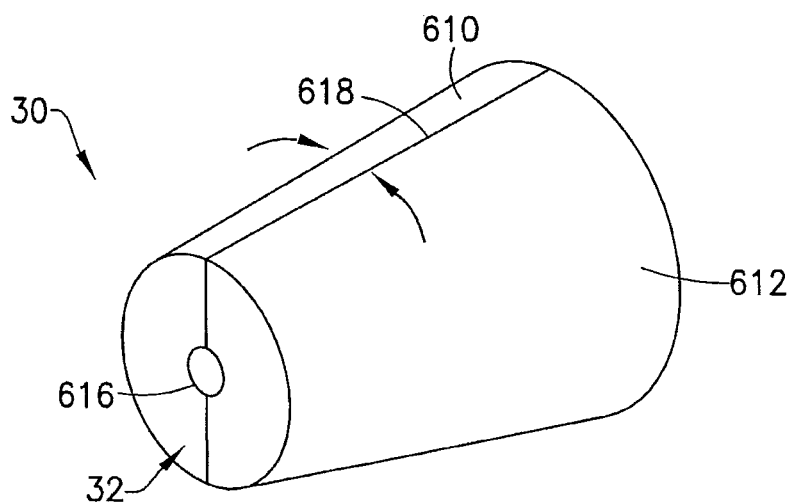

Referring to FIGS. 43A-43B, the cylindrical pressure jacket 30 may be pivotally connected to the housing 18 of the fluid injector 12 by a hinged connection 606. The pressure jacket 30 may be a split-open or clam shell pressure jacket which is opened along a longitudinal hinge joint 608. Thus, the pressure jacket 30 is formed by two (2) pressure jacket portions 610, 612 joined by the longitudinal hinge joint 608. The pressure jacket 30 has a closed front or distal end 32 that defines a central opening or aperture 616 for passage of a fluid tubing set (not shown) connected to the bellows member 120 or another fluid container loaded into the pressure jacket 30. To load the bellows member in the pressure jacket 30, the pressure jacket 30 is pivoted away from the fluid injector housing 18 along the hinged connection 606 and then opened along the longitudinal hinge joint 608. The bellows member 120 is loaded into the pressure jacket 30, while the fluid tubing set is passed through a longitudinal slot 618 formed when the pressure jacket 30 is opened along the longitudinal hinge joint 608.

Figure 44A:
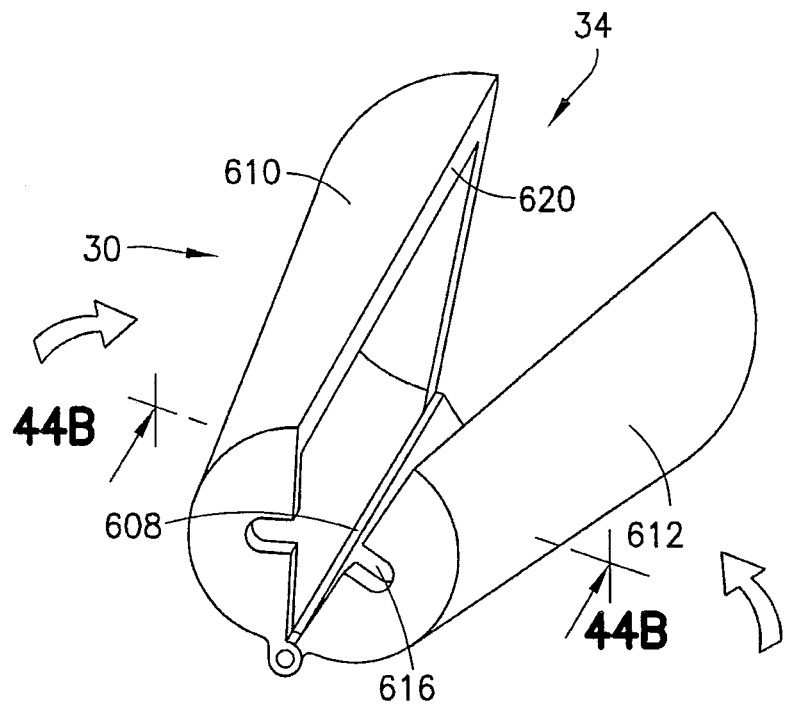
FIG. 44A is schematic perspective view of a clam shell pressure jacket which is held in a closed and locked state by a structure on the bellows member or on a fluid container.
Figure 44B:
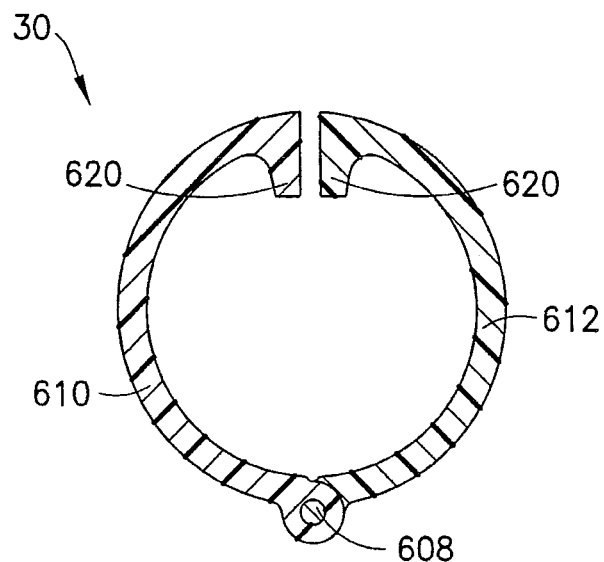
FIG. 44B is a transverse cross-sectional view of the pressure jacket shown in FIG. 44A taken along lines 44B-44B in FIG. 44A.
Figure 44C:
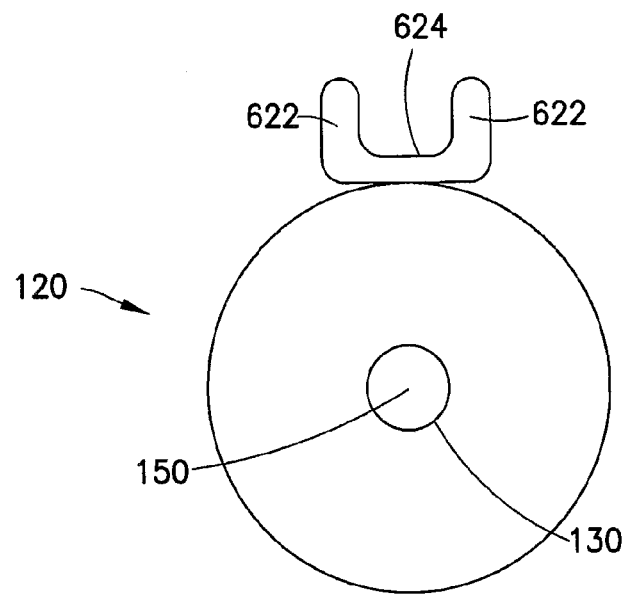
FIG. 44C is a front view of a bellows member or a fluid container adapted to interface with the pressure jacket of FIGS. 44A-44B.
Figure 44D:
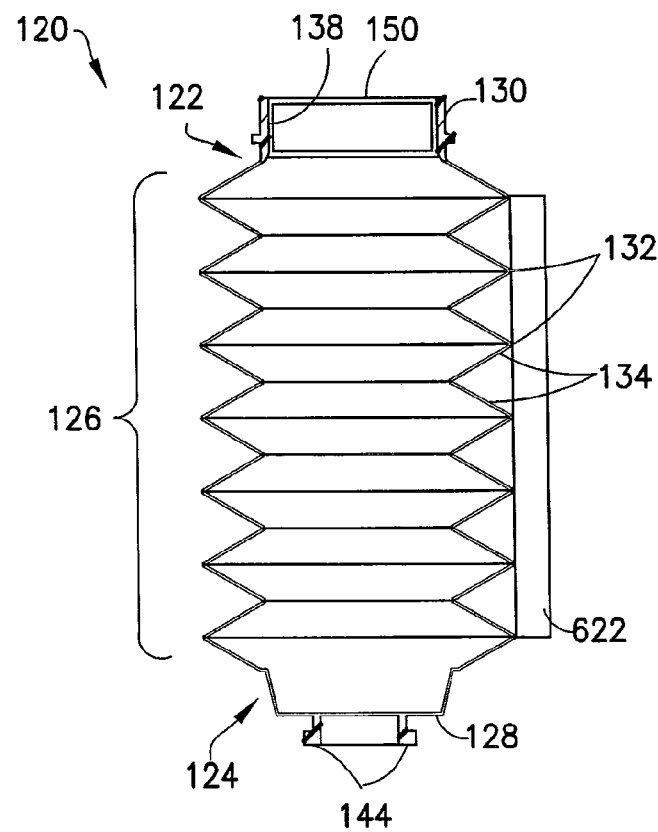
FIG. 44D is a side view of a bellows member or a fluid container adapted to interface with the pressure jacket of FIGS. 44A-44B.

Referring to FIGS. 44A-44D, the pressure jacket 30 is shown according to another embodiment, but having similarities to the pressure jacket 30 described above in connection with FIGS. 43A-43B. The pressure jacket 30 is formed again by two (2) pressure jacket portions 610, 612 joined by a longitudinal hinge joint 608. Additionally, in this embodiment, the pressure jacket portions 610, 612 each have a radially-inward extending flange 620 that extends inward toward the interior of the pressure jacket 30 along the longitudinal slot 618 formed when the pressure jacket 30 is opened along the longitudinal hinge joint 608. In this embodiment, the bellows member 120 or another fluid container adapted for use in the pressure jacket 30 comprises a locking structure, as shown in FIGS. 44C-44D, in the form of two (2) opposed locking flanges 622 that define a U-shaped slot therebetween 624. The U-shaped slot 624 is provided to slidably receive therein the opposed flanges 620 on the pressure jacket portions 610, 612 as the bellows member 120 is loaded into the pressure jacket 30 from the open rear or proximal end 34 opposite the closed front or distal end 32 of the pressure jacket 30. Thus, the locking flanges 622 form a locking structure to maintain the pressure jacket 30 in a closed state. The pressure jacket 30 may be pivotally connected to the fluid injector housing 18 in a similar manner to that shown in FIGS. 43A-43B. The opposed locking tabs 622 may be provided only at the distal end 122 of the bellows member 120, or extend part or all of the length of the bellows portion 126 to receive the opposed flanges 620 of the pressure jacket 30 as illustrated. Alternatively, the locking tabs 622 may be provided additionally or only at the proximal end 124 of the bellows member 120 to receive the opposed flanges 622 provided adjacent the open rear or proximal end 34 of the pressure jacket 30. Moreover, as noted, the locking tabs 622 may be continuous and in the form of opposed flanges along part or all of the length of the bellows member 120 to receive the opposed flanges 622, which may be formed continuously or intermittently along the length of the two (2) pressure jacket portions 610, 612.

Figure 45:
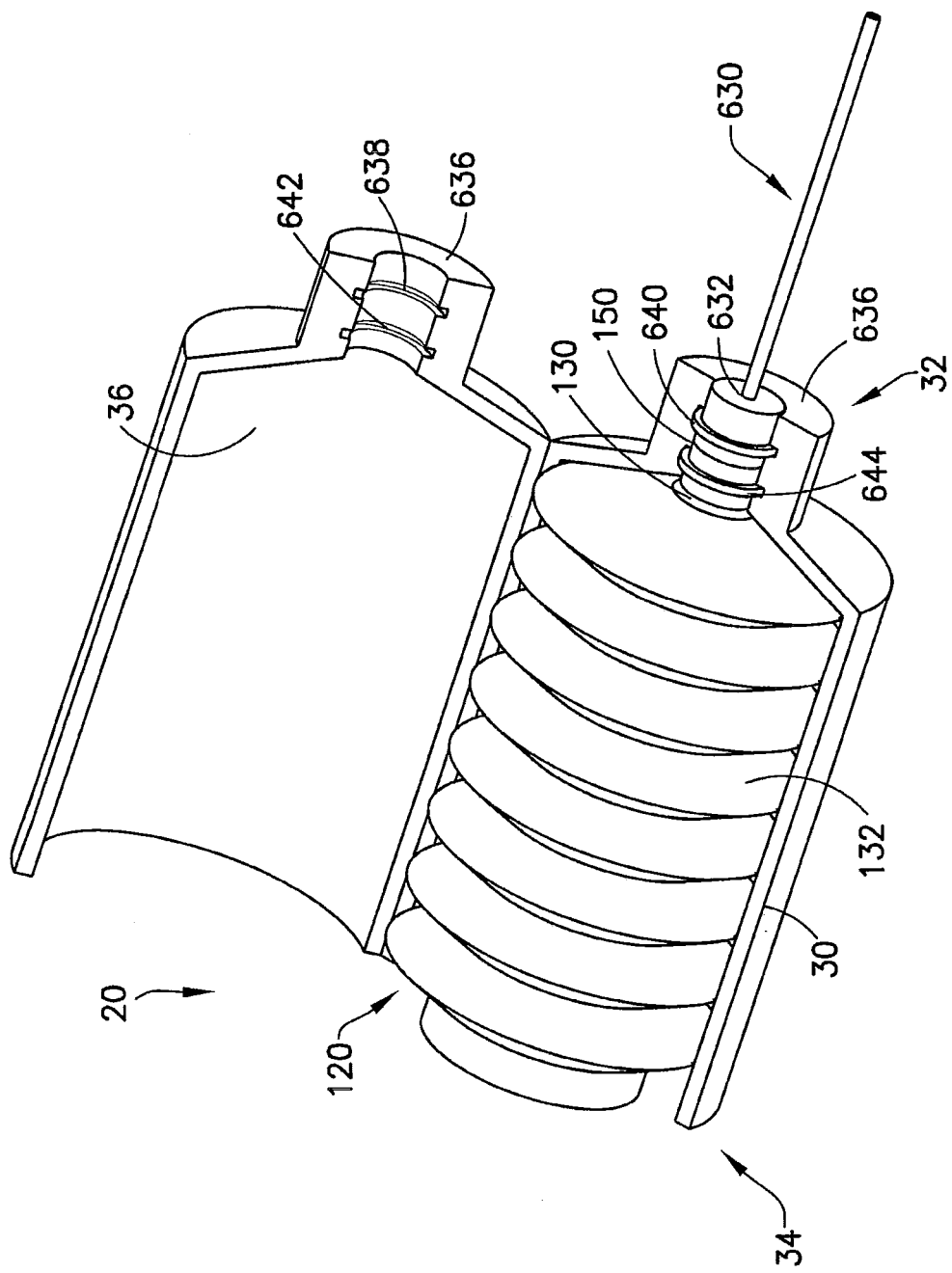
FIG. 45 is a perspective view of a clam shell pressure jacket adapted to maintain a fluid connection between a fluid tubing set and the bellows member when under pressure.

Referring to FIG. 45, the pressure jacket 30, such as the various clam shell opening pressure jacket embodiments set forth in this disclosure, may comprise structure to secure the connection of a fluid tubing set to the discharge port 150 on the bellows member 120, or to another fluid container described in this disclosure. In FIG. 45 a perspective view of the pressure jacket 30 in an opened state is shown to illustrate a concept of using the pressure jacket 30 to radially and axially hold the connection between a fluid tubing set and the discharge port 150. As an illustrative example, the pressure jacket 30 may be the pressure jacket 30 described in connection with FIGS. 43A-43B, but this reference to the embodiment should not be considered as limiting. In FIG. 45, a fluid tubing set 630 having a fluid connector 632 is fluidly connected to the discharge port 150 by any desired method. For example, the fluid connector 632 may comprise a piercing element used to access the discharge port 150. The closed front or distal end 32 of the pressure jacket 30 may define a split-open receiving port or neck 636 for the fluid connector 632 and the discharge neck 130 of the bellows member 130. The receiving port or neck 636 comprises a first or distal receiving recess or groove 638 that receives a radially-outward directed rim or flange 640 on the fluid connector 632, thereby fixing the fluid connector 632 in the receiving port or neck 636 on the pressure jacket closed front or distal end 32. Additionally, the receiving port or neck 636 further comprises a second or proximal receiving recess or groove 642 that receives a similar radially-outward directed rim or flange 644 on the discharge neck 130 on the bellows member 120, thereby also fixing the discharge neck 130 in the receiving port or neck 636 on the pressure jacket closed front end 32. With both the fluid connector 632 and the discharge neck 130 on the bellows member 120 secured in the radial and axial directions in the receiving port or neck 636 in the pressure jacket closed front or distal end 32, the fluid connection interface between the fluid connector 632 and the discharge port 150 on the bellows member 120 is maintained even when the bellows member 120 is under pressure. If desired, the respective locations of the rims or flanges 640, 644 and the respective receiving recesses or grooves 638, 642 may be reversed.

Figure 46:
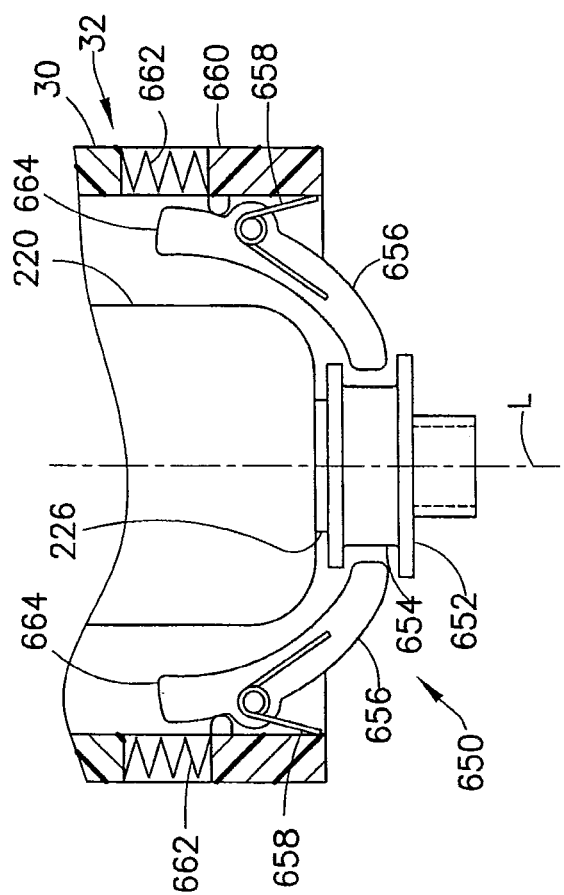
FIG. 46 is a schematic view illustrating a pressure jacket chuck mechanism used to support a fluid connection with the bellows syringe when under pressure according to another embodiment.

Referring to FIG. 46, in another embodiment, a chuck mechanism 650 may be incorporated into an open distal end 32 of the cylindrical body or pressure jacket 30 to engage the discharge port 226 of the fluid container 220, which is formed with an open passageway or opening 240 that is sealed by a fluid connector fitting or element 652 disposed in the discharge port 226 in this embodiment. While a fluid container 220 is illustrated in FIG. 46, the bellows member 120 may also be used in this embodiment. The fluid connector fitting 652 defines an annular recess or groove 654 for engagement by the components of the chuck mechanism 650. The chuck mechanism 650 is adapted to engage the fluid connector fitting 652 so that the fluid can be drawn into the fluid container 220 or bellows member 120 and expelled therefrom while the fluid container 220 or bellows member 120 is held fixed in the pressure jacket 30 by the engagement with the annular recess or groove 654 in the fluid connector fitting 652. The chuck mechanism 650 comprises a plurality of chuck fingers 656 that are spring-biased inward by torsion springs 658 toward a central axis L of the chuck mechanism 650. A release collar 660 is spring-biased outward from the distal end 32 of the pressure jacket 30 by one or more compression springs 662, and the release collar 660 controls operation of the chuck fingers 656. To operate the chuck mechanism 650 to an opened configuration for loading of the bellows member 120 in the pressure jacket 30, a user pushes on the release collar 660 which acts on respective ends 664 of the chuck fingers 656. The chuck fingers 656 pivot radially outward away from the central axis L of the chuck mechanism 650 and disengage from the annular recess or groove 654 in the fluid connector fitting 652 to permit the loading of the fluid container 220 or bellows member 120 or like fluid container into the pressure jacket 30. The user pushes on the release collar 660 against the action of the compression springs 662 to operate the chuck mechanism 650 to the opened configuration or state. When the fluid container 220 or bellows member 120 is loaded into the pressure jacket 30, the user releases the release collar 660 and the action of the compression springs 662 and torsion springs 658 automatically seat the chuck fingers 656 in the receiving recess or groove 654 in the fluid connector fitting 652.

Figure 47:
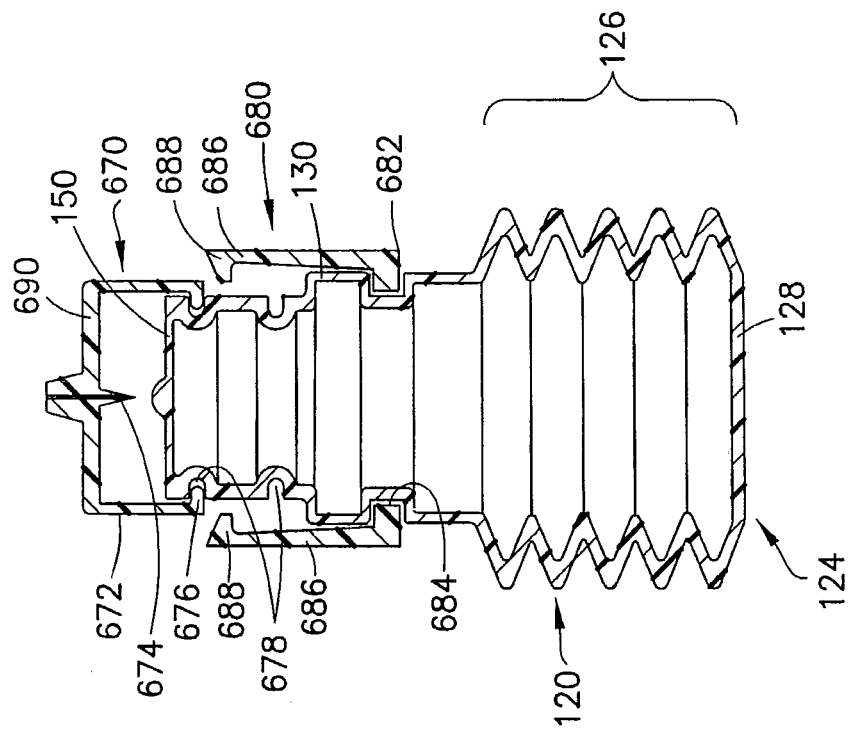
FIG. 47 is a cross-sectional view showing use of an external connector clip used to support a fluid connection with the bellows member and a fluid connector fitting according to another embodiment.

Referring to FIG. 47, another embodiment for securing a fluid connector fitting 670 to the discharge port 150 on the discharge neck 130 of the bellows member 120 is shown. The fluid connector fitting 670 comprises a housing or shield portion 672 that encloses a piercing element or tip 674. The shield portion 672 has a terminal end flange 676 adapted to engage a series of annular distal recesses or grooves 678 in the discharge neck 130 of the bellows member 120. In this embodiment, an external connector clip 680 is disposed on the discharge neck 130. The connector clip 680 has a proximal end 682 thereof seated within an annular recess or groove 684 in the discharge neck 130. The connector clip 680 comprises a plurality of distally-extending spring arms 686 that terminate with tapered end flanges 688.

In use to pierce the discharge port 150, the user presses down on the fluid connector fitting 670 causing the end flange 676 to snap out of engagement with the first or distal recess or groove 678 in the discharge neck 130 of the bellows member 120 and seat into engagement with the second or proximal recess or groove 678 in the discharge neck 130. The movement of the fluid connector fitting 670 causes the piercing element 674 to pierce the discharge port 150 at the end of the discharge neck 130. Further, this movement causes the spring arms 686 to deflect radially outward due to the engagement of the shield portion 672 with the tapered faces on the tapered end flanges 688 on the spring arms 686. The spring arms 686 seat over a closed end 690 of the housing or shield portion 672 of the fluid connector fitting 670 as the end flange 676 on the shield portion 672 seats into engagement with the second or proximal recess or groove 678 in the discharge neck 130, and the spring arms 686 secure the fluid connection established between the fluid connector fitting 670 and the discharge port 150 on the bellows member 120 and, further, limit the possible reuse of the bellows member 120.

Figure 48B:
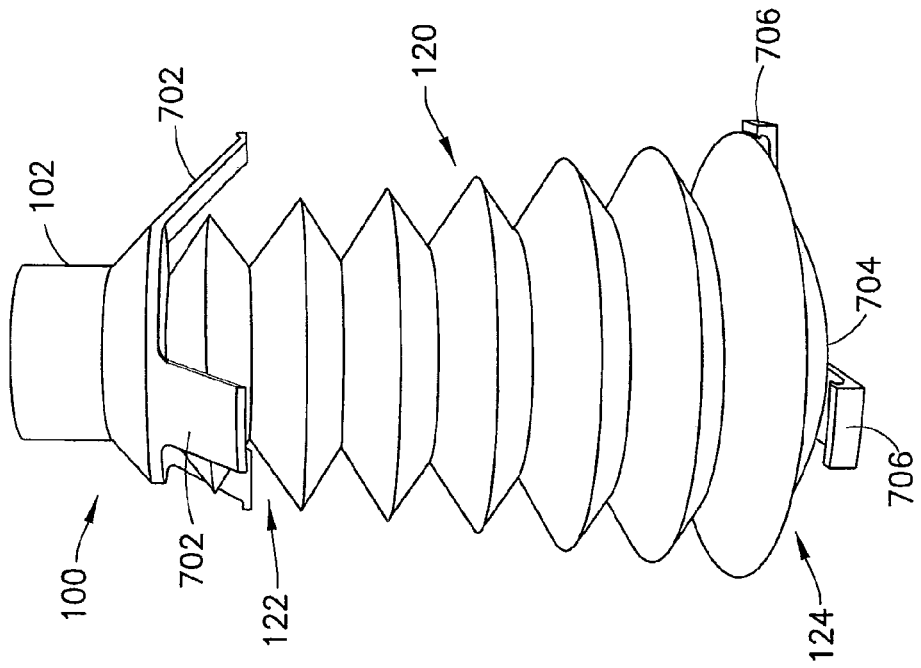
FIGS. 48A and 48B are perspective views showing a pyramidal-shaped bellows syringe shown in a collapsed state and an extended state, respectively.
Figure 48A:
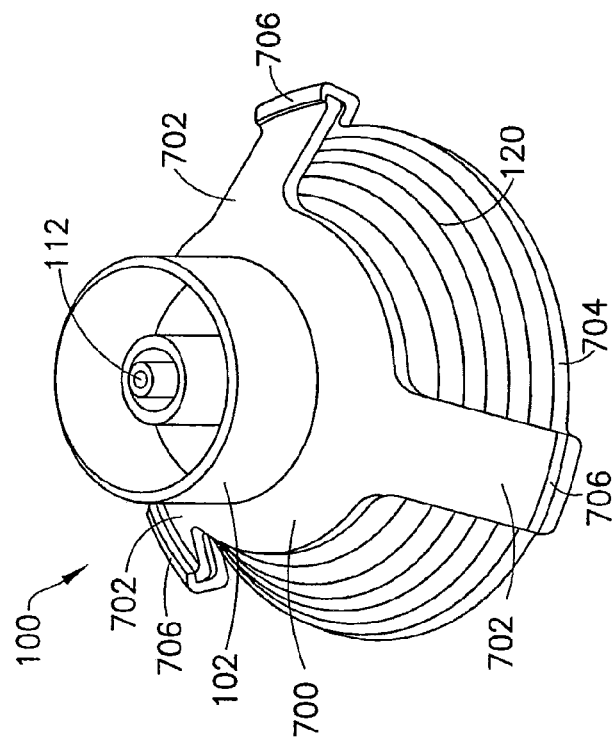

Referring to FIGS. 48A-48B, a pyramidal-shaped bellows syringe 100 is shown. In this embodiment, the cap member 102 comprises a tapered collar 700 with three (3) depending tab members 702. Additionally, a base member or element 704 is provided at the proximal end 124 of the bellows member 120. The base member 704 comprise threes (3) radial catch members 706 adapted to engage the tab members 702 on the tapered collar 700. The engagement of the tab members 702 with the catch members 706 secures the bellows syringe 100 in the collapsed state shown in FIG. 48A. The release of the tab members 702 from the catch members 706 may be done automatically when the bellows syringe 100 is interfaced with the pressure jacket 30, for example, pursuant to any of the concepts described previously or hereinafter.

Figure 49A:
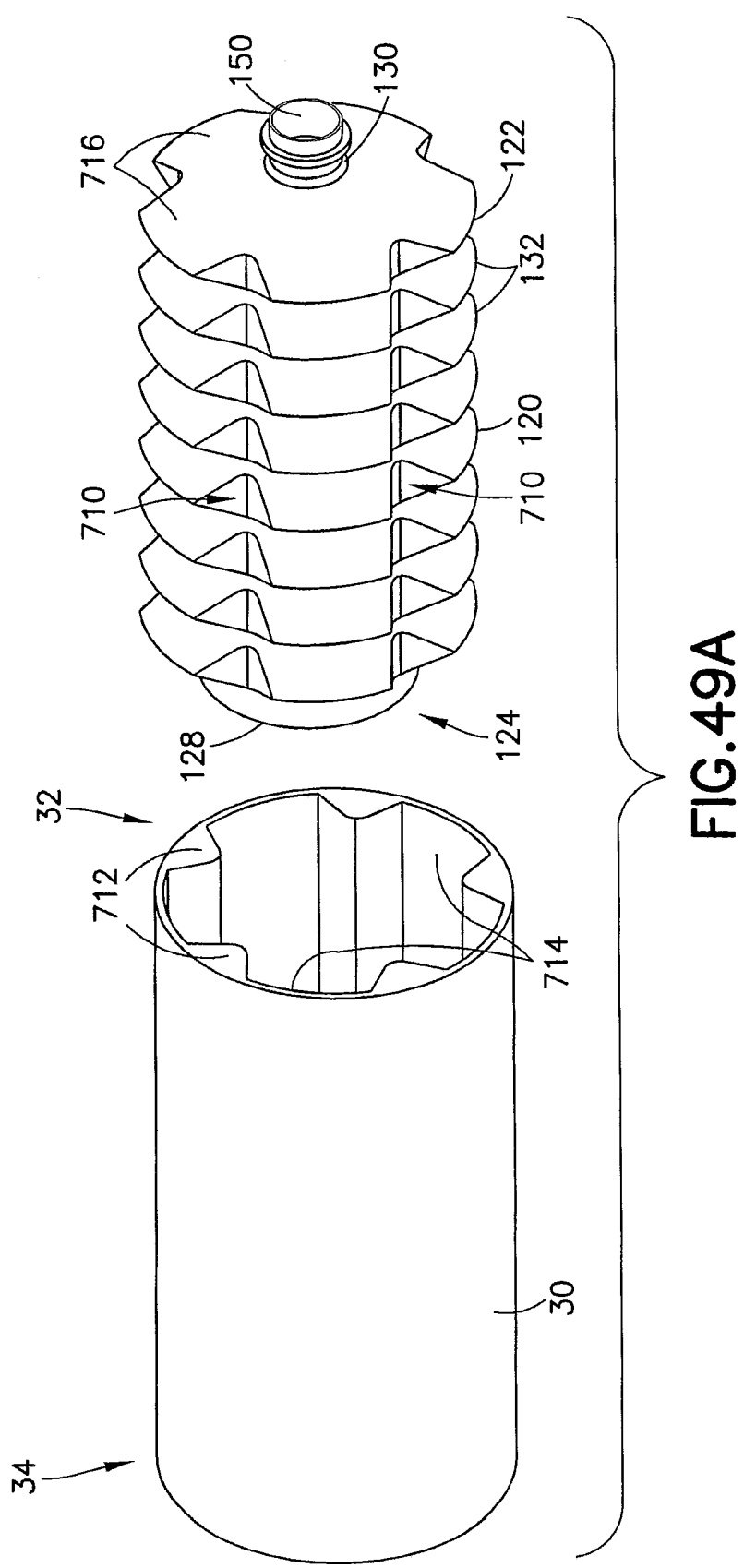
FIG. 49A is an exploded perspective view showing another embodiment of the bellows member disposed within a pressure jacket comprising longitudinal internal support ribs or elements.

Referring to FIGS. 49A-49D, another embodiment of the bellows member 120 and pressure jacket 30 with inter-engaging longitudinal features is shown. In this embodiment, the body of the bellows member 120 is generally scallop-shaped in transverse cross section, as best shown in FIG. 49B, to define a series of longitudinal recesses 710. The interior of the pressure jacket 30 is specifically shaped to receive the scallop-shaped bellows member 120 and comprises a series of longitudinal ridges 712 with intervening or separating longitudinal channels 714 shaped to receive the bellows member 120. The longitudinal ridges 712 fit within the longitudinal recesses 710 in the body of the bellows member 120 as shown in FIG. 49C and support the bellows sections or rings 132 along the longitudinal and radial directions of the bellows member 120. Thus, the bellows member 120 is keyed to fit within the interior of the pressure jacket 30 in this embodiment. The longitudinal ridges 712 also strengthen the pressure jacket 30. While not shown, an end cap or cover may be used to enclose the bellows member 120 in the pressure jacket 30. Further, the longitudinal recesses 710 in the bellows member 120 cause the bellows member 120 to define a series of individual lobes 716 as shown in FIG. 46B.

Figure 50:
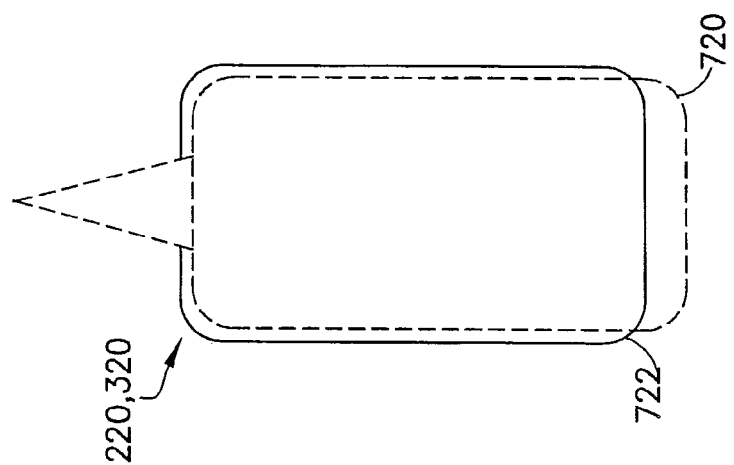
FIG. 50 is a perspective view of a fluid container having an intentionally longer axial length than a receiving pressure jacket.

Referring to FIG. 50, the bellows member 120 or any of the fluid containers described hereinabove, such as containers 220, 320 may be made longer, in the unfilled state, than the space available in the receiving pressure jacket 30 as illustrated by dashed line 720 in FIG. 50. As a result of this intentionally-extended axial length, when the bellows member 120 or fluid container is loaded into the pressure jacket 30, the disposable component is always seated or "sprung" against the piston head 16 of the piston element 14 of the fluid injector 12, particularly when the piston element 14 is retracted to its rearmost position in the fluid injector. The solid line 722 in FIG. 50 represents the volume of the pressure jacket 30.

Figure 51A:
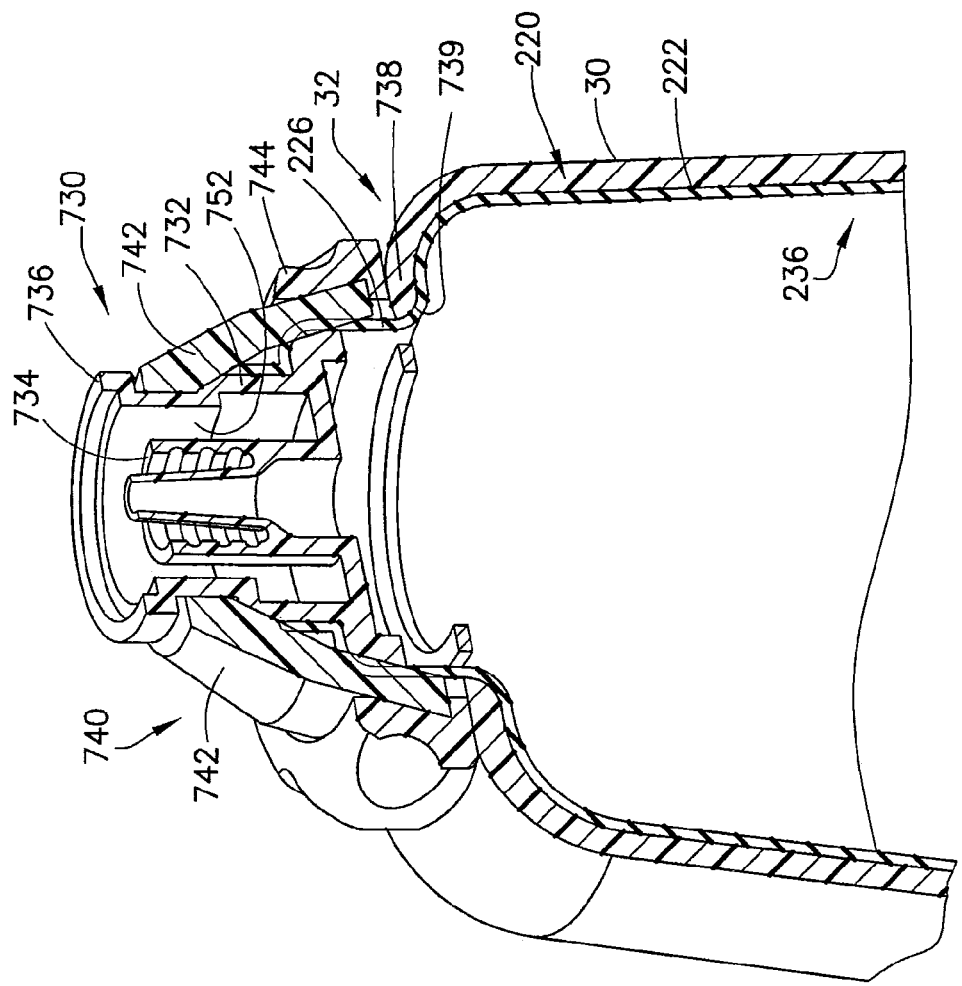
FIG. 51A is a perspective and partial cross-sectional view of a fluid container having a fluid connector fitting and a chuck mechanism used to secure a fluid connection to the fluid connector fitting.

Referring to FIGS. 51A-51C, a fluid container such as fluid container 220 is shown with a luer-type fluid connector fitting 730 situated in the discharge port 226 at the distal end 224 of the fluid container body 222. The fluid connector fitting 730 comprises an annular body 732 surrounding a luer-type fluid connector element 734. The annular body 732 defines an integral end lip or rim 736. A pressure jacket 30 adapted to accept the fluid container 220 is also shown and comprises a distal end 32 with a neck or collar 738 defining a central opening 739 for the fluid connector fitting 730 to pass therethrough. A drill-type chuck mechanism 740 is associated with the neck or collar 738 and surrounds and engages the fluid connector fitting 730. The chuck mechanism 740 is used to secure the connected engagement between an opposing luer-type fluid connector (not shown) and the luer-type fluid connector element 734 disposed in the annular body 732 by radially compressing the annular body 732 and thereby exerting radial pressure on the two connected luer-type connectors.

The chuck mechanism 740 comprises several locking fingers 742 that are adapted to engage with the end lip or rim 736 on the annular body 732. The locking fingers or chucks 742 are similar to locking fingers or chucks on a conventional hand-held power drill. The locking fingers or chucks 742 are actuated by a locking collar 744. The locking collar 744 has internal tabs 746 which force radial tabs 748 on the neck or collar 738 of the pressure jacket 30 into a slot or groove 750 in the exterior of the annular body 732 when the locking collar 744 is rotated in a tightening direction. This tightening rotation of the locking collar 744 causes the locking fingers 742 to press radially inward on the annular body 732 thus compressing an internal abutment surface or wall 752 in the annular body 732 that is disposed opposite of the connection site for the luer-type fluid connector element 734 and an opposing luer-type connector element (not shown). The radial compression of the abutment surface or wall 752 assists in securing this fluid connection when under pressure. If desired, the abutment surface or wall 752 may comprise radial structures or components to physically engage the fluid connector element 734 and/or an opposed connector element (not shown) engaged therewith. While the foregoing embodiment was described in connection with fluid container 220 comprising a tapered sidewall 236, the foregoing embodiment may be adapted for use with the bellows member 120 or any straight-walled fluid container 220, 320 described previously.

Referring to FIGS. 52A-52B, a fluid injector 12 is shown that is adapted to operate with an open-top pressure jacket 30. The pressure jacket 30 is supported by a hinged front or face plate 760 which is pivotally connected to the fluid injector housing 18. The hinged front or face plate 760 defines a U-shaped opening 762 to receive the proximal end 34 of the pressure jacket 30. The pressure jacket 30 in this embodiment is specifically adapted for use with the fluid container 220 comprising a tapered sidewall 236, but this embodiment may also be adapted for use with the bellows member 120 described previously or any straight-walled fluid container. The proximal end 34 of the pressure jacket 30 may comprise a rear circumferential flange 764 for interference engagement with the U-shaped opening 762. The fluid injector housing 18 further has a top face plate 766 above the hinged face plate 760 that has an outward extending roof portion 768 with a collar locking element 770. The top face plate 766 further has a slide lock element 772 that is slidable vertically along the top face plate 766 along one side of the pressure jacket 30. The slide lock element 772 is adapted to engage a locking appendage 774 on the hinged face plate 760 to secure the hinged face plate 760 in the closed position seated against the fluid injector body 18.

The pressure jacket 30 defines a top opening 780 for receiving the fluid container 220 therein. In this embodiment, the fluid container 220 may comprise a fluid connector fitting or element 242 to engage with a fluid tubing set 782 with an end or terminal fluid connector fitting 784. The distal end 32 of the pressure jacket 30 defines a front opening for 786 for passage of the fluid tubing set 782 therethrough. A locking ring 790 is provided on the distal end 32 of the pressure jacket 30 and is used to secure the pressure jacket 30 to fluid injector housing 18 when the hinged face plate 760 is in the closed position. The locking ring 790 is adapted to mechanically lock with the collar locking element 770 by rotating the locking ring 790 to cause internal structures or elements (not shown) on the locking ring 790 to engage the collar locking element 770. In use, the fluid container 220 is loaded into the pressure jacket 30 through the top opening 780 when the hinged face plate 760 is pivoted to the position shown in FIG. 52A. The fluid tubing set 782 may be previously connected to the fluid connector fitting or element 242 on the fluid container 220, and the tubing for this set 782 may be passed through the front opening 786 in the distal end 32 of the pressure jacket 30. The hinged face plate 760 may be pivoted to the closed position shown in FIG. 52B and the slide lock element 770 on the top face plate 766 may be slid into locking engagement with the locking appendage 774 on the hinged face plate 760, securing the same to the fluid injector housing 18 and further covering the top opening 780 in the pressure jacket 30 with the roof portion 768 extending outward from the top face plate 766. The locking ring 790 on the distal end 32 of the pressure jacket 30 may be rotated to secure the pressure jacket 30 to the roof portion 768 extending outward from the top face plate 766. The locking ring 790 defines a slot 792 for passing tubing from the fluid tubing set 782 therethrough during the loading process.

Figure 53:
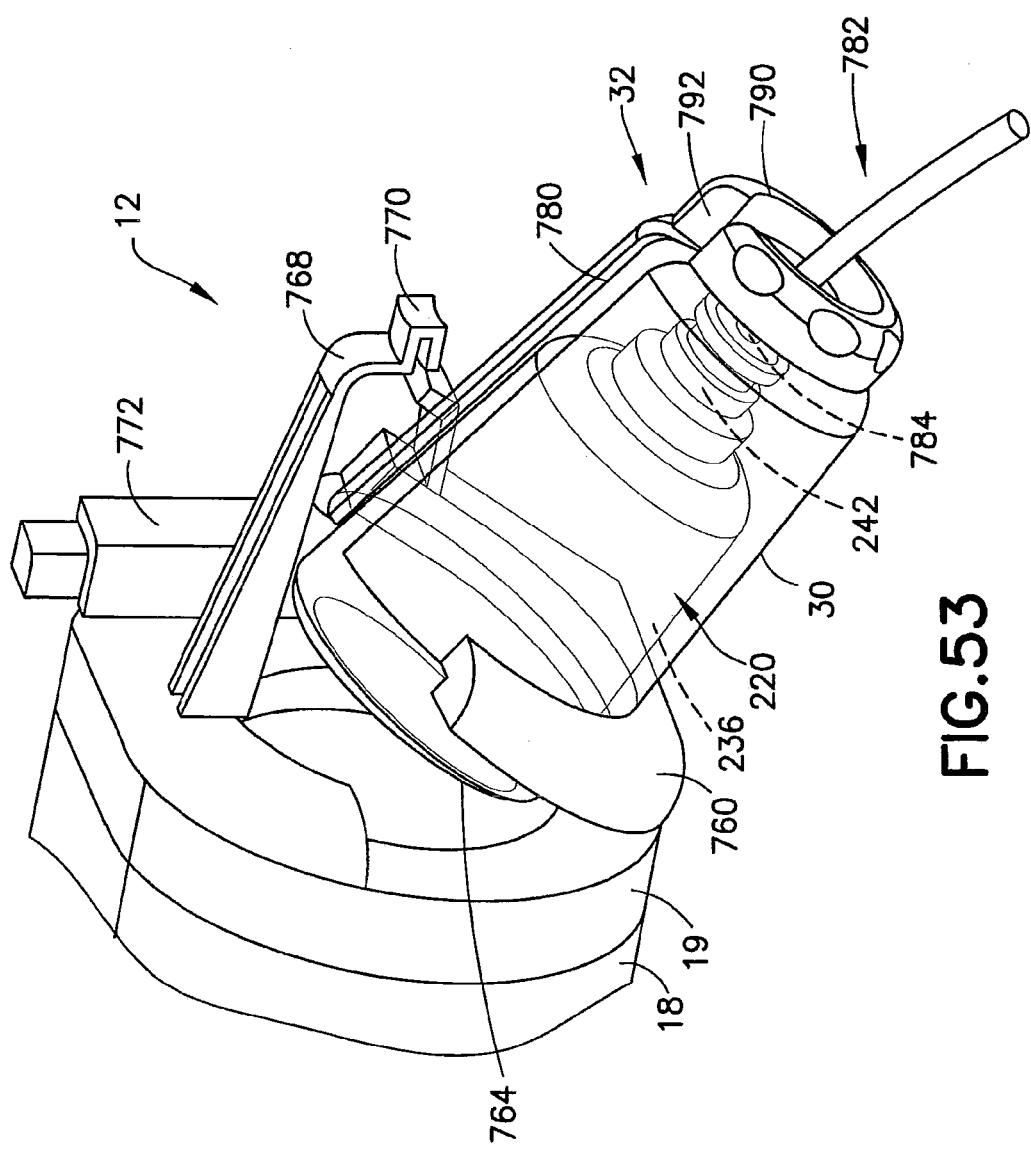
FIG. 53 is a perspective view of a fluid injector in which a split-top pressure jacket is hinged to the fluid injector housing and another embodiment of the locking ring is used to secure the pressure jacket to the fluid injector housing in the closed position.

Referring to FIG. 53, a variation of the foregoing embodiment pressure jacket 30 is shown in which the top opening 780 is formed as a split-top opening. In this embodiment, the fluid container 220 is breach loaded into the open proximal end 34 of the pressure jacket 30 and the tubing of the fluid tubing set 782 is passed through the split-top opening 780. The locking ring 790 in this embodiment also defines a slot 792 for passing the tubing of the fluid tubing set 782 therethrough. Additionally, in this embodiment, the roof portion of the top face plate 766 is formed as an appendage to enclose the split-top opening 780 in the pressure jacket 30 and the slot 792 in the locking ring 790. Further, the top face plate 766 and hinged face plate 760 are generally ring-shaped in this embodiment. Other than the foregoing specified differences, the embodiments of FIGS. 52A-52B and FIG. 53 are substantially identical.

Referring to FIGS. 54A-54D, another embodiment of the pressure jacket 30 is shown having a split or clam shell configuration. In this embodiment, the pressure jacket 30 comprises two (2) opposed portions or sections 796, 798, with the first portion or section 796 fixed to and extending outward from the face plate 19 of the fluid injector housing 18. The second pressure jacket portion 798 has an end 800 pivotally connected to a distal end 802 of the first pressure jacket portion 796, so that the second pressure jacket portion 798 opens upward from the first pressure jacket portion 796 to form a mouth opening 804 facing the fluid injector housing 18. The bellows member 120 or one of the fluid container embodiments described previously may be top-loaded into the first or lower pressure jacket portion 796 through the mouth opening 804. A suitable opening (not shown) may be provided in the closed distal end 32 of the pressure jacket 30 to permit fluid connecting tubing (not shown) to be connected to the disposable component held in the first and second pressure jacket portions 796, 798.

Referring to FIG. 55, an embodiment of the bellows member 120 of the bellows syringe 100 is shown that has a first pair of outward-extending radial tabs 810 at the distal end 122, such as extending outward from the discharge neck 130, and a second larger pair of outward-extending radial tabs 812 at the proximal end 124. The respective pairs of radial tabs 810, 812 may engage corresponding receiving slots (not shown) in the various embodiments of the pressure jacket 30 set forth in this disclosure. The respective pairs of radial tabs 810, 812 are of different sizes so that the bellows member 120 can be keyed into the pressure jacket 30 in only one orientation, hence, the corresponding receiving slots in the pressure jacket 30 are formed to only accept the corresponding pairs of radial tabs, either radial tabs 810 or radial tabs 812.

Figure 56A:
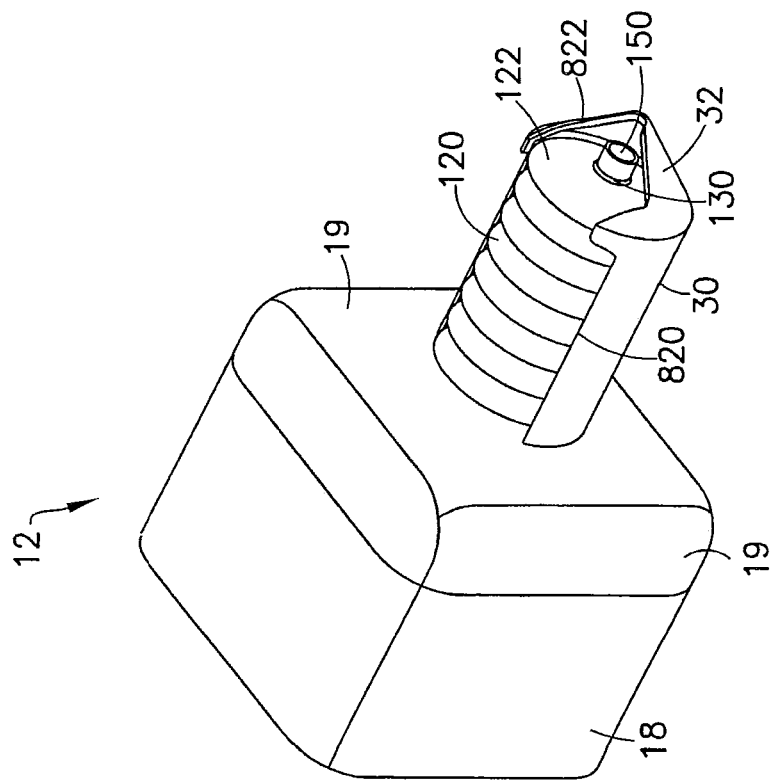
FIG. 56A is a perspective view of a fluid injector having a pressure jacket with a top opening in which a disposable fluid container or bellows member is top-loaded into the pressure jacket.
Figure 56B:
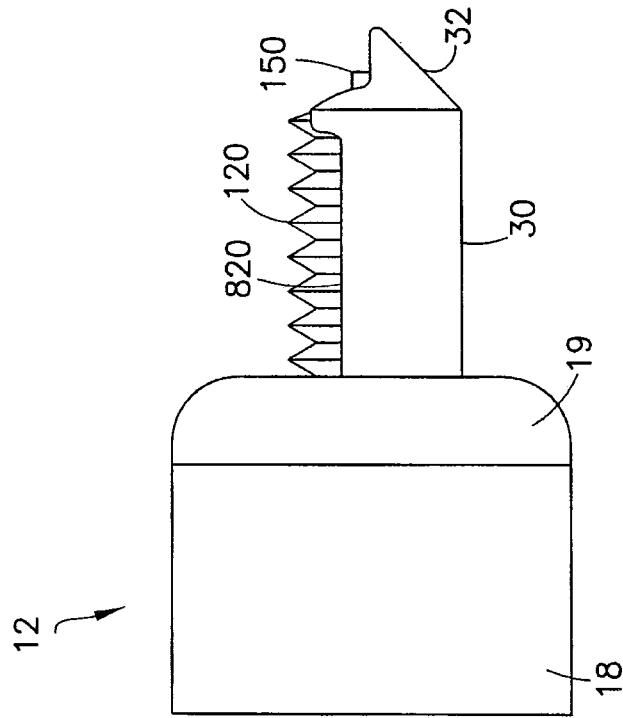
FIG. 56B is a side view of the fluid injector of FIG. 56A.

Referring to FIGS. 56A-56B, a fluid injector 12 is shown in which the top of the pressure jacket 30 is open to define a top opening 820 to accept the bellows member 120 or another fluid container therein. The pressure jacket 30 has a partially closed distal end wall 32 that has a conical shape to accept a similarly shaped distal end 122 of the bellows member 120, or a similarly shaped distal end 224 of fluid container 220. The conical distal end 32 defines a vertical opening 822 so that tubing associated with a fluid tubing set (not shown) may be passed through the vertical opening 822 as the bellows member 120 is loaded into the pressure jacket 30. The disposable container in this embodiment, such as bellows member 120 or fluid containers 220, 320, may be loaded into the pressure jacket 30 in a similar manner to a caulking tube being loaded into a caulking gun, with the pressure jacket 30 and conical distal end 32 thereof having a similar configuration to a mechanical caulking gun.

Figure 57:
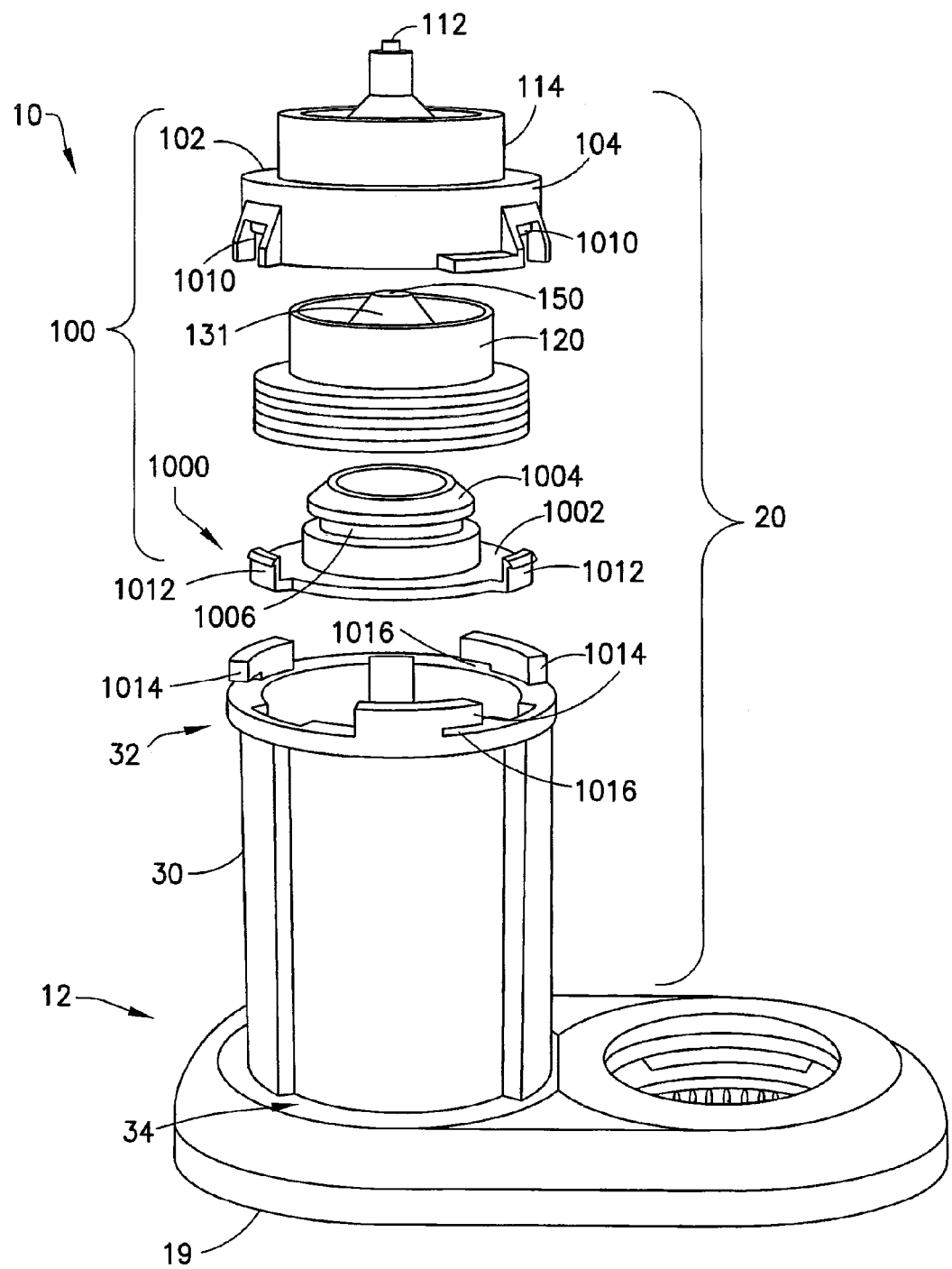
FIG. 57 is a perspective and exploded view of another embodiment of the bellows syringe further comprising a base member and connected to a pressure jacket.
Figure 58:
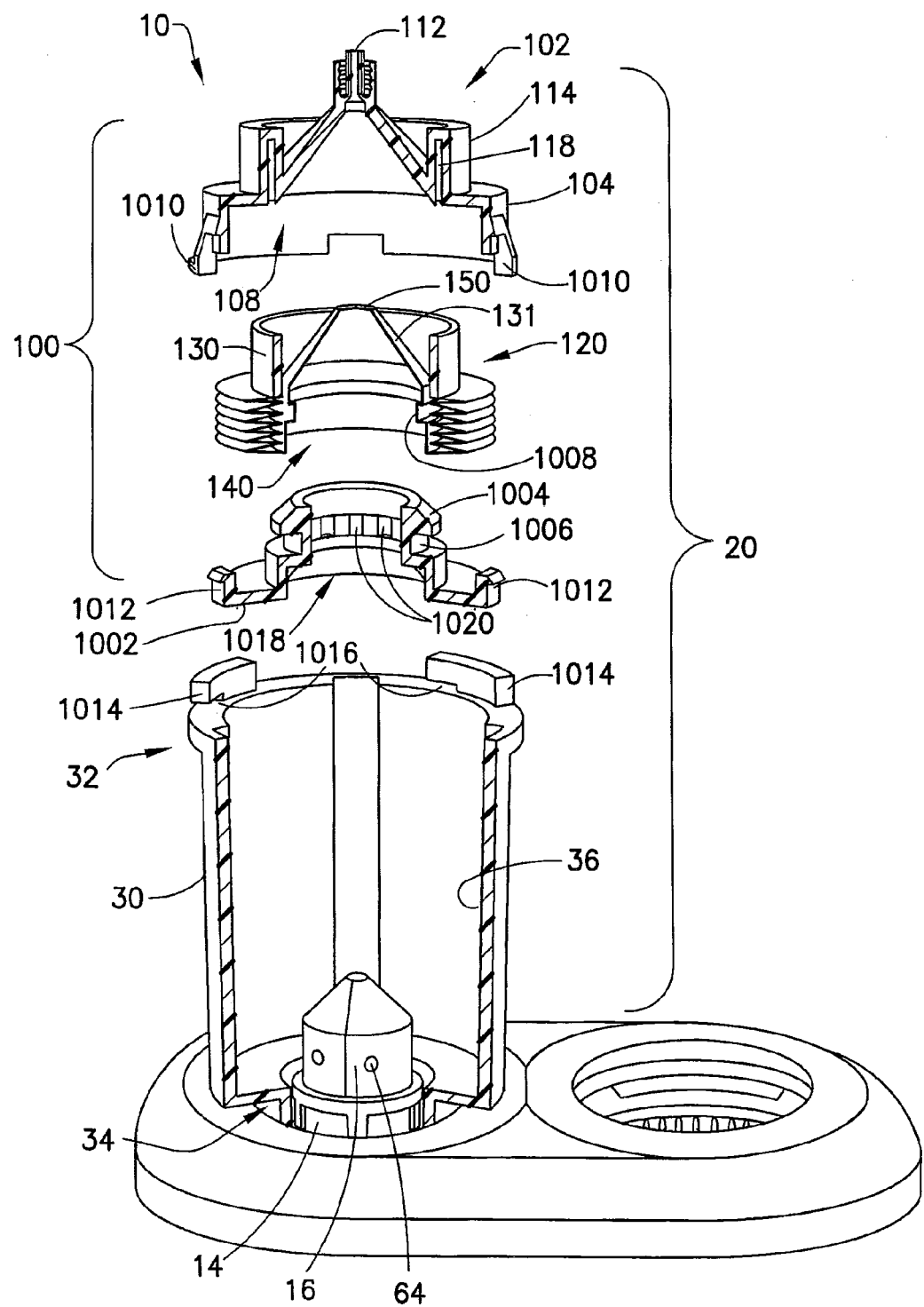
FIG. 58 is a perspective, exploded, and partial cross-sectional view of the embodiment shown in FIG. 57.

Referring to FIGS. 57-66, another embodiment of the bellows assembly 20 as shown and discussed in connection with FIGS. 1-3 and 7 is depicted in connection with a fluid injector face plate 19 of the fluid injector 12. In view of the similarities in the present embodiment in comparison to the embodiment shown in FIGS. 1-3 and 7, only specific differences will be discussed herein. In the present embodiment, the bellows syringe 100 comprises the cap member 102, the bellows member 120 and, now, a base member 1000 adapted to engage the bellows member 120 and the cap member 102. The base member 1000 is formed with a flat plate portion 1002 and a central annular portion 1004 defining a circumferential exterior groove 1006. The central annular portion 1004 is adapted to seat within the receiving end pocket 140 in the bellows member 120, and the receiving end pocket 140 comprises a cooperating internal rim or rib 1008 for engaging the circumferential exterior groove 1006. The bellows member 120 is again intended to be disposed within the interior cavity 106 in the cap member 102 and held therein in a compressed, pre-use state. However, in the present embodiment, the retaining tabs 110 formed as part of the skirt portion 104 of the cap member 102 in the previous embodiment are now replaced by receiving catch members 1010 on the skirt portion 104. The plate portion 1002 comprises upward-extending retaining tabs 1012 which engage the receiving catch members 1010 on the skirt portion 104 to maintain the bellows member 120 in the compressed or pre-use state. Thus, the bellows member 120 is seated onto the annular portion 1004 of the base member 1000 in this embodiment, with the annular portion 1004 disposed within the end pocket 140 in the bellows member 120 and the cooperating internal rim or rib 1008 in the end pocket 140 engaged in the circumferential exterior groove 1006 in the annular portion 1004. Further, the bellows member 120 is held in the compressed or pre-use state by the inter-engagement between the upward-extending retaining tabs 1012 on the base member 1000 with the receiving catch members 1010 on the skirt portion 104 of the cap member 102. Thus, in this embodiment retaining tabs 1012 are in the opposite location than the tab members 110 of the embodiment shown in FIGS. 1-3 and 7. Moreover, it will be appreciated that the locations for the retaining tabs 1012 and the catch member 1010 may be reversed if desired. Additionally, the bellows member 120 may comprise a conical portion 131 that seats into the interior cavity 108 of the cap member 104; the conical portion 131 defines the discharge port 150, as shown in FIGS. 57-58.

In the present embodiment, the distal end 32 of the pressure jacket 30 is modified to comprise a plurality of tab members 1014 each defining a lateral or transverse slot 1016, generally formed as bayonet slots. The flat plate portion 1002 is adapted to engage the bayonet or transverse slots 1016 to secure the bellows syringe 100 to the pressure jacket 30. The proximal end 34 of the pressure jacket 30 is adapted to engage the face plate 19 of the fluid injector 12 in any suitable manner. Further details relating to desirable mounting structures used to properly interface the pressure jacket 30 with the fluid injector 12 may be found in the Medrad, Inc. patents incorporated by reference previously, which discuss interfacing features for securing a Stellant® CT syringe to a Stellant® fluid injector. Additionally, the piston head 16 of the piston element 14 shown in various views in FIGS. 57-66 may have the radially-extendable retaining pins 64 discussed previously in connection with FIGS. 6A-6F, and the overall shape of the piston head 16 shown in FIGS. 6A-6F.

Figure 59:
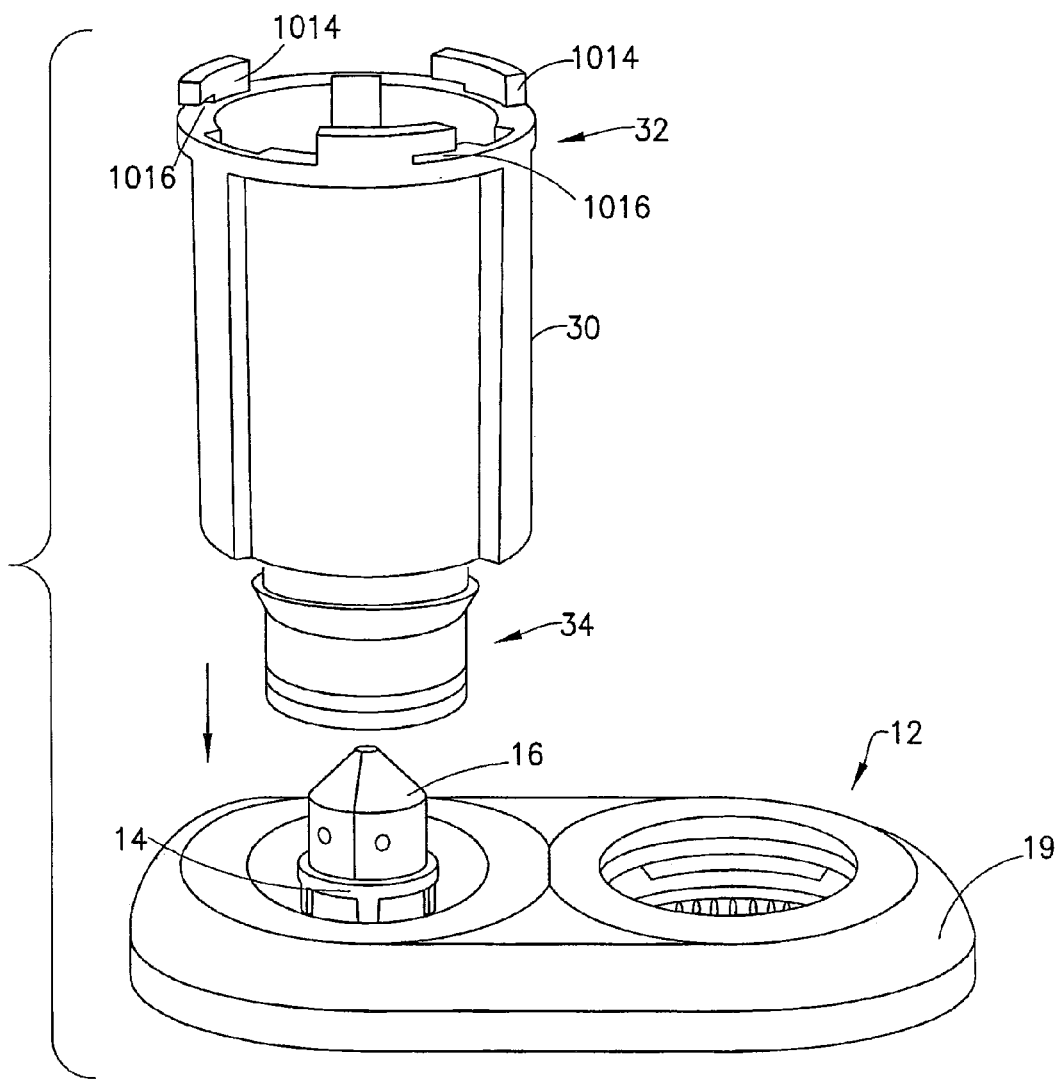
FIG. 59 is a perspective and exploded view showing connection of the pressure jacket to a fluid injector face plate for the embodiment shown in FIGS. 57-58.
Figure 60:
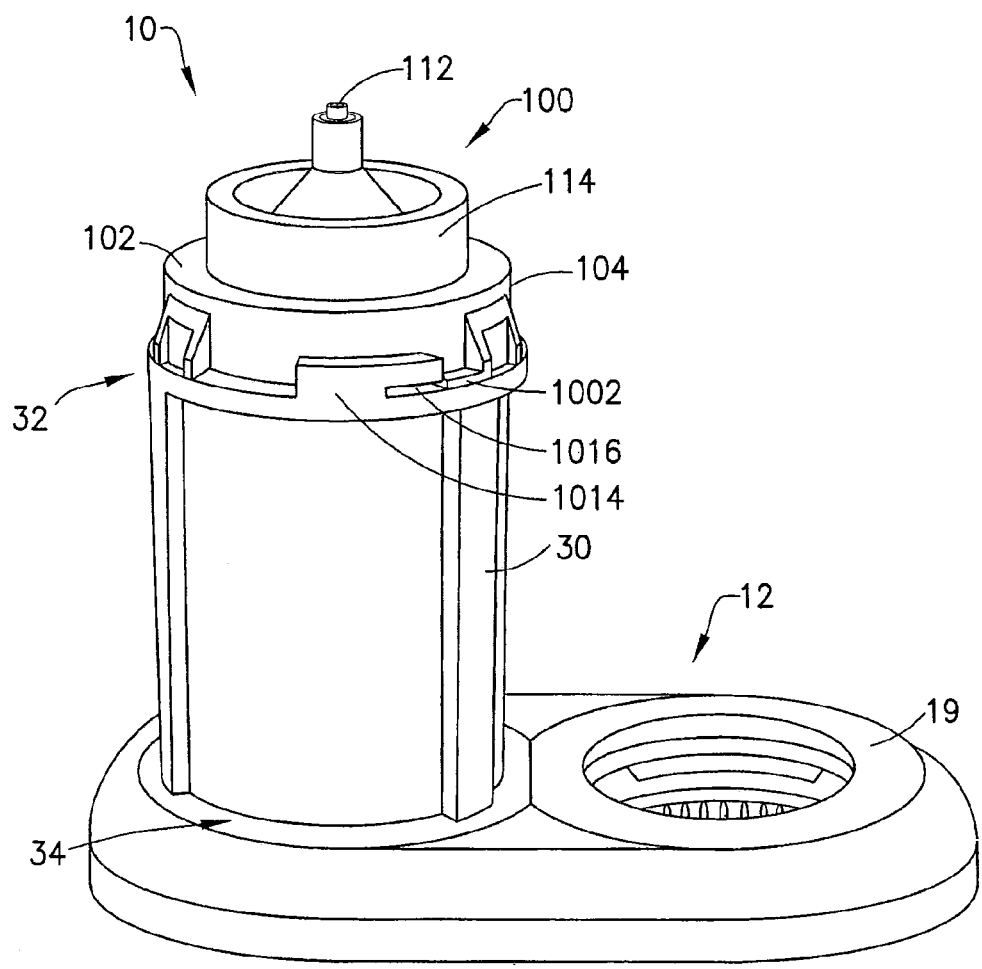
FIGS. 60-61 are sequential perspective views showing attachment of the bellows syringe to the pressure jacket for the embodiment shown in FIGS. 57-58.
Figure 61:
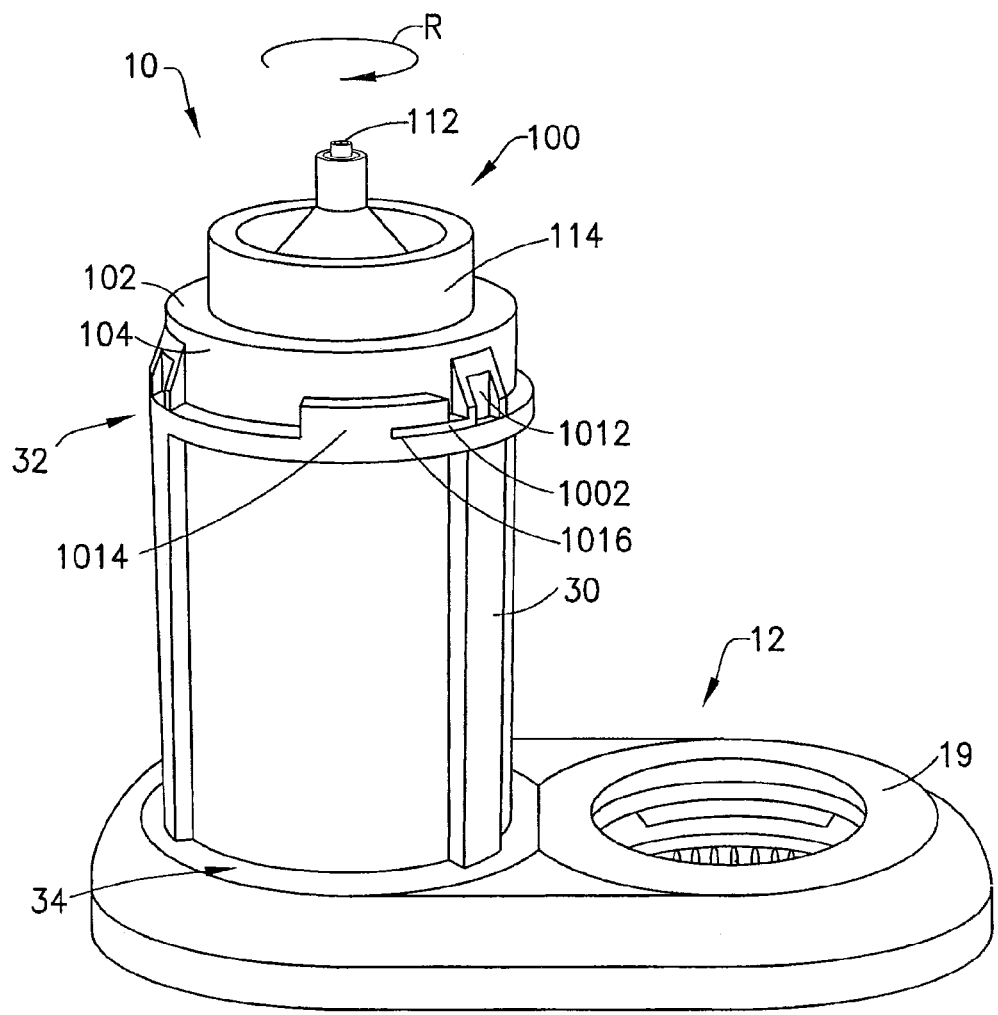
Figure 62:
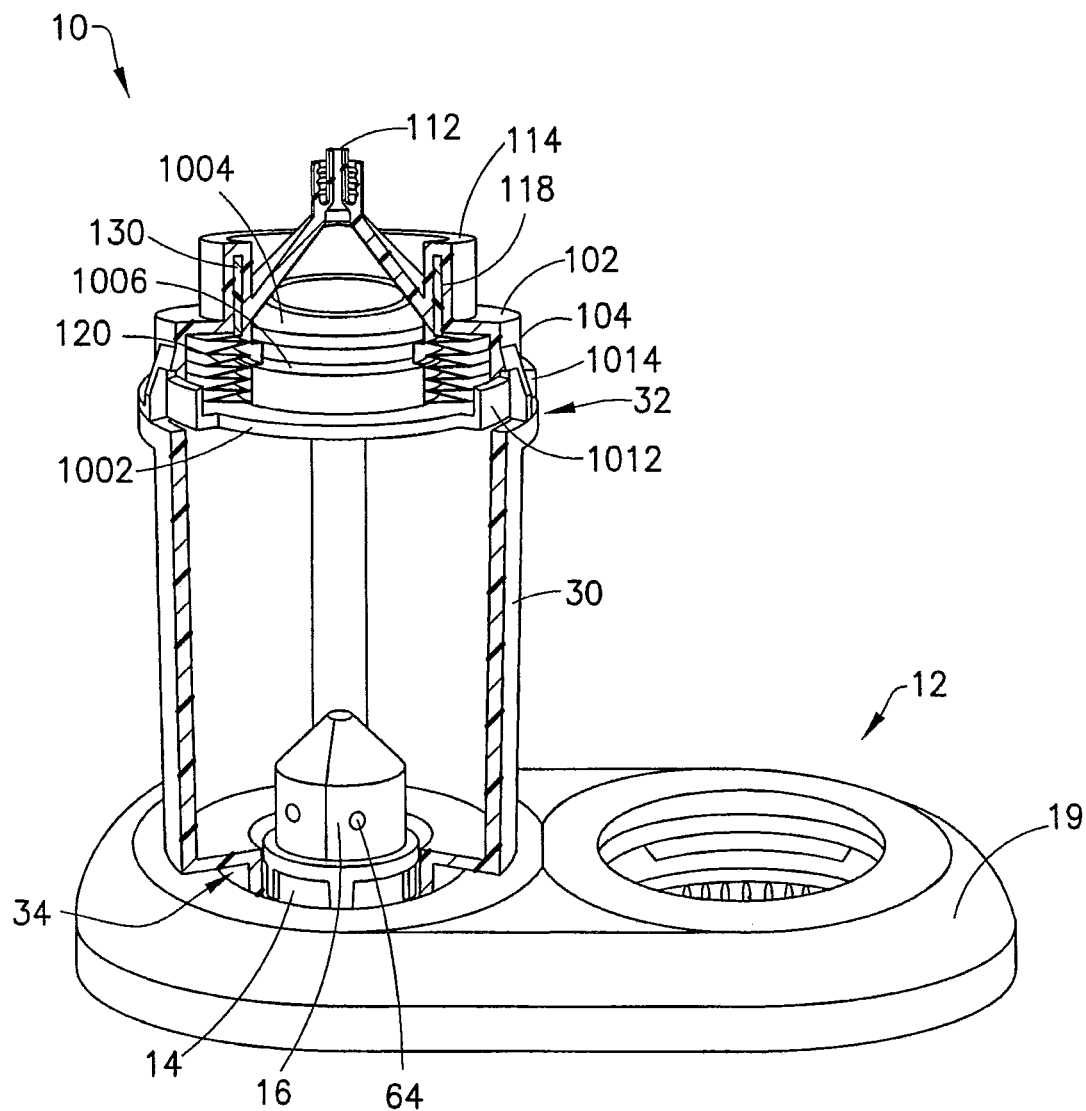
FIGS. 62-64 are sequential perspective and partial cross-sectional views showing operation of the bellows syringe on the pressure jacket for the embodiment shown in FIGS. 57-58.
Figure 63:
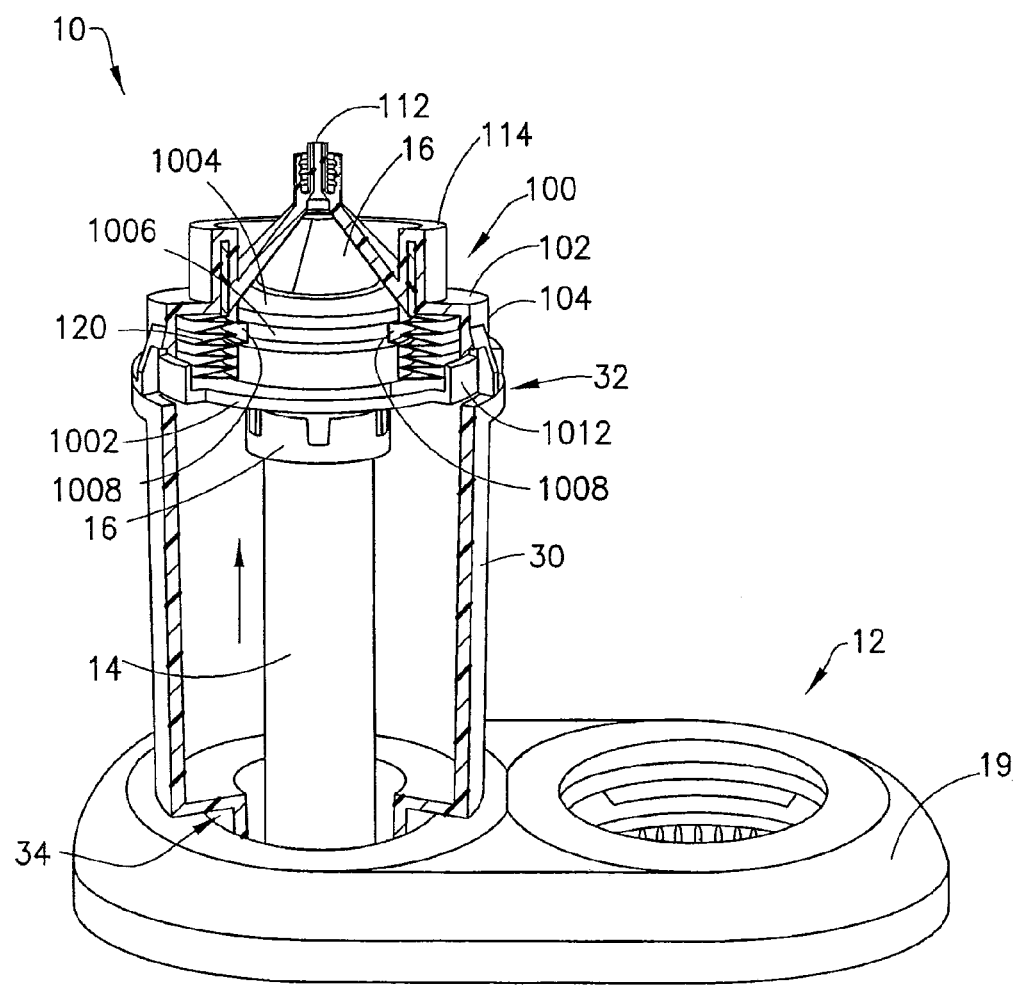
Figure 64:
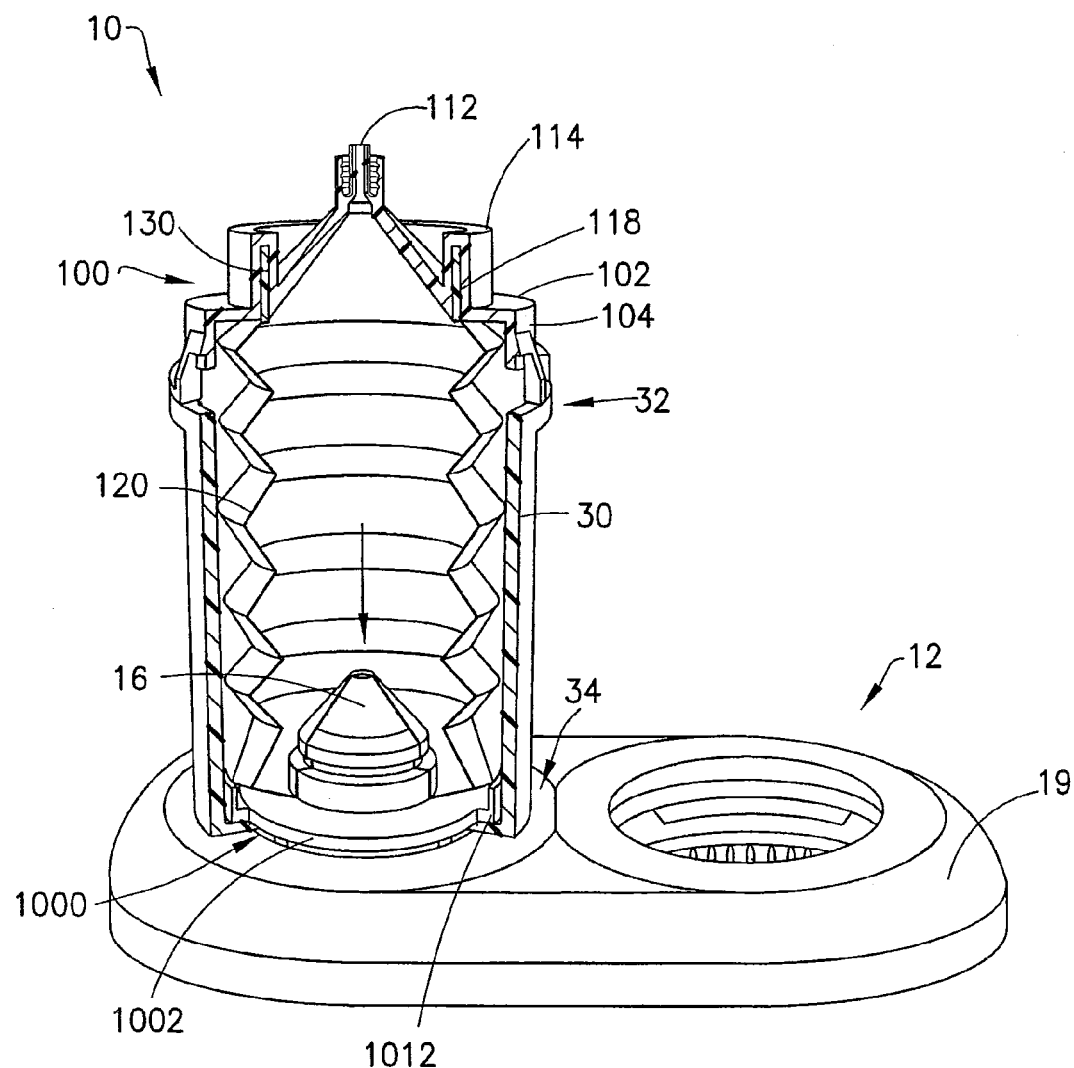
Figure 65:
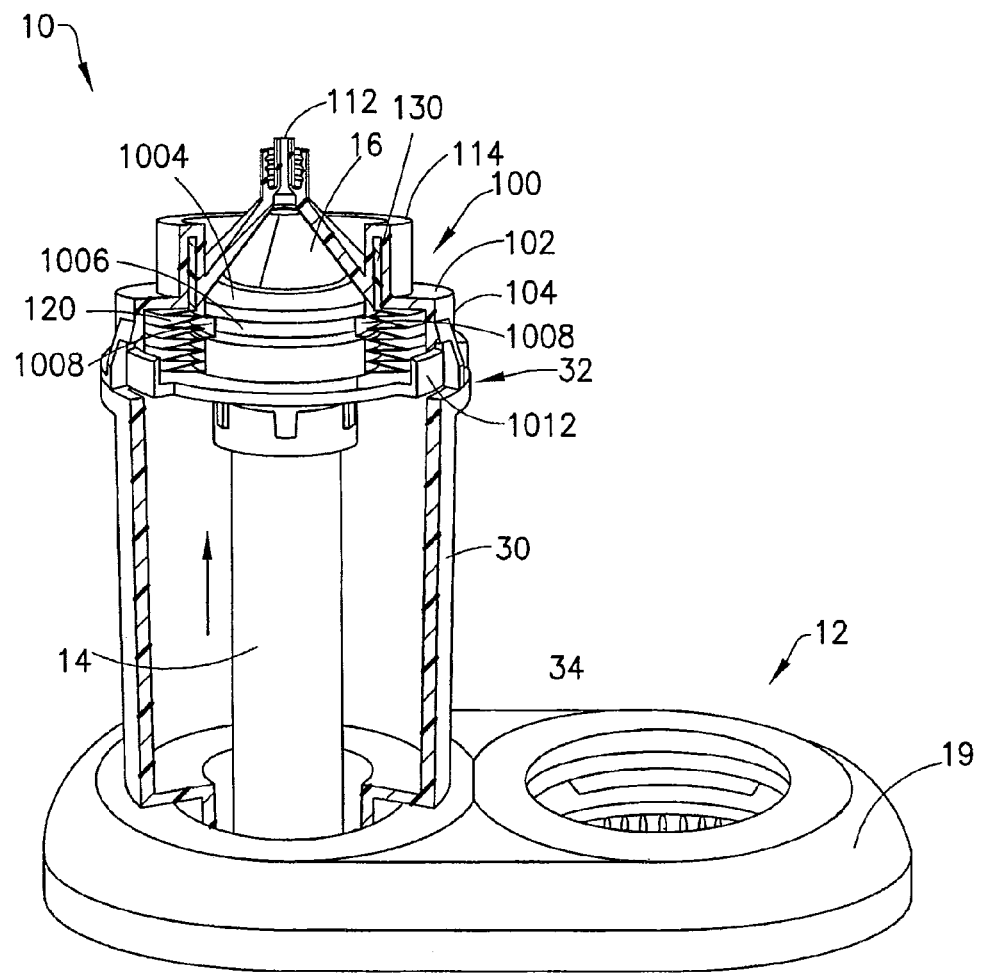
FIGS. 65-66 are sequential perspective and partial cross-sectional views showing detachment of the bellows syringe from the pressure jacket for the embodiment shown in FIGS. 57-58.
Figure 66:
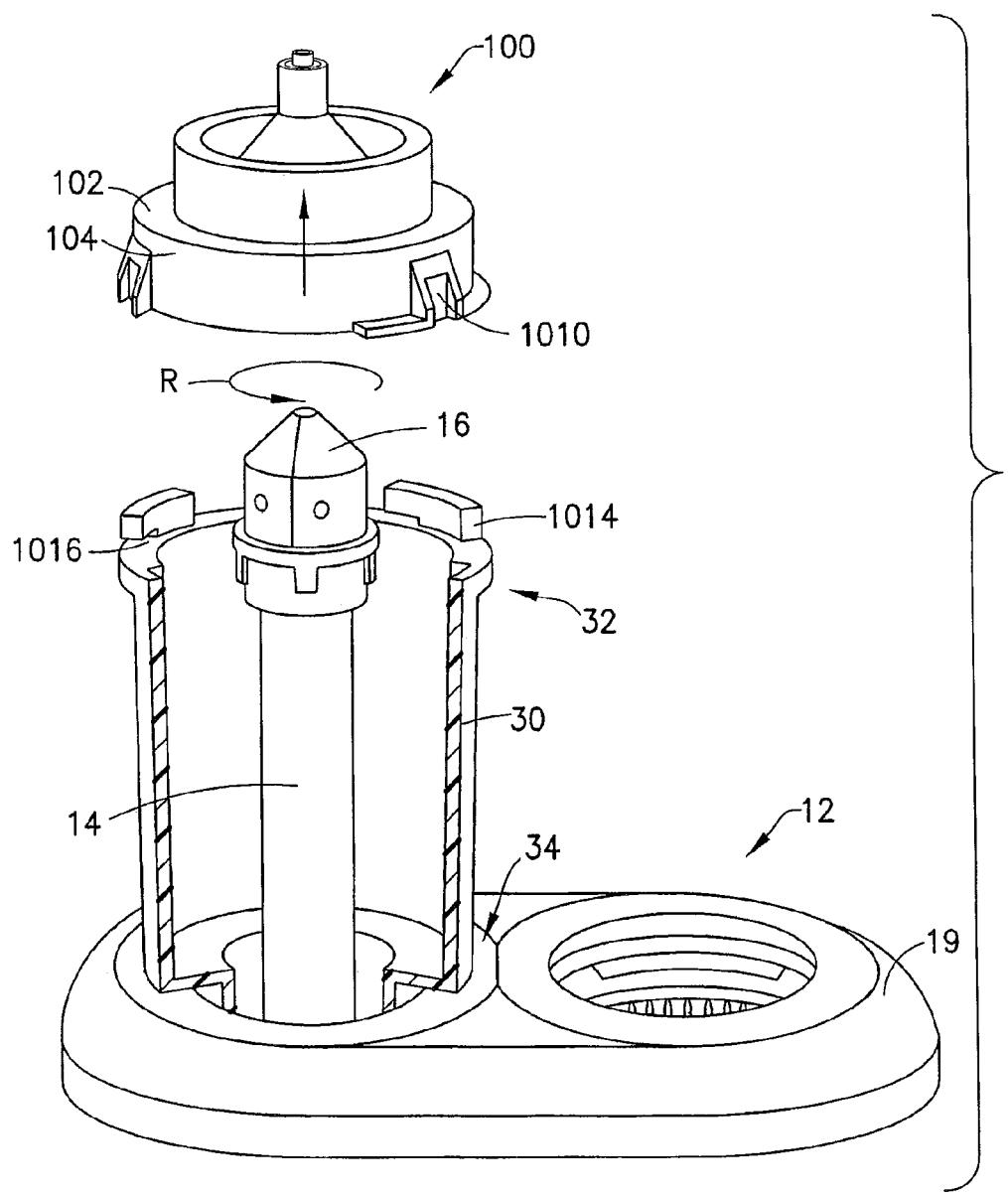

Referring to FIG. 59, the pressure jacket 30 is connected to the face plate 19 by inserting the proximal end 34 into the receiving opening or aperture in the face plate 19. Next, as shown in FIGS. 60-61, the bellows syringe 100 is connected to the distal end 32 of the pressure jacket 30. This connection is made by placing the flat plate portion 1002 of the base member 1000 onto the distal end 32 of the pressure jacket 30 so that the upward-extending retaining tabs 1012 are disposed between the tab members 1014 on the distal end 32. The cap member 102 of the bellows syringe 100 is then rotated in the appropriate direction represented by arrow R to seat the flat plate portion 1002 into the transverse slots 1016 in the tab members 1014 on the distal end 32 of the pressure jacket 30. This engagement secures the bellows syringe 1000 to the pressure jacket 30. Referring further to FIGS. 62-63, the piston element 14 is driven forward so that the piston head 16 engages an end pocket 1018 in the central annular portion 1004 further having internal elements or structures 1020 (see FIG. 58), similar to internal elements or structures 72 discussed previously, that receive the retaining pins 64 on the piston head 16 so that the base member 1000 becomes engaged with the piston head 16. The piston element 14 may be driven sufficiently forward to cause automatic release of the upward-extending retaining tabs 1012 on the base member 1000 with the receiving catch members 1010 on the skirt portion 104 to release the bellows member 120 from the compressed or pre-use state. The bellows member 120 may be expanded as the piston element 14 retracts in the pressure jacket 30 as shown in FIG. 64. When the medical procedure using the bellows syringe 100 is completed, the piston element 14 may be driven forward to the initial position shown in FIG. 65 which permits the upward-extending retaining tabs 1012 on the base member 1000 to reestablish a connection with the receiving catch members 1010 on the skirt portion 104 thereby again placing the bellows member 120 in a compressed, now post-use state. The bellows syringe 100 may be removed from the pressure jacket 30 by reversing the attachment procedure described previously and discarded as medical waste, as shown in FIG. 66.

While embodiments of a bellows syringe or fluid container fluid delivery system and methods of use and operation thereof were provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A bellows syringe for a fluid delivery system, the bellows syringe comprising:
a cap member defining an internal cavity and a discharge port, the cap member further comprising a depending skirt portion;
a bellows member disposed in the internal cavity and held in a compressed state in the internal cavity; and
a base member,
wherein the bellows member is held in the compressed state in the internal cavity by engagement between at least one retaining tab provided on one of the cap member and the base member and engaged with at least one catch member on the other of the cap member and the base member,
and wherein the base member is adapted for connection to a piston head of a piston element of an injector.

2. The bellows syringe of claim 1, wherein the at least one retaining tab comprises a plurality of retaining tabs engaged with a plurality of catch members, respectively, to hold the bellows member in the compressed state in the internal cavity.

3. The bellows syringe of claim 1, wherein a proximal end of the bellows member is closed and a distal end of the bellows member defines a discharge port in fluid communication with the cap member discharge port, and wherein the base member comprises at least one attachment element to attach to the piston head of the piston element.

4. The bellows syringe of claim 3, wherein the base member further comprises an annular portion and the at least one attachment element is disposed in the annular portion.

5. The bellows syringe of claim 1, wherein the base member comprises a plate portion and a central portion, and wherein one of the skirt portion and the plate portion comprises a plurality of retaining tabs engaged with a plurality of catch members provided on the other of the skirt portion and the plate portion to hold the bellows member in the compressed state in the internal cavity.

6. The bellows syringe of claim 5, wherein the central portion defines a circumferential groove and the bellows member comprises a cooperating rib engaging the circumferential groove for securing the plate portion to a proximal end of the bellows member.

7. The bellows syringe of claim 5, wherein the central portion defines an end pocket for receiving the piston head of the piston element, and wherein the end pocket comprises at least one internal element to engage the piston head.

8. A bellows assembly for association with a fluid delivery system, the bellows assembly comprising:
a pressure jacket having a distal end and a proximal end and defining a throughbore therebetween; and
a bellows syringe adapted for connection to the distal end of the pressure jacket, the bellows syringe comprising:
a cap member defining an internal cavity and a discharge port, the cap member further comprising a depending skirt portion;
a bellows member disposed in the internal cavity and held in a compressed state in the internal cavity; and
a base member,
wherein the bellows member is held in the compressed state in the internal cavity by engagement between at least one retaining tab provided on one of the cap member and the base member and engaged with at least one catch member on the other of the cap member and the base member.

9. The bellows assembly of claim 8, wherein the at least one retaining tab comprises a plurality of retaining tabs engaged with a plurality of catch members, respectively, to hold the bellows member in the compressed state in the internal cavity.

10. The bellows assembly of claim 8, wherein a proximal end of the bellows member is closed and a distal end of the bellows member defines a discharge port in fluid communication with the cap member discharge port, and wherein the base member comprises at least one attachment element to attach to a piston head of a piston element operable in the throughbore of the pressure jacket.

11. The bellows assembly of claim 10, wherein the base member further comprises an annular portion and the at least one attachment element is disposed in the annular portion.

12. The bellows assembly of claim 8, wherein the base member comprises a plate portion and a central portion, and wherein one of the skirt portion and the plate portion comprises a plurality of retaining tabs engaged with a plurality of catch members provided on the other of the skirt portion and the plate portion to hold the bellows member in the compressed state in the internal cavity.

13. The bellows assembly of claim 12, wherein the central portion defines a circumferential groove and the bellows member comprises a cooperating rib engaging the circumferential groove for securing the plate portion to a proximal end of the bellows member.

14. The bellows assembly of claim 12, wherein the central portion defines an end pocket for receiving a piston head of a piston element, and wherein the end pocket comprises at least one internal element to engage the piston head.

15. The bellows assembly of claim 12, wherein the distal end of the pressure jacket comprises a plurality of tab members each defining a slot, and wherein the plate portion is adapted to engage the slots to secure the bellows syringe to the pressure jacket.

16. A fluid delivery system comprising:
- a fluid injector comprising a reciprocally operable piston element having a piston head;
- a pressure jacket having a distal end and a proximal end and defining a throughbore therebetween, the pressure jacket proximal end engaged with the fluid injector such that the piston element is operable in the throughbore; and
- a bellows syringe adapted for connection to the distal end of the pressure jacket, the bellows syringe comprising:
  - a cap member defining an internal cavity and a discharge port, the cap member further comprising a depending skirt portion;
  - a bellows member disposed in the internal cavity and held in a compressed state in the internal cavity; and
  - a base member,
- wherein the bellows member is held in the compressed state in the internal cavity by engagement between at least one retaining tab provided on one of the cap member and the base member and engaged with at least one catch member on the other of the cap member and the base member.

17. The fluid delivery system of claim 16, wherein the at least one retaining tab comprises a plurality of retaining tabs engaged with a plurality of catch members, respectively, to hold the bellows member in the compressed state in the internal cavity.

18. The fluid delivery system of claim 16, wherein a proximal end of the bellows member is closed and a distal end of the bellows member defines a discharge port in fluid communication with the cap member discharge port, and wherein the base member comprises at least one attachment element to attach to the piston head of the piston element operable in the throughbore of the pressure jacket.

19. The fluid delivery system of claim 18, wherein the base member further comprises an annular portion and the at least one attachment element is disposed in the annular portion.

20. The fluid delivery system of claim 16, wherein the base member comprises a plate portion and a central portion, and wherein one of the skirt portion and the plate portion comprises a plurality of retaining tabs engaged with a plurality of catch members provided on the other of the skirt portion and the plate portion to hold the bellows member in the compressed state in the internal cavity.

21. The fluid delivery system of claim 20, wherein the central portion defines a circumferential groove and the bellows member comprises a cooperating rib engaging the circumferential groove for securing the plate portion to a proximal end of the bellows member.

22. The fluid delivery system of claim 20, wherein the central portion defines an end pocket for receiving the piston head of the piston element, and wherein the end pocket comprises at least one internal element to engage the piston head.

23. The fluid delivery system of claim 20, wherein the distal end of the pressure jacket comprises a plurality of tab members each defining a slot, and wherein the plate portion is adapted to engage the slots to secure the bellows syringe to the pressure jacket.

* * * * *

UNITED STATES PATENT AND TRADEMARK OFFICE
CERTIFICATE OF CORRECTION

PATENT NO. : 9,180,252 B2  
APPLICATION NO. : 13/834624  
DATED : November 10, 2015  
INVENTOR(S) : Gelblum et al.

Page 1 of 1

It is certified that error appears in the above-identified patent and that said Letters Patent is hereby corrected as shown below:

IN THE SPECIFICATION:
Column 2, Line 4, delete "thereof A" and insert -- thereof. A --, therefor.
Column 2, Line 26, delete "syringe" and insert -- syringe. --, therefor.
Column 13, Line 59, delete "is schematic" and insert -- is a schematic --, therefor.
Column 14, Line 41, delete "is perspective" and insert -- is a perspective --, therefor.
Column 14, Line 46, delete "is perspective" and insert -- is a perspective --, therefor.
Column 14, Line 64, delete "is side" and insert -- is a side --, therefor.
Column 18, Line 45, delete "neck 120" and insert -- discharge neck 130 --, therefor.
Column 29, Line 39, delete "a the shield" and insert -- a shield --, therefor.
Column 31, Line 66, delete "with." and insert -- with --, therefor.
Column 33, Line 21, delete "base 520." and insert -- support base 530. --, therefor.
Column 33, Line 25, delete "base 530" and insert -- support base 530 --, therefor.
Column 34, Line 45, delete "FIG. 40A-40B," and insert -- FIGS. 40A-40B, --, therefor.
Column 42, Lines 14-15, delete "interior cavity 106" and insert -- interior cavity 108 --, therefor.
Column 42, Lines 40-41, delete "cap member 104;" and insert -- cap member 102; --, therefor.

Signed and Sealed this  
Fifteenth Day of March, 2016

Michelle K. Lee  
*Director of the United States Patent and Trademark Office*